United States Patent
Allen et al.

(10) Patent No.: US 7,994,163 B2
(45) Date of Patent: Aug. 9, 2011

(54) 6-SUBSTITUTED-2,3,4,5-TETRAHYDRO-1H-BENZO[D]AZEPINES AS 5-HT$_{2C}$ RECEPTOR AGONISTS

(75) Inventors: John Gordon Allen, Newbury Park, CA (US); Karin Briner, Indianapolis, IN (US); Christopher Stanley Galka, Carmel, IN (US); Richard Charles Hoying, Plainfield, IN (US); Maria Angeles Martinez-Grau, Alcobendas (ES); Julie Miyashiro, Morton Grove, IL (US); Natalia Pokrovskaia, New Westminster (CA); Matthew Robert Reinhard, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 674 days.

(21) Appl. No.: 11/996,457

(22) PCT Filed: Sep. 1, 2006

(86) PCT No.: PCT/US2006/034334
§ 371 (c)(1),
(2), (4) Date: Jan. 22, 2008

(87) PCT Pub. No.: WO2007/028082
PCT Pub. Date: Mar. 8, 2007

(65) Prior Publication Data
US 2008/0255092 A1    Oct. 16, 2008

Related U.S. Application Data

(60) Provisional application No. 60/713,495, filed on Sep. 1, 2005.

(51) Int. Cl.
| | | |
|---|---|---|
| *A61P 3/04* | (2006.01) | |
| *A61P 25/00* | (2006.01) | |
| *A61P 25/22* | (2006.01) | |
| *A61P 25/24* | (2006.01) | |
| *A61K 31/55* | (2006.01) | |
| *C07D 223/16* | (2006.01) | |
| *C07D 401/12* | (2006.01) | |
| *C07D 403/12* | (2006.01) | |
| *C07D 409/12* | (2006.01) | |
| *C07D 417/12* | (2006.01) | |

(52) U.S. Cl. .................. 514/217.01; 540/594
(58) Field of Classification Search ............. 514/217.01; 540/594
See application file for complete search history.

(56) References Cited

U.S. PATENT DOCUMENTS

| | | | |
|---|---|---|---|
| 4,265,890 A | 5/1981 | Holden et al. | |
| 4,985,352 A | 1/1991 | Julius et al. | |
| 5,639,748 A | 6/1997 | DeMarinis et al. | |
| 5,698,766 A | 12/1997 | Julius et al. | |

FOREIGN PATENT DOCUMENTS

| | | |
|---|---|---|
| EP | 0285 287 | 10/1988 |
| EP | 1213017 A2 | 6/2002 |
| WO | WO 93/03015 | 2/1993 |
| WO | WO 93/04686 | 3/1993 |
| WO | WO 93/04866 | 3/1993 |
| WO | WO 02/074746 | 9/2002 |
| WO | WO/02/074746 | 9/2002 |
| WO | WO 03 006466 | 1/2003 |
| WO | WO 03/045940 | 6/2003 |
| WO | WO 2003/086306 | 10/2003 |
| WO | WO 2005/003096 | 1/2005 |
| WO | WO 2005/019179 | 3/2005 |
| WO | WO 2005/019180 | 3/2005 |
| WO | WO 2005/042490 | 5/2005 |
| WO | WO 2005/042491 | 5/2005 |
| WO | WO 2005/082859 | 9/2005 |
| WO | WO 2006/069363 | 6/2006 |
| WO | WO 2006/071740 | 7/2006 |

OTHER PUBLICATIONS

Vikers et al., *Psycholpharmacology*, 167: 274-280 (2003).
Tecott et al., *Nature*, 374: 542-546 (1995).
Martin et al., *Pharmacol. Biochem. Behav.*, 71: 615 (2002).
Chou-Green et al., *Physiology & Behavior*, 78: 641-649 (2003).
Leysen et al., *Trends in Drug Research II*, 29: 49-61 (1998).
Frank et al., *Neuropsychopharmacology* 27: 869-873 (2002).
Upton et al., *Eur. J. Pharmacol.*, 359:33 (1998).
Fitzgerald, Ennis, *Annual Reports in Medicinal Chemistry*, 37: 21-30 (2002).
Nelson et al., *Naunyn-Schmiedeberg's Arch. Pharm.*, 359: 1-6 (1999).
V. Setola et al., *Mol. Pharmacology*, 63: 1223-1229 (2003).
Frishman, Kotob, *Journal of Clinical Pharmacology*, 39: 7-16 (1999).
Seeman, Van Tol, *Trends in Pharmacological Sciences*, 15: 264-270 (1994).
Data Base Registry: XP002419374, Sep. 30, 2005.
Database Registry: XP002419375, Sep. 30, 2005.
Database Registry: XP002419376, Sep. 30, 2005.
Database Registry: XP002419377, Sep. 30, 2005.

*Primary Examiner* — Brenda Coleman
(74) *Attorney, Agent, or Firm* — R. Craig Tucker

(57) ABSTRACT

The present invention provides 6-substituted 2,3,4,5-tetrahydro-1H-benzo[d]azepines of Formula (I) as selective 5-HT2C receptor agonists for the treatment of 5-HT2c associated disorders including obesity, obsessive/compulsive disorder, depression, and anxiety: R6 D R?N—R"R* where R6 is —(CrC3)alkyl-S—(C0-C3)alkyl-R10, —(C1-C3)alkyl-NR11R12, —(CrC3)alkyl-O—R13. and other substituents are as defined in the specification.

5 Claims, No Drawings

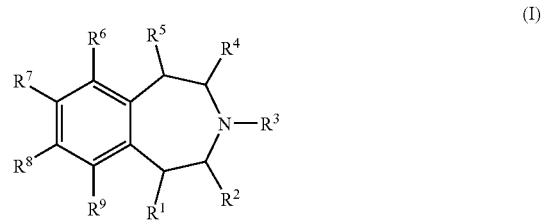

6-SUBSTITUTED-2,3,4,5-TETRAHYDRO-1H-BENZO[D]AZEPINES AS 5-HT$_{2C}$ RECEPTOR AGONISTS

This U.S. national stage application of International Application PCT/US2006/034334, filed Sep. 1, 2006, claims priority to U.S. provisional application Ser. No. 60/713,495, filed Sep. 1, 2005.

The neurotransmitter serotonin (5-hydroxytryptamine, 5-HT) has a rich pharmacology arising from a heterogeneous population of at least seven receptor classes. The serotonin 5-HT$_2$ class is further subdivided into at least three subtypes, designated 5-HT$_{2A}$, 5-HT$_{2B}$, and 5-HT$_{2C}$. The 5-HT$_{2C}$ receptor has been isolated and characterized (Julius, et al., U.S. Pat. No. 4,985,352), and transgenic mice lacking the 5-HT$_{2C}$ receptor have been reported to exhibit seizures and an eating disorder resulting in increased consumption of food (Julius et al., U.S. Pat. No. 5,698,766). The 5-HT$_{2C}$ receptor has also been linked to various other neurological disorders including obesity (Vickers et al., Psychopharmacology, 167: 274-280 (2003)), hyperphagia (Tecott et al., Nature, 374: 542-546 (1995)), obsessive compulsive disorder (Martin et al., Pharmacol. Biochem. Behav., 71: 615 (2002); Chou-Green et al., Physiology & Behavior, 78: 641-649 (2003)), depression (Leysen, Kelder, Trends in Drug Research II, 29: 49-61 (1998)), anxiety (Curr. Opin. Invest. Drugs 2(4), p. 317 (1993)), substance abuse, sleep disorder (Frank et al., Neuropsychopharmacology 27: 869-873 (2002)), hot flashes (EP 1213017 A2), epilepsy (Upton et al., Eur. J. Pharmacol., 359: 33 (1998); Fitzgerald, Ennis, Annual Reports in Medicinal Chemistry, 37: 21-30 (2002)), and hypogonadism (Curr. Opin. Invest. Drugs 2(4), p. 317 (1993)).

Certain substituted 2,3,4,5-tetrahydro-1H-benzo[d]azepine compounds have been disclosed as useful therapeutics as for example:

U.S. Pat. No. 4,265,890 describes certain substituted 2,3,4,5-tetrahydro-1H-benzo[d]azepine compounds as dopaminergic receptor antagonists for use as antipsychotics and antiemetics, inter alia.

EP 0 285 287 describes certain substituted 2,3,4,5-tetrahydro-1H-benzo[d]azepine compounds for use as agents to treat gastrointestinal motility disorders, inter alia.

WO 93/03015 and WO 93/04686 describe certain substituted 2,3,4,5-tetrahydro-1H-benzo[d]azepine compounds as alpha-adrenergic receptor antagonists for use as agents to treat hypertension and cardiovascular diseases in which changes in vascular resistance are desirable, inter alia.

WO 02/074746 A1 describes certain substituted 2,3,4,5-tetrahydro-1H-benzo[d]azepine compounds as 5-HT$_{2C}$ agonists for the treatment of hypogonadism, obesity, hyperphagia, anxiety, depression, sleep disorder, inter alia.

WO 03/006466 A1 describes certain substituted tricyclic hexahydroazepinoindole and indoline compounds as 5-HT ligands and consequently their usefulness for treating diseases wherein modulation of 5-HT activity is desired.

WO 05/019180 describes 6-(2,2,2-trifluoroethylamino)-7-chloro-2,3,4,5-tetrahydro-1H-benzo[d]azepine as a potent and selective 5-HT$_{2C}$ agonist for the treatment of obesity, anxiety, depression, and obsessive-compulsive disorder.

High affinity 5-HT$_{2C}$ receptor agonists would provide useful therapeutics for the treatment of the above mentioned 5-HT$_{2C}$ receptor-associated disorders including obesity, hyperphagia, obsessive/compulsive disorder, depression, anxiety, substance abuse, sleep disorder, hot flashes, and hypogonadism. High affinity 5-HT$_{2C}$ receptor agonists that are also selective for the 5-HT$_{2C}$ receptor, would provide such therapeutic benefit without the undesirable adverse events associated with current therapies. Achieving selectivity for the 5-HT$_{2C}$ receptor, particularly as against the 5-HT$_{2A}$ and 5-HT$_{2B}$ receptors, has proven difficult in designing 5-HT$_{2C}$ agonists. 5-HT$_{2A}$ receptor agonists have been associated with problematic hallucinogenic adverse events. (Nelson et al., Naunyn-Schmiedeberg's Arch. Pharm., 359: 1-6 (1999)). 5-HT$_{2B}$ receptor agonists have been associated with cardiovascular related adverse events, such as valvulopathy. (V. Setola et al., Mol. Pharmacology, 63: 1223-1229 (2003), and ref. cited therein).

Previous references to substituted 2,3,4,5-tetrahydro-1H-benzo[d]azepine compounds as potential therapeutics have predominately recited their uses as alpha adrenergic and/or dopaminergic modulators. Adrenergic modulators are often associated with the treatment of cardiovascular diseases (Frishman, Kotob, Journal of Clinical Pharmacology, 39: 7-16 (1999)). Dopaminergic receptors are primary targets in the treatment of schizophrenia and Parkinson's disease (Seeman, Van Tol, Trends in Pharmacological Sciences, 15: 264-270 (1994)). It will be appreciated by those skilled in the art that selectivity as against these and other physiologically important receptors will generally also be preferred characteristics for therapeutics for the specific treatment of 5-HT$_{2C}$ associated disorders as described above.

In continued research on selective 5-HT$_{2C}$ agonists over those disclosed earlier in commonly assigned PCT application US 05/05418, it was found that many earlier compounds could metabolize in part to their corresponding 6-alkylthio-, 6-alkylamino-, or 6-alkoxy-tetrahydrobenzazepine counterparts, which themselves were relatively potent, but non-selective serotonin agonists. This was found to be particularly relevant to the 6-alkylthio-, particularly the 6-methylthio-linked series of compounds. To avoid this metabolism to active, but non-selective compounds, applicants have now discovered potent and selective 5-HT$_{2C}$ agonists according to the present disclosure, wherein the reversal of the respective 6-position alkylthio-, alkylamino-, and alkoxy-linkers reduces or avoids the formation of such metabolites while maintaining many of the desirable characteristics of their prior-disclosed analogs.

Therefore, the present invention provides selective 5-HT$_{2C}$ agonist compounds of Formula I:

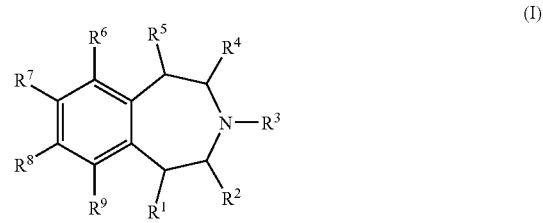

(I)

where:
R$^1$ is hydrogen, fluoro, or (C$_1$-C$_3$)alkyl;
R$^2$, R$^3$, and R$^4$ are each independently hydrogen, methyl, or ethyl;
R$^5$ is hydrogen, fluoro, methyl, or ethyl;
R$^6$ is —(C$_1$-C$_3$)alkyl-S—(C$_0$-C$_3$)alkyl-R$^{10}$, —(C$_1$-C$_3$)alkyl-NR$^{12}$—(C$_0$-C$_3$)alkyl-R$^{11}$, or —(C$_1$-C$_3$)alkyl-O—(C$_0$-C$_3$)alkyl-R$^{13}$;
R$^7$ is hydrogen, halo, cyano, (C$_1$-C$_6$)alkyl optionally substituted with 1 to 6 fluoro substituents, (C$_2$-C$_6$)alkenyl optionally substituted with 1 to 6 fluoro substituents, (C$_3$-C$_7$)cycloalkyl optionally substituted with 1 to 4 fluoro substituents, (C$_1$-C$_6$)alkoxy optionally substituted with 1 to 6 fluoro substituents, (C$_1$-C$_6$)alkylthio optionally substituted with 1 to 6 fluoro substituents, $Ph^1$-$(C_0$-$C_3)$alkyl optionally substituted with 1 to 6 fluoro substituents, $Ph^1$-$(C_0$-$C_3)$alkyl-O— optionally substituted with 1 to 6 fluoro substituents, or $Ph^1$-$(C_0$-$C_3)$alkyl-S— optionally substituted with 1 to 6 fluoro substituents;

$R^8$ is hydrogen, halo, cyano, —$SCF_3$, or hydroxy;

$R^9$ is hydrogen, halo, cyano, —$CF_3$, —$SCF_3$, hydroxy, or $(C_1$-$C_3)$alkoxy optionally substituted with 1 to 6 fluoro substituents;

$R^{10}$ is
  a) an aromatic heterocycle substituent selected from the group consisting of tetrazolyl, 1,2,3-thiadiazolyl, 1,3,4-thiadiazolyl, 1,2,4-thiadiazolyl, 1,2,3-oxadiazolyl, 1,3,4-oxadiazolyl, and 1,2,4-oxadiazolyl, any one of which may optionally be substituted with a substituent selected from the group consisting of $(C_1$-$C_4)$alkyl optionally substituted with 1 to 5 fluoro substituents, $Ph^1$-$(C_0$-$C_3)$alkyl, $Ar^1$—$(C_0$-$C_3)$alkyl, $(C_1$-$C_4)$alkyl-C(O)—, $Ph^1$-$(C_0$-$C_3)$alkyl-C(O)—, $Ar^1$—$(C_0$-$C_3)$alkyl-C(O)—, $(C_1$-$C_4)$alkyl-$NR^{12}$—$(C_0$-$C_3)$alkyl- optionally substituted on the on the and $(C_1$-$C_4)$alkyl moiety with 1 to 5 fluoro substituents, $(C_3$-$C_7)$cycloalkyl-$(C_0$-$C_3)$alkyl-$NR^{12}$—$(C_0$-$C_3)$alkyl, $Ph^1$-$(C_0$-$C_3)$alkyl-$NR^{12}$—$(C_0$-$C_3)$alkyl, $Ar^1$—$(C_0$-$C_3)$alkyl-$NR^{12}$—$(C_0$-$C_3)$alkyl;
  b) an aromatic heterocycle substituent selected from the group consisting of imidazolyl, thiazolyl, isothiazolyl, thiophenyl, pyrazolyl, oxazolyl, isoxazolyl, 1,2,3-triazolyl, 1,2,4-triazolyl, or a heterocycle selected from thiazolinyl, any one of which may be optionally substituted with one to two substituents selected from the group consisting of
    $(C_1$-$C_6)$alkyl optionally substituted with 1 to 6 fluoro substituents,
    $Ph^1$-$(C_0$-$C_3)$alkyl optionally substituted on the alkyl moiety with 1 to 6 fluoro substituents,
    $Ar^1$—$(C_0$-$C_3)$alkyl optionally substituted on the alkyl moiety with 1 to 6 fluoro substituents,
    $(C_1$-$C_6)$alkyl-C(O)—,
    $Ph^1$-$(C_0$-$C_3)$alkyl-C(O)—,
    $Ar^1$—$(C_0$-$C_3)$alkyl-C(O)—,
    $(C_1$-$C_6)$alkyl-NH—C(O)— optionally substituted with 1 to 6 fluoro substituents,
    $Ph^1$-$(C_0$-$C_3)$alkyl-NH—C(O)— optionally substituted on the alkyl moiety with 1 to 6 fluoro substituents, and
    $Ar^1$—$(C_0$-$C_3)$alkyl-NH—C(O)— optionally substituted on the alkyl moiety with 1 to 6 fluoro substituents,
    or optionally substituted on ring carbon atoms with one or two substituents selected from the group consisting of
    halo,
    cyano,
    $(C_1$-$C_6)$alkyl-CH=CH— optionally substituted with 1 to 6 fluoro substituents,
    $(C_1$-$C_6)$alkoxy optionally substituted with 1 to 6 fluoro substituents,
    $(C_1$-$C_6)$alkylthio optionally substituted with 1 to 6 fluoro substituents,
    $Ph^1$-$(C_0$-$C_3)$alkylthio,
    $(C_1$-$C_6)$alkyl-$NR^{12}$—$(C_0$-$C_3)$alkyl- optionally substituted on the $(C_1$-$C_6)$alkyl moiety with 1 to 6 fluoro substituents,
    $(C_3$-$C_7)$cycloalkyl-$(C_0$-$C_3)$alkyl-$NR^{12}$—$(C_0$-$C_3)$alkyl,
    $Ph^1$-$(C_0$-$C_3)$alkyl-$NR^{12}$—$(C_0$-$C_3)$alkyl-,
    $Ar^1$—$(C_0$-$C_3)$alkyl-$NR^{12}$—$(C_0$-$C_3)$alkyl-,
    $Het^1$-$(C_0$-$C_3)$alkyl-,
    $(C_1$-$C_6)$alkyl-C(O)—NH—,
    $Ph^1$-$(C_0$-$C_3)$alkyl-C(O)—NH—,
    $Ar^1$—$(C_0$-$C_3)$alkyl-C(O)—NH—,
    $(C_1$-$C_6)$alkyl-O—C(O)—NH— optionally substituted with 1 to 6 fluoro substituents,
    $Ph^1$-$(C_0$-$C_3)$alkyl-O—C(O)—NH— optionally substituted on the alkyl moiety with 1 to 6 fluoro substituents, and
    $Ar^1$—$(C_0$-$C_3)$alkyl-O—C(O)—NH— optionally substituted on the alkyl moiety with 1 to 6 fluoro substituents,
    or optionally substituted on two adjacent ring atoms with a bivalent 3 to 4 carbon hydrocarbon substituent which, together with the ring atoms to which it is attached, form a benzene ring or a partially saturated five- or six-membered ring;
  c) phenyl optionally substituted with:
    i) 1 to 5 independently selected halo substituents; or
    ii) 1 to 3 substituents independently selected from the group consisting of halo, cyano, —$SCF_3$, nitro, hydroxy, $(C_1$-$C_6)$alkyl optionally further substituted with 1 to 6 fluoro substituents, and $(C_1$-$C_6)$alkoxy optionally further substituted with 1 to 6 fluoro substituents; or
    iii) 0, 1, or 2 substituents independently selected from the group consisting of halo, cyano, —$SCF_3$, methyl, —$CF_3$, methoxy, —$OCF_3$, nitro, and hydroxy, together with one substituent selected from the group consisting of
      $(C_3$-$C_7)$cycloalkyl-$(C_0$-$C_5)$alkyl optionally substituted on the alkyl moiety with 1 to 6 fluoro substituents and optionally substituted independently on the cycloalkyl moiety with 1 to 6 substituents selected from fluoro and methyl provided that no more than 2 substituents are methyl,
      $Ph^1$-$(C_0$-$C_5)$alkyl,
      $Ar^1$—$(C_0$-$C_5)$alkyl,
      thiazolyl-$(C_0$-$C_6)$alkyl optionally substituted with a substituent independently selected from the group consisting of halo, $(C_1$-$C_6)$alkyl optionally further substituted with 1 to 6 fluoro substituents, $(C_1$-$C_6)$alkyl-$NR^{12}$—$(C_0$-$C_3)$alkyl- optionally substituted on the $(C_1$-$C_6)$alkyl moiety with 1 to 6 fluoro substituents, and $(C_3$-$C_7)$cycloalkyl-$(C_0$-$C_3)$alkyl-$NR^{12}$—$(C_0$-$C_3)$alkyl,
      $(C_1$-$C_6)$alkyl-CH=CH— optionally substituted with 1 to 6 fluoro substituents, $(C_3$-$C_7)$cycloalkyl-$(C_0$-$C_3)$alkyl-CH=CH— optionally substituted with 1 to 6 fluoro substituents on alkyl and optionally substituted independently on the cycloalkyl moiety with 1 to 6 substituents selected from fluoro and methyl provided that no more than 2 substituents are methyl,
      $(C_1$-$C_6)$alkyl-S—$(C_0$-$C_5)$alkyl optionally substituted on the $(C_1$-$C_6)$alkyl moiety with 1 to 6 fluoro substituents,
      $(C_3$-$C_7)$cycloalkyl-$(C_0$-$C_3)$alkyl-S—$(C_0$-$C_5)$alkyl,
      $Ph^1$-$(C_0$-$C_3)$alkyl-S—$(C_0$-$C_5)$alkyl,
      $Ar^1$—$(C_0$-$C_3)$alkyl-S—$(C_0$-$C_5)$alkyl,
      $(C_1$-$C_6)$alkyl-O—$(C_0$-$C_5)$alkyl optionally substituted on the $(C_1$-$C_6)$alkyl moiety with 1 to 6 fluoro substituents,
      $(C_3$-$C_7)$cycloalkyl-$(C_0$-$C_3)$alkyl-O—$(C_0$-$C_5)$alkyl,
      $Ph^1$-$(C_0$-$C_3)$alkyl-O—$(C_0$-$C_5)$alkyl,
      $Ar^1$—$(C_0$-$C_3)$alkyl-O—$(C_0$-$C_5)$alkyl,
      $(C_1$-$C_6)$alkyl-$SO_2$—$(C_0$-$C_5)$alkyl optionally substituted on the $(C_1$-$C_6)$alkyl moiety with 1 to 6 fluoro substituents, ($C_3$-$C_7$)cycloalkyl-($C_0$-$C_3$)alkyl-$SO_2$—($C_0$-$C_5$)alkyl,
$Ph^1$-($C_0$-$C_3$)alkyl-$SO_2$—($C_0$-$C_5$)alkyl,
$Ar^1$—($C_0$-$C_3$)alkyl-$SO_2$—($C_0$-$C_5$)alkyl,
($C_1$-$C_6$)alkyl-C(O)—($C_0$-$C_5$)alkyl,
($C_3$-$C_7$)cycloalkyl-($C_0$-$C_3$)alkyl-C(O)—($C_0$-$C_5$)alkyl,
$Ph^1$-($C_0$-$C_3$)alkyl-C(O)—($C_0$-$C_5$)alkyl,
$Ar^1$—($C_0$-$C_3$)alkyl-C(O)—($C_0$-$C_5$)alkyl,
($C_1$-$C_6$)alkyl-NH—($C_0$-$C_5$)alkyl optionally substituted on the ($C_1$-$C_6$)alkyl moiety with 1 to 6 fluoro substituents,
($C_3$-$C_7$)cycloalkyl-($C_0$-$C_3$)alkyl-NH—($C_0$-$C_5$)alkyl,
$Ph^1$-($C_0$-$C_3$)alkyl-NH—($C_0$-$C_5$)alkyl,
$Ar^1$—($C_0$-$C_3$)alkyl-NH—($C_0$-$C_5$)alkyl,
$Het^1$-($C_0$-$C_3$)alkyl-,
($C_1$-$C_6$)alkyl-NH—C(O)—($C_0$-$C_5$)alkyl optionally substituted on the ($C_1$-$C_6$)alkyl moiety with 1 to 6 fluoro substituents,
($C_3$-$C_7$)cycloalkyl-($C_0$-$C_3$)alkyl-NH—C(O)—($C_0$-$C_5$)alkyl,
$Ph^1$-($C_0$-$C_3$)alkyl-NH—C(O)—($C_0$-$C_5$)alkyl,
$Ar^1$—($C_0$-$C_3$)alkyl-NH—C(O)—($C_0$-$C_5$)alkyl,
($C_1$-$C_6$)alkyl-($C_0$-$C_3$)alkyl-C(O)—NH—($C_0$-$C_5$)alkyl,
($C_3$-$C_7$)cycloalkyl-C(O)—NH—($C_0$-$C_5$)alkyl,
$Ph^1$-($C_0$-$C_3$)alkyl-C(O)—NH—($C_0$-$C_5$)alkyl,
$Ar^1$—($C_0$-$C_3$)alkyl-C(O)—NH—($C_0$-$C_5$)alkyl,
($C_1$-$C_6$)alkyl-NH—$SO_2$—($C_0$-$C_5$)alkyl optionally substituted on the ($C_1$-$C_6$)alkyl moiety with 1 to 6 fluoro substituents,
($C_3$-$C_7$)cycloalkyl-($C_0$-$C_3$)alkyl-NH—$SO_2$—($C_0$-$C_5$)alkyl,
($C_1$-$C_6$)alkyl-$SO_2$—NH—($C_0$-$C_5$)alkyl,
($C_3$-$C_7$)cycloalkyl-($C_0$-$C_3$)alkyl-$SO_2$—NH—($C_0$-$C_5$)alkyl;

d) an aromatic heterocycle substituent selected from the group consisting of pyridyl, pyridazinyl, pyrimidinyl, pyrazinyl, any of which may be optionally substituted with 1 or 2 substituents independently selected from the group consisting of halo, cyano, —$SCF_3$, methyl, —$CF_3$, methoxy, —$OCF_3$, nitro, hydroxy, and optionally further substituted with a substituent selected from the group consisting of ($C_3$-$C_7$)cycloalkyl-($C_0$-$C_5$)alkyl optionally further substituted on the alkyl moiety with 1 to 6 fluoro substituents and optionally substituted independently on the cycloalkyl moiety with 1 to 6 substituents selected from fluoro and methyl provided that no more than 2 substituents are methyl,
$Ph^1$-($C_0$-$C_5$)alkyl,
$Ar^1$—($C_0$-$C_5$)alkyl,
thiazolyl-($C_0$-$C_1$)alkyl optionally substituted with a substituent independently selected from the group consisting of halo, ($C_1$-$C_6$)alkyl optionally further substituted with 1 to 6 fluoro substituents, ($C_1$-$C_6$)alkyl-$NR^{12}$—($C_0$-$C_3$)alkyl- optionally substituted on the ($C_1$-$C_6$)alkyl moiety with 1 to 6 fluoro substituents, and ($C_3$-$C_7$)cycloalkyl-($C_0$-$C_3$)alkyl-$NR^{12}$—($C_0$-$C_3$)alkyl,
($C_1$-$C_6$)alkyl-CH=CH— optionally substituted with 1 to 6 fluoro substituents,
($C_3$-$C_7$)cycloalkyl-($C_0$-$C_3$)alkyl-CH=CH— optionally substituted with 1 to 6 fluoro substituents on alkyl and optionally substituted independently on the cycloalkyl moiety with 1 to 6 substituents selected from fluoro and methyl provided that no more than 2 substituents are methyl,
($C_1$-$C_6$)alkyl-S—($C_0$-$C_5$)alkyl optionally substituted on the ($C_1$-$C_6$)alkyl moiety with 1 to 6 fluoro substituents,
($C_3$-$C_7$)cycloalkyl-($C_0$-$C_3$)alkyl-S—($C_0$-$C_5$)alkyl,
$Ph^1$-($C_0$-$C_3$)alkyl-S—($C_0$-$C_5$)alkyl,
$Ar^1$—($C_0$-$C_3$)alkyl-S—($C_0$-$C_5$)alkyl,
($C_1$-$C_6$)alkyl-O—($C_0$-$C_5$)alkyl optionally substituted on the ($C_1$-$C_6$)alkyl moiety with 1 to 6 fluoro substituents,
($C_3$-$C_7$)cycloalkyl-($C_0$-$C_3$)alkyl-O—($C_0$-$C_5$)alkyl,
$Ph^1$-($C_0$-$C_3$)alkyl-O—($C_0$-$C_5$)alkyl,
$Ar^1$—($C_0$-$C_3$)alkyl-O—($C_0$-$C_5$)alkyl,
($C_1$-$C_6$)alkyl-$SO_2$—($C_0$-$C_5$)alkyl optionally substituted on the ($C_1$-$C_6$)alkyl moiety with 1 to 6 fluoro substituents,
($C_3$-$C_7$)cycloalkyl-($C_0$-$C_3$)alkyl-$SO_2$—($C_0$-$C_5$)alkyl,
$Ph^1$-($C_0$-$C_3$)alkyl-$SO_2$—($C_0$-$C_5$)alkyl,
$Ar^1$—($C_0$-$C_3$)alkyl-$SO_2$—($C_0$-$C_5$)alkyl,
($C_1$-$C_6$)alkyl-C(O)—($C_0$-$C_5$)alkyl,
($C_3$-$C_7$)cycloalkyl-($C_0$-$C_3$)alkyl-C(O)—($C_0$-$C_5$)alkyl,
$Ph^1$-($C_0$-$C_3$)alkyl-C(O)—($C_0$-$C_5$)alkyl,
$Ar^1$—($C_0$-$C_3$)alkyl-C(O)—($C_0$-$C_5$)alkyl,
($C_1$-$C_6$)alkyl-NH—($C_0$-$C_5$)alkyl optionally substituted on the ($C_1$-$C_6$)alkyl moiety with 1 to 6 fluoro substituents,
($C_3$-$C_7$)cycloalkyl-($C_0$-$C_3$)alkyl-NH—($C_0$-$C_5$)alkyl,
$Ph^1$-($C_0$-$C_3$)alkyl-NH—($C_0$-$C_5$)alkyl,
$Ar^1$—($C_0$-$C_3$)alkyl-NH—($C_0$-$C_5$)alkyl,
$Het^1$-($C_0$-$C_5$)alkyl-,
($C_1$-$C_6$)alkyl-NH—C(O)—($C_0$-$C_5$)alkyl optionally substituted on the ($C_1$-$C_6$)alkyl moiety with 1 to 6 fluoro substituents,
($C_3$-$C_7$)cycloalkyl-($C_0$-$C_3$)alkyl-NH—C(O)—($C_0$-$C_5$)alkyl,
$Ph^1$-($C_0$-$C_3$)alkyl-NH—C(O)—($C_0$-$C_5$)alkyl,
$Ar^1$—($C_0$-$C_3$)alkyl-N—H—C(O)—($C_0$-$C_5$)alkyl,
($C_1$-$C_6$)alkyl-C(O)—NH—($C_0$-$C_5$)alkyl,
($C_3$-$C_7$)cycloalkyl-($C_0$-$C_3$)alkyl-C(O)—NH—($C_0$-$C_5$)alkyl,
$Ph^1$-($C_0$-$C_3$)alkyl-C(O)—NH—($C_0$-$C_5$)alkyl,
$Ar^1$—($C_0$-$C_3$)alkyl-C(O)—NH—($C_0$-$C_5$)alkyl; or e) alpha-naphthalyl, quinolin-2-yl, quinolin-3-yl, or quinolin-4-yl;

$R^{11}$ is a) phenyl optionally substituted with:
i) 1 to 5 independently selected halo substituents; or
ii) 1 to 3 substituents independently selected from the group consisting of halo, cyano, methyl, —$CF_3$, —$SCF_3$, methoxy, nitro, and hydroxy; or
iii) 0, 1 or 2 substituents independently selected from the group consisting of halo, cyano, methyl, —$CF_3$, —$SCF_3$, methoxy, nitro, and hydroxy and further substituted with a substituent selected from the group consisting of:
($C_1$-$C_6$)alkyl optionally further substituted with 1 to 6 fluoro substituents,
($C_1$-$C_6$)alkyl-O—($C_0$-$C_5$)alkyl optionally further substituted with 1 to 6 fluoro substituents,
($C_1$-$C_6$)alkyl-CH=CH— optionally substituted with 1 to 6 fluoro substituents,
($C_3$-$C_7$)cycloalkyl-($C_0$-$C_3$)alkyl-CH=CH— optionally substituted with 1 to 6 fluoro substituents on alkyl and optionally substituted independently on the cycloalkyl moiety with 1 to 6 substituents selected from fluoro and methyl provided that no more than 2 substituents are methyl,
$(C_3-C_7)$cycloalkyl-$(C_0-C_3)$alkyl-O—$(C_0-C_5)$alkyl,
$Ph^1$-$(C_0-C_3)$alkyl-O—$(C_0-C_5)$alkyl,
$Ar^1$—$(C_0-C_3)$alkyl-O—$(C_0-C_5)$alkyl,
$(C_1-C_6)$alkyl-S—$(C_0-C_5)$alkyl optionally substituted on the $(C_1-C_6)$alkyl moiety with 1 to 6 fluoro substituents,
$(C_3-C_7)$cycloalkyl-$(C_0-C_3)$alkyl-S—$(C_0-C_5)$alkyl,
$Ph^1$-$(C_0-C_3)$alkyl-S—$(C_0-C_5)$alkyl,
$Ar^1$—$(C_0-C_3)$alkyl-S—$(C_0-C_5)$alkyl,
$(C_1-C_6)$alkyl-$SO_2$—$(C_0-C_5)$alkyl optionally substituted on the $(C_1-C_6)$alkyl moiety with 1 to 6 fluoro substituents,
$(C_3-C_7)$cycloalkyl-$(C_0-C_3)$alkyl-$SO_2$—$(C_0-C_5)$alkyl,
$Ph^1$-$(C_0-C_3)$alkyl-$SO_2$—$(C_0-C_5)$alkyl,
$Ar^1$—$(C_0-C_3)$alkyl-$SO_2$—$(C_0-C_5)$alkyl,
$(C_1-C_6)$alkyl-C(O)—$(C_0-C_5)$alkyl,
$(C_3-C_7)$cycloalkyl-$(C_0-C_3)$alkyl-C(O)—$(C_0-C_5)$alkyl,
$Ph^1$-$(C_0-C_3)$alkyl-C(O)—$(C_0-C_5)$alkyl,
$Ar^1$—$(C_0-C_3)$alkyl-C(O)—$(C_0-C_5)$alkyl,
$(C_1-C_6)$alkyl-NH—$(C_0-C_5)$alkyl optionally substituted on the $(C_1-C_6)$alkyl moiety with 1 to 6 fluoro substituents,
$(C_3-C_7)$cycloalkyl-$(C_0-C_3)$alkyl-NH—$(C_0-C_5)$alkyl,
$Ph^1$-$(C_0-C_3)$alkyl-NH—$(C_0-C_5)$alkyl,
$Ar^1$—$(C_0-C_3)$alkyl-NH—$(C_0-C_5)$alkyl,
$(C_1-C_6)$alkyl-NH—C(O)—$(C_0-C_5)$alkyl optionally substituted on the $(C_1-C_6)$alkyl moiety with 1 to 6 fluoro substituents,
$(C_3-C_7)$cycloalkyl-$(C_0-C_3)$alkyl-NH—C(O)—$(C_0-C_5)$alkyl,
$Ph^1$-$(C_0-C_3)$alkyl-NH—C(O)—$(C_0-C_5)$alkyl,
$Ar^1$—$(C_0-C_3)$alkyl-NH—C(O)—$(C_0-C_5)$alkyl,
$Het^1$-$(C_0-C_5)$alkyl-,
$(C_1-C_6)$alkyl-C(O)—NH—$(C_0-C_5)$alkyl,
$(C_3-C_7)$cycloalkyl-$(C_0-C_3)$alkyl-C(O)—NH—$(C_0-C_5)$alkyl,
$Ph^1$-$(C_0-C_3)$alkyl-C(O)—NH—$(C_0-C_5)$alkyl, and
$Ar^1$—$(C_0-C_3)$alkyl-C(O)—NH—$(C_0-C_5)$alkyl;
b) pyridyl optionally substituted with
  i) 1 to 3 substituents independently selected from the group consisting of halo, cyano, methyl, —$CF_3$, —$SCF_3$, methoxy, nitro, and hydroxy; or
  ii) 0, 1 or 2 substituents independently selected from the group consisting of halo, cyano, methyl, —$CF_3$, —$SCF_3$, methoxy, nitro, and hydroxy, and further substituted with a substituent selected from the group consisting of:
    $(C_1-C_6)$alkyl optionally further substituted with 1 to 6 fluoro substituents,
    $(C_1-C_6)$alkyl-O—$(C_0-C_5)$alkyl optionally further substituted with 1 to 6 fluoro substituents,
    $(C_1-C_6)$alkyl-CH=CH— optionally substituted with 1 to 6 fluoro substituents,
    $(C_3-C_7)$cycloalkyl-$(C_0-C_3)$alkyl-CH=CH— optionally substituted with 1 to 6 fluoro substituents on alkyl and optionally substituted independently on the cycloalkyl moiety with 1 to 6 substituents selected from fluoro and methyl provided that no more than 2 substituents are methyl,
    $(C_3-C_7)$cycloalkyl-$(C_0-C_3)$alkyl-O—$(C_0-C_5)$alkyl,
    $Ph^1$-$(C_0-C_3)$alkyl-O—$(C_0-C_5)$alkyl,
    $(C_1-C_6)$alkyl-S—$(C_0-C_5)$alkyl optionally substituted on the $(C_1-C_6)$alkyl moiety with 1 to 6 fluoro substituents,
    $(C_3-C_7)$cycloalkyl-$(C_0-C_3)$alkyl-S—$(C_0-C_5)$alkyl,
    $Ph^1$-$(C_0-C_3)$alkyl-S—$(C_0-C_5)$alkyl,
    $(C_1-C_6)$alkyl-$SO_2$—$(C_0-C_5)$alkyl optionally substituted on the $(C_1-C_6)$alkyl moiety with 1 to 6 fluoro substituents,
    $(C_3-C_7)$cycloalkyl-$(C_0-C_3)$alkyl-$SO_2$—$(C_0-C_5)$alkyl,
    $Ph^1$-$(C_0-C_3)$alkyl-$SO_2$—$(C_0-C_5)$alkyl,
    $(C_1-C_6)$alkyl-C(O)—$(C_0-C_5)$alkyl,
    $(C_3-C_7)$cycloalkyl-$(C_0-C_3)$alkyl-C(O)—$(C_0-C_5)$alkyl,
    $Ph^1$-$(C_0-C_3)$alkyl-C(O)—$(C_0-C_5)$alkyl,
    $(C_1-C_6)$alkyl-NH—$(C_0-C_5)$alkyl optionally substituted on the $(C_1-C_6)$alkyl moiety with 1 to 6 fluoro substituents,
    $(C_3-C_7)$cycloalkyl-$(C_0-C_3)$alkyl-NH—$(C_0-C_5)$alkyl,
    $Ph^1$-$(C_0-C_3)$alkyl-NH—$(C_0-C_5)$alkyl,
    $(C_1-C_6)$alkyl-NH—C(O)—$(C_0-C_5)$alkyl optionally substituted on the $(C_1-C_6)$alkyl moiety with 1 to 6 fluoro substituents,
    $(C_3-C_7)$cycloalkyl-$(C_0-C_3)$alkyl-NH—C(O)—$(C_0-C_5)$alkyl,
    $Ph^1$-$(C_0-C_3)$alkyl-NH—C(O)—$(C_0-C_5)$alkyl,
    $(C_1-C_6)$alkyl-C(O)—NH—$(C_0-C_5)$alkyl,
    $(C_3-C_7)$cycloalkyl-$(C_0-C_3)$alkyl-C(O)—NH—$(C_0-C_5)$alkyl, and
    $Ph^1$-$(C_0-C_3)$alkyl-C(O)—NH—$(C_0-C_5)$alkyl;
c) pyridazinyl optionally substituted with 1 or 2 substituents independently selected from the group consisting of halo, cyano, hydroxy, $(C_1-C_6)$alkyl optionally further substituted with 1 to 6 fluoro substituents, $(C_1-C_6)$alkoxy optionally further substituted with 1 to 6 fluoro substituents; and $(C_1-C_6)$alkylthio optionally further substituted with 1 to 6 fluoro substituents; or
d) a five-membered aromatic heterocycle selected from the group of thiophenyl, thiazole, isothiazole optionally substituted with 1 or 2 substituents independently selected from the group consisting of halo, cyano, hydroxy, $(C_1-C_6)$alkyl optionally further substituted with 1 to 6 fluoro substituents, $(C_1-C_6)$alkoxy optionally further substituted with 1 to 6 fluoro substituents, $(C_1-C_6)$alkylthio optionally further substituted with 1 to 6 fluoro substituents, $(C_1-C_6)$alkylamino optionally further substituted with 1 to 6 fluoro substituents, and $(C_1-C_6)$alkyl-C(O)—;

$R^{12}$ is hydrogen or methyl
$R^{13}$ is a) phenyl optionally substituted with:
  i) 1 to 5 independently selected halo substituents; or
  ii) 1 to 3 substituents independently selected from the group consisting of halo, cyano, —$SCF_3$, nitro, hydroxy, $(C_1-C_6)$alkyl optionally further substituted with 1 to 6 fluoro substituents, and $(C_1-C_6)$alkoxy optionally further substituted with 1 to 6 fluoro substituents; or
  iii) 0, 1, or 2 substituents independently selected from the group consisting of halo, cyano, —$SCF_3$, methyl, —$CF_3$, methoxy, —$OCF_3$, nitro, and hydroxy, together with one substituent selected from the group consisting of
    $(C_3-C_7)$cycloalkyl-$(C_0-C_5)$alkyl optionally substituted on the alkyl moiety with 1 to 6 fluoro substituents and optionally substituted independently on the cycloalkyl moiety with 1 to 6 substituents selected from fluoro and methyl provided that no more than 2 substituents are methyl, $Ph^1$-$(C_0$-$C_5)$alkyl, $Ar^1$—$(C_0$-$C_5)$alkyl, $(C_1$-$C_6)$alkyl-CH=CH— optionally substituted with 1 to 6 fluoro substituents, $(C_3$-$C_7)$cycloalkyl-$(C_0$-$C_3)$alkyl-CH=CH— optionally substituted with 1 to 6 fluoro substituents on alkyl and optionally substituted independently on the cycloalkyl moiety with 1 to 6 substituents selected from fluoro and methyl provided that no more than 2 substituents are methyl, $(C_1$-$C_6)$alkyl-S—$(C_0$-$C_5)$alkyl optionally substituted on the $(C_1$-$C_6)$alkyl moiety with 1 to 6 fluoro substituents, $(C_3$-$C_7)$cycloalkyl-$(C_0$-$C_3)$alkyl-S—$(C_0$-$C_5)$alkyl, $Ph^1$-$(C_0$-$C_3)$alkyl-S—$(C_0$-$C_5)$alkyl, $Ar^1$—$(C_0$-$C_3)$alkyl-S—$(C_0$-$C_5)$alkyl, $(C_1$-$C_6)$alkyl-O—$(C_0$-$C_5)$alkyl optionally substituted on the $(C_1$-$C_6)$alkyl moiety with 1 to 6 fluoro substituents, $(C_3$-$C_7)$cycloalkyl-$(C_0$-$C_3)$alkyl-O—$(C_0$-$C_5)$alkyl, $Ph^1$-$(C_0$-$C_3)$alkyl-O—$(C_0$-$C_5)$alkyl, $Ar^1$—$(C_0$-$C_3)$alkyl-O—$(C_0$-$C_5)$alkyl, $(C_1$-$C_6)$alkyl-$SO_2$—$(C_0$-$C_5)$alkyl optionally substituted on the $(C_1$-$C_6)$alkyl moiety with 1 to 6 fluoro substituents, $(C_3$-$C_7)$cycloalkyl-$(C_0$-$C_3)$alkyl-$SO_2$—$(C_0$-$C_5)$alkyl, $Ph^1$-$(C_0$-$C_3)$alkyl-$SO_2$—$(C_0$-$C_5)$alkyl, $Ar^1$—$(C_0$-$C_3)$alkyl-$SO_2$—$(C_0$-$C_5)$alkyl, $(C_1$-$C_6)$alkyl-C(O)—$(C_0$-$C_5)$alkyl, $(C_3$-$C_7)$cycloalkyl-$(C_0$-$C_3)$alkyl-C(O)—$(C_0$-$C_5)$alkyl, $Ph^1$-$(C_0$-$C_3)$alkyl-C(O)—$(C_0$-$C_5)$alkyl, $Ar^1$—$(C_0$-$C_3)$alkyl-C(O)—$(C_0$-$C_5)$alkyl, $(C_1$-$C_6)$alkyl-NH—$(C_0$-$C_5)$alkyl optionally substituted on the $(C_1$-$C_6)$alkyl moiety with 1 to 6 fluoro substituents, $(C_3$-$C_7)$cycloalkyl-$(C_0$-$C_3)$alkyl-NH—$(C_0$-$C_5)$alkyl, $Ph^1$-$(C_0$-$C_3)$alkyl-NH—$(C_0$-$C_5)$alkyl, $Ar^1$—$(C_0$-$C_3)$alkyl-NH—$(C_0$-$C_5)$alkyl, $Het^1$-$(C_0$-$C_3)$alkyl-, $(C_1$-$C_6)$alkyl-NH—C(O)—$(C_0$-$C_5)$alkyl optionally substituted on the $(C_1$-$C_6)$alkyl moiety with 1 to 6 fluoro substituents, $(C_3$-$C_7)$cycloalkyl-$(C_0$-$C_3)$alkyl-NH—C(O)—$(C_0$-$C_5)$alkyl, $Ph^1$-$(C_0$-$C_3)$alkyl-NH—C(O)—$(C_0$-$C_5)$alkyl, $Ar^1$—$(C_0$-$C_3)$alkyl-NH—C(O)—$(C_0$-$C_5)$alkyl, $(C_1$-$C_6)$alkyl-$(C_0$-$C_3)$alkyl-C(O)—NH—$(C_0$-$C_5)$alkyl, $(C_3$-$C_7)$cycloalkyl-C(O)—NH—$(C_0$-$C_5)$alkyl, $Ph^1$-$(C_0$-$C_3)$alkyl-C(O)—NH—$(C_0$-$C_5)$alkyl, $Ar^1$—$(C_0$-$C_3)$alkyl-C(O)—NH—$(C_0$-$C_5)$alkyl, $(C_1$-$C_6)$alkyl-NH—$SO_2$—$(C_0$-$C_5)$alkyl optionally substituted on the $(C_1$-$C_6)$alkyl moiety with 1 to 6 fluoro substituents, $(C_3$-$C_7)$cycloalkyl-$(C_0$-$C_3)$alkyl-NH—$SO_2$—$(C_0$-$C_5)$alkyl, $(C_1$-$C_6)$alkyl-$SO_2$—NH—$(C_0$-$C_5)$allyl, $(C_3$-$C_7)$cycloalkyl-$(C_0$-$C_3)$alkyl-$SO_2$—NH—$(C_0$-$C_5)$alkyl; or b) thiophenyl optionally substituted with one to two substituents selected from the group consisting of
halo,
cyano,
$(C_1$-$C_6)$alkyl optionally substituted with 1 to 6 fluoro substituents, $Ph^1$-$(C_0$-$C_3)$alkyl optionally substituted on the alkyl moiety with 1 to 6 fluoro substituents, $Ar^1$—$(C_0$-$C_3)$alkyl optionally substituted on the alkyl moiety with 1 to 6 fluoro substituents, $(C_1$-$C_6)$alkyl-C(O)—, $Ph^1$-$(C_0$-$C_3)$alkyl-C(O)—, $Ar^1$—$(C_0$-$C_3)$alkyl-C(O)—, $(C_1$-$C_6)$alkyl-NH—C(O)— optionally substituted with 1 to 6 fluoro substituents, $Ph^1$-$(C_0$-$C_3)$alkyl-NH—C(O)— optionally substituted on the alkyl moiety with 1 to 6 fluoro substituents, $Ar^1$—$(C_0$-$C_3)$alkyl-NH—C(O)— optionally substituted on the alkyl moiety with 1 to 6 fluoro substituents, $(C_1$-$C_6)$alkyl-CH=CH— optionally substituted with 1 to 6 fluoro substituents, $(C_1$-$C_6)$alkoxy optionally substituted with 1 to 6 fluoro substituents, $(C_1$-$C_6)$alkylthio optionally substituted with 1 to 6 fluoro substituents, $Ph^1$-$(C_0$-$C_3)$alkylthio, $(C_1$-$C_6)$alkyl-$NR^{12}$—$(C_0$-$C_3)$alkyl- optionally substituted on the $(C_1$-$C_6)$alkyl moiety with 1 to 6 fluoro substituents, $(C_3$-$C_7)$cycloalkyl-$(C_0$-$C_3)$alkyl-$NR^{12}$—$(C_0$-$C_3)$alkyl, $Ph^1$-$(C_0$-$C_3)$alkyl-$NR^{12}$—$(C_0$-$C_3)$alkyl-, $Ar^1$—$(C_0$-$C_3)$alkyl-$NR^{12}$$(C_0$-$C_3)$alkyl-, $Het^1$-$(C_0$-$C_3)$alkyl-, $(C_1$-$C_6)$alkyl-C(O)—NH—, $Ph^1$-$(C_0$-$C_3)$alkyl-C(O)—NH—, $Ar^1$—$(C_0$-$C_3)$alkyl-C(O)—NH—, $(C_1$-$C_6)$alkyl-O—C(O)—NH— optionally substituted with 1 to 6 fluoro substituents, $Ph^1$-$(C_0$-$C_3)$alkyl-O—C(O)—NH— optionally substituted on the alkyl moiety with 1 to 6 fluoro substituents, and $Ar^1$—$(C_0$-$C_3)$alkyl-O—C(O)—NH— optionally substituted on the alkyl moiety with 1 to 6 fluoro substituents;

$Ar^1$ is pyridyl, optionally substituted with 1 to 4 independently selected halo substituents, or with 1 to 3 substituents independently selected from the group consisting of halo, cyano, hydroxy, acetyl, methyl, —$CF_3$, methoxy, —$OCF_3$, methylthio, —$SCF_3$;

$Ph^1$ is phenyl optionally substituted with 1 to 5 independently selected halo substituents, or with 1 to 3 substituents independently selected from the group consisting of halo, cyano, hydroxy, acetyl, methylthio, —$SCF_3$, $(C_1$-$C_6)$alkyl optionally further substituted with 1 to 6 fluoro substituents, and $(C_1$-$C_6)$alkoxy optionally further substituted with 1 to 6 fluoro substituents;

$Het^1$ is a saturated, nitrogen-containing heterocycle substituent selected from the group consisting of pyrrolidinyl, piperidinyl, homopiperidinyl, morpholinyl, thiomorpholinyl, homomorpholinyl, and homothiomorpholinyl, any of which may optionally be substituted with $(C_1$-$C_6)$alkyl or with 2 methyl substituents;

or a pharmaceutically acceptable salt or solvate thereof.

This invention also provides pharmaceutical compositions which comprise a compound of Formula I, or a pharmaceutically acceptable salt thereof, in association with a pharmaceutically acceptable carrier, diluent, or excipient.

In another aspect of the present invention, there is provided a method for increasing activation of the 5-$HT_{2C}$ receptor in mammals comprising administering to a mammal in need of such activation an effective amount of a compound of Formula I, or a pharmaceutically acceptable salt thereof.

The present invention also provides a method for treating obesity in mammals comprising administering to a mammal in need of such treatment an effective amount of a compound of Formula I, or a pharmaceutically acceptable salt thereof.

The present invention also provides a method for treating obsessive/compulsive disorder in mammals comprising administering to a mammal in need of such treatment an effective amount of a compound of Formula I, or a pharmaceutically acceptable salt thereof.

Furthermore, the present invention provides a method for treating depression in mammals comprising administering to a mammal in need of such treatment an effective amount of a compound of Formula I, or a pharmaceutically acceptable salt thereof.

Furthermore, the present invention provides a method for treating anxiety in mammals comprising administering to a mammal in need of such treatment an effective amount of a compound of Formula I, or a pharmaceutically acceptable salt thereof.

In preferred embodiments of the above methods of treatment utilizing a compound of Formula I, or a pharmaceutically acceptable salt thereof, the mammal is a human.

In another aspect of the present invention, there is provided a compound of Formula I for use in selectively increasing activation of the 5-$HT_{2C}$ receptor and/or for use in treating a variety of disorders associated with decreased activation of 5-$HT_{2C}$ receptors. Preferred embodiments of this aspect of the invention include a compound of Formula I for use in the treatment of obesity, hyperphagia, obsessive/compulsive disorder, depression, anxiety, substance abuse, sleep disorder, hot flashes, and/or hypogonadism. Particularly preferred embodiments of this aspect of the invention include the treatment of obesity, obsessive/compulsive disorder, depression, and/or anxiety.

In another aspect of the present invention, there is provided the use of one or more compounds of Formula I in the manufacture of a medicament for the activation of 5-$HT_{2C}$ receptors in a mammal. In preferred embodiments of this aspect of the invention, there is provided the use of one or more compounds of Formula I in the manufacture of a medicament for the treatment of obesity, hyperphagia, obsessive/compulsive disorder, depression, anxiety, substance abuse, sleep disorder, hot flashes, and/or hypdgonadism. Particularly preferred embodiments of this aspect of the invention include the use of one or more compounds of Formula I in the manufacture of medicaments for the treatment of obesity, obsessive/compulsive disorder, depression, and/or anxiety.

Additionally, the present invention provides a pharmaceutical formulation adapted for the treatment of obesity, or for the treatment of obsessive/compulsive disorder, or for the treatment of depression, or for the treatment of anxiety, each of which comprise a compound of Formula I in association with a pharmaceutically acceptable carrier, diluent or excipient.

In those instances where the disorders which can be treated by 5-$HT_{2C}$ agonists are known by established and accepted classifications, their classifications can be found in various sources. For example, at present, the fourth edition of the Diagnostic and Statistical Manual of Mental Disorders (DSM-IV™) (1994, American Psychiatric Association, Washington, D.C.), provides a diagnostic tool for identifying many of the disorders described herein. Also, the International Classification of Diseases, Tenth Revision (ICD-10), provides classifications for many of the disorders described herein. The skilled artisan will recognize that there are alternative nomenclatures, nosologies, and classification systems for disorders described herein, including those as described in the DSM-IV and ICD-10, and that terminology and classification systems evolve with medical scientific progress.

The general chemical terms used throughout have their usual meanings. For example, the term "alkyl" refers to a branched or unbranched saturated hydrocarbon group. The term "n-alkyl" refers to an unbranched alkyl group. By way of illustration, but without limitation, the term "($C_1$-$C_2$)alkyl" refers to methyl and ethyl. The term "($C_1$-$C_3$) n-alkyl" refers to methyl, ethyl, and propyl. The term "($C_1$-$C_3$)alkyl" refers to methyl, ethyl, propyl, and isopropyl. The term "($C_1$-$C_5$)alkyl" refers to all branched and unbranched alkyl groups having from one to five carbon atoms. The term "($C_1$-$C_6$)alkyl" refers to all branched and unbranched alkyl groups having from one to six carbon atoms. The term "($C_3$-$C_6$)alkyl" refers to all branched and unbranched alkyl groups having from three to six carbon atoms. The term "($C_2$-$C_6$)alkyl" refers to all branched and unbranched alkyl groups having from two to six carbon atoms.

($C_x$-$C_y$)alkyl may also be used in conjunction with other substituents to indicate a branched or unbranched saturated hydrocarbon linker for the substituent, where x and y indicate the range of carbon atoms permitted in the linker moiety. By way of illustration, but without limitation, —($C_0$-$C_1$)alkyl refers to a single bond or a methylene linker moiety; —($C_0$-$C_2$)alkyl refers to a single bond, methylene, methyl-methylene, or ethylene linker moiety; —($C_0$-$C_3$)alkyl further includes trimethylene, alpha- or beta-methyl ethylene, or ethyl methylene; —($C_0$-$C_5$)alkyl refers to a bond or a saturated, branched or unbranched hydrocarbon linker having from 1 to 5 carbon atoms. —($C_1$-$C_2$)alkyl, —($C_1$-$C_3$)alkyl, —($C_1$-$C_5$)alkyl, and —($C_1$-$C_6$)alkyl refer to branched or unbranched alkylene linkers having from 1 to 2, 3, 5, or 6 carbon atoms, respectively.

The term "alkenyl" refers to a branched or unbranched hydrocarbon group having one or more carbon-carbon double bonds. By way of illustration, but without limitation, the term "($C_2$-$C_6$)alkenyl" refers to a branched or unbranched hydrocarbon group having from 2 to 6 carbon atoms and 1 or more carbon-carbon double bonds. Allyl means a propyl-2-en-1-yl moiety ($CH_2$=CH—$CH_2$—).

The term "($C_3$-$C_7$)cycloalkyl" refers to cyclopropyl, cyclobutyl, cyclopentyl, cyclohexyl and cycloheptyl. Cycloalkylalkyl refers to a cycloalkyl moiety linked through a branched or unbranched alkylene linker, as for example, but without limitation, —$CH_2$—, —$CH_2CH_2$—, —$CH(CH_3)$—, —$CH_2CH_2CH_2$—, —$CH_2CH(CH_3)$—, —$CH(CH_3)CH_2$—, —$CH(CH_2CH_3)$—, and the like. ($C_3$-$C_7$)cycloalkyl($C_{0-}$$C_{1, 2 \, or \, 3}$)alkyl, refers to a cycloalkyl moiety linked through a single bond (i.e. $C_0$-alkyl) or an alkylene linker having 1, 2, or 3 carbon atoms, respectively. Each alkyl, cycloalkyl, and cycloalkylalkyl group may be optionally substituted as provided for herein.

The terms "alkoxy", "phenyloxy", "sulfonyloxy", and "carbonyloxy" refer to an alkyl group, phenyl group, sulfonyl group, or carbonyl group, respectively, that is bonded through an oxygen atom.

The terms "alkylthio", "trifluoromethylthio", "cycloalkylthio" ("cyclohexylthio"), "phenylthio", and "furanylthio" refer to an alkyl group, trifluoromethyl group, cycloalkyl (cyclohexyl) group, phenyl group, or furanyl group, respectively, that is bonded through a sulfur atom.

The terms "alkylcarbonyl", "alkoxycarbonyl", "phenylcarbonyl", and "phenyloxycarbonyl", refer to an alkyl, alkoxy, phenyl, or phenyloxy group bonded through a carbonyl moiety.

The terms "alkylsulfonyl" (t-butylsulfonyl), "($C_3$-$C_7$)cycloalkylsulfonyl", "phenylsulfonyl", "$Ph^1$-($C_0$-$C_3$)alkylsulfonyl", and "Ar²—(C₀-C₃)alkylsulfonyl", refer to an alkyl (t-butyl), (C₃-C₇)cycloalkyl, phenyl, Ph¹-(C₀-C₃)alkyl, or Ar²—(C₀-C₃)alkyl group bonded through a sulfonyl moiety (—SO₂—).

The term "N-linked" means that the referenced moiety is linked through its nitrogen atom, by way of illustration, but without limitation, N-linked Het¹ means the Het¹ moiety is linked through a nitrogen atom in the ring of the Het¹ moiety.

The term "halo" refers to fluoro, chloro, bromo, or iodo. Preferred halo groups are fluoro, chloro, and bromo. More preferred halo groups are fluoro and chloro.

The term "heterocycle" is taken to mean a saturated or unsaturated 4 to 7 membered ring containing from 1 to 3 heteroatoms selected from nitrogen, oxygen and sulfur, said ring optionally being benzofused. Exemplary saturated heterocycles, for the purposes of the present invention, include azetidinyl, pyrrolidinyl, piperidinyl, homopiperidinyl, tetrahydrofuranyl, tetrahydropyranyl, morpholinyl, thiomorpholinyl, piperazinyl, and the like. Exemplary unsaturated heterocycles include, but are not limited to, pyrrolyl, pyrazolyl, imidazolyl, 1,2,3-triazolyl, 1,2,4-triazolyl, furanyl, oxazolyl, isoxazolyl, 1,2,3-oxadiazolyl, 1,2,4-oxadiazolyl, 1,3,4-oxadiazolyl, thiophenyl, thiazolyl, isothiazolyl, 1,2,3-thiadiazolyl, 1,2,4-thiadiazolyl, 1,3,4-thiadiazolyl, pyridyl, pyridazinyl, and the like. Exemplary benzofused heterocyclic rings include, but are not limited to, indolyl, dihydroindolyl, indazolyl, benzisoxazolyl, benzimidazolyl, benzofuranyl, dihydrobenzofuranyl, benzoxazolyl, benzo[1,3]dioxolyl, benzothiophenyl, benzothiazolyl, quinolinyl, isoquinolinyl, benzopyranyl, dihydrobenzopyranyl, cinnolinyl, quinazolinyl and the like, all of which may be optionally substituted as provided for herein, which also includes optionally substituted on the benzene ring when the heterocycle is benzofused.

In one embodiment, preferred saturated heterocycles include pyrrolidinyl, piperidinyl, homopiperidinyl, tetrahydrofuranyl, tetrahydropyranyl, morpholinyl, thiomorpliolinyl, homomorpholinyl, and homothiomotpholinyl, all of which may be optionally substituted as provided for herein.

In one embodiment, preferred unsaturated heterocycles include [pyrrolyl,?]pyrazolyl, imidazolyl, furanyl, oxazolyl, isoxazolyl, 1,2,3-oxadiazolyl, 1,2,4-oxadiazolyl, 1,3,4-oxadiazolyl, thiophenyl, thiazolyl, isothiazolyl, 1,2,3-thiadiazolyl, 1,2,4-thiadiazolyl, 1,3,4-thiadiazolyl, and pyridyl, all of which may be optionally substituted as provided for herein.

The terms "gem-", "geminal", or "geminate" refer to two identical substituents bonded to a common carbon atom, as for example, but without limitation, gem-methyl, meaning two methyl groups bound to a common carbon atom, as for instance in a 3,3-dimethyltetrahydrobenzofuranyl group. For the purposes of this application, gem-ethano means an ethylene substituent wherein both carbons are bound to the same carbon atom of the substituted group to form a cyclopropyl moiety, as for example, but without limitation, the ethano substituent on the 2-phenyl-(1,1-ethano)ethylamino group below:

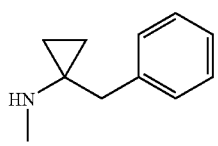

The term "amino protecting group" as used in this specification refers to a substituent commonly employed to block or protect the amino functionality while reacting other functional groups on the compound. Examples of such amino protecting groups include the formyl group, the trityl group, the acetyl group, the trichloroacetyl group, the trifluoroacetyl group, the chloroacetyl, bromoacetyl, and iodoacetyl groups, carbamoyl-type blocking groups such as benzyloxycarbonyl, 9-fluorenylmethoxycarbonyl ("FMOC"), t-butoxycarbonyl (t-BOC), and like amino protecting groups. The species of amino protecting group employed is not critical so long as the derivatized amino group is stable to the conditions of subsequent reactions on other positions of the molecule and can be removed at the appropriate point without disrupting the remainder of the molecule. The selection and use (addition and subsequent removal) of amino protecting groups is well known within the ordinary skill of the art. Further examples of groups referred to by the above terms are described by T. W. Greene and P. G. M. Wuts, "Protective Groups in Organic Synthesis", 3rd edition, John Wiley and Sons, New York, N.Y., 1999, chapter 7, hereafter referred to as "Greene".

The term "pharmaceutical" or "pharmaceutically acceptable" when used herein as an adjective, means substantially non-toxic and substantially non-deleterious to the recipient.

By "pharmaceutical composition" it is further meant that the carrier, solvent, excipients and/or salt must be compatible with the active ingredient of the composition (e.g. a compound of Formula I). It is understood by those of ordinary skill in this art that the terms "pharmaceutical formulation" and "pharmaceutical composition" are generally interchangeable, and they are so used for the purposes of this application.

The term "effective amount" means an amount of a compound of Formula I which is capable of activating 5-HT$_{2C}$ receptors and/or eliciting a given pharmacological effect.

The term "suitable solvent" refers to any solvent, or mixture of solvents, inert to the ongoing reaction that sufficiently solubilizes the reactants to afford a medium within which to effect the desired reaction.

It is understood that compounds of the present invention may exist as stereoisomers. As such, all enantiomers, diastereomers, and mixtures thereof, are included within the scope of the present invention. Where specific stereochemistries are identified in this application, the Cahn-Prelog-Ingold designations of (R)- and (S)- and the cis and trans designation of relative stereochemistry are used to refer to specific isomers and relative stereochemistry. Known optical rotations are designated by (+) and (−) for dextrorotatary and levorotatary, respectively. Where a chiral compound is resolved into its isomers, but absolute configurations or optical rotations are not determined, the isomers are arbitrarily designated as isomer 1, isomer 2, etc. While all enantiomers, diastereomers, and mixtures thereof, are contemplated within the present invention, preferred embodiments are single enantiomers and single diastereomers.

It is generally understood by those skilled in this art, that compounds intended for use in pharmaceutical compositions are routinely, though not necessarily, converted to a salt form in efforts to optimize such characteristics as the handling properties, stability, pharmacokinetic, and/or bioavailability, etc. Methods for converting a compound to a given salt form are well known in the art (see for example, Berge, S. M, Bighley, L. D., and Monkhouse, D. C., J. Pharm. Sci., 66:1, (1977)). In that the compounds of the present invention are amines and therefore basic in nature, they readily react with a wide variety of pharmaceutically acceptable organic and inorganic acids to form pharmaceutically acceptable acid addition salts therewith. Such salts are also embodiments of this invention.

Typical inorganic acids used to form such salts include hydrochloric, hydrobromic, hydroiodic, nitric, sulfuric, phosphoric, hypophosphoric, metaphosphoric, pyrophosphoric acid, and the like. Salts derived from organic acids, such as aliphatic mono and dicarboxylic acids, phenyl substituted alkanoic acids, hydroxyalkanoic and hydroxyalkandioic acids, aromatic acids, aliphatic and aromatic sulfonic acids, may also be used. Such pharmaceutically acceptable salts thus include chloride, bromide, iodide, nitrate, acetate, phenylacetate, trifluoroacetate, acrylate, ascorbate, benzoate, chlorobenzoate, dinitrobenzoate, hydroxybenzoate, methoxybenzoate, methylbenzoate, o-acetoxybenzoate, isobutyrate, phenylbutyrate, α-hydroxybutyrate, butyne-1,4-dicarboxylate, hexyne-1,4-dicarboxylate, caprate, caprylate, cinnamate, citrate, formate, fumarate, glycolate, heptanoate, hippurate, lactate, malate, maleate, hydroxymaleate, malonate, mandelate, nicotinate, isonicotinate, oxalate, phthalate, terephthalate, propiolate, propionate, phenylpropionate, salicylate, sebacate, succinate, suberate, benzenesulfonate, p-bromobenzenesulfonate, chlorobenzenesulfonate, ethylsulfonate, 2-hydroxyethylsulfonate, methylsulfonate (mesylate), naphthalene-1-sulfonate, naphthalene-2-sulfonate, naphthalene-1,5-sulfonate, p-toluenesulfonate, xylenesulfonate, tartrate, and the like.

It is well known that such compounds can form salts in various molar ratios with the acid to provide, for example, the hemi-acid, mono-acid, di-acid salt, etc. Where in the salt formation procedure, the acid is added in a specific stoichiometric ratio, unless otherwise analyzed to confirm, the salt is presumed, but not known, to form in that molar ratio. Terms such as "(acid)$_x$," are understood to mean that the molar ratio of the salt formed is not known and can not be presumed, as for example, but without limitation, (HCl)$_x$ and (methanesulfonic acid)$_x$.

Abbreviations used herein are defined as follows:
"2B-3 ethanol" means ethanol denatured with toluene.
"Anal. Calc'd" or "Anal. Calcd" means calculated elemental analysis.
"BINAP" means (±)-2,2'-bis(diphenylphosphino)-1,1'-binaphthalene.
"Boc" means tert-butoxycarbonyl.
"bp" means boiling point.
"Brine" means a saturated aqueous sodium chloride solution.
"t-Bu" means tert-butyl.
"CV" means calorific value of oxygen.
"DABCO" means 1,4-diazabicyclo[2.2.2]octane.
"DBU" means 1,8-diazabicyclo[5.4.0]undec-7-ene.
"DCM" means dichloromethane (i.e. methylene chloride, $CH_2Cl_2$).
"DMF" means N,N-dimethylformamide.
"DMSO" means dimethylsulfoxide.
"DOI" means (±)-1-(2,5-dimethoxy-4-[$^{125}$I]-iodophenyl)-2-aminopropane.
"DPPF" means 1,1'-bis(diphenylphosphino)ferrocene.
"DPPP" means 1,3-bis(diphenylphosphino)propane.
"DSC" means differential scanning calorimetry.
"ee" means enantiomeric excess.
"EDTA" means ethylenediaminetetraacetic acid.
"EE" means energy expenditure.
"EEDQ" means 2-ethoxy-1-ethoxycarbonyl-1,2-dihydroquinoline.
"EtOAc" means ethyl acetate.
"GDP" means guanosine diphosphate.
"GTP" means guanosine triphosphate.

"GTPγ[$^{35}$S]" means guanosine triphosphate having the terminal phosphate substituted with $^{35}$S in place of an oxygen.
"HPLC" means high-pressure liquid chromatography.
"HRMS" means high-resolution mass spectrometry.
"IR" means Infrared.
"ISPA" means immunoadsorption scintillation proximity assay.
"mp" means melting point.
"Ms" in a chemical structure means the methanesulfonyl moiety (—$SO_2CH_3$).
"MS (APCI+)" means mass spectroscopy using atmospheric pressure chemical ionization.
"MS (ES+)" means mass spectroscopy using electrospray ionization.
"MTBE" means methyl tert-butyl ether.
"NMR" means nuclear magnetic resonance.
"psi" means pounds per square inch.
"RQ" means respiratory quotient.
"SCX chromatography" means chromatography on an SCX column or cartridge.
"SCX column" or "SCX cartridge", as used herein, refers to a Varian Bond Elute® silica based strong cation exchange resin column or disposable cartridge or equivalent.
"Sudan III" means 1-[(4-phenylazo)phenylazo]-2-naphthalenol.
"Tf" in a chemical structure means the trifluoromethanesulfonyl moiety (—$SO_2CF_3$).
"TFA" means trifluoroacetic acid.
"THF" means tetrahydrofuran.
"TLC" means thin layer chromatography.

While all of the compounds of the present invention are useful as 5-$HT_{2C}$ agonists, certain classes are preferred, as for example, compounds having any of the following enumerated selections of substituents: Compounds wherein 1) $R^7$ is halo;
2) $R^7$ is chloro;
3) $R^7$ is fluoro;
4) $R^7$ is ($C_1$-$C_6$)alkyl optionally substituted with 1 to 6 fluoro substituents;
5) $R^7$ is ($C_1$-$C_3$)alkyl optionally substituted with 1 to 6 fluoro substituents;
6) $R^7$ is —$CF_3$;
7) $R^7$ is ($C_3$-$C_6$)alkenyl optionally substituted with 1 to 6 fluoro substituents;
8) $R^7$ is ($C_3$-$C_6$)alkenyl;
9) $R^7$ is cyano;
10) $R^{1-5}$ are each hydrogen;
11) $R^5$ is methyl or ethyl;
12) $R^5$ is methyl;
13) $R^3$ is methyl;
14) $R^8$ is hydrogen;
15) $R^9$ is ($C_1$-$C_3$)alkoxy;
16) $R^9$ is methoxy;
17) $R^9$ is halo;
18) $R^9$ is chloro;
19) $R^9$ is cyano;
20) $R^9$ is —$CF_3$;
21) $R^6$ is —($C_1$-$C_3$)alkyl-S—($C_0$-$C_3$)alkyl-$R^{10}$;
22) $R^6$ is —$CH_2$—S—($C_0$-$C_3$)alkyl-$R^{10}$;
23) $R^6$ is —($C_1$-$C_3$)alkyl-S—$R^{10}$;
24) $R^6$ is —$CH_2$—S—$R^{10}$;
25) $R^6$ is —($C_1$-$C_3$)alkyl-$NR^{11}R^{12}$;
26) $R^6$ is —$CH_2$—$NR^{11}R^{12}$;
27) $R^6$ is —($C_1$-$C_3$)alkyl-O—$R^{13}$;
28) $R^6$ is —$CH_2$—O—$R^{13}$;

29) $R^{10}$ is phenyl substituted with fluoro;
30) $R^{10}$ is phenyl substituted with 1 to 3 independently selected halo subsituents;
31) $R^{10}$ is phenyl substituted with 1 to 3 substituents independently selected from the group consisting of halo, cyano, —$SCF_3$, nitro, hydroxy, $(C_1-C_6)$alkyl optionally further substituted with 1 to 6 fluoro substituents, and $(C_1-C_6)$alkoxy optionally further substituted with 1 to 6 fluoro substituents;
32) $R^{10}$ is phenyl substituted with 0, 1, or 2 substituents independently selected from the group consisting of halo, cyano, —$SCF_3$, methyl, —$CF_3$, methoxy, —$OCF_3$, nitro, and hydroxy, together with one substituent selected from the group consisting of
   $(C_3-C_7)$cycloalkyl-$(C_0-C_5)$alkyl optionally substituted on the alkyl moiety with 1 to 6 fluoro substituents and optionally substituted independently on the cycloalkyl moiety with 1 to 6 substituents selected from fluoro and methyl provided that no more than 2 substituents are methyl,
   $Ph^1$—$(C_0-C_5)$alkyl,
   $Ar^1$—$(C_0-C_5)$alkyl,
   $(C_1-C_6)$alkyl-CH═CH— optionally substituted with 1 to 6 fluoro substituents, $(C_3-C_7)$cycloalkyl-$(C_0-C_3)$alkyl-CH═CH— optionally substituted with 1 to 6 fluoro substituents on alkyl and optionally substituted independently on the cycloalkyl moiety with 1 to 6 substituents selected from fluoro and methyl provided that no more than 2 substituents are methyl,
   $(C_1-C_6)$alkyl-S—$(C_0-C_5)$alkyl,
   $(C_3-C_7)$cycloalkyl-S—$(C_0-C_5)$alkyl,
   $Ph^1$-$(C_0-C_3)$alkyl-S—$(C_0-C_5)$alkyl,
   $Ar^1$—$(C_0-C_3)$alkyl-S—$(C_0-C_5)$alkyl,
   $(C_1-C_6)$alkyl-O—$(C_0-C_5)$alkyl,
   $(C_3-C_7)$cycloalkyl-O—$(C_0-C_5)$alkyl,
   $Ph^1$-$(C_0-C_3)$alkyl-O—$(C_0-C_5)$alkyl,
   $Ar^1$—$(C_0-C_3)$alkyl-O—$(C_0-C_5)$alkyl,
   $(C_1-C_6)$alkyl-$SO_2$—$(C_0-C_5)$alkyl,
   $(C_3-C_7)$cycloalkyl-$SO_2$—$(C_0-C_5)$alkyl,
   $Ph^1$-$(C_0-C_3)$alkyl-$SO_2$—$(C_0-C_5)$alkyl,
   $Ar^1$—$(C_0-C_3)$alkyl-$SO_2$—$(C_0-C_5)$alkyl,
   $(C_1-C_6)$alkyl-C(O)—$(C_0-C_5)$alkyl,
   $(C_3-C_7)$cycloalkyl-C(O)—$(C_0-C_5)$alkyl,
   $Ph^1$-$(C_0-C_3)$alkyl-C(O)—$(C_0-C_5)$alkyl,
   $Ar^1$—$(C_0-C_3)$alkyl-C(O)—$(C_0-C_5)$alkyl,
   $(C_1-C_6)$alkyl-NH—$(C_0-C_5)$alkyl,
   $(C_3-C_7)$cycloalkyl-NH—$(C_0-C_5)$alkyl,
   $Ph^1$-$(C_0-C_3)$alkyl-NH—$(C_0-C_5)$alkyl,
   $Ar^1$—$(C_0-C_3)$alkyl-NH—$(C_0-C_5)$alkyl,
   $(C_1-C_6)$alkyl-NH—C(O)—$(C_0-C_5)$alkyl,
   $(C_3-C_7)$cycloalkyl-NH—C(O)—$(C_0-C_5)$alkyl,
   $Ph^1$-$(C_0-C_3)$alkyl-NH—C(O)—$(C_0-C_5)$alkyl,
   $Ar^1$—$(C_0-C_3)$alkyl-NH—C(O)—$(C_0-C_5)$alkyl,
   $(C_1-C_6)$alkyl-C(O)—NH—$(C_0-C_5)$alkyl,
   $(C_3-C_7)$cycloalkyl-C(O)—NH—$(C_0-C_5)$alkyl,
   $Ph^1$-$(C_0-C_3)$alkyl-C(O)—NH—$(C_0-C_5)$alkyl,
   $Ar^1$—$(C_0-C_3)$alkyl-C(O)—NH—$(C_0-C_5)$alkyl,
   $(C_1-C_6)$alkyl-NH—$SO_2$—$(C_0-C_5)$alkyl,
   $(C_3-C_7)$cycloalkyl-NH—$SO_2$—$(C_0-C_5)$alkyl,
   $(C_1-C_6)$alkyl-$SO_2$—NH—$(C_0-C_5)$alkyl,
   $(C_3-C_7)$cycloalkyl-$SO_2$—NH—$(C_0-C_5)$alkyl;
33) $R^{10}$ is phenyl substituted with 0, 1, or 2 substituents independently selected from the group consisting of halo, cyano, —$SCF_3$, methyl, —$CF_3$, methoxy, —$OCF_3$, nitro, and hydroxy, together with one substituent selected from the group consisting of
   $Ph^1$-$(C_0-C_5)$alkyl,
   $Ar^1$—$(C_0-C_5)$alkyl,
   $(C_1-C_6)$alkyl-CH═CH— optionally substituted with 1 to 6 fluoro substituents,
   $(C_3-C_7)$cycloalkyl-$(C_0-C_3)$alkyl-CH═CH— optionally substituted with 1 to 6 fluoro substituents on alkyl and optionally substituted independently on the cycloalkyl moiety with 1 to 6 substituents selected from fluoro and methyl provided that no more than 2 substituents are methyl,
   $(C_1-C_6)$alkyl-C(O)—$(C_0-C_5)$alkyl,
   $(C_3-C_7)$cycloalkyl-C(O)—$(C_0-C_5)$alkyl,
   $Ph^1$-$(C_0-C_3)$alkyl-C(O)—$(C_0-C_5)$alkyl,
   $Ar^1$—$(C_0-C_3)$alkyl-C(O)—$(C_0-C_5)$alkyl,
   $(C_1-C_6)$alkyl-NH—C(O)—$(C_0-C_5)$alkyl,
   $(C_3-C_7)$cycloalkyl-NH—C(O)—$(C_0-C_5)$alkyl,
   $Ph^1$-$(C_0-C_3)$alkyl-NH—C(O)—$(C_0-C_5)$alkyl,
   $Ar^1$—$(C_0-C_3)$alkyl-NH—C(O)—$(C_0-C_5)$alkyl,
34) $R^{10}$ is an aromatic heterocycle substituent selected from the group consisting of tetrazolyl, 1,2,3-thiadiazolyl, 1,3,4-thiadiazolyl, 1,2,4-thiadiazolyl, 1,2,3-oxadiazolyl, 1,3,4-oxadiazolyl, and 1,2,4-oxadiazolyl, any one of which may optionally be substituted with a substituent selected from the group consisting of $(C_1-C_4)$alkyl optionally substituted with 1 to 4 fluoro substituents, $Ph^1$-$(C_0-C_3)$alkyl, $Ar^1$—$(C_0-C_3)$alkyl, $(C_1-C_4)$alkyl-C(O)—, $Ph^1$-$(C_0-C_3)$alkyl-C(O)—, and $Ar^1$—$(C_0-C_3)$alkyl-C(O)—;
35) $R^{10}$ is an aromatic heterocycle substituent selected from the group consisting of 1,3,4-thiadiazolyl optionally be substituted with $(C_1-C_4)$alkyl optionally substituted with 1 to 4 fluoro substituents;
36) $R^{10}$ is imidazolyl optionally substituted with a substituent selected from the group consisting of $(C_1-C_6)$alkyl optionally substituted with 1 to 6 fluoro substituents, $Ph^1$-$(C_0-C_3)$alkyl optionally substituted on the alkyl moiety with 1 to 6 fluoro substituents, or $Ar^1$—$(C_0-C_3)$alkyl optionally substituted on the alkyl moiety with 1 to 6 fluoro substituents;
37) $R^{10}$ is an aromatic heterocycle substituent selected from the group consisting of imidazolyl, thiazolyl, isothiazolyl, thiophenyl, pyrazolyl, oxazolyl, isoxazolyl, 1,2,3-triazolyl, 1,2,4-triazolyl, any one of which may be optionally substituted with one to two substituents selected from the group consisting of
   $(C_1-C_6)$alkyl optionally substituted with 1 to 6 fluoro substituents,
   $Ph^1$-$(C_0-C_3)$alkyl optionally substituted on the alkyl moiety with 1 to 6 fluoro substituents,
   $Ar^1$—$(C_0-C_3)$alkyl optionally substituted on the alkyl moiety with 1 to 6 fluoro substituents,
   $(C_1-C_6)$alkyl-C(O)—,
   $Ph^1$-$(C_0-C_3)$alkyl-C(O)—,
   $Ar^1$—$(C_0-C_3)$alkyl-C(O)—,
   $(C_1-C_6)$alkyl-NH—C(O)— optionally substituted with 1 to 6 fluoro substituents,
   $Ph^1$-$(C_0-C_3)$alkyl-NH—C(O)— optionally substituted on the alkyl moiety with 1 to 6 fluoro substituents, and
   $Ar^1$—$(C_0-C_3)$alkyl-NH—C(O)— optionally substituted on the alkyl moiety with 1 to 6 fluoro substituents,
or optionally substituted on ring carbon atoms with one or two substituents selected from the group consisting of halo,
cyano,
$(C_1-C_6)$alkyl-CH═CH— optionally substituted with 1 to 6 fluoro substituents, (C$_1$-C$_6$)alkoxy optionally substituted with 1 to 6 fluoro substituents,
(C$_1$-C$_6$)alkylthio optionally substituted with 1 to 6 fluoro substituents,
Ph$^1$-(C$_0$-C$_3$)alkylthio,
(C$_1$-C$_6$)alkyl-NH— optionally substituted with 1 to 6 fluoro substituents,
Ph$^1$-(C$_0$-C$_3$)alkyl-NH—,
Ar$^1$—(C$_0$-C$_3$)alkyl-NH—,
(C$_1$-C$_6$)alkyl-C(O)—NH—,
Ph$^1$-(C$_0$-C$_3$)alkyl-C(O)—NH—,
Ar$^1$—(C$_0$-C$_3$)alkyl-C(O)—NH—,
(C$_1$-C$_6$)alkyl-O—C(O)—NH— optionally substituted with 1 to 6 fluoro substituents,
Ph$^1$-(C$_0$-C$_3$)alkyl-O—C(O)—NH— optionally substituted on the alkyl moiety with 1 to 6 fluoro substituents, and
Ar$^1$—(C$_0$-C$_3$)alkyl-O—C(O)—NH— optionally substituted on the alkyl moiety with 1 to 6 fluoro substituents, or optionally substituted on two adjacent ring atoms with a bivalent 3 to 4 carbon hydrocarbon substituent which, together with the ring atoms to which it is attached, form a benzene ring or a partially saturated five- or six-membered ring;

38) R$^{10}$ is an aromatic heterocycle substituent selected from the group consisting of pyridyl, pyridazinyl, pyrimidinyl, pyrazinyl, any of which may be optionally substituted with 1 or 2 substituents independently selected from the group consisting of halo, cyano, —SCF$_3$, methyl, —CF$_3$, methoxy, —OCF$_3$, nitro, hydroxy, and optionally further substituted with a substituent selected from the group consisting of
(C$_3$-C$_7$)cycloalkyl-(C$_0$-C$_5$)alkyl optionally further substituted on the alkyl moiety with 1 to 6 fluoro substituents and optionally substituted independently on the cycloalkyl moiety with 1 to 6 substituents selected from fluoro and methyl provided that no more than 2 substituents are methyl,
Ph$^1$-(C$_0$-C$_5$)alkyl,
Ar$^1$—(C$_0$-C$_5$)alkyl,
(C$_1$-C$_6$)alkyl-CH═CH— optionally substituted with 1 to 6 fluoro substituents,
(C$_3$-C$_7$)cycloalkyl-(C$_0$-C$_3$)alkyl-CH═CH— optionally substituted with 1 to 6 fluoro substituents on alkyl and optionally substituted independently on the cycloalkyl moiety with 1 to 6 substituents selected from fluoro and methyl provided that no more than 2 substituents are methyl,
(C$_1$-C$_6$)alkyl-S—(C$_0$-C$_5$)alkyl,
(C$_3$-C$_7$)cycloalkyl-S—(C$_0$-C$_5$)alkyl,
Ph$^1$-(C$_0$-C$_3$)alkyl-S—(C$_0$-C$_5$)alkyl,
Ar$^1$—(C$_0$-C$_3$)alkyl-S—(C$_0$-C$_5$)alkyl,
(C$_1$-C$_6$)alkyl-O—(C$_0$-C$_5$)alkyl,
(C$_3$-C$_7$)cycloalkyl-O—(C$_0$-C$_5$)alkyl,
Ph$^1$-(C$_0$-C$_3$)alkyl-O—(C$_0$-C$_5$)alkyl,
Ar$^1$—(C$_0$-C$_3$)alkyl-O—(C$_0$-C$_5$)alkyl,
(C$_1$-C$_6$)alkyl-SO$_2$—(C$_0$-C$_5$)alkyl,
(C$_3$-C$_7$)cycloalkyl-SO$_2$—(C$_0$-C$_5$)alkyl,
Ph$^1$-(C$_0$-C$_3$)alkyl-SO$_2$—(C$_0$-C$_5$)alkyl,
Ar$^1$—(C$_0$-C$_3$)alkyl-SO$_2$—(C$_0$-C$_5$)alkyl,
(C$_1$-C$_6$)alkyl-C(O)—(C$_0$-C$_5$)alkyl,
(C$_3$-C$_7$)cycloalkyl-C(O)—(C$_0$-C$_5$)alkyl,
Ph$^1$-(C$_0$-C$_3$)alkyl-C(O)—(C$_0$-C$_5$)alkyl,
Ar$^1$—(C$_0$-C$_3$)alkyl-C(O)—(C$_0$-C$_5$)alkyl,
(C$_1$-C$_6$)alkyl-NH—(C$_0$-C$_5$)alkyl,
(C$_3$-C$_7$)cycloalkyl-NH—(C$_0$-C$_5$)alkyl,
Ph$^1$-(C$_0$-C$_3$)alkyl-NH—(C$_0$-C$_5$)alkyl,
Ar$^1$—(C$_0$-C$_3$)alkyl-NH—(C$_0$-C$_5$)alkyl,
(C$_1$-C$_6$)alkyl-NH—C(O)—(C$_0$-C$_5$)alkyl,
(C$_3$-C$_7$)cycloalkyl-NH—C(O)—(C$_0$-C$_5$)alkyl,
Ph$^1$-(C$_0$-C$_3$)alkyl-NH—C(O)—(C$_0$-C$_5$)alkyl,
Ar$^1$—(C$_0$-C$_3$)alkyl-NH—C(O)—(C$_0$-C$_5$)alkyl,
(C$_1$-C$_6$)alkyl-C(O)—NH—(C$_0$-C$_5$)alkyl,
(C$_3$-C$_7$)cycloalkyl-C(O)—NH—(C$_0$-C$_5$)alkyl,
Ph$^1$-(C$_0$-C$_3$)alkyl-C(O)—NH—(C$_0$-C$_5$)alkyl,
Ar$^1$—(C$_0$-C$_3$)alkyl-C(O)—NH—(C$_0$-C$_5$)alkyl;

39) R$^{11}$ is optionally substituted phenyl;
40) R$^{11}$ is substituted with 1 to 5 independently selected halo substituents;
41) R$^{11}$ is substituted with 1 to 3 substituents independently selected from the group consisting of halo, cyano, —SCF$_3$, nitro, and hydroxy, and optionally further substituted with a substituent selected from the group consisting of
(C$_1$-C$_6$)alkyl optionally further substituted with 1 to 6 fluoro substituents,
(C$_1$-C$_6$)alkyl-O—(C$_0$-C$_5$)alkyl optionally further substituted with 1 to 6 fluoro substituents,
(C$_1$-C$_6$)alkyl-CH═CH— optionally substituted with 1 to 6 fluoro substituents,
(C$_3$-C$_7$)cycloalkyl-(C$_0$-C$_3$)alkyl-CH═CH— optionally substituted with; 1 to 6 fluoro substituents on alkyl and optionally substituted independently on the cycloalkyl moiety with 1 to 6 substituents selected from fluoro and methyl provided that no more than 2 substituents are methyl,
(C$_3$-C$_7$)cycloalkyl-O—(C$_0$-C$_5$)alkyl,
Ph$^1$-(C$_0$-C$_3$)alkyl-O—(C$_0$-C$_5$)alkyl,
Ar$^1$—(C$_0$-C$_3$)alkyl-O—(C$_0$-C$_5$)alkyl,
(C$_1$-C$_6$)alkyl-S—(C$_0$-C$_5$)alkyl,
(C$_3$-C$_7$)cycloalkyl-S—(C$_0$-C$_5$)alkyl,
Ph$^1$-(C$_0$-C$_3$)alkyl-S—(C$_0$-C$_5$)alkyl,
Ar$^1$—(C$_0$-C$_3$)alkyl-S—(C$_0$-C$_5$)alkyl,
(C$_1$-C$_6$)alkyl-SO$_2$—(C$_0$-C$_5$)alkyl,
(C$_3$-C$_7$)cycloalkyl-SO$_2$—(C$_0$-C$_5$)alkyl,
Ph$^1$-(C$_0$-C$_3$)alkyl-SO$_2$—(C$_0$-C$_5$)alkyl,
Ar$^1$—(C$_0$-C$_3$)alkyl-SO$_2$—(C$_0$-C$_5$)alkyl,
(C$_1$-C$_6$)alkyl-C(O)—(C$_0$-C$_5$)alkyl,
(C$_3$-C$_7$)cycloalkyl-C(O)—(C$_0$-C$_5$)alkyl,
Ph$^1$-(C$_0$-C$_3$)alkyl-C(O)—(C$_0$-C$_5$)alkyl,
Ar$^1$—(C$_0$-C$_3$)alkyl-C(O)—(C$_0$-C$_5$)alkyl,
(C$_1$-C$_6$)alkyl-NH—(C$_0$-C$_5$)alkyl,
(C$_3$-C$_7$)cycloalkyl-NH—(C$_0$-C$_5$)alkyl,
Ph$^1$-(C$_0$-C$_3$)alkyl-NH—(C$_0$-C$_5$)alkyl,
Ar$^1$—(C$_0$-C$_3$)alkyl-NH—(C$_0$-C$_5$)alkyl,
(C$_1$-C$_6$)alkyl-NH—C(O)—(C$_0$-C$_5$)alkyl,
(C$_3$-C$_7$)cycloalkyl-NH—C(O)—(C$_0$-C$_5$)alkyl,
Ph$^1$-(C$_0$-C$_3$)alkyl-NH—C(O)—(C$_0$-C$_5$)alkyl,
Ar$^1$—(C$_0$-C$_3$)alkyl-NH—C(O)—(C$_0$-C$_5$)alkyl,
(C$_1$-C$_6$)alkyl-C(O)—NH—(C$_0$-C$_5$)alkyl,
(C$_3$-C$_7$)cycloalkyl-C(O)—NH—(C$_0$-C$_5$)alkyl,
Ph$^1$-(C$_0$-C$_3$)alkyl-C(O)—NH—(C$_0$-C$_5$)alkyl, and
Ar$^1$—(C$_0$-C$_3$)alkyl-C(O)—NH—(C$_0$-C$_5$)alkyl;

42) R$^{11}$ is optionally substituted pyridyl;
43) R$^{11}$ is pyridyl optionally substituted with 1 or 3 substituents independently selected from the group consisting of halo, cyano, —SCF$_3$, nitro, and hydroxy, and optionally further substituted with a substituent selected from the group consisting of
(C$_1$-C$_6$)alkyl optionally further substituted with 1 to 6 fluoro substituents,
(C$_1$-C$_6$)alkyl-O—(C$_0$-C$_5$)alkyl optionally further substituted with 1 to 6 fluoro substituents, $(C_1-C_6)$alkyl-CH=CH— optionally substituted with 1 to 6 fluoro substituents,
$(C_3-C_7)$cycloalkyl-$(C_0-C_3)$alkyl-CH=CH— optionally substituted with 1 to 6 fluoro substituents on alkyl and optionally substituted independently on the cycloalkyl moiety with 1 to 6 substituents selected from fluoro and methyl provided that no more than 2 substituents are methyl,
$(C_3-C_7)$cycloalkyl-O—$(C_0-C_5)$alkyl,
$Ph^1$-$(C_0-C_3)$alkyl-O—$(C_0-C_5)$alkyl,
$(C_1-C_6)$alkyl-S—$(C_0-C_5)$alkyl,
$(C_3-C_7)$cycloalkyl-S—$(C_0-C_5)$alkyl,
$Ph^1$-$(C_0-C_3)$alkyl-S—$(C_0-C_5)$alkyl,
$(C_1-C_6)$alkyl-$SO_2$—$(C_0-C_5)$alkyl,
$(C_3-C_7)$cycloalkyl-$SO_2$—$(C_0-C_5)$alkyl,
$Ph^1$-$(C_0-C_3)$alkyl-$SO_2$—$(C_0-C_5)$alkyl,
$(C_1-C_6)$alkyl-C(O)—$(C_0-C_5)$alkyl,
$(C_3-C_7)$cycloalkyl-C(O)—$(C_0-C_5)$alkyl,
$Ph^1$-$(C_0-C_3)$alkyl-C(O)—$(C_0-C_5)$alkyl,
$(C_1-C_6)$alkyl-NH—$(C_0-C_5)$alkyl,
$(C_3-C_7)$cycloalkyl-NH—$(C_0-C_5)$alkyl,
$Ph^1$-$(C_0-C_3)$alkyl-NH—$(C_0-C_5)$alkyl,
$(C_1-C_6)$alkyl-NH—C(O)—$(C_0-C_5)$alkyl,
$(C_3-C_7)$cycloalkyl-NH—C(O)—$(C_0-C_5)$alkyl,
$Ph^1$-$(C_0-C_3)$alkyl-NH—C(O)—$(C_0-C_5)$alkyl,
$(C_1-C_6)$alkyl-C(O)—NH—$(C_0-C_5)$alkyl,
$(C_3-C_7)$cycloalkyl-C(O)—NH—$(C_0-C_5)$alkyl, and
$Ph^1$-$(C_0-C_3)$alkyl-C(O)—NH—$(C_0-C_5)$alkyl;

44) $R^{11}$ is pyridazinyl optionally substituted with 1 or 2 substituents independently selected from the group consisting of halo, cyano, hydroxy, $(C_1-C_6)$alkyl optionally further substituted with 1 to 6 fluoro substituents, $(C_1-C_6)$alkoxy optionally further substituted with 1 to 6 fluoro substituents; and $(C_1-C_6)$alkylthio optionally further substituted with 1 to 6 fluoro substituents;

45) $R^{11}$ is a five-membered aromatic heterocycle selected from the group of thiophenyl, thiazole, isothiazole optionally substituted with 1 or 2 substituents independently selected from the group consisting of halo, cyano, hydroxy, $(C_1-C_6)$alkyl optionally further substituted with 1 to 6 fluoro substituents, $(C_1-C_6)$alkoxy optionally further substituted with 1 to 6 fluoro substituents, $(C_1-C_6)$alkylthio optionally further substituted with 1 to 6 fluoro substituents, and $(C_1-C_6)$alkyl-C(O)—;

46) $R^{12}$ is hydrogen;
47) $R^{12}$ is methyl;
48) $R^{13}$ is optionally substituted phenyl;
49) $R^{13}$ is phenyl substituted with 0, 1, or 2 substituents independently selected from the group consisting of halo, cyano, —$SCF_3$, methyl, —$CF_3$, methoxy, —$OCF_3$, nitro, and hydroxy, together with one substituent selected from the group consisting of
$(C_3-C_7)$cycloalkyl-$(C_0-C_5)$alkyl optionally substituted on the alkyl moiety with 1 to 6 fluoro substituents and optionally substituted independently on the cycloalkyl moiety with 1 to 6 substituents selected from fluoro and methyl provided that no more than 2 substituents are methyl,
$Ph^1$-$(C_0-C_5)$alkyl,
$Ar^1$—$(C_0-C_5)$alkyl,
$(C_1-C_6)$alkyl-CH=CH— optionally substituted with 1 to 6 fluoro substituents, $(C_3-C_7)$cycloalkyl-$(C_0-C_3)$alkyl-CH=CH— optionally substituted with 1 to 6 fluoro substituents on alkyl and optionally substituted independently on the cycloalkyl moiety with 1 to 6 substituents selected from fluoro and methyl provided that no more than 2 substituents are methyl,
$(C_1-C_6)$alkyl-S—$(C_0-C_5)$alkyl optionally substituted on the $(C_1-C_6)$alkyl moiety with 1 to 6 fluoro substituents,
$(C_3-C_7)$cycloalkyl-$(C_0-C_3)$alkyl-S—$(C_0-C_5)$alkyl,
$Ph^1$-$(C_0-C_3)$alkyl-S—$(C_0-C_5)$alkyl,
$Ar^1$—$(C_0-C_3)$alkyl-S—$(C_0-C_5)$alkyl,
$(C_1-C_6)$alkyl-O—$(C_0-C_5)$alkyl optionally substituted on the $(C_1-C_6)$alkyl moiety with 1 to 6 fluoro substituents,
$(C_3-C_7)$cycloalkyl-$(C_0-C_3)$alkyl-O—$(C_0-C_5)$alkyl,
$Ph^1$-$(C_0-C_3)$alkyl-O—$(C_0-C_5)$alkyl,
$Ar^1$—$(C_0-C_3)$alkyl-O—$(C_0-C_5)$alkyl,
$(C_1-C_6)$alkyl-$SO_2$—$(C_0-C_5)$alkyl optionally substituted on the $(C_1-C_6)$alkyl moiety with 1 to 6 fluoro substituents,
$(C_3-C_7)$cycloalkyl-$(C_0-C_3)$alkyl-$SO_2$—$(C_0-C_5)$alkyl,
$Ph^1$-$(C_0-C_3)$alkyl-$SO_2$—$(C_0-C_5)$alkyl,
$Ar^1$—$(C_0-C_3)$alkyl-$SO_2$—$(C_0-C_5)$alkyl,
$(C_1-C_6)$alkyl-C(O)—$(C_0-C_5)$alkyl,
$(C_3-C_7)$cycloalkyl-$(C_0-C_3)$alkyl-C(O)—$(C_0-C_5)$alkyl,
$Ph^1$-$(C_0-C_3)$alkyl-C(O)—$(C_0-C_5)$alkyl,
$Ar^1$—$(C_0-C_3)$alkyl-C(O)—$(C_0-C_5)$alkyl,
$(C_1-C_6)$alkyl-NH—$(C_0-C_5)$alkyl optionally substituted on the $(C_1-C_6)$alkyl moiety with 1 to 6 fluoro substituents,
$(C_3-C_7)$cycloalkyl-$(C_0-C_3)$alkyl-NH—$(C_0-C_5)$alkyl,
$Ph^1$-$(C_0-C_3)$alkyl-NH—$(C_0-C_5)$alkyl,
$Ar^1$—$(C_0-C_3)$alkyl-NH—$(C_0-C_5)$alkyl,
$Het^1$-$(C_0-C_3)$alkyl-,
$(C_1-C_6)$alkyl-NH—C(O)—$(C_0-C_5)$alkyl optionally substituted on the $(C_1-C_6)$alkyl moiety with 1 to 6 fluoro substituents,
$(C_3-C_7)$cycloalkyl-$(C_0-C_3)$alkyl-NH—C(O)—$(C_0-C_5)$alkyl,
$Ph^1$-$(C_0-C_3)$alkyl-NH—C(O)—$(C_0-C_5)$alkyl,
$Ar^1$—$(C_0-C_3)$alkyl-NH—C(O)—$(C_0-C_5)$alkyl,
$(C_1-C_6)$alkyl-$(C_0-C_3)$alkyl-C(O)—NH—$(C_0-C_5)$alkyl,
$(C_3-C_7)$cycloalkyl-C(O)—NH—$(C_0-C_5)$alkyl,
$Ph^1$-$(C_0-C_3)$alkyl-C(O)—NH—$(C_0-C_5)$alkyl,
$Ar^1$—$(C_0-C_3)$alkyl-C(O)—NH—$(C_0-C_5)$alkyl,
$(C_1-C_6)$alkyl-NH—$SO_2$—$(C_0-C_5)$alkyl optionally substituted on the $(C_1-C_6)$alkyl moiety with 1 to 6 fluoro substituents,
$(C_3-C_7)$cycloalkyl-$(C_0-C_3)$alkyl-NH—$SO_2$—$(C_0-C_5)$alkyl,
$(C_1-C_6)$alkyl-$SO_2$—NH—$(C_0-C_5)$alkyl, and
$(C_3-C_7)$cycloalkyl-$(C_0-C_3)$alkyl-$SO_2$—NH—$(C_0-C_5)$alkyl;

50) $R^{13}$ is optionally substituted thiophenyl;
$R^{13}$ is thiophenyl substituted with one substituent selected from the group consisting of halo, cyano, and $(C_1-C_6)$alkyl optionally substituted with 1 to 6 fluoro substituents, and further substituted with a substituent selected from the group consisting of $Ph^1$-$(C_0-C_3)$alkyl optionally substituted on the alkyl moiety with 1 to 6 fluoro substituents,
$Ar^1$—$(C_0-C_3)$alkyl optionally substituted on the alkyl moiety with 1 to 6 fluoro substituents, 51) $R^{13}$ is thiophenyl substituted with one to two substituents selected from the group consisting of
halo,
cyano, and
$(C_1-C_6)$alkyl optionally substituted with 1 to 6 fluoro substituents, It will be understood that the above classes are preferred selections for each substitutent and may be combined with preferred selections for other substituents to form additional preferred classes. Exemplary combinations include, but are not limited to:

52) Any one of preferred embodiments 1) through 9) (the preferred selections for $R^7$), combined with any one of preferred embodiments 21) through 24) (certain preferred selections for $R^6$);
53) A preferred combination according to 52), combined with any one of preferred embodiments 29) through 38) (the preferred selections for $R^{10}$);
54) Any one of preferred embodiments 1) through 9) (the preferred selections for $R^7$), combined with preferred embodiment 25) or 26) (certain preferred selections for $R^6$);
55) A preferred combination according to 54), combined with any one of preferred embodiments 39) through 45) (the preferred selections for $R^{11}$);
56) A preferred combination according to 55), combined with preferred embodiment 46) or 47) (the preferred selections for $R^{12}$), wherein the more preferred compounds are those wherein $R^{12}$ is hydrogen;
57) Any one of preferred embodiments 1) through 9) (the preferred selections for $R^7$), combined with preferred embodiment 27) or 28) (certain preferred selections for $R^6$);
58) A preferred combination according to 57), combined with any one of preferred embodiments 48) through 51) (the preferred selections for $R^{13}$);
59) Any one of preferred embodiments 22) through 51) (the preferred selections for $R^6$) or a preferred combination according to any one of 52) through 58), wherein $R^7$ is halogen;
60) Any one of preferred embodiments 22) through 51) (the preferred selections for $R^6$) or a preferred combination according to any one of 52) through 58), wherein $R^7$ is chloro;
61) Any one of preferred embodiments 22) through 51) (the preferred selections for $R^6$) or a preferred combination according to any one of 52) through 60), wherein $R^{1-5}$, $R^8$ and $R^9$ are each hydrogen.

Generally, when $R^{10}$ or $R^{11}$ is optionally substituted pyridyl, then pyrid-2-yls are preferred over pyrid-3-yls (ring numbering being with respect to the pyridyl nitrogen to the attachment position of the pyridyl moiety to the core structure irrespective of further substituents on the pyridyl that might change the ring numbering of the final compound according to IUPAC nomenclature rules).

Also generally, for compounds wherein $R^{10}$ or $R^{11}$ is phenyl, substitution at the para-position of the phenyl moiety is particularly preferred. Likewise, when $R^{10}$ or $R^{11}$ is a 6 member heterocycle, substitution at 4-position relative to the attachment point of the heterocycle to the core structure is also particularly preferred.

When $R^{10}$, $R^{11}$, or $R^{13}$ is a 5 member heterocycle, substitution at the 3- and 4-positions is particularly preferred over substitution at the 2 or 5-position, relative to the attachment point of the heterocycle to the core structure.

Generally, compounds wherein $R^6$ is —($C_1$-$C_3$)alkyl-S—($C_0$-$C_3$)alkyl-$R^{10}$ are preferred over compounds wherein $R^6$ is —($C_1$-$C_3$)alkyl-$NR^{11}R^{12}$, which are generally preferred over compounds wherein $R^6$ is —($C_1$-$C_3$)alkyl-O—$R^{13}$.

Within each of these sub-families of compounds, preferred compounds are those having a methylene (($C_1$)alkyl) linker between the tetrahydrobenzazepine core structure and the heteroatom (i.e. compounds wherein $R^6$ is —$CH_2$—S—($C_0$-$C_3$)alkyl-$R^{10}$). Additional preferred compounds within the thioether sub-family of compounds are those having a direct bond (($C_0$)alkyl) between the sulfur atom and the $R^{10}$ moiety (i.e. compounds wherein $R^6$ is —($C_1$-$C_3$)alkyl-S—$R^{10}$). Furthermore, particularly preferred compounds within the thioether sub-family of compounds are those having both a methylene linker between the tetrahydrobenzazepine core structure and the sulfur atom and a direct bond to $R^{10}$ (i.e. compounds wherein $R^6$ is —$CH_2$—S—$R^{10}$). These preferences can be combined with the preferences for $R^7$ to be halo, more particularly chloro, and/or for $R^{1-5, 8, 9}$ to each be hydrogen to provide yet more preferred embodiments of the present invention.

One favored group of compounds of the present invention is that represented by formula (Ia), and pharmaceutically acceptable salts thereof:

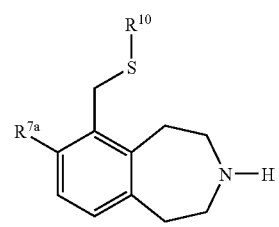

Ia wherein
$R^{7a}$ is halogen, and especially chloro; and
$R^{10}$ is as defined in formula (I).

Another favored group of compounds of the present invention is that represented by formula (Ib), and pharmaceutically acceptable salts thereof:

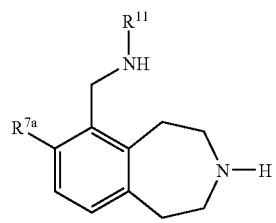

Ib wherein
$R^{7a}$ is halogen, and especially chloro; and
$R^{11}$ is as defined in relation to formula (I).

Yet another favored group of compounds of the present invention is that represented by formula (Ic), and pharmaceutically acceptable salts thereof:

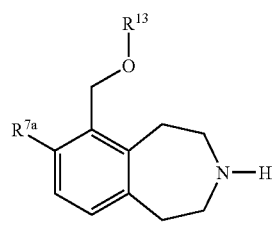

Ic wherein
$R^{17a}$ is halogen, and especially chloro; and
$R^{13}$ is as defined in formula (I).

Specific preferred compounds of the present invention are those described in the Examples herein, including the free bases and the pharmaceutically acceptable salts thereof.

a suitable protecting group for a secondary amine such as, but not limited to, tert-butoxycarbonyl, and variables $R^1$, $R^2$, $R^3$, $R^4$, $R^5$, $R^7$, $R^8$, $R^9$ and $R^{10}$ are as previously defined.

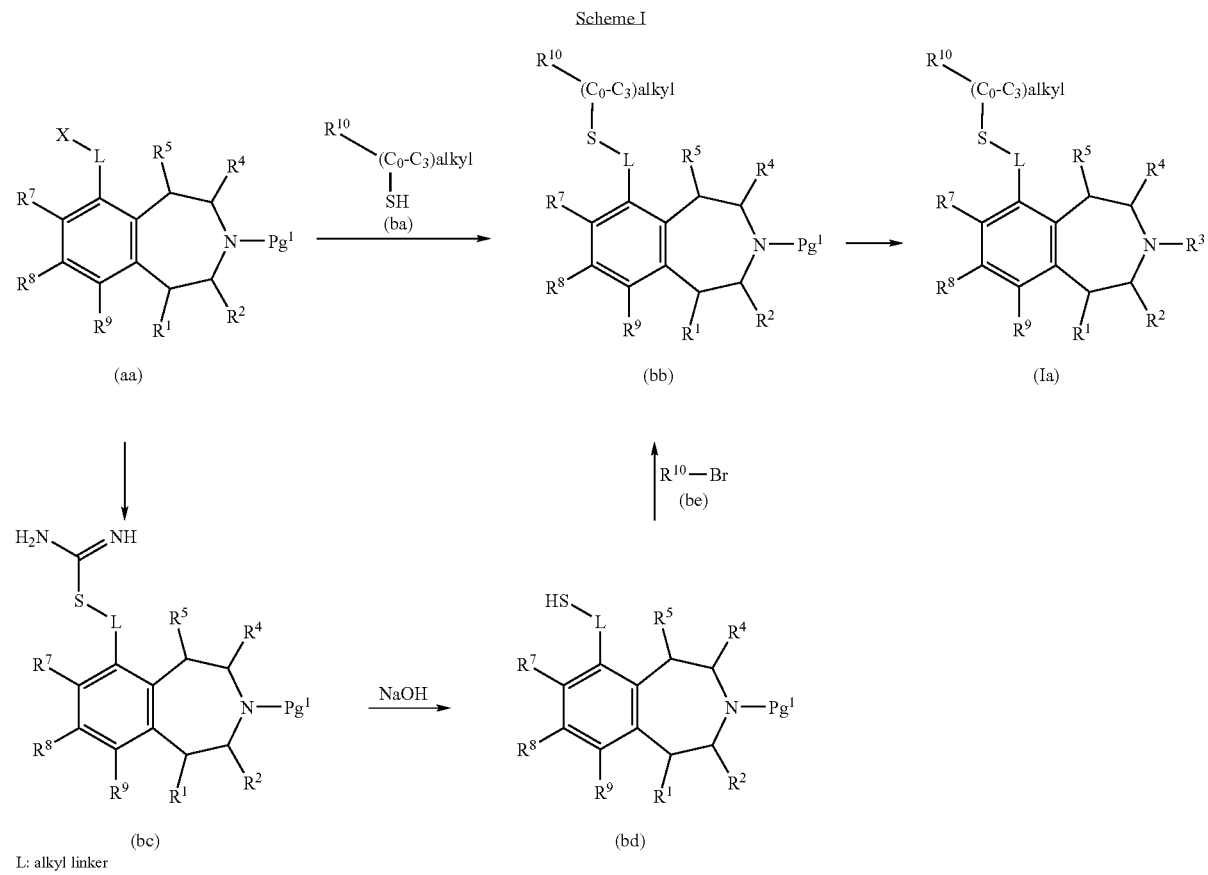

L: alkyl linker
X: Cl, Br, I, O-SO$_2$R (R = methyl, trifluoromethyl, p-tolyl)

It will be appreciated that the preferred definitions of the various substituents recited herein may be taken alone or in combination and, unless otherwise stated, apply to the generic formula (I) for compounds of the present invention, as well as to the preferred classes of compounds represented by formulae (Ia), (Ib), and/or (Ic).

The compounds of the invention can be prepared according to the following synthetic schemes by methods well known and appreciated in the art. Suitable reaction conditions for the steps of these schemes are well known in the art and appropriate substitutions of solvents and co-reagents are within the skill of the art. Likewise, it will be appreciated by those skilled in the art that synthetic intermediates may by isolated and/or purified by various well known techniques as needed or desired, and that frequently, it will be possible to use various intermediates directly in subsequent synthetic steps with little or no purification. Furthermore, the skilled artisan will appreciate that in some circumstances, the order in which moieties are introduced is not critical. The particular order of steps required to produce the compounds of Formula I is dependent upon the particular compound being synthesized, the starting compound, and the relative, liability of the substituted moieties as is well appreciated by those of ordinary skill in the art. All substituents, unless otherwise indicated, are as previously defined, and all reagents are well known and appreciated in the art.

Compounds of Formula I where $R^6$ is an alkyl-linked thioether may be prepared as illustrated in Scheme I where Pg$^1$ is Mix a 6-alkyl-2,3,4,5-tetrahydro-1H-benzo[d]azepine derivative (aa) that is substituted with a leaving group X, for example a 6-chloroalkyl derivative of the 2,3,4,5-tetrahydro-1H-benzo[d]azepines (aa) with an appropriately substituted thiol (ba), and a base in a suitable solvent, typically sodium hydride in DMF, and stir at room temperature or heat to afford the desired compound (bb) after applying standard extractive and chromatographic techniques. Alternately, a thiolate salt, for example potassium thiolate, can be preformed and then be treated with the electrophile (aa) in DMF at room temperature or with heat. Thiols are either commercially available or may be prepared by methods well known to the skilled artisan. Deprotection of the ring nitrogen gives the desired compound (Ia) where $R^3$ is H. Final compounds (Ia) where $R^3$ is methyl or ethyl can be obtained by alkylation of the secondary amine after removal of Pg$^1$. Another possible synthetic route to the N-protected thioether derivatives (bb) via intermediates (bc) and (bd) is also illustrated in Scheme I. A 6-alkyl-2,3,4,5-tetrahydro-1H-benzo[d]azepine derivative (aa) that is substituted with a leaving group X, for example a 6-chloroalkyl derivative of the 2,3,4,5-tetrahydro-1H-benzo[d]azepines (aa), may react with thiourea in a suitable solvent and usually under heat to give after workup intermediate (bc). Treatment of intermediates (bc) in a suitable solvent with aqueous sodium hydroxide and heat may afford after applying extractive and chromatographic techniques thiol intermediates (bd).

The thioether derivatives (bb) may be prepared from the thiols (bd) by palladium-catalyzed reactions with an appropriately substituted aryl or heteroaryl bromide. The aryl or heteroaryl bromides are either commercially available or can be synthesized by methods well known to the skilled artisan.

Compounds of Formula I where $R^6$ is an alkyl-linked ether may be prepared as illustrated in Scheme II where $Pg^1$ is a suitable protecting group for a secondary amine such as, but not limited to, tert-butoxycarbonyl, and variables $R^1$, $R^2$, $R^3$, $R^4$, $R^5$, $R^7$, $R^8$, $R^9$ and $R^{13}$ are as previously defined.

azepines (d) following reaction processes well known to the skilled artisan, some of which are described in Schemes III to V.

For example, the appropriate 6-chloromethyl derivatives of 2,3,4,5-tetrahydro-1H-benzo[d]azepines (ac) may be prepared as described in Scheme III. Mix the 6-triflate of 2,3,4,5-tetrahydro-1H-benzo[d]azepines (d) with an alcohol, a suitable palladium catalyst/ligand mixture in a solvent, typically DMSO, using triethylamine as base, in an autoclave at 50 psi of carbon monoxide and heat to afford the desired

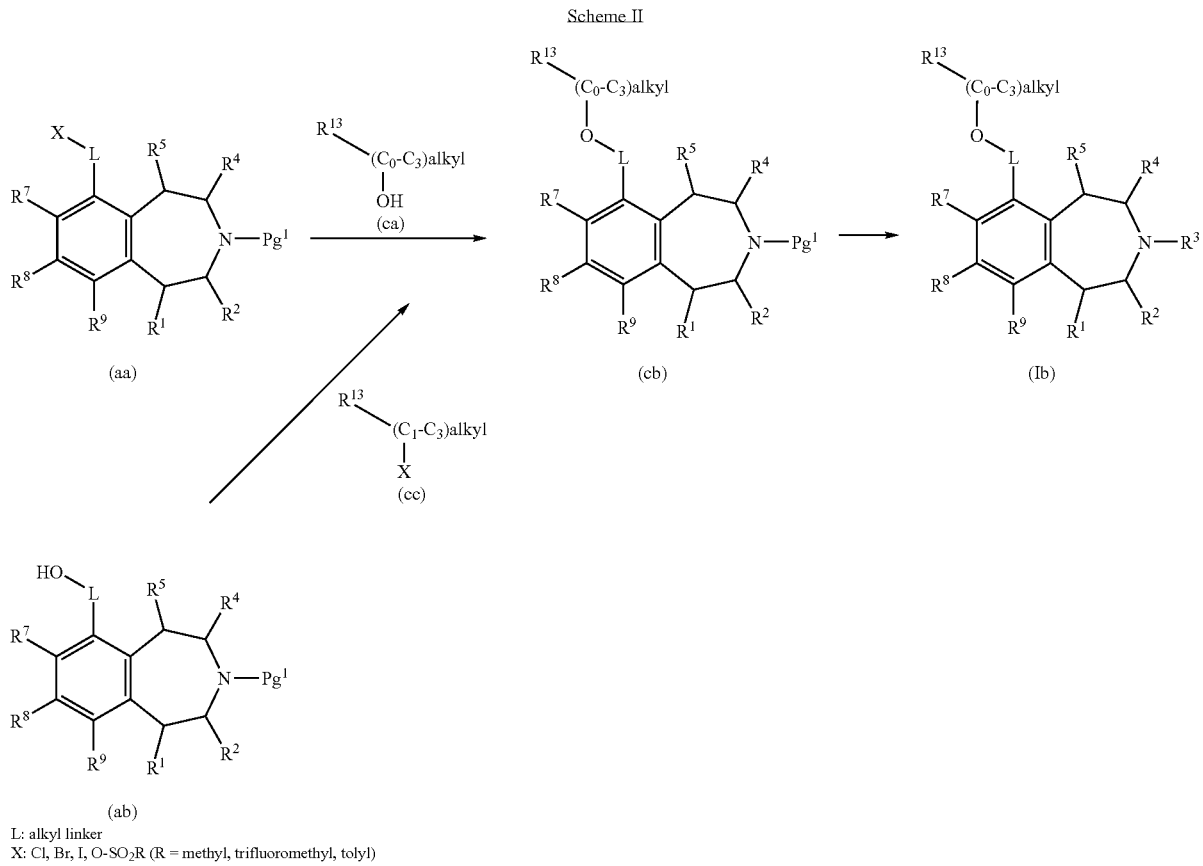

Scheme II

L: alkyl linker
X: Cl, Br, I, O-SO$_2$R (R = methyl, trifluoromethyl, tolyl)

Mix a 6-alkyl-2,3,4,5-tetrahydro-1H-benzo[d]azepines (aa) that is substituted with a leaving group X, with an appropriately substituted alcohol (ca), and a base in a suitable solvent, typically sodium hydride in DMF, and stir at room temperature or heat to afford the desired compound (cb) after applying standard extractive and chromatographic techniques. Alcohols are either commercially available or may be prepared by methods well known to the skilled artisan. Alternately, compounds (cb) may be obtained by reaction of 6-alkyl alcohols (ab) with an appropriately substituted alkyl halide (cc) or alkyl sulfonate (cc) in the presence of a suitable base and in a suitable solvent. Deprotection of the ring nitrogen gives the desired compounds (Ib) where $R^3$ is H. Final compounds (Ib), where $R^3$ is methyl or ethyl, can be obtained by alkylation of the secondary amine after removal of $Pg^1$.

The appropriate 2,3,4,5-tetrahydro-1H-benzo[d]azepines (aa) containing a suitable leaving group may be prepared from the appropriate alcohols (ab) via transformations well known in the art. The alcohols (ab) may be obtained from the appropriate 6-triflates of 2,3,4,5-tetrahydro-1H-benzo[d]

carboxylic esters (e). Deprotection of the ring nitrogen gives the compounds (f). Reduction of the carboxylic ester with a reducing agent, such as lithium aluminum hydride, and subsequent protection of the nitrogen with a suitable protecting group for a secondary amine such as, but not limited to, tert-butoxycarbonyl, provides compounds (ad). The alcohol (ad) may be converted into the chloride (ac), for example, by treatment with methanesulfonyl chloride in a solvent, typically dichloromethane, using triethylamine as base.

Scheme III

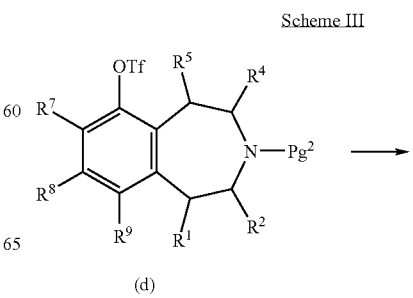

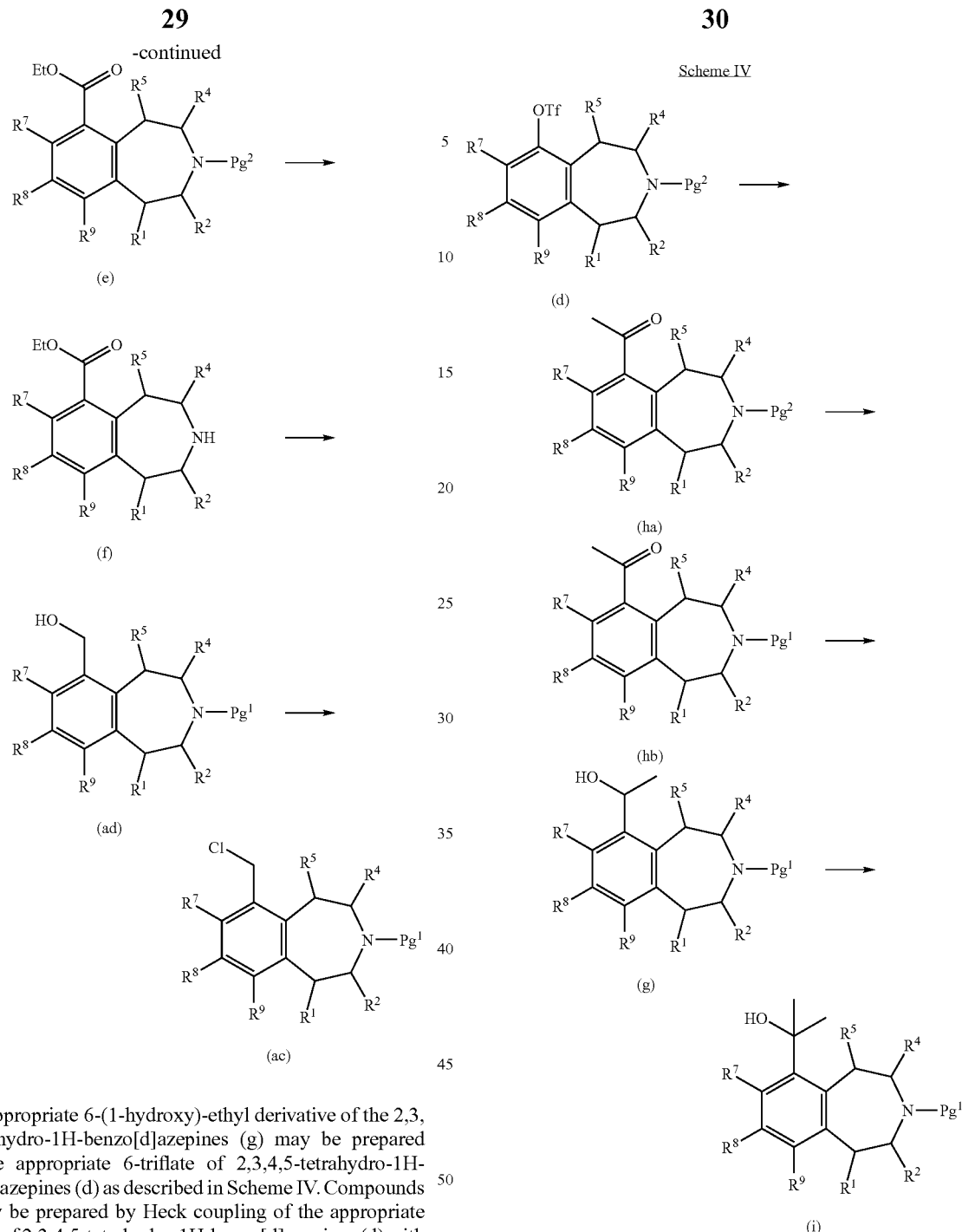

Scheme IV

The appropriate 6-(1-hydroxy)-ethyl derivative of the 2,3,4,5-tetrahydro-1H-benzo[d]azepines (g) may be prepared from the appropriate 6-triflate of 2,3,4,5-tetrahydro-1H-benzo[d]azepines (d) as described in Scheme IV. Compounds (ha) may be prepared by Heck coupling of the appropriate 6-triflate of 2,3,4,5-tetrahydro-1H-benzo[d]azepines (d) with butyl vinyl ether, using a suitable palladium catalyst/ligand mixture in a solvent, typically DMF, and triethylamine as base. Acid hydrolysis and standard extractive and chromatographic techniques afford the desired compounds (ha). Deprotection of the ring nitrogen and subsequent protection of the nitrogen with a suitable protecting group for a secondary amine such as, but not limited to, tert-butoxycarbonyl, provide compounds (hb). Reduction of the carbonyl group with a reducing agent, such as sodium borohydride in an alcoholic solvent, typically methanol, ethanol or iso-propanol, afford compound (g) after applying standard extractive and chromatographic techniques. Alternately, ketones (hb) may be converted in tertiary alcohols (i) by addition of a carbon nucleophile.

Alcohols with a 2-carbon linker (b) or a 3-carbon linker (kb) may be prepared from the appropriate 6-triflate of 2,3,4,5-tetrahydro-1H-benzo[d]azepines (d) as described in Scheme V. Compounds (ja) may be prepared by Heck coupling of the appropriate 6-triflate of 2,3,4,5-tetrahydro-1H-benzo[d]azepines (d) with, for example, 1-methoxy-trimethylsilyloxy-ethylene using a suitable palladium catalyst/ligand mixture in a solvent, typically DMF, and in the presence of lithium acetate. Standard work-up and isolation techniques afford the desired compounds (ja). Reduction of the ester group with a reducing agent, affords compound (jb) after applying standard extractive and chromatographic techniques. Compounds (ka) may be prepared by Heck coupling of the appropriate 6-triflate of 2,3,4,5-tetrahydro-1H-benzo[d]azepines (d) with, for example, t-butyl acrylate using a suitable palladium catalyst/ligand mixture, for example Pd(II) acetate/tri-o-tolylphosphine, in a solvent, typically DMF, and triethylamine as base. Standard work-up and isolation techniques afford the desired compounds (ka). Reduction of the double bond, for example with hydrogen and Pd/C in a solvent such as methanol, affords esters (kb). The esters may be reduced to the alcohols (kc) under conditions well known in the literature. The skilled artisan will also appreciate that the intermediate esters (ja), (ka), and (kb), might be further alkylated under methods well known in the art to provide eventually alcohols with branched alkyl chains.

Compounds of Formula I where $R^6$ is an alkyl-linked amine may be prepared as illustrated in Scheme VI where $Pg^1$ is a suitable protecting group for a secondary amine such as, but not limited to, tert-butoxycarbonyl, and variables $R^1$, $R^2$, $R^3$, $R^4$, $R^5$, $R^7$, $R^8$, $R^9$, $R^{11}$ and $R^{12}$ are as previously defined.

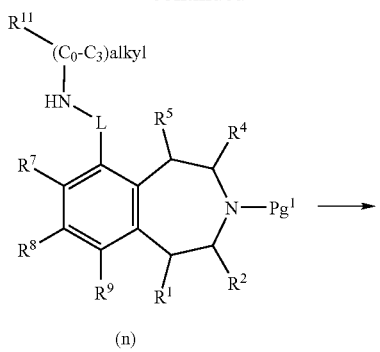

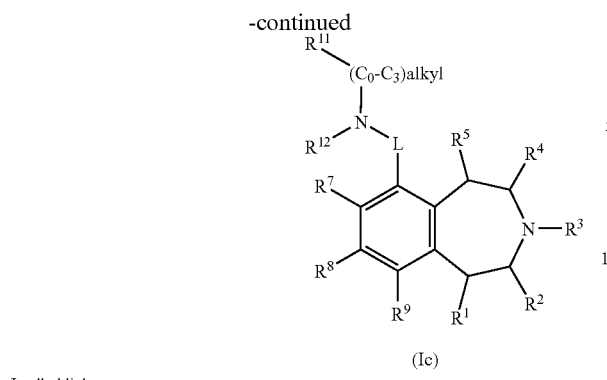

(Ic)

L: alkyl linker

The appropriate 6-aminoalkyl derivatives of 2,3,4,5-tetrahydro-1H-benzo[d]azepines (m) can be converted to the compounds (n), where $R^{11}$ is directly attached to the nitrogen (-L-HN—$R^{11}$), under Buchwald coupling conditions, by treatment with an appropriate aryl bromide, chloride, iodide, or triflate in the presence of an effective palladium catalyst/ligand system, and a base in a suitable solvent, typically toluene or 1,4-dioxane under an inert atmosphere and heat. The aryl halides or triflate are either commercially available or may be prepared by methods well known to the skilled artisan. Introduction of a second substituent $R^{12}$, if needed, may be performed to provide compounds (o). Standard workup and chromatographic techniques followed by deprotection of the ring nitrogen give the compounds (Ic), where $R^3$ is H. Final compounds (Ic) where $R^3$ is methyl or ethyl can be obtained by alkylation of the secondary amine after removal of $Pg^1$. The compounds (n), where $R^{11}$ is linked to the nitrogen via an alkyl chain (-L-HN—($C_1$-$C_3$)alkyl-$R^{11}$), may be obtained for example by reductive amination of a suitable aldehyde or ketone with amines (m).

The appropriate 6-aminoalkyl derivative of 2,3,4,5-tetrahydro-1H-benzo[d]azepines (m) may be prepared from the appropriate 6-triflate of 2,3,4,5-tetrahydro-1H-benzo[d]azepines (d) as described in Schemes VII and VIII. Mix the appropriate 6-triflate of 2,3,4,5-tetrahydro-1H-benzo[d]azepines (d) with zinc cyanide and a suitable palladium catalyst/ligand mixture in a solvent, typically DMF, to obtain the desired 6-cyano-2,3,4,5-tetrahydro-1H-benzo[d]azepines (p) after standard extractive and chromatographic techniques. Deprotection of the ring nitrogen and subsequent protection of the nitrogen with a suitable protecting group for a secondary amine such as, but not limited to, tert-butoxycarbonyl, provide compound (q). Reduction of the cyano group with borane affords compounds (r) after standard extractive and chromatographic techniques.

Scheme VII

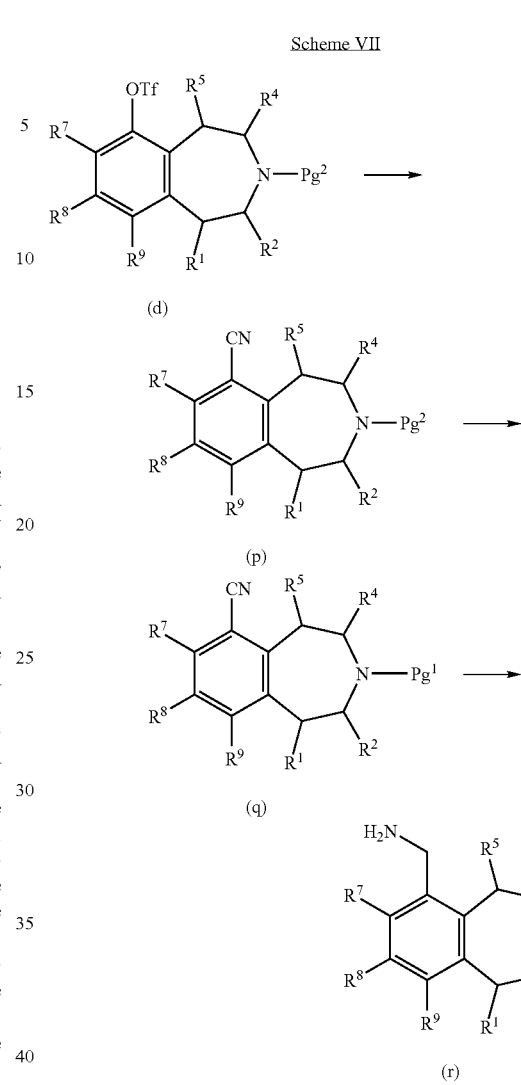

Other 6-aminoalkyl derivatives (m) may be prepared as described in Scheme VIII. Reaction of the 6-alkyl halides or sulfonates (aa) with a nitrogen nucleophile, such as sodium azide, in a suitable solvent, such as DMF, can afford azides (s), which may be reduced to the amino derivatives (m) by methods well known to the skilled artisan. Alternately, reaction of the 6-alkyl halides or sulfonates (aa) with cyanide can lead to compounds (t), which may be reduced to the amino derivatives (u) by methods well known to the skilled artisan.

Scheme VIII

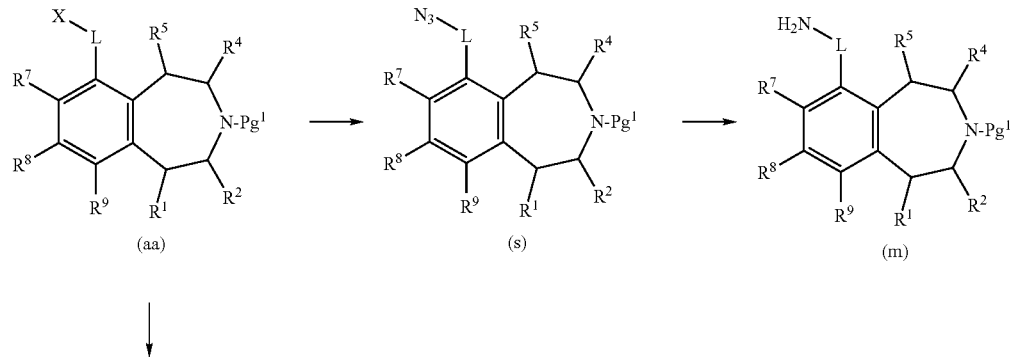

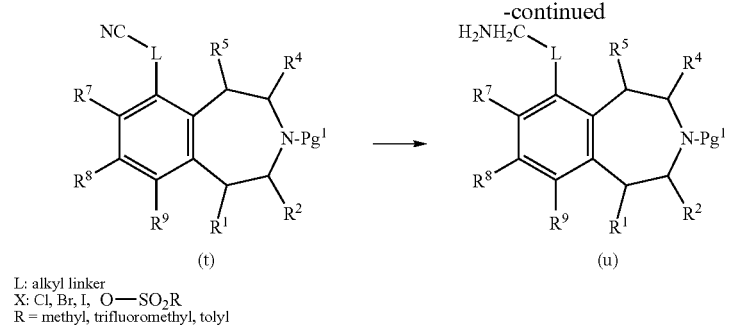

L: alkyl linker
X: Cl, Br, I, O—SO$_2$R
R = methyl, trifluoromethyl, tolyl

The appropriate 6-triflate of 2,3,4,5-tetrahydro-1H-benzo[d]azepines (d) may be prepared as described in Scheme IX. Compound (d) may be prepared from 1-naphthol. 1-Naphthol can be converted to 5-hydroxy-1,4-dihydronaphthalene (va) by Birch reduction using ammonia and lithium metal at low temperature. Methylation of the 6-hydroxy group affords the compound (vb). Ozonolysis of compound (vb) and subsequent reduction with sodium borohydride provide the diol (vc). After converting the two hydroxyl groups into two good leaving groups, for example methanesulfonates, cyclize the compound (vd) to the 6-methoxy-2,3,4,5-tetrahydro-1H-benzo[d]azepines (ve) with aqueous ammonia under pressure. Protect the ring nitrogen with a variety of alkyl halides, acid chlorides or anhydrides such as trifluoroacetic anhydride to give compound (vf). Subsequently convert the methyl ether (vf) to the phenol (vg) with BBr$_3$ in dichloromethane or other methods well known in the literature [see for example, Greene and Wuts, Protective Groups in Organic Synthesis, 3$^{rd}$ Ed., John Wiley and sons, Chapter III, New York (1999)].

Functionalization of the aromatic ring to introduce substituents R$^7$, R$^8$ and R$^9$ are well known in the art and very depending on the substitution desired. Subsequent trifluoromethanesulfonylation of the phenol (vh) affords the desired 2,3,4,5-tetrahydro-1H-benzo[d]azepines (d).

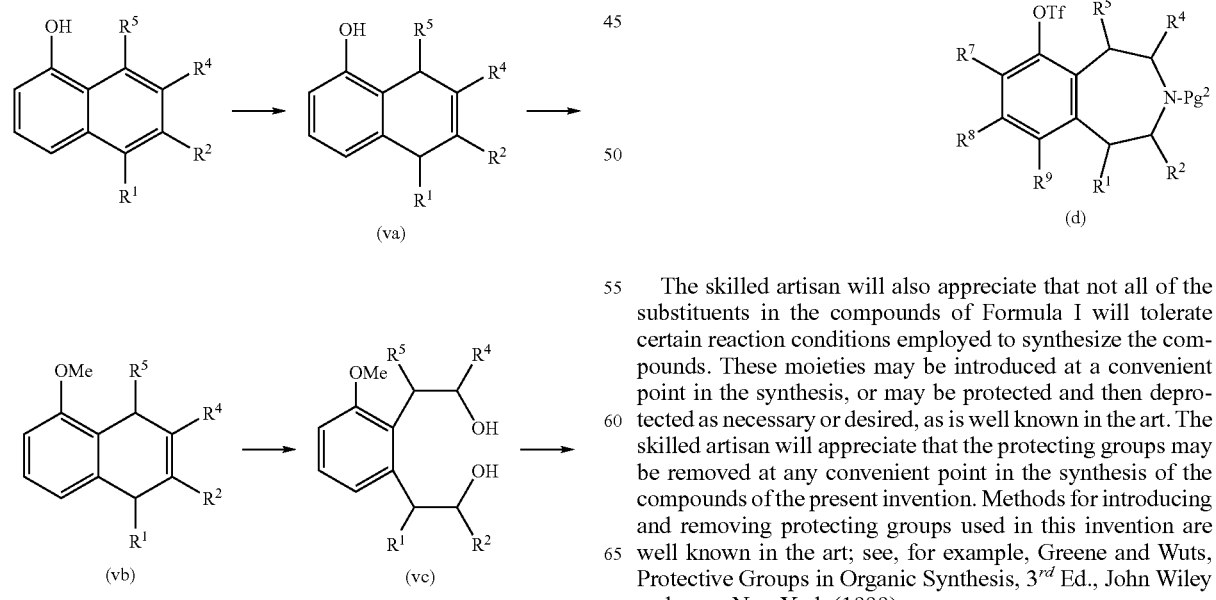

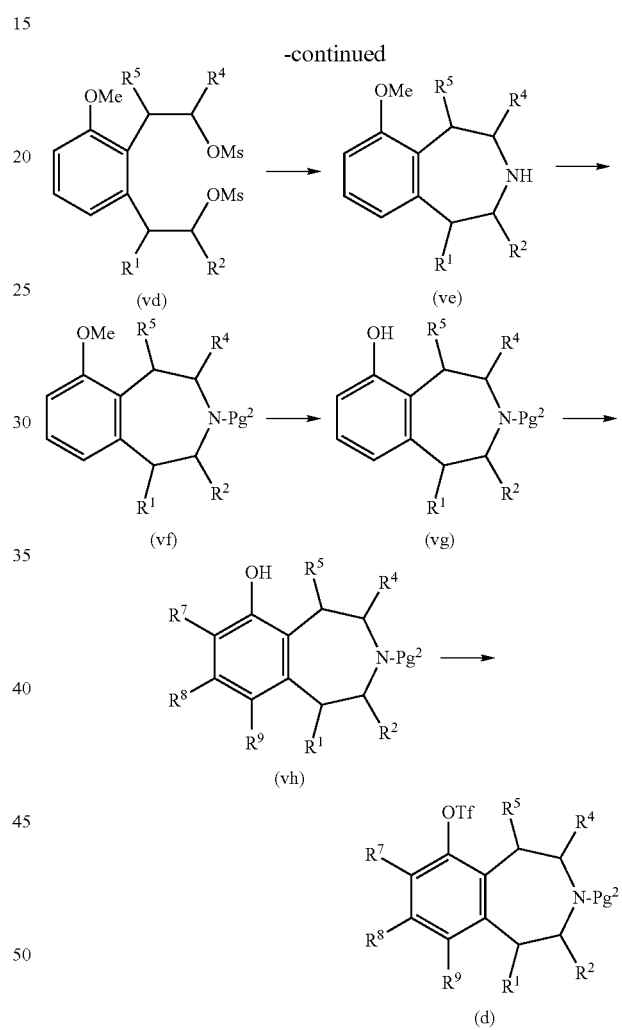

The skilled artisan will also appreciate that not all of the substituents in the compounds of Formula I will tolerate certain reaction conditions employed to synthesize the compounds. These moieties may be introduced at a convenient point in the synthesis, or may be protected and then deprotected as necessary or desired, as is well known in the art. The skilled artisan will appreciate that the protecting groups may be removed at any convenient point in the synthesis of the compounds of the present invention. Methods for introducing and removing protecting groups used in this invention are well known in the art; see, for example, Greene and Wuts, Protective Groups in Organic Synthesis, 3$^{rd}$ Ed., John Wiley and sons, New York (1999).

The appropriate 6-triflate of 2,3,4,5-tetrahydro-1H-benzo[d]azepines (a) may be prepared as described in Scheme II. Compound (a) may be prepared from 1-naphthol. 1-Naphthol can be converted to 5-hydroxy-1,4-dihydronaphthalene (c) by Birch reduction using ammonia and lithium metal at low temperature. Methylation of the 6-hydroxy group affords the compound (d). Ozonolysis of (d) and subsequent reduction with sodium borohydride provide the diol (e). After converting the two hydroxyl groups into two good leaving groups, for example methanesulfonates, cyclize the compound (f) to the 6-methoxy-2,3,4,5-tetrahydro-1H-benzo[d]azepines (g) with aqueous ammonia under pressure. Protect the ring nitrogen with a variety of alkyl halides, acid chlorides or anhydrides such as trifluoroacetic anhydride to give compound (h). Subsequently convert the methyl ether (h) to the phenol (i) with BBr$_3$ in dichloromethane or other methods well known in the literature [see for example, Greene and Wuts, Protective Groups in Organic Synthesis, 3$^{rd}$ Ed., John Wiley and sons, Chapter III, New York (1999)].

The following Preparations and Examples are illustrative of methods useful for the synthesis of the compounds of the present invention. Exemplified compounds are also particularly preferred compounds of the present invention.

General Procedure 1

Dissolve the appropriately substituted 3-tert-butoxycarbonyl-2,3,4,5-tetrahydro-1H-benzo[d]azepine in a mixture of trifluoroacetic acid/dichloromethane (from 1:0 to 1:10 ratio) and stir the reaction for 1-16 h at room temperature. Concentrate in vacuo and either subject the residue to SCX chromatography or partition the residue between saturated aqueous NaHCO$_3$ and dichloromethane or EtOAc. Dry the organic layer over Na$_2$SO$_4$ and concentrate in vacuo. Purify by chromatography on silica gel eluting with 1-20% 2M ammonia/methanol in dichloromethane, or by SCX chromatography eluting with methanol followed by 1.0-7.0 M ammonia in methanol or by reverse phase HPLC.

General Procedure 2-1

Dissolve the purified free base (1 equiv.) in acetone, diethyl ether or methanol and add a solution of succinic acid (1 equiv.) in a minimal volume of acetone or methanol. Stir for 1 h at room temperature. Concentrate to an oil, add a minimal volume of dichloromethane and ether to precipitate out the salt. Alternatively, to precipitate out the salt, allow the reaction mixture to stand 1-16 h at room temperature, 4° C. or −10° C. and add ether or hexane. Filter and wash the solid with ether or hexane to obtain the succinate salt. Alternatively, evaporate the solvent in vacuo, wash the solid with ether and filter or decant the solvent to obtain the succinate salt as a solid. Dry the solid in vacuo or under a stream of nitrogen.

General Procedure 2-2

Dissolve the purified free base (1 equiv.) in a minimal volume of acetone, 1,4-dioxane, methanol or dichloromethane and add an excess of 4M hydrogen chloride in dioxane or a 1M solution of hydrogen chloride in diethyl ether. Stir for 1 h and evaporate the solvent to obtain the salt as a solid. Alternatively, allow the reaction mixture to stand 1 to 16 h at room temperature and add ether or hexane to precipitate out the salt. Filter and wash the solid with ether or hexane to obtain the salt as a solid. Alternatively, evaporate the solvent in vacuo, wash the solid with ether, filter or decant the solvent to obtain the hydrochloride salt as a solid. Dry the solid in vacuo or under a stream of nitrogen.

General Procedure 2-3

Dissolve the purified free base (1 equiv.) in methanol, add a solution of aminonium chloride (1 equiv.) in methanol and stir for 1 h. Slowly remove the volatiles in vacuo. Dissolve the residue in methanol and remove most of the solvent in vacuo. Add anhydrous ether or EtOAc to precipitate out the hydrochloride salt. Collect the solid, wash the solid with ether and then dry the solid in vacuo or under a stream of nitrogen.

General Procedure 2-4

Dissolve the purified free base (1 equiv.) in a minimal volume of dichloromethane, ether, methanol or chloroform and add a solution of (L)-tartaric acid (1 equiv.) in a minimal volume of methanol. Allow the mixture to stand 10 min to 16 h at room temperature and evaporate the solvent to obtain the salt as a solid. Alternatively add ether or hexane to precipitate out the solid. Dry the solid in vacuo or under a stream of nitrogen. Alternatively evaporate the solvent and dissolve the resulting oil with acetonitrile/water (2:1) and water (so that the final solution has an excess of water) and freeze dry the solution.

Preparation 1

7-Chloro-3-(2,2,2-trifluoroacetyl)-6-trifluoromethanesulfonyloxy-2,3,4,5-tetrahydro-1H-benzo[d]azepine

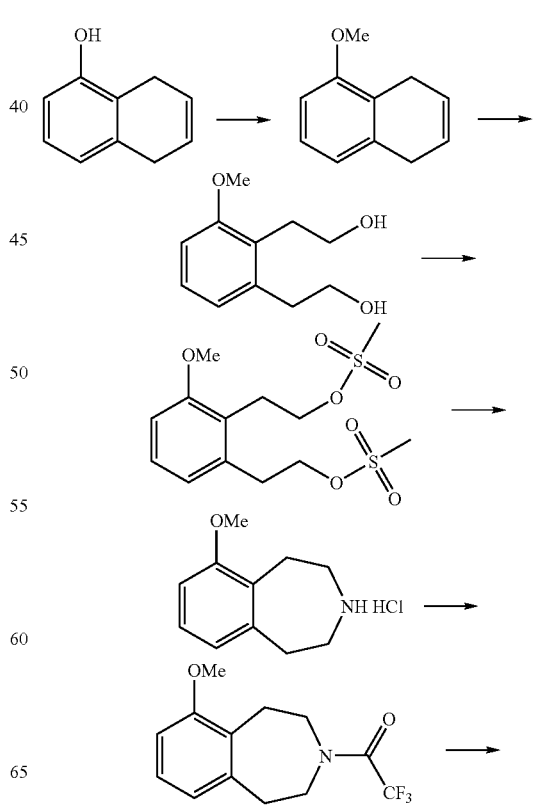

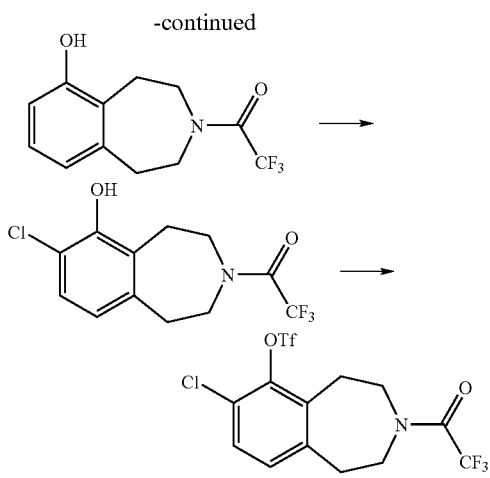

5-Methoxy-1,4-dihydronaphthalene: Add powdered potassium carbonate (193.1 g, 1.397 mol) to a solution of 5-hydroxy-1,4-dihydronaphthalene [68.08 g, 90% potency based on $^1$H-NMR, 0.4657 mol, from Societa Italiana Medicinala Scandicci, s.r.l., Reggello (Firenze), Italy] in ethanol (700 mL). Cool the solution to 0° C. with ice/water and add dimethyl sulfate (88.1 g, 66.1 mL, 0.699 mol) dropwise, maintaining the temperature between 5° C. and 10° C. Then heat the reaction mixture to 40° C. until the TLC (10:1 hexane/EtOAc) shows the absence of starting material (about 2 h). Filter off the solids by vacuum filtration and remove the solvent in vacuo. Dilute the residual brown oil with diethyl ether (500 mL), wash with 10% aqueous NH$_4$OH (500 mL), water (500 mL), brine (500 mL), dry the organic layer over Na$_2$SO$_4$, filter and concentrate in vacuo to give the crude product as a brown oil (73 g). Purify the crude product by short path distillation under vacuum (bp 120-130° C./5 Torr) to give the desired intermediate as a clear oil (69.0 g, 92.5% potency corrected) (contains some 1,2,3,4-tetrahydro-5-methoxynaphthalene as an impurity). $^1$H NMR (300 MHz, CDCl$_3$), δ 7.15 (t, 1H, J=7.9), 6.72 (dd, 2H, J=15.7, 7.9), 5.93-5.88 (m, 2H), 3.83 (s, 3H), 3.42-3.39 (m, 2H), 3.30-3.28 (m, 2H); R$_f$=0.58 eluting with 10:1 hexane/EtOAc.

2,3-Bis-(2-hydroxyethyl)-1-methoxybenzene: Charge a four-neck 5 L flask equipped with an over-head mechanical stirrer, reflux condenser, thermocouple, and gas dispersion apparatus with 5-methoxy-1,4-dilydronaphthalene (264.54 g, 89.5% potency based on $^1$H-NMR, 1.478 mol) in DCM (1.3 L) and 2B-3 ethanol (1 L). Add sudan III (10 mg) to give a faint red color. Cool the solution to −65° C. or lower, then pass O$_3$ through the solution until the solution turns a light yellow color and the TLC (10:1 hexane/EtOAc, KMnO$_4$ stain) shows the absence of the starting material (about 30 h). Transfer the solution via cannula into a slurry of NaBH$_4$ (97.8 g, 2.59 mol) in 2B-3 ethanol (500 mL) cooled in ice/water. It is important that the temperature be maintained at or above 0° C., as for example between 0° C. and 10° C., throughout the transfer to ensure the ozonide is completely reduced to the diol. After the transfer is complete, warm the solution to ambient temperature and stir for about 30 min. Cool the slurry to 0° C. with ice/water then slowly add acetone (540 mL, 7.4 mol) to remove excess NaBH$_4$. After all the solids dissolve, remove the solvent in vacuo. Dissolve the yellow solid in DCM (1 L) and water (1 L), separate the layers and extract the aqueous layer with DCM (750 mL). Wash the combined organic layers with brine (1.5 L), add toluene (750 mL) and remove the solvent in vacuo. Dissolve the solid in DCM (500 mL) with heating, then add toluene (750 mL) and concentrate the solution in vacuo to give the desired intermediate as a light yellow solid (283.7 g, 89% potency corrected, mp 82-83° C.) (contains 1,2,3,4-tetrahydro-5-methoxynaphthalene as an impurity (8.6%)). Further purify the product by vacuum drying overnight at 75° C., 5 Torr, to remove all but trace amount of the 1,2,3,4-tetrahydro-5-methoxynaphthalene impurity. $^1$H NMR (300 MHz, CDCl$_3$), δ 7.16 (dd, 1H, J=8.2, 7.6), 6.83 (s, 1H, J=7.0), 6.76 (s, 1H, J=8.2), 3.85-3.77 (m, 7H), 3.01-2.91 (m, 4H), 2.35 (s, 2H); $^{13}$C NMR (300 MHz, DMSO-d$_6$), δ 157.5, 138.9, 126.5, 125.2, 122.0, 108.4, 62.1, 60.5, 55.3, 36.1, 29.6; IR (KBr): 3006, 2960, 2886, 2829, 1583, 1461, 1440, 1264, 1091, 1041 cm$^{-1}$; MS (ES+) m/z 178 (M+H)$^+$; Anal. Calc'd for C$_{11}$H$_{16}$O$_3$: C, 67.32; H, 8.22; N, 0. Found: C, 67.26, H, 8.10; N, 0.21. R$_f$=0.23 eluting with 95:5 DCM/methanol.

2,3-Bis-(2-methanesulfonyloxyethyl)-1-methoxybenzene: To a slurry of 2,3-bis-(2-hydroxyethyl)-1-methoxybenzene (50.6 g, 0.258 mol, 1 equiv.) and triethylamine (78.3 g, 0.774 mol, 3 equiv.) in DCM (500 mL) at 0° C., add dropwise a solution of methanesulfonyl chloride (65.0 g, 0.567 mol, 2.2 equiv.) in DCM (100 mL) over 45 min. The addition is exothermic and the methanesulfonyl chloride is added at a rate to keep the temperature below 10° C. After the addition is complete, warm the reaction to ambient temperature. Wash the solution with water (2×500 mL), and then brine (750 mL). Dry the organic layer over Na$_2$SO$_4$, filter and concentrate in vacuo to obtain the desired intermediate as a dark yellow oil (87.4 g, 96.2%), which is used in the next reaction without further purification. An analytical sample is obtained by flash column chromatography eluting with 100% diethyl ether. $^1$H NMR (300 MHz, CDCl$_3$), δ 7.20 (t, 1H, J=7.9), 6.82 (s, 1H, J=7.2), 6.80 (s, 1H, J=8.2), 4.41-4.34 (m, 4H), 3.83 (s, 3H), 3.16-3.09 (m, 4H), 2.91 (s, 3H), 2.87 (s, 3H); $^{13}$C NMR (300 MHz, CDCl$_3$), δ 158.07, 136.55, 128.26, 123.34, 122.39, 109.24, 69.88, 69.08, 55.55, 37.35, 37.14, 32.57, 26.47; $^{13}$C NMR (300 MHz, DMSO-d$_6$), δ157.58, 136.79, 127.81, 122.91, 122.00, 109.33, 70.19, 68.88, 55.55, 36.49, 36.47, 31.56, 25.72; IR (KBr): 1586.8, 1469.4, 1358.51, 1267.3, 1173.9, 1105.4, 972.4, 954.6, 914.3 cm$^{-1}$; MS (ES+) m/z 257 (M+H)$^+$; Anal. Calc'd. for C$_{13}$H$_{20}$O$_7$S$_2$: C, 44.31; H, 5.72; N, 0. Found: C, 44.22, H, 5.68; N, 0.13. R$_f$=0.72 eluting with 95:5 DCM/methanol.

6-Methoxy-2,3,4,5-tetrahydro-1H-benzo[d]azepine: Dissolve 2,3-bis-(2-methanesulfonyloxyethyl)-1-methoxybenzene (474.4 g, 1.346 mol) in acetonitrile (7 L) and split the mixture into two equal lots. In two separate runs, add concentrated aqueous NH$_4$OH (3.5 L) and charge the solution to a pressure vessel (PARR apparatus). Heat the solution in a closed reactor to 100° C. over 20 min (internal pressure reaches about 100 psi), and maintain at 100° C. until the reaction is complete (about 1 h, HPLC monitored). Cool the reaction mixture to ambient temperature. Combine the two lots and remove the solvent in vacuo. Dissolve the residue in MTBE (3.5 L) and water (3.5 L). Adjust the pH to 6.5 using 2M aqueous NaOH or 1M aqueous HCl as appropriate (typically the pH is about pH=5.1 and the adjustment requires about 50 mL 2M aqueous NaOH). Discard the organic layer, adjust the aqueous layer to pH=13 using 50% NaOH (about 150 mL). Extract with MTBE (2×3.5 L), wash the combined organic layers with brine (3.5 L), dry over Na$_2$SO$_4$, filter and concentrate in vacuo to give the title compound as a crude yellow oil that solidifies upon standing (179.3 g). Use the material for the next step without further purification. Prepare an analytical sample by purification by two Kugelrohr distillations to give a clear oil that solidifies upon standing, mp 44.3-45.0° C. $^{13}$C NMR (300 MHz, DMSO-d$_6$), δ 156.1, 144.4, 130.3, 126.2, 121.5, 108.9, 55.5, 48.2, 47.9, 39.9, 29.1; MS (ES+) m/z, 163 (M+H)$^+$; Anal. Calc'd for $C_{11}H_{15}NO$: C, 74.54; H, 8.53; N, 7.90. Found: C, 74.28, H, 8.62; N, 7.86.

6-Methoxy-2,3,4,5-tetrahydro-1H-benzo[d]azepine Hydrochloride: Dissolve crude 6-methoxy-2,3,4,5-tetrahydro-1H-benzo[d]azepine (35.1 g, 0.198 mol) in 2B-3 ethanol (250 mL), heat the solution to reflux and add 2M HCl in ethanol (108.9 mL, 0.218 mol, 1.1 equiv.). Slowly add heptane (700 mL) over 10 min, then remove the heating mantle and cool the solution to ambient temperature, and finally continue the cooling with an ice/water mixture. Collect the resulting solid by vacuum filtration and wash with cold ethanol:heptane (1:2) (3×100 mL), air-dry for 15 min under vacuum, then further dry the product in a vacuum oven at 60° C. for 1 h to give the desired intermediate as a white granular solid 35.53 g, 63%): mp 246.6-246.9° C.; $^1$H NMR (300 MHz, DMSO-d$_6$), δ 9.82 (broad s, 1H), 7.12 (dd, 1H, J=7.6, 7.9), 6.88 (d, 1H, J=8.2), 6.78 (d, 1H, J=7.3), 3.75 (s, 3H), 3.20-3.00 (m, 8H); $^{13}$C NMR (300 MHz, DMSO-d$_6$), δ 156.2, 141.3, 127.4, 127.2, 121.6, 109.7, 55.7, 44.9, 44.7, 31.6, 21.7; MS (ES+) m/z 178 (M+H)$^+$; Anal. Calc'd for $C_{11}H_{15}ClNO$: C, 62.12; H, 7.11; N, 6.59. Found: C, 61.95, H, 7.64; N, 6.58.

6-Methoxy-3-(2,2,2-trifluoroacetyl)-2,3,4,5-tetrahydro-1H-benzo[d]azepine: To a slurry of 6-methoxy-2,3,4,5-tetrahydro-1H-benzo[d]azepine hydrochloride (35.3 g, 0.165 mol, 1 equiv.) and triethylamine (69.1 mL, 0.496 mol, 3 equiv.) in DCM (300 mL) cooled at 0° C. with ice/water, add dropwise a solution of trifluoroacetic anhydride (25.7 mL, 0.182 mol, 1.1 equiv.) in DCM (40 mL) over 30 min, but at a rate that maintains the temperature below 10° C. After the addition is complete, warm the reaction mixture to ambient temperature and stir until the reaction is complete (verify by TLC using 9:1 CH$_2$Cl$_2$:methanol, about 2 h.). Wash the solution with water (2×350 mL), and then brine (350 mL), dry the organic layer over Na$_2$SO$_4$, filter and concentrate in vacuo to give desired intermediate as a yellow oil that solidifies upon standing (44.9 g, 96%). Use the material without further purification in the next step. Prepare an analytical sample by chromatography on silica gel eluting with 40% diethyl ether in hexane, mp 74-76° C. $^1$H NMR (300 MHz, CDCl$_3$), δ 7.16-7.11 (m, 1H), 6.81-6.74 (m, 2H), 3.81 (s, 3H), 3.79-3.64 (m, 4H), 3.11-3.07 (m, 2H), 2.99-2.95 (m, 2H); $^1$H NMR (300 MHz, DMSO-d$_6$), δ 7.13 (dd, 1H, J=1.5, 7.0), 7.08 (d, 1H, J=1.5), 6.88-6.74 (m, 1H), 3.75 (s, 3H), 3.67-3.61 (m, 4H), 3.04-2.92 (m, 4H); $^{13}$C NMR (300 MHz, DMSO-d$_6$), δ 156.43, 156.38, 155.06, 155.00, 154.60, 154.54, 154.14, 154.08, 141.31, 141.04, 127.44, 127.18, 127.05, 127.01, 122.27, 121.94, 121.90, 118.46, 114.64, 110.80, 109.52, 109.41, 55.63, 55.61, 47.11, 47.07, 46.67, 46.63, 45.61, 45.16, 35.90, 34.65, 26.18, 24.91; Anal. Calc'd for $C_{13}H_{14}F_3NO_2$: C, 57.14; H, 5.16; N, 5.13. Found: C, 57.17, H, 5.27; N, 5.08.

6-Hydroxy-3-(2,2,2-trifluoroacetyl)-2,3,4,5-tetrahydro-1H-benzo[d]azepine: To a 1M solution of BBr$_3$ (1.1 L, 1.6 equiv.), cooled at 0° C. with an ice-water bath, add 6-methoxy-3-(2,2,2-trifluoroacetyl)-2,3,4,5-tetrahydro-1H-benzo[d]azepine (187 g, 0.684 mol) in DCM (200 mL) over 1 h., while maintaining the temperature between 0° C. and 10° C. Warm the reaction mixture to ambient temperature and stir until HPLC indicates completion of the reaction (about 2 h.). Cool the solution to 0° C. and transfer it via cannula into an ice/water solution (1.2 L), thereby precipitating the product as a white solid. Add EtOAc (2 L) to dissolve most of the precipitate, separate the layers and concentrate the organic layer in vacuo. Extract the aqueous layer three times with EtOAc (2×2 L, 1×1 L). Wash the combined organic layers with water (2 L), and then brine (2 L), dry over Na$_2$SO$_4$, filter and concentrate in vacuo to give the desired intermediate as a light yellow solid (166.3 g, 94%). Use the product for the next step without further purification. Prepare an analytical sample by chromatography on silica gel eluting with 40% diethyl ether in hexane: mp 183.0-185.2° C. $^1$H NMR (300 MHz, DMSO-d$_6$), δ 9.39 (s, 1H), 6.94-6.88 (m, 1H), 6.72-6.68 (m, 1H), 6.61-6.57 (m, 1H), 3.67-3.32 (m, 4H), 2.99-2.86 (m, 4H); $^{13}$C NMR (300 MHz, DMSO-d$_6$), δ 154.50, 141.47, 141.18, 126.77, 126.64, 125.77, 125.33, 120.38, 120.32, 118.49, 114.67, 113.64, 113.47, 47.31, 47.27, 47.00, 46.96, 45.83, 45.49, 36.17, 34.93, 26.46, 25.18, 20.66, 14.00; MS (ES+) m/z 260 (M+H)$^+$; Anal. Calc'd for $C_{12}H_{12}F_3NO_2$: C, 55.60; H, 4.67; N, 5.40. Found: C, 55.51, H, 4.71; N, 5.29.

7-Chloro-6-hydroxy-3-(2,2,2-trifluoroacetyl)-2,3,4,5-tetrahydro-1H-benzo[d]azepine: Heat a mixture of 6-hydroxy-3-(2,2,2-trifluoroacetyl)-2,3,4,5-tetrahydro-1H-benzo[d]azepine (120 g, 0.4629 mol) and toluene (14.4 L) to 70° C. for 45 min until most of the starting material is dissolved. Add diisobutylamine (1.197 g, 1.62 mL, 9.26 mmol) followed by addition of sulfuryl chloride (62.48 g, 37.19 mL, 0.463 mol) in toluene (360 mL) over 20 min. Stir the reaction mixture for 50 min and then add additional sulfuryl chloride (4.536 g, 2.70 mL, 0.0336 mol) neat and stir the reaction mixture for 15 min at 70° C. Cool the reaction mixture to 24° C. over 30 min and then add 1N hydrochloric acid (2 L). Separate, wash the organic layer with saturated aqueous NaHCO$_3$ (2 L), brine (2 L) and then dry over Na2SO4. Filter and remove the solvent with a rotary evaporator at 70° C. until about 672.5 g remains using the minimum effective vacuum in order to maintain a vapor phase sufficient to prevent drying above the solvent line and self-seeding, thus preventing crystallization under these conditions. Using toluene heated to 70° C., transfer the light-yellow solution to a preheated (70° C.) 3-neck flask equipped with a mechanical stirrer. Lower the temperature to 58° C. over 1 h. If available, seed the solution with crystals of 7-chloro-6-hydroxy-3-(2,2,2-trifluoroacetyl)-2,3,4,5-tetrahydro-1H-benzo[d]azepine from a prior synthesis to enhance crystallization. After 30 min, reduce the temperature further to 55° C. and observe the initiation of the crystallization process. Hold the temperature at 55° C. for 2 h. followed by 4 h. at 45° C., then turn off the heat allowing the mixture to slowly reach 24° C. (ambient temperature). After stirring for 8 h. with the heat off, cool the mixture to 0° C. for 2 h. followed by 2 h. at −10° C. Collect the resulting dense, white, granular crystals by vacuum filtration at −10° C. Rinse the crystals twice with cold (−10° C.) toluene and vacuum dry at 50° C., 5 Torr, for 12 h., to obtain the desired intermediate as a white solid (120.7 g, 99.5% purity, 88.8%): mp 133-134° C. MS (ES+) m/z 294 (M+H)$^+$. Anal. Calc'd for $C_{12}H_{11}ClF_3NO_2$: C, 49.08; H, 3.78; N, 4.77; Cl, 12.07. Found: C, 49.01; H, 3.63; N, 4.72; Cl, 12.32.

7-Chloro-3-(2,2,2-trifluoroacetyl)-6-trifluoromethanesulfonaloxy-2,3,4,5-tetrahydro-1H-benzo[d]azepine: Cool a solution of 7-chloro-6-hydroxy-3-(2,2,2-trifluoroacetyl)-2,3,4,5-tetrahydro-1H-benzo[d]azepine (60 g, 0.204 mol), triethylamine (62.6 mL, 0.448 mol, 2.2 equiv.), and DCM (590 mL) in an ice bath and add dropwise trifluoromethanesulfonic anhydride (43.5 mL, 0.258 mol, 1.26 equiv.) over 70 min. Remove the ice bath and stir the reaction mixture for 2 h. Wash the reaction mixture sequentially with water (500 mL), 1N aqueous HCl (500 mL), water (500 mL), and brine (500 mL). Dry the organic layer over Na$_2$SO$_4$ and concentrate in vacuo to give the crude product as a brown solid (90 g). Dissolve the solid in warm toluene (200 mL). Further purify by plug filtration chromatography over silica gel (500 g) eluting sequentially with hexane (1 L), hexane/EtOAc (9:1, 1 L), hexane/EtOAc (4:1, 1 L), and hexane/EtOAc (7:3, 9 L).

Pool the eluents and evaporate the solvent to obtain the product as a yellow tan solid (86.3 g). Dissolve the solid in warm EtOAc (86 mL) and then add hexane (700 mL). If available, seed the solution with crystals of 7-chloro-3-(2,2,2-trifluoro-acetyl)-6-trifluoromethanelsulfonyloxy-2,3,4,5-tetrahydro-1H-benzo[d]azepine from a prior synthesis to enhance crystallization. Allow the mixture to stand at ambient temperature for 30 min. Cool the mixture at about −10° C. for 2 h., filter, rinse the crystals with cold (−10° C.) hexane/EtOAc, and air-dry on the filter under vacuum to obtain the title compound as a first crop of crystals (73.54 g). Concentrate the mother liquor to obtain a solid (12.7 g). Recrystallize the solid in a mixture of EtOAc/hexane (15 mL: 121 mL) to obtain additional title compound (7.65 g, total yield: 81.19 g, 93%).

Preparation 2

3-tert-Butoxycarbonyl-7-chloro-6-chloromethyl-2,3,4,5-tetrahydro-1H-benzo[d]azepine

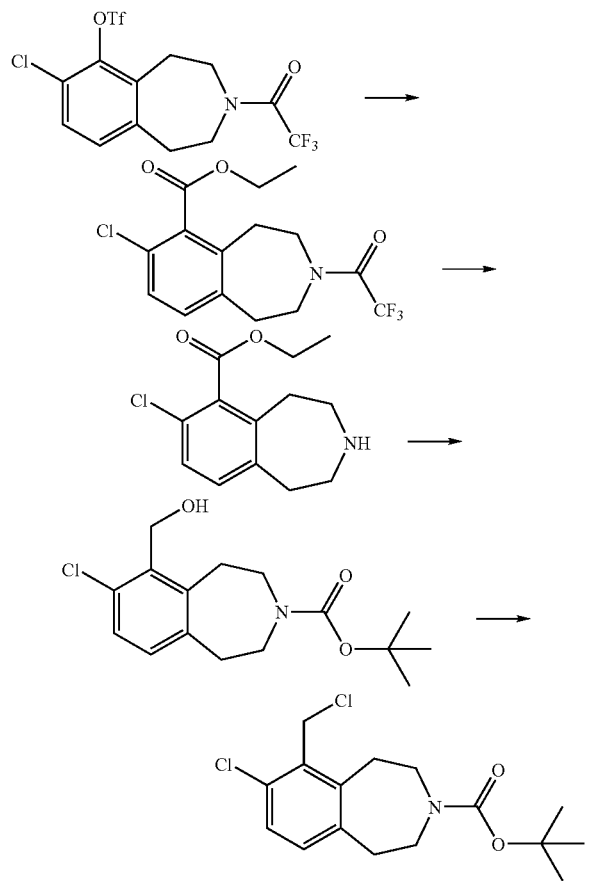

7-Chloro-6-(ethoxycarbonyl)-3-(2,2,2-trifluoroacetyl)-2,3,4,5-tetrahydro-1H-benzo[d]azepine: Add 7-chloro-3-(2,2,2-trifluoroacetyl)-6-trifluoromethanesulfonyloxy-2,3,4,5-tetrahydro-1H-benzo[d]azepine (213 g, 500 mmol), triethylamine (118 g, 1150 mmol), palladium(II) acetate (5.6 g, 25 mmol) and 1,3-bis(diphenylphosphino)propane (6.4 g, 15 mmol) to anhydrous DMSO (2.1 L) and ethanol (640 mL) in a 1 gallon autoclave. Inert the autoclave with nitrogen then charge the mixture with carbon monoxide at 50 psi and heat at 100° C. for 2 h (monitor reaction by HPLC). Cool the autoclave to room temperature and add the dark reaction mixture to a flask containing water (3.2 L) and EtOAc (3.2 L). Collect the organic layer and back extract the aqueous layer with EtOAc (2.1 L). Wash the combined organic extracts with water (2.1 L). Concentrate the organic layer in vacuo to a dark oil. Purify the crude mixture by chromatography on silica gel eluting with heptane/EtOAc (5:1) to give the desired intermediate as a pale green oil (144 g, 82%).

7-Chloro-6-(ethoxycarbonyl)-2,3,4,5-tetrahydro-1H-benzo[d]azepine: Slurry 7-chloro-6-(ethoxycarbonyl)-3-(2,2,2-trifluoroacetyl)-2,3,4,5-tetrahydro-1H-benzo[d]azepine (176 g, 503 mmol) and potassium carbonate (348 g, 2516 mmol) in ethanol (1.4 L) and water (1.4 L). Stir the mixture at room temperature for 42 h. Partition the mixture between water (2.6 L) and EtOAc (2.6 L). Collect the organic layer and back extract the aqueous layer with EtOAc (1.8 L). Wash the combined organic extracts successively with water (1.8 L) and brine (1.8 L). Collect the organic layer, dry over Na$_2$SO$_4$ and concentrate in vacuo to obtain the desired intermediate as a green oil (120 g, 94%).

3-tert-Butoxycarbonyl-7-chloro-6-hydroxymethyl-2,3,4,5-tetrahydro-1H-benzo[d]azepine: Add a solution of 7-chloro-6-(ethoxycarbonyl)-2,3,4,5-tetrahydro-1H-benzo[d]azepine (108 g, 426 mmol) in anhydrous THF (540 mL) over 30 min to a cold slurry of 1M lithium aluminum hydride in THF (533 mL, 533 mmol) in heptane (1.1 L). Maintain the reaction temperature below 5° C. during the addition. Warm the reaction to 40° C. and stir for 4 h (monitor reaction by HPLC). Cool the reaction to 0° C. and cautiously add water (162 mL). To the resulting heterogeneous off-white slurry, add triethylamine (217 g, 2130 mmol) and di-tert-butyl dicarbonate (139 g, 639 mmol). Stir the reaction mixture for 16 h at room temperature. Filter off any solids and wash with THF. Add dimethylethylenediamine (119 g, 1277 mmol) to the filtrate and stir for 30 min at room temperature. Partition the mixture between 20% citric acid and EtOAc. Collect the organic layer and wash with aqueous saturated NaHCO$_3$. Collect the organic layer, dry over Na$_2$SO$_4$ and concentrate in vacuo to give an off-white solid. Slurry the solid in heptane at 60° C. with vigorous stirring for 1 h. Cool the slurry to room temperature, filter and wash the solid with heptane, and dry in vacuo to obtain the desired intermediate as a white solid (115 g, 87%). MS (ES+) m/z: 212 (M-Boc+H)$^+$.

3-tert-Butoxycarbonyl-7-chloro-6-chloromethyl-2,3,45-tetrahydro-1H-benzo[d]azepine: Add methanesulfonyl chloride (1.1 g, 9.63 mmol; alternatively 2.36 g, 20.7 mmol) to 3-tert-butoxycarbonyl-7-chloro-6-hydroxymethyl-2,3,4,5-tetrahydro-1H-benzo[d]azepine (2.5 g, 8.03 mmol; alternatively 3.2 g, 10.3 mmol) and triethylamine (2.2 mL, 16.06 mmol; alternatively 4.3 mL, 30.8 mmol) in DCM (50 mL; alternatively 60 mL) at 0° C. Warm the mixture to room temperature and stir for 1 h., alternatively for 16 h. Dilute the reaction with DCM and wash the organic phase with water. Dry the organic phase over Na$_2$SO$_4$, filter and concentrate in vacuo to afford the title compound as a clear oil that was used immediately without any further purification. MS (ES+) m/z: 274 [M-(t-Bu)+H]$^+$.

Preparation 3

3-tert-Butoxycarbonyl-7-chloro-6-(1-hydroxy-ethyl)-2,3,4,5-tetrahydro-1H-benzo[d]azepine

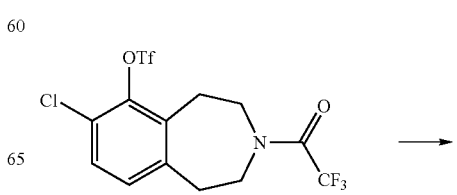

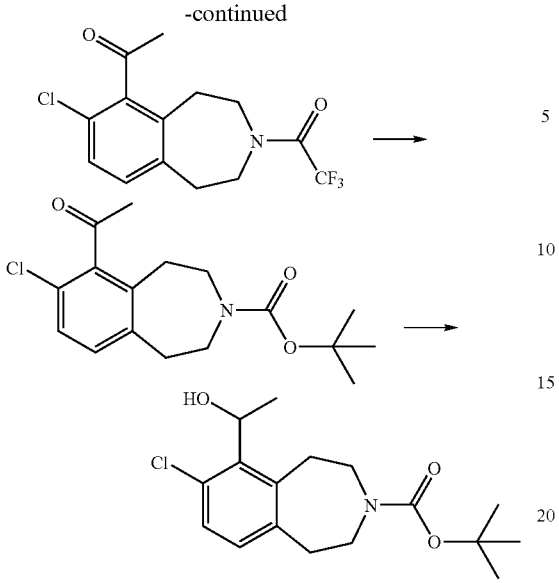

6-Acetyl-7-chloro-3-(2,2,2-trifluoroacetyl)-2,3,4,5-tetrahydro-1H-benzo[d]azepine: Combine 7-chloro-3-(2,2,2-trifluoroacetyl)-6-trifluoromethanesulfonyloxy-2,3,4,5-tetrahydro-1H-benzo[d]azepine (0.6 g, 1.41 mmol), butyl vinyl ether (0.9 mL, 7.06 mmol), palladium(II) acetate (32 mg, 0.14 mmol), DPPP (58 mg, 0.14 mmol), triethylamine (90.4 mL, 2.82 mmol), anhydrous DMF (10 mL) and stir at 90° C. for 2 h. Cool the reaction mixture to room temperature, add diethyl ether (25 mL) and wash with brine (15 mL). Separate the organic layer, dry over anhydrous $Na_2SO_4$, filter and concentrate in vacuo. Dissolve the residue in methanol (20 mL), add 1N aqueous HCl (18 mL) and stir at 70° C. for 2 h. Cool the reaction mixture to room temperature and remove methanol by evaporation. Dissolve the residue in diethyl ether (20 mL), wash with brine, collect the organic layer and dry over $Na_2SO_4$. Concentrate in vacuo and purify the crude mixture by chromatography on silica gel eluting with hexane/EtOAc (1:0 to 3:2 gradient) to obtain the desired intermediate as a colorless oil (0.4 g, 90%). MS (ES+) m/z: 320 (M+H)$^+$.

6-Acetyl-3-tert-butoxycarbonyl-7-chloro-2,3,4,5-tetrahydro-1H-benzo[d]azepine: Dissolve 6-acetyl-7-chloro-3-(2,2,2-trifluoroacetyl)-2,3,4,5-tetrahydro-1H-benzo[d]azepine (1.3 g, 4.24 mmol) in methanol (42 mL). Add $K_2CO_3$ (1.2 g, 8.49 mmol) and stir at 80° C. for 2 h. Cool the reaction mixture to room temperature, add di-tert-butyl-dicarbonate (1.9 g, 8.48 mmol) in DCM (5 mL) and stir at room temperature for 15 h. Remove the solvent in vacuo, dissolve the residue in diethyl ether (40 mL) and wash with water (10 mL). Dry the organic layer over anhydrous $Na_2SO_4$, filter and concentrate in vacuo. Purify the crude mixture by chromatography on silica gel eluting with hexane/EtOAc (1:0 to 3:2 gradient) to give the desired intermediate as a clear oil (1.33 g, 97%). MS (ES+) m/z: 324 (M+H)$^+$.

3-tert-Butoxycarbonyl-7-chloro-6-(1-hydroxy-ethyl)-2,3,4,5-tetrahydro-1H-benzo[d]azepine: Combine 6-acetyl-3-tert-butoxycarbonyl-7-chloro-2,3,4,5-tetrahydro-1H-benzo[d]azepine (0.5 g, 1.64 mmol), sodium borohydride (0.3 g, 6.55 mmol), 2-propanol (15 mL) and stir at 80° C. for 15 h. Cool the reaction mixture to room temperature, dilute with diethyl ether (50 mL) and wash with brine (3×15 mL). Dry the organic layer over anhydrous $Na_2SO_4$, filter and concentrate in vacuo. Purify the crude mixture by chromatography on silica gel eluting with hexane/EtOAc (1:0 to 4:1 gradient) to obtain the desired intermediate as a colorless oil (0.4 g, 80%). Treat an aliquot with trifluoroacetic acid to obtain the mass spectrum: MS (ES+) m/z: 225 (M+H)$^+$.

Preparation 4

6-Aminomethyl-3-tert-butoxycarbonyl-7-chloro-2,3,4,5-tetrahydro-1H-benzo[d]azepine

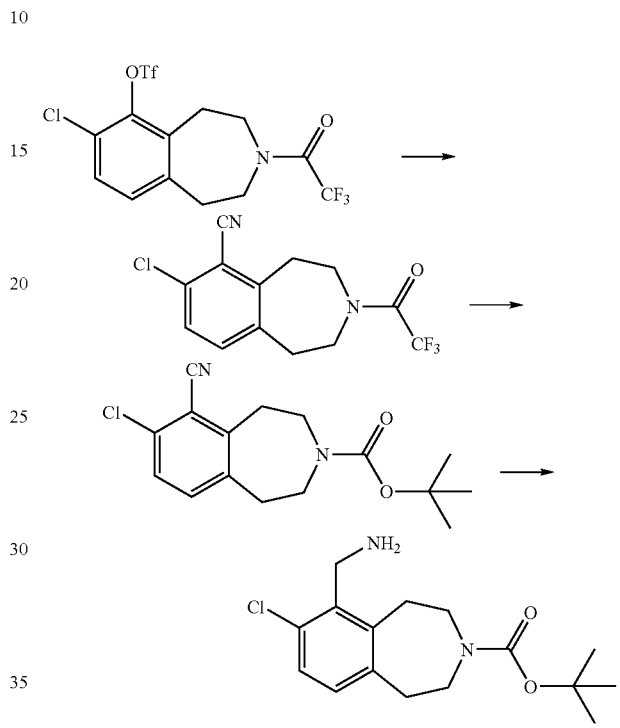

7-Chloro-6-cyano-3-(2,2,2-trifluoroacetyl)-2,3,4,5-tetrahydro-1H-benzo[d]azepine: Combine 7-chloro-3-(2,2,2-trifluoroacetyl)-6-trifluoromethanesulfonyloxy-2,3,4,5-tetrahydro-1H-benzo[d]azepine (5.015 g, 11.8 mmol), zinc cyanide (2.09 g, 17.7 mmol), tris(dibenzylideneacetone)dipalladium(0) (0.59 g, 0.59 mmol) and DPPF (0.659 g, 1.18 mmol) in anhydrous DMF (40 mL), and stir at 95° C. for 3 h. Cool the reaction mixture to room temperature, add DCM and water. Extract the aqueous phase with DCM. Dry the combined organic extracts over anhydrous $Na_2SO_4$, filter and concentrate in vacuo. Purify the crude mixture by chromatography on silica gel eluting with hexane/EtOAc (20:1, 10:1 and 5:1) to obtain the desired intermediate (3.2 g, 90%). MS (ES+) m/z: 303 (M+H)$^+$.

3-tert-Butoxycarbonyl-7-chloro-6-cyano-2,3,4,5-tetrahydro-1H-benzo[d]azepine: Combine 7-chloro-6-cyano-3-(2,2,2-trifluoroacetyl)-2,3,4,5-tetrahydro-1H-benzo[d]azepine (3.08 g, 10.19 mmol) and $K_2CO_3$ (5.637 g, 40.79 mmol) in methanol (60 mL) and water (15 mL) and stir at room temperature for 1 h. Evaporate methanol in vacuo. Dissolve the residue in THF (50 mL) and water (20 mL), add di-tert-butyl-dicarbonate (2.22 g, 10.19 mmol) slowly at room temperature and stir for 30 min. Dilute with DCM and wash with water. Collect the organic layer, dry over anhydrous $Na_2SO_4$, filter and concentrate in vacuo to provide the desired intermediate that was used without further purification. MS (ES+) m/z: 207 (M-Boc+H)$^+$.

6-(Aminomethyl)-3-tert-butoxycarbonyl-7-chloro-2,3,4,5-tetrahydro-1H-benzo[d]azepine: Add borane-methyl sulfide complex (40 mL, 80 mmol, 2M solution in THF) to a solution of 3-tert-butoxycarbonyl-7-chloro-6-cyano-2,3,4,5-tetrahydro-1H-benzo[d]azepine (4.79 g, 10.2 mmol) in anhydrous THF (120 mL). Reflux the mixture overnight under nitrogen. Cool the mixture to room temperature and quench with methanol. Add KHSO$_4$ (20 g in water) and stir for 1 h. Remove the organic solvent in vacuo and basify by addition of solid K$_2$CO$_3$. Extract with DCM and wash with brine. Collect the organic layer, dry over anhydrous Na$_2$SO$_4$, filter and concentrate in vacuo. Purify by chromatography on silica gel eluting with hexane/EtOAc (1:0 and 3:1), DCM and DCM/(chloroform:methanol:concentrated ammonium hydroxide 88:18: 2) (20:1, 10:1 and 5:1) to give the title compound (2.56 g, 81% over 2 steps). MS (ES+) m/z: 311 (M+H)$^+$.

Preparation 5

4-Bromo-N-cycloheptyl-benzamide

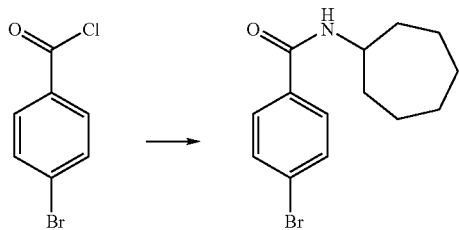

Dissolve 4-bromo-benzoyl chloride (2.0 g, 9.1 mmol) in DCM (20 mL). Cool the solution to 0° C. and add triethylamine (2.54 mL, 18.2 mmol) followed by cycloheptylamine (1.24 g, 10.9 mmol). Warm the mixture to room temperature over 1 h. Wash the mixture with saturated NaHCO$_3$ (15 mL). Collect the organic layer, and extract the aqueous layer with DCM. Dry the combined organic extracts over Na$_2$SO$_4$, filter and concentrate in vacuo. Purify the residue by chromatography on silica gel (120 g) eluting with hexane/EtOAc (1:1) to obtain the title compound as a solid (2.5 g, 93%). MS (APCI+) m/z: 296 (M)$^+$.

Preparation 6

N-Benzyl-6-mercapto-nicotinamide

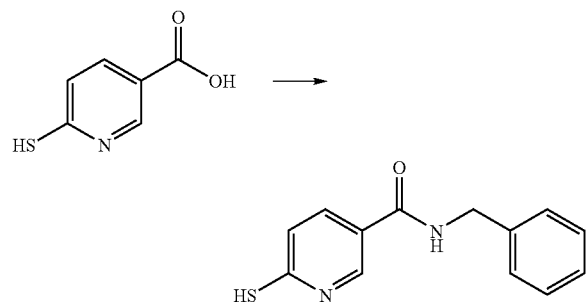

Combine 6-mercapto-nicotinic acid (0.64 g, 4.1 mmol), benzylamine (0.45 mL, 4.1 mmol) and EEDQ (1 g, 4 mmol) in anhydrous DMF (3 mL). Stir at room temperature for 12 h. Dilute the reaction with water and extract with DCM. Dry over MgSO$_4$, filter and concentrate in vacuo to give a yellow solid. Purify by chromatography on silica gel eluting with 2M ammonia in methanol/DCM (2:98 and 10:90) to give the title compound as a yellow solid (440 mg, 44%). MS (ES+) m/z: 245 (M+H)$^+$.

Preparation 7

2H-Pyridazine-3-thione

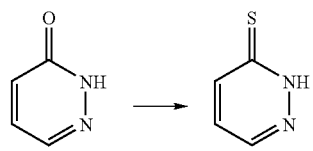

Combine 2H-pyridazin-3-one (5 g, 52 mmol) and phosphorous pentasulfide (4.6 g, 10.3 mmol) in pyridine (30 mL). Stir at room temperature for 5 min then reflux for 3 h. Cool to room temperature and concentrate in vacuo to give a dark green oil. Triturate the oil with water to give the title compound as dark green crystals (3.02 g, 52%).

Preparation 8

4-(1,1-Dimethyl-propyl)-benzenethiol

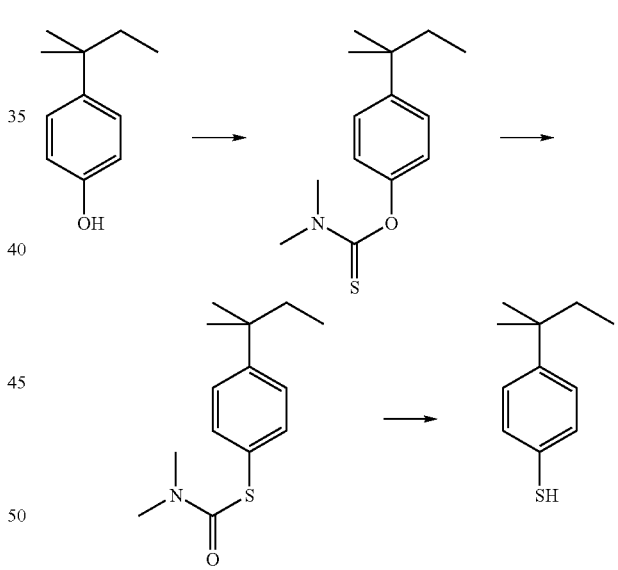

4-(1,1-Dimethyl-propyl)-1-dimethylthiocarbamoyloxy-benzene: Stir a mixture of 4-(1,1-dimethyl-propyl)-phenol (1.96 g, 11.9 mmol), N,N-dimethylthiocarbamoyl chloride (2.94 g, 23.8 mmol) and DABCO (2.82 g, 25.1 mmol) in anhydrous DMF (30 mL) at room temperature for 16 h under a nitrogen atmosphere. Pour reaction onto ice and extract the mixture with EtOAc (3×75 mL). Combine the organic extracts and wash with 0.5 M aqueous HCl. Dry the organic phase over MgSO$_4$ and concentrate in vacuo. Purify the crude mixture by chromatography on silica gel eluting with hexane/EtOAc (4:1) to obtain the desired intermediate as a yellow solid (2.28 g, 76%). MS (ES+) m/z: 252.3 (M+H)$^+$.

1-Dimethylcarbamoylthio-4-(1,1-dimethyl-propyl)-benzene: Heat 4-(1,1-dimethyl-propyl)-1-dimethylthiocarbamoyloxy-benzene (2.28 g, 9.1 mmol) neat in an oil bath at 230° C. for 6 h. Cool to room temperature and purify by chromatography on silica gel eluting with hexane/EtOAc (4:1) to obtain the desired intermediate as a yellow solid (520 mg, 23%).

4-(1,1-Dimethyl-propyl)-benzenethiol: Reflux a mixture of 1-dimethylcarbamoylthio-4-(1,1-dimethyl-propyl)-benzene (520 mg, 2.1 mmol) and K$_2$CO$_3$ (1.28 g, 9.3 mmol) in methanol (40 mL) for 6 h. Cool to room temperature and concentrate in vacuo. Suspend the residue in water and acidify to pH 1 with 1M aqueous HCl. Extract the aqueous phase with EtOAc (3×40 mL). Dry the combined organic extracts over MgSO$_4$, filter and concentrate in vacuo. Purify the crude mixture by chromatography on silica gel eluting with hexane/EtOAc (1:0 to 97:3) to obtain the title compound (100 mg, 26%).

Preparation 9

2-Mercapto-5-(3-methyl-butyryl)-pyridine

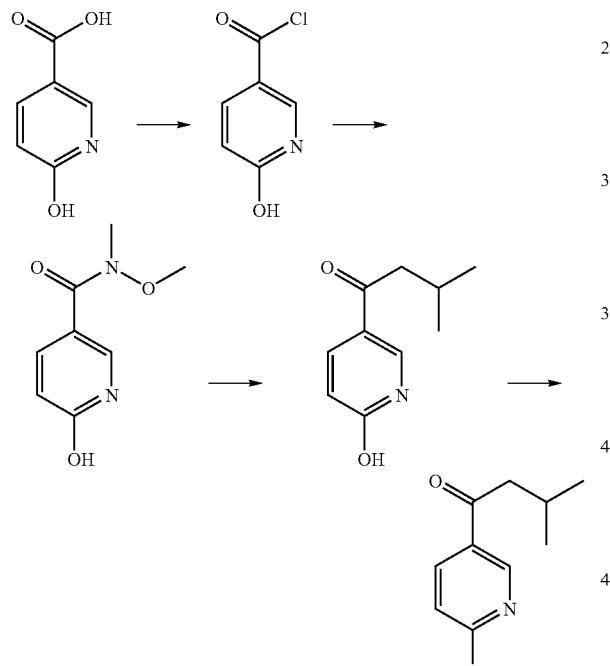

6-Hydroxy-nicotinoyl chloride: Mix 6-hydroxy-nicotinic acid (14 g, 101 mmol) and pyridine (0.41 mL, 0.49 mmol) in acetonitrile (60 mL). Heat the mixture at 80° C. for 30 min. Add thionyl chloride (7.6 mL, 104 mmol) and continue heating at 80° C. for an additional 1.5 h. Cool to room temperature (reaction solidifies). Filter off the solid using a minimal amount of cold acetonitrile. Dry the solid in vacuo to obtain the desired intermediate as a tan solid (11.2 g, 70%).

6-Hydroxy-N-methoxy-N-methyl-nicotinamide: Add 6-hydroxy-nicotinoyl chloride (11.2 g, 71 mmol) and N,O-dimethylhydroxylamine hydrochloride (7.76 g, 79.5 mmol) to ethanol-free chloroform (100 mL, wash chloroform with water, dry over MgSO$_4$, then filter through neutral alumina to obtain ethanol-free chloroform). Cool the mixture to 0° C. under a nitrogen atmosphere. Add pyridine (12.6 mL, 155.8 mmol), warm reaction up to room temperature and stir for 16 h under a nitrogen atmosphere. Wash reaction with water (2×75 mL) followed by brine (75 mL). Dry the organic layer over MgSO$_4$, filter and concentrate in vacuo. Purify the crude mixture by chromatography on silica gel eluting with DCM/2M ammonia in methanol (44:1) to obtain the desired intermediate as a yellow solid (8.6 g, 67%). MS (ES+) m/z: 183.2 (M+H)$^+$.

2-Hydroxy-5-(3-methyl-butyryl)-pyridine: Dissolve 6-hydroxy-N-methoxy-N-methyl-nicotinamide (1.89 g, 10.4 mmol) in anhydrous THF (40 mL), then cool the solution to 0° C. Add isobutyl magnesium chloride (16 mL, 32 mmol, 2M solution in diethyl ether) under nitrogen, allow the mixture to warm gradually to room temperature and then stir for 16 h. Quench the reaction with 1M aqueous HCl and concentrate the mixture in vacuo. Extract the aqueous mixture with EtOAc (4×50 mL). Dry the combined organic extracts over MgSO$_4$, filter and concentrate in vacuo to obtain a yellow solid. Purify by chromatography on silica gel eluting with DCM/2M ammonia in methanol (23:2) to obtain the desired intermediate as a white solid (1.28 g, 69%). MS (ES+) m/z: 180.2 (M+H)$^+$.

2-Mercapto-5-(3-methyl-butyryl)-pyridine: Combine 2-hydroxy-5-(3-methyl-butyryl)-pyridine (742 mg, 4.1 mmol) and phosphorus pentasulfide (1.88 g, 4.2 mmol) in pyridine (5 mL). Heat the mixture at 120° C. for 5 h under a nitrogen atmosphere. Cool the mixture to room temperature and partition between water and EtOAc. Collect the aqueous layer, wash with additional EtOAc and DCM. Acidify the aqueous layer with 1M aqueous HCl and extract with DCM (4×30 mL). Dry the combined organic extracts over MgSO$_4$, filter and concentrate in vacuo to obtain the title compound (120 mg, 15%). MS (ES+) m/z: 196.2 (M+H)$^+$.

Preparation 10

(R)-1-Methyl-2,2,2-trifluoro-ethylamine Hydrochloride

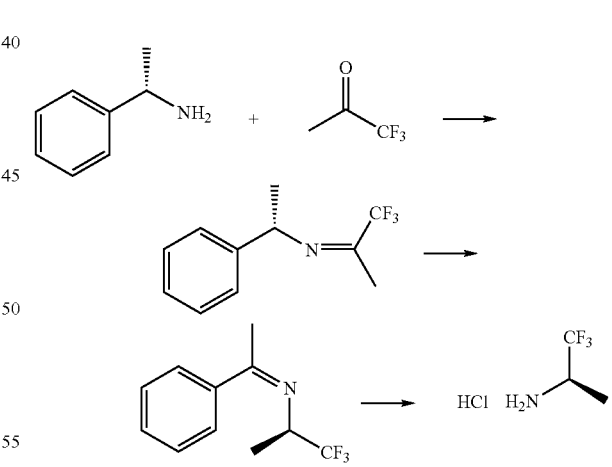

(S)-(1-Phenylethyl)-(2',2',2'-trifluoro-1-methylethylidene)-amine: Use a 22 liter 3-neck round-bottom flask equipped with a dry ice condenser and inlet tube in one side neck, mechanical stirrer in center neck and a Dean-Stark trap with dry ice condenser at top in other side neck. Chill a solution of cold 1,1,1-trifluoroacetone (2100 g, 18.74 mol) and cold toluene (1000 mL) in a wet ice-acetone bath at all times. To a cold mixture of (S)-(−)-α-methylbenzylamine (550 g, 4.54 mol) and p-toluenesulfonic acid monohydrate (8.63 g, 0.0454 mol) in toluene (1000 mL) at 0° C. add a cooled solution of 1,1,1-trifluoroacetone (753 g, 6.72 mol) in cold toluene via teflon tubing under positive pressure of nitrogen (with the Teflon tubing below the surface of the reaction mixture and stopcock to prevent back-up). Remove the dry ice condenser in side neck and replace it with inlet with tubing. However, keep the Dean-Stark trap and dry ice condenser on the other side neck. Heat the reaction mixture slowly to 111° C. Remove water distillate and turn off heat. Slowly add the organic distillate to the reaction mixture at a rate to keep trifluoroacetone distillation under control. Heat the reaction slowly to 111° C. Turn off heat and remove water and organic distillate. Add a cooled solution of 1,1,1-trifluoroacetone (789 g, 7.04 mol) in toluene to the hot reaction mixture at a rate to keep trifluoroacetone distillation under control. Heat the reaction mixture slowly to 111° C. Turn off heat and remove the distillate. Cool the reaction mixture and concentrate in vacuo at 60° C. Add hexane (4 L) in portions to aid in removal of toluene to obtain the desired intermediate as a pale yellow oil of the crude product (1410 g).

(R)-(1'-Phenylethylidene)-(2,2,2-trifluoro-1-methylethyl)-amine: To crude (S)-(1-phenylethyl)-(2',2',2'-trifluoro-1-methylethylidene)-amine (1410 g, 4.54 mol theory) and washings with 20 g of toluene at room temperature, add DBU (1050 g, 6.897 mol) in portions to keep temperature below 60° C. Heat the reaction at 60° C. overnight (14 h) under nitrogen until the starting material rearranges to the desired intermediate (2460 g of solution). MS (ES+) m/z: 216.2 (M+H)⁻.

(R)-1-Methyl-2,2,2-trifluoro-ethylamine Hydrochloride: Dilute the first half (1230 g) of the above reaction mixture with heptane (1500 mL) and DCM (1500 mL). Add 5N aqueous HCl (1250 mL) to the solution mixture and stir for 30 min until only acetophenone is present in the organic phase. Wash the bottom aqueous phase with 1:1 heptane/DCM (2×500 mL) and then cool the aqueous phase in an ice bath. Add ice-cold DCM (1500 mL) and then cold 5N aqueous NaOH (1250 mL) dropwise to the biphasic mixture and stir for 15 min. Separate the bottom organic phase. Extract the aqueous phase with DCM (2×500 mL) and distill the combined organic phase carefully (40-60° C. pot temperature) while cooling the receiving flask in a dry ice/acetone bath. Collect the distillate. Add cold 5N aqueous HCl (500 mL) dropwise and stir for 30 min. Concentrate the mixture in vacuo, using toluene for azeotropic removal of water, to afford the title compound as a white solid. Repeat the procedure with the second half of the previous reaction mixture to obtain the title compound as a white solid (451 g total, 66%). MS (ES+) m/z: 114.1 (M+H)⁺. [α]$_D$=−1.4° (c 0.5, MeOH).

Preparation 11

(R)-6-Mercapto-N-(1-methyl-2,2,2-trifluoro-ethyl)-nicotinamide

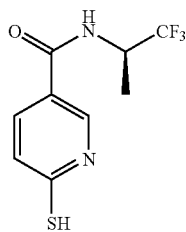

Combine 6-mercapto-nicotinic acid (655 mg, 4.2 mmol), (R)-1-methyl-2,2,2-trifluoro-ethylamine hydrochloride (634 mg, 4.2 mmol) and EEDQ (1.06 g, 4.3 mmol) in anhydrous DMF (3 mL). Add triethylamine (0.6 mL, 4.3 mmol) and stir at room temperature for 16 h. Dilute the reaction mixture with water and extract with EtOAc (4×40 mL). Wash the combined organic extracts with brine, dry over MgSO₄, filter and concentrate in vacuo. Purify the crude mixture by chromatography on silica gel eluting with hexane/EtOAc (3:2) to obtain the title compound as a yellow solid (180 mg, 18%). MS (ES+) m/z: 251.2 (M+H)⁺.

Preparation 12

4-Isobutyl-1H-imidazole-2-thiol

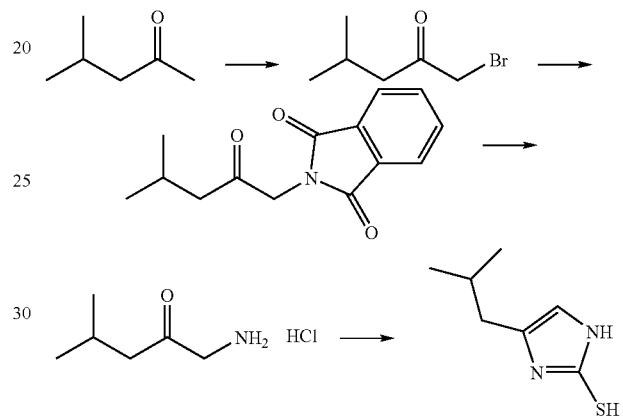

1-Bromo-4-methyl-2-pentanone: Dissolve 4-methyl-2-pentanone (8 g, 80.3 mmol) in methanol (60 mL). Cool the solution to 0° C. under a nitrogen atmosphere and add bromine (4.8 mL, 80.3 mmol) via addition funnel over 2 min. Stir the resulting red solution at 10-15° C. until a clear solution remains (approximately 15 min). Add water (30 mL) and stir the reaction overnight at room temperature. Extract the mixture with diethyl ether (4×70 mL). Wash the combined organic extracts with 10% aqueous K₂CO₃ (2×100 mL, off-gassing during base wash). Dry the organic layer over Na₂SO₄ and concentrate in vacuo to obtain the desired intermediate as an oil (11 g, 76%). MS (APCI+) m/z: 180 (M)⁺.

2-(4-Methyl-2-oxo-pentyl)-isoindole-1,3-dione: Dissolve 1-bromo-4-methyl-2-pentanone (11.0 g, 61.4 mmol) and potassium phthalimide (11.9 g, 64.5 mmol) in toluene (60 mL) at room temperature under a nitrogen atmosphere. Heat the mixture to 100° C. and stir for 16 h. Cool the resulting slurry to room temperature, filter off solids, and concentrate the filtrate in vacuo to a solid. Purify the residue by chromatography on silica gel (40 g) eluting with hexane/EtOAc (1:1) to obtain the desired intermediate (3.6 g, 24%). MS (ES+) m/z: 246.3 (M+H)⁺.

1-Amino-4-methyl-2-pentanone Hydrochloride: Slurry 2-(4-methyl-2-oxo-pentyl)-isoindole-1,3-dione (2.8 g, 11.4 mmol) in concentrated HCl (18 mL), glacial acetic acid (16 mL) and water (13 mL). Stir the mixture at reflux for 16 h. Cool to room temperature and pour the solution onto ice (25 mL). Filter off the solids, wash the filtrate with cold water (20 mL) and concentrate in vacuo to a solid. Recrystallize the solid in ethanol (15 mL) and diethyl ether (50 mL). Decant off the solvent and dry the white paste under reduced pressure to obtain the desired intermediate as a white solid (1.4 g, 81%).

4-Isobutyl-1H-imidazole-2-thiol: Dissolve 1-amino-4-methyl-2-pentanone hydrochloride (1.4 g, 9.2 mmol) and potassium thiocyanate (1.3 g, 12.9 mmol) in water (3 mL). Stir the solution at 100° C. in a sealed flask for 2 h. Cool the mixture and concentrate in vacuo. Purify the residue by chromatography on silica gel (10 g) eluting with EtOAc to obtain a yellow solid (980 mg, estimated 1:1 product to starting material by NMR). Dissolve the yellow solid (980 mg) in water (2 mL) and concentrated hydrochloric acid (0.5 mL). Add potassium thiocyanate (0.7 g, 7.2 mmol) and heat the mixture at 100° C. for 16 h. Cool the mixture and concentrate in vacuo. Purify the residue by chromatography on silica gel (25 g) eluting with hexane/EtOAc (1:1) to obtain the title compound as a yellow solid (550 mg, 38%). MS (ES+) m/z: 157.2 (M+H)+.

Preparation 13

The compound of Preparation 13 may be prepared essentially as described in Preparation 12 using 1-bromo-2-butanone. Overall yield and MS (ES+) data are shown in the Table below.

| Prep. | Structure | Compound | Yield (%) | MS (ES+) m/z |
|---|---|---|---|---|
| 13 | 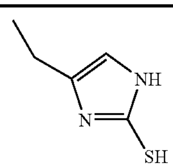 | 4-Ethyl-1H-imidazole-2-thiol | 63 | 129 (M + H)+ |

Preparation 14

4,5,6,7-Tetrahydro-1H-benzoimidazole-2-thiol

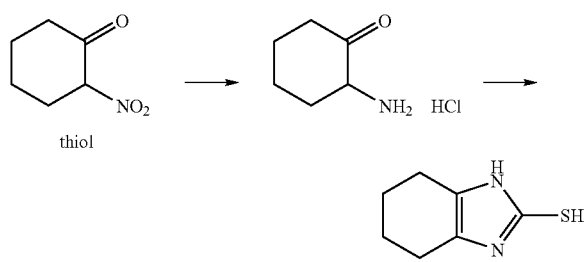

thiol

2-Amino-cyclohexanone Hydrochloride: Add 2-nitrocyclohexanone (7.0 g, 48.9 mmol), 5% platinum sulfided on carbon (500 mg), ethanol (120 mL) and concentrated hydrochloric acid (6 mL) to a pressure vessel under a nitrogen atmosphere. Pressurize the vessel to 50 psi with hydrogen and stir the mixture for 3 h. Filter the mixture through Celite® and wash with ethanol followed by DCM under a nitrogen atmosphere. Concentrate the filtrate in vacuo. Slurry the residue in acetone (50 mL) and filter. Collect the solid to obtain the desired intermediate (2.2 g, 40%).

4,5,6,7-Tetrahydro-1H-benzoimidazole-2-thiol: Dissolve 2-amino-cyclohexanone hydrochloride (2.2 g, 14.7 mmol) and potassium thiocyanate (1.4 g, 14.7 mmol) in water (10 mL). Stir the solution at 100° C. in a sealed flask for 16 h. Cool the mixture and store the mixture at 4° C. for 16 h. Filter off the resulting solid and wash with water (20 mL). Collect the solid, slurry in diethyl ether (20 mL) and filter. Dry the solid in a vacuum oven at 50° C. for 2 h to obtain the title compound as a tan solid (1.4 g, 62%). MS (ES+) m/z: 155.1 (M+H)+.

Preparation 15

5-Ethyl-1H-1,3,4-triazole-2-thione

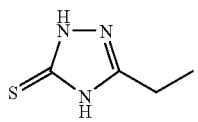

Add dropwise over 10 min a solution of propionyl chloride (0.56 mL, 6.4 mmol) in benzene (10 mL) to a solution of thiosemicarbazide (580 mg, 6.4 mmol) in anhydrous pyridine (20 mL, 128 mmol) at 0° C. Warm to room temperature and stir overnight. Concentrate the mixture in vacuo, dissolve the residue in anhydrous methanol (15 mL) and add solid sodium methoxide (700 mg, 12.8 mmol). Heat the resulting mixture to reflux for 16 h. Concentrate in vacuo and dissolve the resulting residue in water (ca. 150 mL). Acidify to pH 1-2 with 5N aqueous HCl and extract with EtOAc (3×50 mL). Wash the combined organic extracts with water (100 mL) and brine (100 mL). Dry the organic phase over Na2SO4 and concentrate in vacuo. Triturate the residue with DCM (ca. 15 mL). Filter and collect the desired intermediate as a tan solid (550 mg, 67%). MS (ES+) m/z: 130 (M+H)+.

Preparation 16

The compound of Preparation 16 may be prepared essentially as described in Preparation 15 using isovaleryl chloride. Yield is shown in the Table below.

| Prep. | Structure | Compound | Yield (%) |
|---|---|---|---|
| 16 | 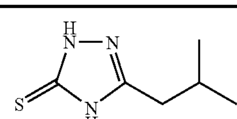 | 5-iso-Butyl-1H-1,3,4-triazole-2-thione | 60 |

Preparation 17

3-tert-Butoxycarbonyl-7-chloro-6-mercaptomethyl-2,3,4,5-tetrahydro-1H-benzo[d]azepine

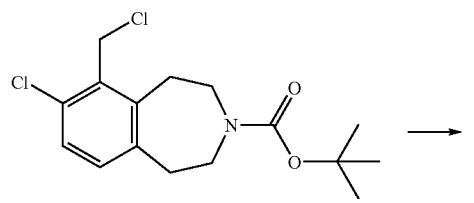

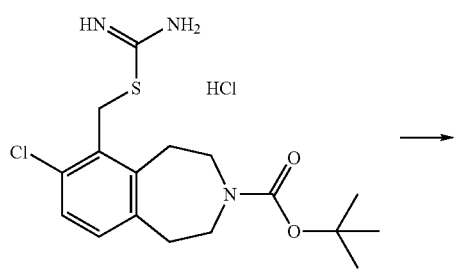

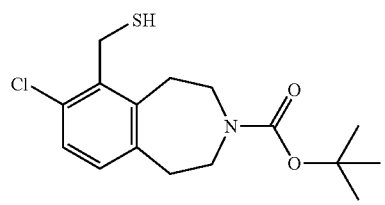

3-tert-Butoxycarbonyl-6-carbamimidoylthiomethyl-7-chloro-2,3,4,5-tetrahydro-1H-benzo[d]azepine hydrochloride: To a solution of 3-tert-butoxycarbonyl-7-chloro-6-chloromethyl-2,3,4,5-tetrahydro-1H-benzo[d]azepine (0.742 g, 2.247 mmol) in anhydrous dioxane (9.4 mL) add thiourea (0.17 g, 2.2 mmol) at room temperature. Heat the mixture at 95° C. overnight. Cool the mixture to room temperature and add anhydrous ether (25 mL). Stir the mixture for 1 h and filter the slurry. Wash the solid with ether (25 mL) and dry to afford the desired intermediate as a white solid (0.780 g, 85%). MS (ES+) m/z: 370.2 (M+H)$^+$.

3-tert-Butoxycarbonyl-7-chloro-6-mercaptomethyl-2,3,4,5-tetrahydro-1H-benzo[d]azepine: To a slurry of 3-tert-butoxycarbonyl-6-carbamimidoylthiomethyl-7-chloro-2,3,4,5-tetrahydro-1H-benzo[d]azepine hydrochloride (1.582 g, 3.895 mmol) in anhydrous dioxane (16.3 mL) add at room temperature a solution of NaOH (0.17 g, 4.3 mmol) in water (0.48 mL). Heat the reaction mixture at 100° C. overnight. After cooling the reaction mixture to 12-15° C., add 1M aqueous KHSO$_4$ (3.9 mL, 3.9 mol). Partition the mixture between water (25 mL) and hexane (50 mL). Dry the organic phase over Na$_2$SO$_4$, filter and concentrate in vacuo. Dissolve the residue in DCM, load the solution on to an Analogix® column (150 g) and purify the crude mixture by preparative liquid chromatography (0:100 to 20:80 EtOAc/hexane over 33 min; 20:80 EtOAc/hexane over 33 min; 35 mL/min) to afford the title compound (1.042 g, 82%) as a colorless oil. MS (ES+) m/z: 328.1 (M+H)$^+$.

Preparation 18

6-Bromomethyl-3-tert-butoxycarbonyl-7-chloro-2,3,4,5-tetrahydro-1H-benzo[d]azepine

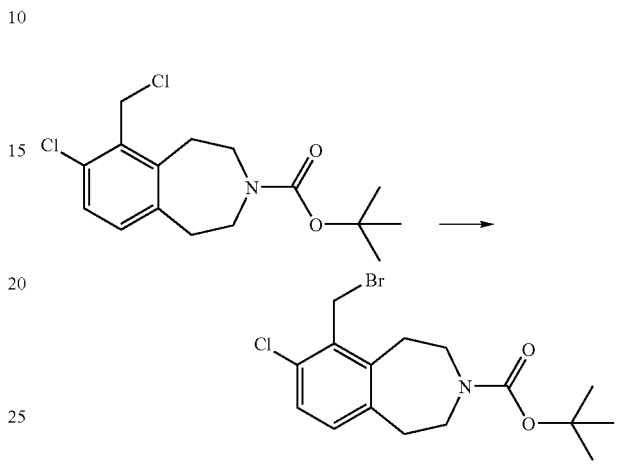

Combine 3-tert-butoxycarbonyl-7-chloro-6-chloromethyl-2,3,4,5-tetrahydro-1H-benzo[d]azepine (3.17 g, 8.14 mmol) and lithium bromide (0.98 g, 11.3 mmol) in anhydrous THF (60 mL) and stir at room temperature for 1 h. Concentrate in vacuo and partition the residue between dichloromethane/water. Dry the organic phase over Na$_2$SO$_4$, filter and concentrate in vacuo. Purify the crude mixture by chromatography on silica gel eluting with hexane/EtOAc (1:0 and 10:1) to obtain the title compound as a white solid (2.6 g, 85%). MS (APCI+) m/z: 274 (M-Boc+H)$^+$.

Preparation 19

N-(5-bromothiazol-2-yl)-cyclopropylmethylamine

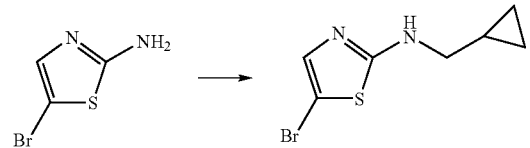

Add acetic acid (2 mL, 33.4 mmol) to a mixture of 5-bromo-thiazol-2-ylamine (1 g, 5.6 mmol), sodium triacetoxyborohydride (3.5 g, 16.7 mmol) and cyclopropane carboxaldehyde (820 mg, 11.7 mmol) at room temperature under a nitrogen atmosphere. Stir the resulting solution for 1.5 h at ambient temperature. Dilute the solution with DCM (50 mL) and wash with saturated aqueous NaHCO$_3$ (80 mL). Dry the organic layer over Na$_2$SO$_4$, filter and concentrate in vacuo. Purify the residue by chromatography on silica gel (40 g) eluting with hexane/EtOAc (9:1 to 7:3 gradient) to obtain the title compound (970 mg, 75%). MS (ES+) m/z: 233.1 (M$^+$).

Preparation 20

4-Acetylsulfanyl-1-tert-butoxycarbonyl-2-methyl-imidazole

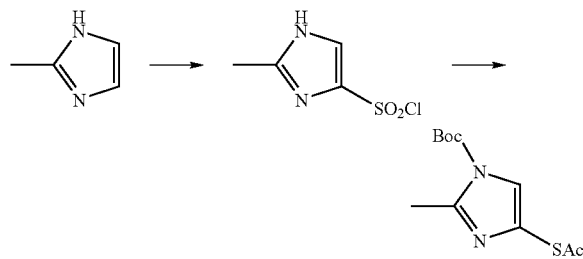

2-Methyl-1H-imidazole-4-sulfonyl chloride: Carefully add chlorosulfonic acid (30 mL) to neat 2-methylimidazole (5 g, 60.9 mmol). Heat the mixture at 150° C. for 3 h and cool to room temperature. Add thionyl chloride (10 mL), heat at 100° C. for 3 h and cool to room temperature. Carefully pour the mixture into ice. Slowly add solid sodium carbonate to neutralize the solution. Filter the precipitate formed and wash with water. Dry the solid under high vacuum overnight at 45° C. to give the desired intermediate (4.38 g, 40%). MS (ES+) m/z: 181 (M+H)$^+$.

4-Acetylsulfanyl-1-tert-butoxycarbonyl-2-methyl-imidazole: Dissolve 2-methyl-1H-imidazole-4-sulfonyl chloride (430 mg, 2.38 mmol) in acetic acid (13 mL). Add a solution of tin(II) chloride dihydrate (2.80 g, 12.4 mmol) in concentrated hydrochloric acid (2.2 mL) and heat at 75° C. for 45 min. Cool the mixture to room temperature and concentrate in vacuo. Dissolve the yellow precipitate in DCM (15 mL), basify with triethylamine and add di-tert-butyl dicarbonate (1.04 g, 4.76 mmol). Stir the mixture at room temperature for 72 h. Partition the mixture between water and DCM and filter the mixture through Celite®. Separate and dry the organic phase over MgSO$_4$, filter, and concentrate the filtrate in vacuo. Purify the crude mixture by chromatography on silica gel (40 g) eluting with DCM/(chloroform:methanol:concentrated NH$_4$OH) [100:0 (5 min), 19:1 (5 min), 9:1 (5 min), 4:1 (5 min), 3:1; flow rate: 50 mL/min)]. Purify the material by additional chromatography on silica gel (40 g) eluting with DCM/(chloroform:methanol:concentrated NH$_4$OH) [100:0 (5 min), 19:1 (5 min), 9:1 (5 min), 4:1; flow rate: 50 mL/min] to give the title compound (205 mg, 34%). MS (ES+) m/z: 257 (M+H)$^+$.

Preparation 21

N-[4-(4-Bromo-phenyl)-thiazol-2-yl]-cyclopropylmethylamine

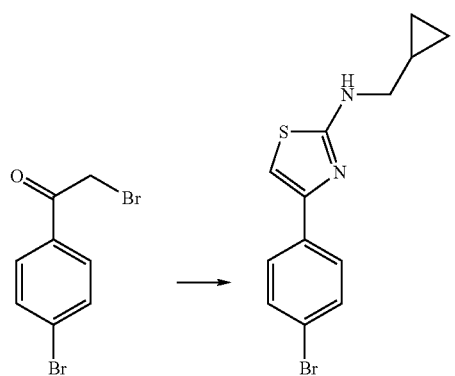

Slurry 4-bromophenacyl bromide (11.2 g, 50 mmol) in absolute ethanol (50 mL). Add N-cyclopropylmethyl-thiourea (6.5 g, 50 mmol) and sodium bicarbonate (4.2 g, 50 mmol), heat to reflux for 2 h, then stir at room temperature overnight. Concentrate to ¼ volume and partition between water/EtOAc (4:1, 500 mL). Extract the aqueous layer with EtOAc (2×75 mL). Dry the combined organic extracts over Na$_2$SO$_4$, filter and concentrate in vacuo to obtain the title compound (14.0 g, 91%) as an off-white solid that was used without further purification. MS (ES+) m/z: 310 (M+H)$^+$.

Preparation 22

N-[4-(6-Bromo-pyridin-3-yl)-thiazol-2-yl]-cyclopropylmethylamine

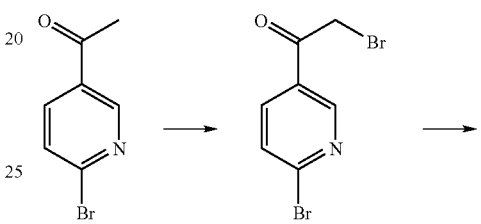

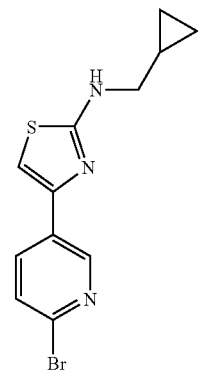

2-Bromo-1-(6-bromo-pyridin-3-yl)-ethanone: Add pyridinium tribromide (7 g, 22 mmol) to a solution of 5-acetyl-2-bromo-pyridine (4 g, 20 mmol) in THF (100 mL) at room temperature. Stir the mixture for 16 h at ambient temperature under a nitrogen atmosphere. Quench the mixture with saturated aqueous NaHCO$_3$ (50 mL, pH at 7.8). Extract the mixture with EtOAc (150 mL). Wash the organic layer with brine (50 mL) and concentrate in vacuo to obtain the desired intermediate as a dark brown oil (11.5 g) that was used without further purification. MS (ES+) m/z: 280.0 (M+H)$^+$.

N-[4-(6-Bromo-pyridin-3-yl)-thiazol-2-yl]-cyclopropylmethylamine: Slurry crude 2-bromo-1-(6-bromo-pyridin-3-yl)-ethanone (11.5 g, ca. 48%), N-cyclopropylmethyl thiourea (2.2 g, 16.9 mmol) and sodium bicarbonate (1.7 g, 20 mmol) in ethanol (100 mL) at room temperature. Stir the mixture at reflux for 1 h under a nitrogen atmosphere. Turn off heat and stir the mixture for an additional 16 h at room temperature. Filter the slurry, then wash the solids with ethanol (50 mL), water (2×50 mL) and hexane (excess). Dry the solid in a vacuum oven for 20 h at 50° C. to obtain the title compound as a tan solid (3.2 g, 61% yield over 2 steps). MS (ES+) m/z: 312 (M+2)$^+$.

Example 1

7-Chloro-6-(pyridin-2-ylaminomethyl)-2,3,4,5-tetrahydro-1H-benzo[d]azepine Succinate

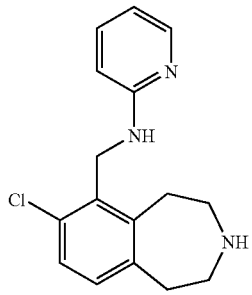 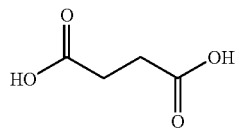

Add tris(dibenzylideneacetone)dipalladium(0) (52 mg, 0.06 mmol), DPPP (47 mg, 0.11 mmol), sodium tert-butoxide (26 mg, 0.27 mmol) and 2-bromopyridine (23 µl, 0.23 mmol) to a solution of 6-aminomethyl-3-tert-butoxycarbonyl-7-chloro-2,3,4,5-tetrahydro-1H-benzo[d]azepine (60 mg, 0.19 mmol) in anhydrous toluene (3 mL). Degas the slurry under house vacuum, then flush with nitrogen. Stir the mixture at 95° C. for 20 h. Cool the mixture to room temperature, dilute with diethyl ether (20 mL) and filter through Celite®. Concentrate the filtrate in vacuo to obtain crude 3-tert-butoxycarbonyl-7-chloro-6-(pyridin-2-ylaminomethyl)-2,3,4,5-tetrahydro-1H-benzo[d]azepine (150 mg). Continue processing with the crude mixture. MS (ES+) m/z: 388.2 (M+H)$^+$.

Use a method similar to the General Procedure 1 to deprotect 3-tert-butoxycarbonyl-7-chloro-6-(pyridin-2-ylaminomethyl)-2,3,4,5-tetrahydro-1H-benzo[d]azepine. Purify by chromatography on silica gel eluting with DCM/2M ammonia in methanol (99:1 to 93:7 gradient) to give 7-chloro-6-(pyridin-2-ylaminomethyl)-2,3,4,5-tetrahydro-1H-benzo[d]azepine. Use a method similar to the General Procedure 2-1 to obtain the title compound (30 mg, 39% overall yield). MS (ES+) m/z: 288.2 (M+H)$^+$.

Example 2

Example 2 may be prepared essentially as described in Example 1 by using 6-aminomethyl-3-tert-butoxycarbonyl-7-chloro-2,3,4,5-tetrahydro-1H-benzo[d]azepine and bromobenzene. The overall yield and MS (ES+) data are shown in the Table below.

Example 3

7-Chloro-6-[(4-cycloheptylcarbamoyl-phenylamino)-methyl]-2,3,4,5-tetrahydro-1H-benzo[d]azepine Succinate

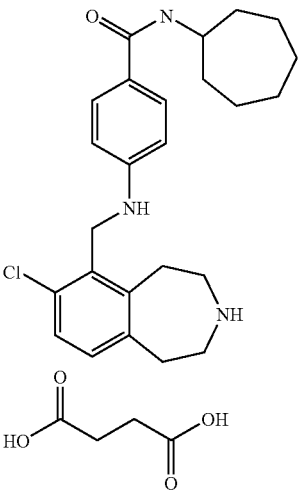

Under a nitrogen atmosphere, add 6-aminomethyl-3-tert-butoxycarbonyl-7-chloro-2,3,4,5-tetrahydro-1H-benzo[d]azepine (500 mg, 1.6 mmol), 4-bromo-N-cycloheptyl-benzamide (520 mg, 1.8 mmol), palladium(II) acetate (35 mg, 0.16 mmol), BINAP (150 mg, 0.24 mmol) and sodium-t-butoxide (460 mg, 4.8 mmol) to toluene (10 mL). Heat the mixture at 70° C. for 1 h. Cool the mixture to room temperature and dilute with water and DCM. Separate the layers and extract the aqueous phase with DCM. Wash the combined organic extracts with water and brine. Dry the organic layer over Na$_2$SO$_4$, filter and concentrate in vacuo. Purify the residue by chromatography on silica gel eluting with hexane/EtOAc (1:0 to 17:1 gradient) to obtain 3-tert-butoxycarbonyl-7-chloro-6-[(4-cycloheptylcarbamoyl-phenylamino)-methyl]-2,3,4,5-tetrahydro-1H-benzo[d]azepine (460 mg, 54%). MS (APCI+) m/z: 526 (M+H)$^+$.

Add hydrogen chloride into a mixture of 3-tert-butoxycarbonyl-7-chloro-6-[(4-cycloheptylcarbamoyl-phenylamino)-methyl]-2,3,4,5-tetrahydro-1H-benzo[d]azepine (590 mg, 1.12 mmol) in EtOAc/methanol (1:1, 60 mL) until the mixture is saturated. Stir for 1 h at 40° C. and concentrate in

| Ex. | Structure | Compound | Yield (%) | MS (ES+) m/z |
|---|---|---|---|---|
| 2 | 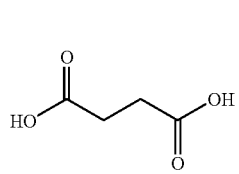 | 7-Chloro-6-phenylaminomethyl-2,3,4,5-tetrahydro-1H-benzo[d]azepine Succinate | 23 | 287.2 (M + H)$^+$ | vacuo. Purify the residue by SCX chromatography to obtain 7-chloro-6-[(4-cycloheptylcarbamoyl-phenylamino)-methyl]-2,3,4,5-tetrahydro-1H-benzo[d]azepine (450 mg, 1.06 mmol). Use a method similar to the General Procedure 2-1 to obtain the title compound as an off-white solid (560 mg, 92%). MS (ES+) m/z: 426 (M+H)+.

Example 4

7-Chloro-6-phenylthiomethyl-2,3,4,5-tetrahydro-1H-benzo[d]azepine Succinate

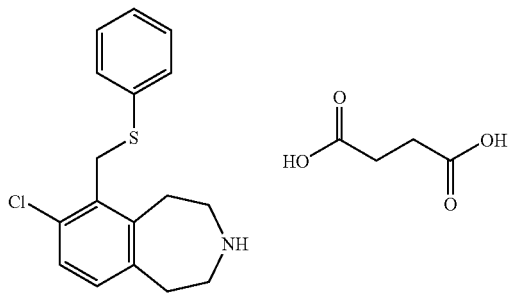

Add sodium hydride (25 mg, 0.62 mmol, 60% dispersion in mineral oil) to benzenethiol (0.06 mL, 0.51 mmol) in anhydrous DMF (2 mL). Stir the mixture under nitrogen for 5 min and then add 3-tert-butoxycarbonyl-7-chloro-6-chloromethyl-2,3,4,5-tetrahydro-1H-benzo[d]azepine (198 mg, 0.51 mmol) in anhydrous DMF (2 mL) followed by catalytic potassium iodide (1 mg). Stir the reaction at 45° C. for 12 h then cool to room temperature and partition between EtOAc/water. Wash the organic phase with brine. Dry the organic phase over MgSO4, filter and concentrate in vacuo to give a yellow oil. Purify the crude mixture by chromatography on silica gel eluting with hexane/EtOAc (9:1) to give 3-tert-butoxycarbonyl-7-chloro-6-phenylthiomethyl-2,3,4,5-tetrahydro-1H-benzo[d]azepine as a yellow oil (200 mg, 98%).

Use a method similar to the General Procedure 1 to deprotect 3-tert-butoxycarbonyl-7-chloro-6-phenylthiomethyl-2,3,4,5-tetrahydro-1H-benzo[d]azepine. Purify by chromatography on silica gel eluting with DCM/2M ammonia in methanol to give 7-chloro-6-phenylthiomethyl-2,3,4,5-tetrahydro-1H-benzo[d]azepine. Use a method similar to the General Procedure 2-1 to give the title compound as a white solid (130 mg, 79%). HRMS (ES+) m/z: 304.0946 (M+H)+.

Examples 5-9

Examples 5-9 may be prepared essentially as described in Example 4 by using 3-tert-butoxycarbonyl-7-chloro-6-chloromethyl-2,3,4,5-tetrahydro-1H-benzo[d]azepine and the appropriate thiol. Example 8 may be prepared essentially as described in Example 4 by using 3-tert-butoxycarbonyl-7-chloro-3-tert-butoxycarbonyl-7-chloro-6-chloromethyl-2,3,4,5-tetrahydro-1H-benzo[d]azepine and 2H-pyridazine-3-thione. Example 9 may be prepared essentially as described in Example 4 by using 3-tert-butoxycarbonyl-7-chloro-3-tert-butoxycarbonyl-7-chloro-6-chloromethyl-2,3,4,5-tetrahydro-1H-benzo[d]azepine and 4-fluorophenol. Overall yields and MS (ES+) data are shown in the Table below.

| Ex. | Structure | Compound | Yield (%) | HRMS (ES+) m/z |
|---|---|---|---|---|
| 5 | 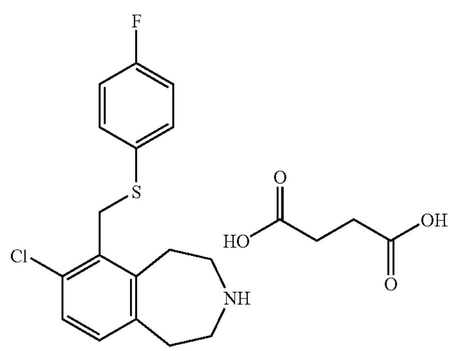 | 7-Chloro-6-(4-fluorophenylthiomethyl)-2,3,4,5-tetrahydro-1H-benzo[d]azepine Succinate | 83 | 322.0831 (M + H)+ |
| 6 | 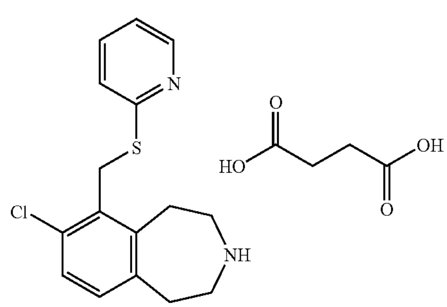 | 7-Chloro-6-(pyridin-2-ylthiomethyl)-2,3,4,5-tetrahydro-1H-benzo[d]azepine Succinate | 36 | 305.0900 (M + H)+ |

-continued
| Ex. | Structure | Compound | Yield (%) | HRMS (ES+) m/z |
|---|---|---|---|---|
| 7 | 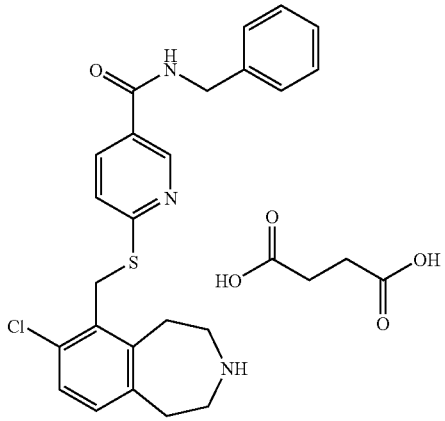 | 7-Chloro-6-[5-(N-benzylcarbamoyl)-pyridin-2-ylthiomethyl]-2,3,4,5-tetrahydro-1H-benzo[d]azepine Succinate | 64 | 438.1407 (M + H)+ |
| 8 | 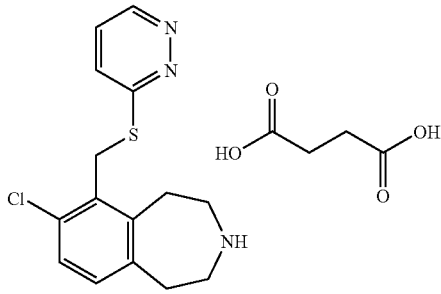 | 7-Chloro-6-(pyridazin-3-ylthiomethyl)-2,3,4,5-tetrahydro-1H-benzo[d]azepine Succinate | 78 | 306.0842 (M + H)+ |
| 9 | 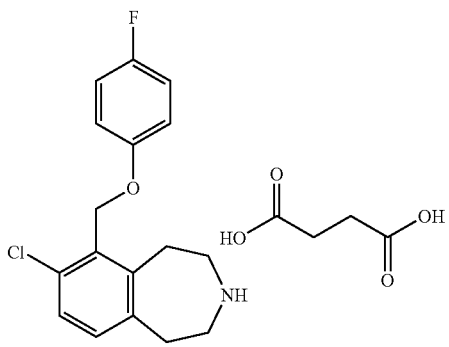 | 7-Chloro-6-(4-fluoro-phenoxymethyl)-2,3,4,5-tetrahydro-1H-benzo[d]azepine Succinate | 67 | 306.1078 (M + H)+ |

Example 10

(−)-7-Chloro-6-(1-phenylthio-ethyl)-2,3,4,5-tetrahydro-1H-benzo[d]azepine Hydrochloride

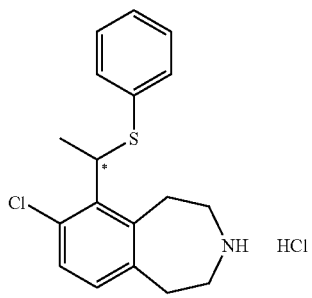

Dissolve 3-tert-butoxycarbonyl-7-chloro-6-(1-hydroxyethyl)-2,3,4,5-tetrahydro-1H-benzo[d]azepine (969 mg, 3.0 mmol) in anhydrous DCM (50 mL). Add triethylamine (1.25 mL, 9.0 mmol) and cool the reaction mixture to 0° C. Add methanesulfonyl chloride (0.46 mL, 6.0 mmol) dropwise to the reaction mixture, warm to room temperature and stir for 3 h. Wash the reaction mixture with saturated aqueous NaHCO$_3$ (15 mL) and brine (15 mL). Dry the organic phase over anhydrous Na$_2$SO$_4$, filter and concentrate in vacuo to obtain the intermediate as a yellow oil (1.2 g) that was used without further purification.

Suspend sodium hydride (131 mg, 3.3 mmol, 60% dispersion in mineral oil) in anhydrous DMF (3 mL) and add thiophenol (0.3 mL, 3.0 mmol) at room temperature. After 5 min add the intermediate (1.2 g, described above) and catalytic potassium iodide (1 mg) in anhydrous DMF (3 mL) and stir at 45° C. for 16 h. Cool the reaction mixture and dilute with EtOAc (20 mL). Wash the mixture with brine (2×5 mL). Collect the organic layer, dry over anhydrous Na$_2$SO$_4$, filter and concentrate in vacuo onto silica gel. Purify the mixture by chromatography on silica gel eluting with hexane/EtOAc (1:0 to 6:4 gradient) to obtain (±)-3-tert-butoxycarbonyl-7-chloro-6-(1-phenylthio-ethyl)-2,3,4,5-tetrahydro-1H-benzo[d]azepine (1.0 g, 80%).

Separate (±)-3-tert-butoxycarbonyl-7-chloro-6-(1-phenylthio-ethyl)-2,3,4,5-tetrahydro-1H-benzo[d]azepin by normal phase chiral chromatography [Chiralcel OJ-H, eluting with acetonitrile/methanol (4:1)].

Use a method similar to the General Procedure 1 to deprotect the first eluting isomer of 3-tert-butoxycarbonyl-7-chloro-6-(1-phenylthio-ethyl)-2,3,4,5-tetrahydro-1H-benzo[d]azepine. Purify by SCX chromatography to obtain (−)-7-chloro-6-(1-phenylthio-ethyl)-2,3,4,5-tetrahydro-1H-benzo[d]azepine. Use a method similar to the General Procedure 2-3 to obtain the title compound (365 mg). MS (ES+) m/z: 318 (M+H)$^+$. $[\alpha]_D$ −212.1° (c 0.5, MeOH).

Example 11

7-Chloro-6-[4-(1,1-dimethyl-propyl)-phenylthiomethyl]-2,3,4,5-tetrahydro-1H-benzo[d]azepine Succinate

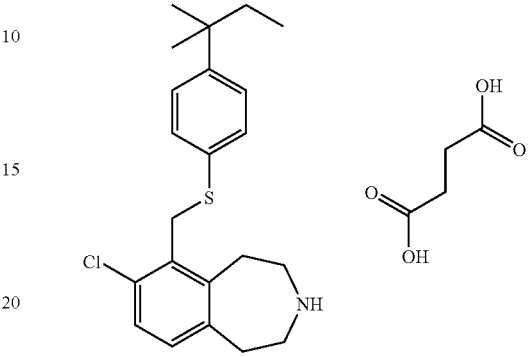

Dissolve 4-(1,1-dimethyl-propyl)-benzenethiol (100 mg, 0.55 mmol) in anhydrous DMF (2 mL). Add sodium hydride (32 mg, 0.78 mmol, 60% dispersion in mineral oil) at room temperature under a nitrogen atmosphere. Stir the mixture for 5 min, then add a solution of 3-tert-butoxycarbonyl-7-chloro-6-chloromethyl-2,3,4,5-tetrahydro-1H-benzo[d]azepine (214 mg, 0.55 mmol) in anhydrous DMF (2 mL). Heat the mixture to 45° C., add catalytic sodium iodide and stir the mixture at 45° C. for 6 h. Cool the reaction mixture to room temperature and quench with water. Extract the mixture with EtOAc (4×25 mL). Wash the combined organic extracts with brine. Dry the organic layer over MgSO$_4$, filter and concentrate in vacuo. Purify the crude mixture by chromatography on silica gel eluting with hexane/EtOAc (20:1 to 17:3 gradient) to obtain 3-tert-butoxycarbonyl-7-chloro-6-[4-(1,1-dimethyl-propyl)-phenylthiomethyl]-2,3,4,5-tetrahydro-1H-benzo[d]azepine (105 mg, 40%).

Use a method similar to the General Procedure 1 to deprotect 3-tert-butoxycarbonyl-7-chloro-6-[4-(1,1-dimethyl-propyl)-phenylthiomethyl]-2,3,4,5-tetrahydro-1H-benzo[d]azepine (105 mg, 0.22 mmol). Purify by chromatography on silica gel eluting with DCM/2M ammonia in methanol (1:0 to 20:1 gradient) to give 7-chloro-6-[4-(1,1-dimethyl-propyl)-phenylthiomethyl]-2,3,4,5-tetrahydro-1H-benzo[d]azepine. Use a method similar to the General Procedure 2-1 to obtain the title compound (103 mg, 95%). MS (ES+) m/z: 374.3 (M+H)$^+$.

Examples 12-14

Examples 12-14 may be prepared essentially as described in Example 11 by using 3-tert-butoxycarbonyl-7-chloro-6-chloromethyl-2,3,4,5-tetrahydro-1H-benzo[d]azepine and the appropriate thiol. Overall yields, MS (ES+) data and optical rotation (where applicable) are shown in the Table below.

| Ex. | Structure | Compound | Yield (%) | MS (ES+) m/z [α]$_D$ (c, solvent) |
|---|---|---|---|---|
| 12 | 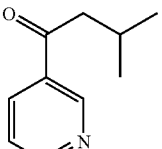 | 7-Chloro-6-[5-(3-methyl-butyryl)-pyridin-2-ylthiomethyl]-2,3,4,5-tetrahydro-1H-benzo[d]azepine Succinate | 10 | 389.2 (M + H)$^+$ |
| 13 | 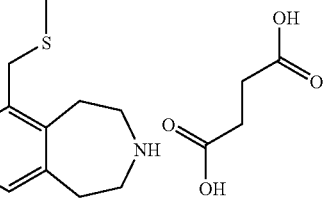 | 7-Chloro-6-(pyrimidin-2-ylthiomethyl)-2,3,4,5-tetrahydro-1H-benzo[d]azepine Succinate | 93 | 306.2 (M + H)$^+$ |
| 14 | 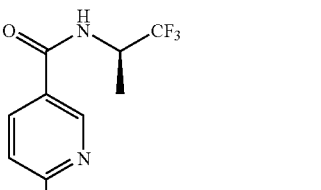 | (R)-7-Chloro-6-[5-(1-methyl-2,2,2-trifluoro-ethylcarbamoyl)-pyridin-2-ylthiomethyl]-2,3,4,5-tetrahydro-1H-benzo[d]azepine Succinate | 94 | 444.1 (M + H)$^+$ +2.0° (c 0.5, MeOH) |

Example 15

7-Chloro-6-phenoxymethyl-2,3,4,5-tetrahydro-1H-benzo[d]azepine Hydrochloride

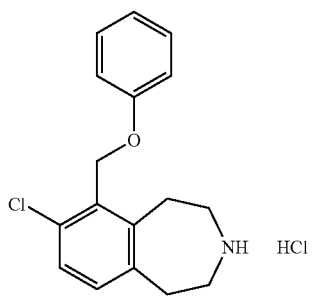

Add sodium hydride (22 mg, 0.54 mmol, 60% dispersion in mineral oil) to phenol (42 mg, 0.04 mL, 0.45 mmol) in anhydrous DMF (2 mL). Stir the mixture under nitrogen for 5 min and then add 3-tert-butoxycarbonyl-7-chloro-6-chloromethyl-2,3,4,5-tetrahydro-1H-benzo[d]azepine (175 mg, 0.45 mmol) in anhydrous DMF (2 mL) followed by catalytic potassium iodide (1 mg). Stir the reaction at 45° C. for 12 h then cool to room temperature and partition between EtOAc/water. Wash the organic phase with brine. Dry the organic phase over MgSO$_4$, filter and concentrate in vacuo to give a yellow oil. Purify the crude mixture by chromatography on silica gel eluting with hexane/EtOAc (9:1) to give 3-tert-butoxycarbonyl-7-chloro-6-phenoxymethyl-2,3,4,5-tetrahydro-1H-benzo[d]azepine as a colorless oil (59 mg, 36%).

Use a method similar to the General Procedure 1 to deprotect 3-tert-butoxycarbonyl-7-chloro-6-phenoxymethyl-2,3,4,5-tetrahydro-1H-benzo[d]azepine. Purify by chromatography on silica gel eluting with DCM/2M ammonia in methanol to give 7-chloro-6-phenoxymethyl-2,3,4,5-tetrahydro-1H-benzo[d]azepine. Use a method similar to the General Procedure 2-2 to give the title compound as a colorless oil (27 mg, 60%). HRMS (ES+) m/z: 288.1160 (M+H)$^+$.

Example 16

7-Chloro-6-(thiophen-2-ylthiomethyl)-2,3,4,5-tetrahydro-1H-benzo[d]azepine Hydrochloride

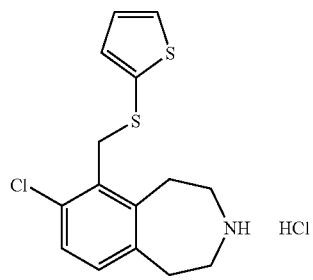

Suspend sodium hydride (20 mg, 60% dispersion in mineral oil) in anhydrous DMF (2 mL) and add thiophene-2-thiol (35 mg, 0.38 mmol) at room temperature. After 5 min add 3-tert-butoxycarbonyl-7-chloro-6-chloromethyl-2,3,4,5-tetrahydro-1H-benzo[d]azepine (150 mg, 0.38 mmol) and catalytic potassium iodide (1 mg) in anhydrous DMF (1 mL) and stir at 45° C. for 13 h. Cool the mixture to room temperature and partition between brine and EtOAc. Dry the organic layer over Na$_2$SO$_4$, filter and concentrate in vacuo. Purify the crude mixture by chromatography on silica gel eluting with hexane/EtOAc (1:0 to 7:3 gradient) to give 3-tert-butoxycarbonyl-7-chloro-6-(thiophen-2-ylthiomethyl)-2,3,4,5-tetrahydro-1H-benzo[d]azepine (110 mg).

Use a method similar to the General Procedure 1 to deprotect 3-tert-butoxycarbonyl-7-chloro-6-(thiophen-2-ylthiomethyl)-2,3,4,5-tetrahydro-1H-benzo[d]azepine. Use a method similar to the General Procedure 2-3 to give the title compound (86 mg, 66%). MS (ES+) m/z: 310 (M+H)$^+$.

Examples 17-21

Examples 17-21 may be prepared essentially as described in Example 16 by using 3-tert-butoxycarbonyl-7-chloro-6-chloromethyl-2,3,4,5-tetrahydro-1H-benzo[d]azepine and the appropriate thiol. Example 21 was prepared as Succinate by following the procedure described in General Procedure 2-1. Overall yields and MS (ES+) data are shown in the Table below.

| Ex. | Structure | Compound | Yield (%) | MS (ES+) m/z |
|---|---|---|---|---|
| 17 | 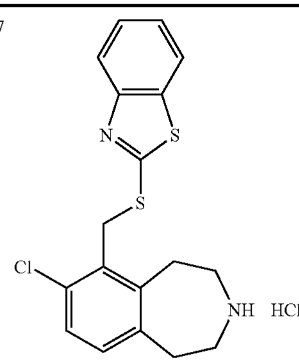 | 7-Chloro-6-(benzothiazol-2-ylthiomethyl)-2,3,4,5-tetrahydro-1H-benzo[d]azepine Hydrochloride | 68 | 361 (M + H)$^+$ |
| 18 | 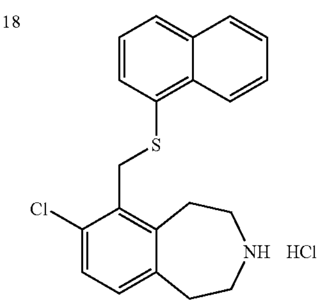 | 7-Chloro-6-(naphth-1-ylthiomethyl)-2,3,4,5-tetrahydro-1H-benzo[d]azepine Hydrochloride | 66 | 253 (M + H)$^+$ |
| 19 | 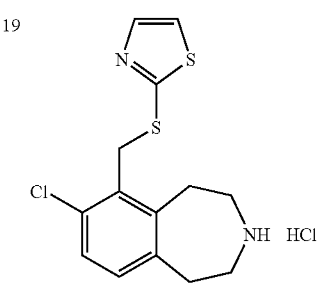 | 7-Chloro-6-(thiazol-2-ylthiomethyl)-2,3,4,5-tetrahydro-1H-benzo[d]azepine Hydrochloride | 51 | 311 (M + H)$^+$ |

-continued

| Ex. | Structure | Compound | Yield (%) | MS (ES+) m/z |
|---|---|---|---|---|
| 20 | 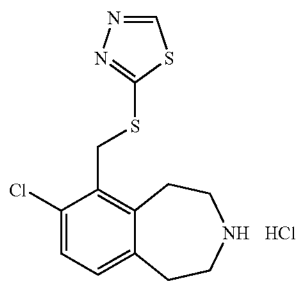 | 7-Chloro-6-([1,3,4]-thiadiazol-2-ylthiomethyl)-2,3,4,5-tetrahydro-1H-benzo[d]azepine Hydrochloride | 61 | 312 (M + H)+ |
| 21 | 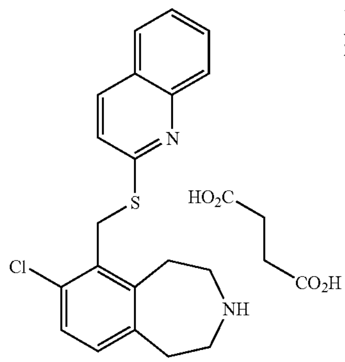 | 7-Chloro-6-(quinolin-2-ylthiomethyl)-2,3,4,5-tetrahydro-1H-benzo[d]azepine Succinate | 11 | 254 (M + H)+ |

Example 22

7-Chloro-6-(4-methyl-thiazol-2-ylthiomethyl)-2,3,4,5-tetrahydro-1H-benzo[d]azepine Succinate

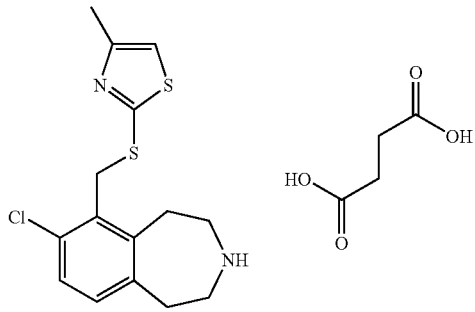

To a solution of 4-methylthiazole-2-thiol (0.32 g, 2.5 mmol) in anhydrous DMF (8.4 mL) add sodium hydride (0.10 g, 2.6 mmol, 60% dispersion in mineral oil) in portions at room temperature. After stirring at room temperature for 10 min, add a solution of 3-tert-butoxycarbonyl-7-chloro-6-chloromethyl-2,3,4,5-tetrahydro-1H-benzo[d]azepine (0.74 g, 2.2 mmol) in anhydrous DMF (5.6 mL). Heat the reaction mixture at 45° C. for 2 h under nitrogen atmosphere, cool to room temperature and stir overnight. Quench the reaction mixture with 10% aqueous NaHCO₃ (14 mL) and extract the mixture three times with EtOAc. Dry the combined organic extracts over Na₂SO₄, filter and concentrate in vacuo. Purify the crude mixture by chromatography on silica gel (40 g) eluting with hexane/EtOAc (1:0 to 85:15 gradient over 30 min; 35 mL/min) to obtain 3-tert-butoxycarbonyl-7-chloro-6-(4-methyl-thiazol-2-ylthiomethyl)-2,3,4,5-tetrahydro-1H-benzo[d]azepine (0.753 g, 79%) as a white foam.

Add TFA (19 mL) to a solution of 3-tert-butoxycarbonyl-7-chloro-6-(4-methyl-thiazol-2-ylthiomethyl)-2,3,4,5-tetrahydro-1H-benzo[d]azepine (0.395 g, 0.93 mmol) in anhydrous DCM (19 mL) at room temperature and stir under nitrogen overnight. Concentrate the reaction mixture in vacuo and purify by SCX chromatography (10 g) eluting with DCM and then DCM/2M ammonia in methanol (1:1). Purify again by chromatography on silica gel (40 g) eluting with DCM/2M ammonia in methanol (1:0 to 9:1 gradient over 30 min; 35 mL/min) to obtain 7-chloro-6-(4-methyl-thiazol-2-ylthiomethyl)-2,3,4,5-tetrahydro-1H-benzo[d]azepine (0.297 g, 99%).

To a solution of 7-chloro-6-(4-methyl-thiazol-2-ylthiomethyl)-2,3,4,5-tetrahydro-1H-benzo[d]azepine (0.297 g, 0.914 mmol) in absolute ethanol (10 mL), add succinic acid (0.108 g, 0.915 mmol). After acid dissolves, concentrate the reaction mixture to an oil. Add MTBE and concentrate in vacuo several times to remove ethanol. Dry the residue in oven at 45-50° C. for 2 days to afford a cloudy white oil. Dilute product in methanol and concentrate in vacuo. Add DCM to the residue and concentrate several times to remove methanol. Dry under high vacuum to afford the title compound (0.405 g, 100%) as a hygroscopic white foam. MS (ES+) m/z: 325.1 (M+H)+.

Examples 23-24

Examples 23-24 may be prepared essentially as described in Example 22 by using 3-tert-butoxycarbonyl-7-chloro-6-chloromethyl-2,3,4,5-tetrahydro-1H-benzo[d]azepine and the appropriately substituted thiol. Overall yields and MS (ES+) data are shown in the Table below.

| Ex. | Structure | Compound | Yield (%) | MS (ES+) m/z |
|---|---|---|---|---|
| 23 | 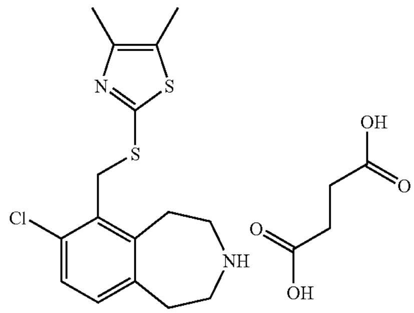 | 7-Chloro-6-(4,5-dimethyl-thiazol-2-ylthiomethyl)-2,3,4,5-tetrahydro-1H-benzo[d]azepine Succinate | 74 | 339.1 (M + H)+ |
| 24 | 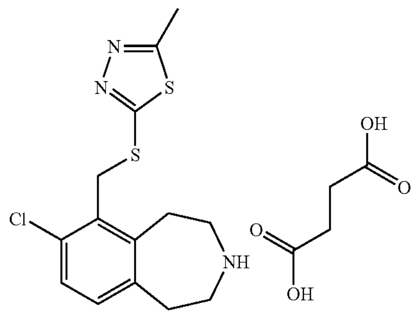 | 7-Chloro-6-(5-methyl-[1,3,4]thiadiazol-2-ylthiomethyl)-2,3,4,5-tetrahydro-1H-benzo[d]azepine Succinate | 90 | 326 (M + H)+ |

Example 25

7-Chloro-6-(1H-imidazol-2-ylthiomethyl)-2,3,4,5-tetrahydro-1H-benzo[d]azepine Phosphate Monohydrate

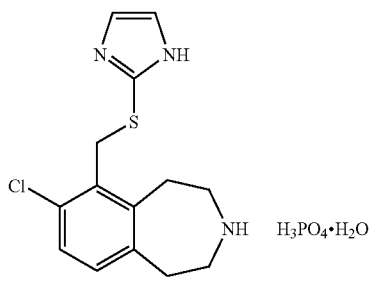

Dissolve 3-tert-butoxycarbonyl-7-chloro-6-chloromethyl-2,3,4,5-tetrahydro-1H-benzo[d]azepine (42.3 g, 128 mmol) in acetone (400 mL). Warm to 50° C., and then add potassium carbonate (26.5 g, 192 mmol) and sodium iodide (1.92 g, 12.8 mmol). With stirring, add 2-mercaptoimidazole (13.46 g, 134.4 mmol). Allow the mixture to stir at room temperature for 16 h. Filter the solid from this mixture, and wash the solid with acetone. Concentrate the filtrate in vacuo to a pink solid. Add DCM (400 mL) and 3% aqueous NaHCO$_3$ (400 mL). Collect the organic layer, and back extract the aqueous with DCM (2×100 mL). Combine the organic extracts and wash successively with brine (2×100 mL) and saturated aqueous NaHCO$_3$ (1×50 mL). Dry the organic layer over Na$_2$SO$_4$, filter, and concentrate in vacuo to obtain 3-tert-butoxycarbonyl-7-chloro-6-(1H-imidazol-2-ylthiomethyl)-2,3,4,5-tetrahydro-1H-benzo[d]azepine as an off-white solid (46.3 g, 92%). MS (ES+) m/z: 394.3 (M+H)+.

Dissolve 3-tert-butoxycarbonyl-7-chloro-6-(1H-imidazol-2-ylthiomethyl)-2,3,4,5-tetrahydro-1H-benzo[d]azepine (10.11 g, 25.65 mmol) in absolute ethanol (125 mL). Add acetyl chloride (20.13 g, 256.5 mmol) dropwise. On addition, the reaction mixture exotherms to 40-50° C. Stir the reaction at 50 to 60° C. for 2.5 h. Cool the mixture to 0 to ° 5 C. Filter, wash with ethanol, and dry solid in vacuo to obtain 7-chloro-6-(1H-imidazol-2-ylthiomethyl)-2,3,4,5-tetrahydro-1H-benzo[d]azepine hydrochloride (8.64 g). MS (ES+) m/z: 294.3 (M+H)+.

Dissolve 7-chloro-6-(1H-imidazol-2-ylthiomethyl)-2,3,4,5-tetrahydro-1H-benzo[d]azepine hydrochloride (9.85 g, 29.85 mmol) in water (60 mL) and absolute ethanol (40 mL) in a flask. Add a solution of Na$_2$CO$_3$ (15.8 g, 149 mmol) in water (100 mL) followed by DCM (125 mL) to the flask. Stir the mixture vigorously, then separate layers. Extract the aqueous layer twice with a solution of DCM (100 mL) and ethanol (10 mL). Dry the combined organic extracts over Na$_2$SO$_4$. Filter and concentrate in vacuo to obtain 7-chloro-6-(1H-imidazol-2-ylthiomethyl)-2,3,4,5-tetrahydro-1H-benzo[d]azepine as a light yellow foam (7.4 g, 75% weight recovery). MS (APCI+) m/z: 294.25 (M+H)+.

Dissolve 7-chloro-6-(1H-imidazol-2-ylthiomethyl)-2,3,4,5-tetrahydro-1H-benzo[d]azepine (41.4 g, 140.9 mmol) in absolute ethanol (500 mL) and water (52 mL). Warm to 70° C. to give a solution. Stir the solution at 65 to 70° C. and add 5M phosphoric acid (28.9 mL, 144.5 mmol). Heavy crystallization occurs. Cool to room temperature, then cool to 0 to 5° C. Filter the solid and rinse with cold ethanol. Dry the collected solid in vacuo to obtain the title compound as a white solid (53.7 g, 93%). MS (APCI+) m/z: 294.25 (M+H)+. mp (DSC)=243-245° C.

Example 26

7-Chloro-6-(4,5-dimethyl-1H-imidazol-2-ylthiomethyl)-2,3,4,5-tetrahydro-1H-benzo[d]azepine (L)-Tartrate

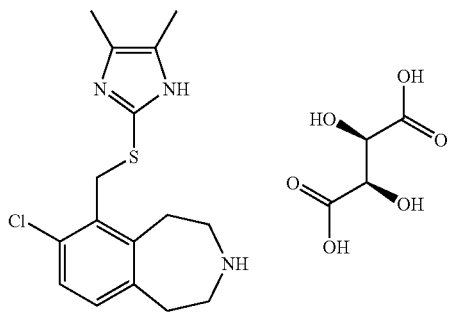

Dissolve 4,5-dimethyl-1H-imidazole-2-thiol (1.9 g, 14.5 mmol) in anhydrous DMF (55 mL). Add sodium hydride (635 mg, 15.9 mmol, 60% dispersion in mineral oil) portionwise over 5 min at room temperature under a nitrogen atmosphere. Stir the mixture for 15 min, then add a solution of 3-tert-butoxycarbonyl-7-chloro-6-chloromethyl-2,3,4,5-tetrahydro-1H-benzo[d]azepine (5 g, 13.8 mmol) in anhydrous DMF (15 mL) at room temperature over 3 min. Heat the mixture at 45° C. for 16 h under nitrogen. Cool the mixture to room temperature and quench with 10% aqueous sodium chloride (80 mL). Extract the mixture three times with EtOAc (1×200 mL, 2×75 mL). Dry the combined organic extracts over $Na_2SO_4$, filter and concentrate in vacuo. Purify the crude mixture by chromatography on silica gel eluting with hexane/EtOAc (7:3 to 1:1 gradient) to obtain 3-tert-butoxycarbonyl-7-chloro-6-(4,5-dimethyl-1H-imidazol-2-ylthiomethyl)-2,3,4,5-tetraydro-1H-benzo[d]azepine (4.5 g, 77%). MS (ES+) m/z: 422.0 (M+H)$^+$.

Use a method similar to the General Procedure 1 to deprotect 3-tert-butoxycarbonyl-7-chloro-6-(4,5-dimethyl-1H-imidazol-2-ylthiomethyl)-2,3,4,5-tetraydro-1H-benzo[d]azepine (4.5 g, 10.7 mmol). Purify by SCX chromatography followed by silica gel chromatography eluting with DCM/2M ammonia in methanol (97:3 to 88:12 gradient) to obtain 7-chloro-6-(4,5-dimethyl-1H-imidazol-2-ylthiomethyl)-2,3,4,5-tetrahydro-1H-benzo[d]azepine (3.1 g). Dissolve 7-chloro-6-(4,5-dimethyl-H-imidazol-2-ylthiomethyl)-2,3,4,5-tetrahydro-1H-benzo[d]azepine (3.1 g, 9.6 mmol) and (L)-tartaric acid (1.44 g, 9.6 mmol) in ethanol at 60° C., cool the solution until solids begin to form then add MTBE (150 mL) slowly until a thick slurry is obtained. Cool the slurry in an ice bath, filter and wash with cold MTBE (50 mL). Collect the solid and dry in vacuo to obtain the title compound as a white solid (4.1 g, 81%). MS (ES+) m/z: 322.2 (M+H)$^+$.

Examples 27-31

Examples 27-31 may be prepared essentially as described in Example 26 by using 3-tert-butoxycarbonyl-7-chloro-6-chloromethyl-2,3,4,5-tetrahydro-1H-benzo[d]azepine and the appropriate thiol. Overall yields and MS (ES+) data are shown in the Table below.

| Ex. | Structure | Compound | Yield (%) | MS (ES+) m/z |
|---|---|---|---|---|
| 27 | 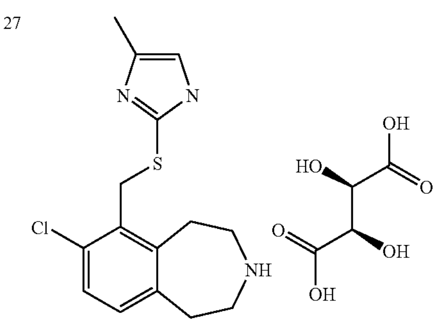 | 7-Chloro-6-(4-methyl-1H-imidazol-2-ylthiomethyl)-2,3,4,5-tetrahydro-1H-benzo[d]azepine (L)-Tartrate | 49 | 308.1 (M + H)$^+$ |
| 28 | 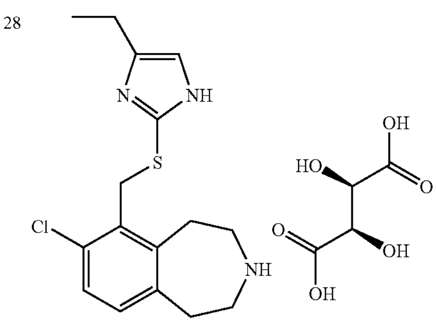 | 7-Chloro-6-(4-ethyl-1H-imidazol-2-ylthiomethyl)-2,3,4,5-tetrahydro-1H-benzo[d]azepine (L)-Tartrate | 66 | 322.2 (M + H)$^+$ |

| Ex. | Structure | Compound | Yield (%) | MS (ES+) m/z |
|---|---|---|---|---|
| 29 | 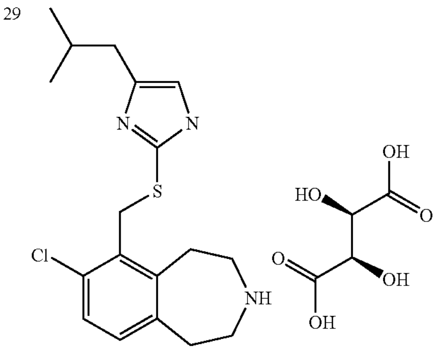 | 7-Chloro-6-(4-isobutyl-1H-imidazol-2-ylthiomethyl)-2,3,4,5-tetrahydro-1H-benzo[d]azepine (L)-Tartrate | 64 | 350.2 (M + H)+ |
| 30 | 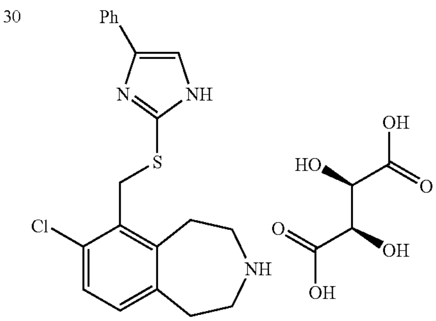 | 7-Chloro-6-(4-phenyl-1H-imidazol-2-ylthiomethyl)-2,3,4,5-tetrahydro-1H-benzo[d]azepine (L)-Tartrate | 52 | 370.2 (M + H)+ |
| 31 | 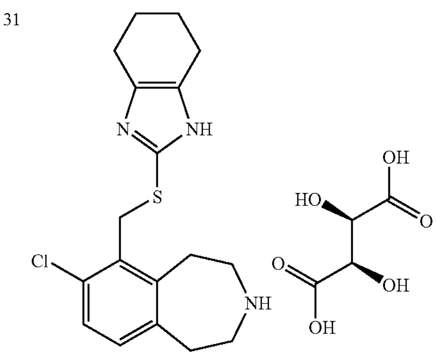 | 7-Chloro-6-(4,5,6,7-tetrahydro-1H-benzoimidazol-2-ylthiomethyl)-2,3,4,5-tetrahydro-1H-benzo[d]azepine (L)-Tartrate | 44 | 348.2 (M + H)+ |

Example 32

(−)-7-Chloro-6-[1-(1H-imidazol-2-ylthio)-ethyl]-2,3,4,5-tetrahydro-1H-benzo[d]azepine (L)-Tartrate

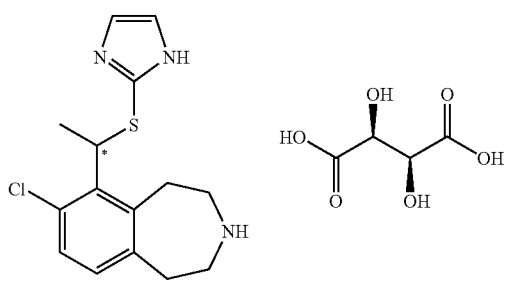

Dissolve 3-tert-butoxycarbonyl-7-chloro-6-(1-hydroxyethyl)-2,3,4,5-tetrahydro-1H-benzo[d]azepine (1.0 g, 3.1 mmol) in anhydrous DCM (20 mL) and triethylamine (1.3 mL, 9.3 mmol). Add methanesulfonyl chloride (0.5 mL, 6.5 mmol) to the reaction mixture, and stir at room temperature for 16 h. Wash the reaction mixture successively with saturated aqueous NaHCO$_3$ (2×30 mL) and brine. Dry the organic phase over anhydrous Na$_2$SO$_4$, filter and concentrate in vacuo to obtain the intermediate as a yellow foam that was used without further purification.

Suspend sodium hydride (156 mg, 3.8 mmol, 60% dispersion in mineral oil) in anhydrous DMF (4 mL) and add 2-mercaptoimidazole (310 mg, 3.1 mmol) at room temperature under a nitrogen atmosphere. After 5 min add the intermediate (described above) and catalytic potassium iodide (1 mg) in anhydrous DMF (4 mL) and stir at 45° C. for 12 h. Cool to room temperature and quench the reaction with water. Extract the mixture with EtOAc (4×40 mL). Wash the combined organic extracts with brine. Dry the organic layer over MgSO$_4$, filter and concentrate in vacuo. Purify the residue by chromatography on silica gel (40 g) eluting with hexane/EtOAc (3:2) to obtain (±)-3-tert-butoxycarbonyl-7-chloro-6-[1-(1H-imidazol-2-ylthio)-ethyl]-2,3,4,5-tetrahydro-1H-benzo[d]azepine (700 mg, 56%).

Separate (±)-3-tert-butoxycarbonyl-7-chloro-6-[1-(1H-imidazol-2-ylthio)-ethyl]-2,3,4,5-tetrahydro-1H-benzo[d]azepine by normal phase chiral chromatography [Chiralcel OD column 8×35 cm, eluting with heptane/n-propanol (9:1)]. First eluting isomer had 99.7% ee [Analytical chiral conditions: Chiralcel OD-H column 0.46×15 cm, eluting with heptane/n-propanol (9:1)]. Second eluting isomer had 96.6% ee [Analytical chiral conditions: Chiralcel OD-H column 0.46× 15 cm, eluting with heptane/n-propanol (9:1)].

Use a method similar to the General Procedure 1 to deprotect the second eluting isomer of 3-tert-butoxycarbonyl-7-chloro-6-[1-(1H-imidazol-2-ylthio)-ethyl]-2,3,4,5-tetrahydro-1H-benzo[d]azepine. Purify by SCX chromatography followed by chromatography on silica gel (12 g) eluting with DCM/2M ammonia in MeOH (9:1) to give (−)-7-chloro-6-[1-(1H-imidazol-2-ylthio)-ethyl]-2,3,4,5-tetrahydro-1H-benzo[d]azepine. Use a method similar to the General Procedure 2-4 to give the title compound as a white solid (369 mg). MS (ES+) m/z: 308.1 (M+H)⁺. [α]$_D$-157° (c 0.5, MeOH).

Example 33

7-Chloro-6-(1,2-dimethyl-1H-imidazol-4-ylthiomethyl)-2,3,4,5-tetrahydro-1H-benzo[d]azepine (L)-Tartrate

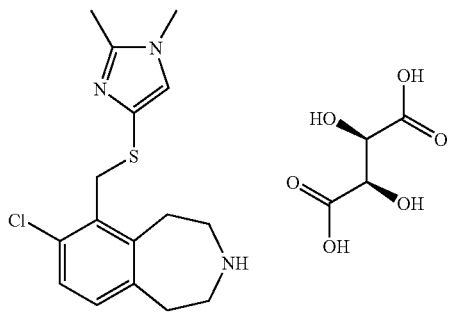

Dissolve 1,2-dimethyl-1H-imidazole-4-thiol (450 mg, 1.8 mmol, prepared as described in *J. Heterocyclic Chem.* 1998, 35, 141) in anhydrous DMF (3 mL). Add sodium hydride (55 mg, 1.4 mmol, 60% dispersion in mineral oil) portionwise over 2 min at room temperature under a nitrogen atmosphere. Stir the yellow solution for 5 min, then add a solution of 3-tert-butoxycarbonyl-7-chloro-6-chloromethyl-2,3,4,5-tetrahydro-1H-benzo[d]azepine (300 mg, 0.9 mmol) in anhydrous DMF (3 mL) at room temperature over 2 min. Heat the mixture at 45° C. for 16 h under a nitrogen atmosphere. Cool the mixture to room temperature and quench with 10% aqueous sodium chloride (10 mL). Extract the mixture with EtOAc (2×30 mL). Dry the combined organic extracts over Na$_2$SO$_4$, filter and concentrate in vacuo. Purify the residue by chromatography on silica gel eluting with hexane/EtOAc (7:3 to 1:1 gradient) to obtain 3-tert-butoxycarbonyl-7-chloro-6-(1,2-dimethyl-1H-imidazol-4-ylthiomethyl)-2,3,4,5-tetrahydro-1H-benzo[d]azepine (160 mg, 42%). MS (ES+) m/z: 422.0 (M+H)⁺.

Use a method similar to the General Procedure 1 to deprotect 3-tert-butoxycarbonyl-7-chloro-6-(1,2-dimethyl-1H-imidazol-4-ylthiomethyl)-2,3,4,5-tetrahydro-1H-benzo[d]azepine (160 mg, 0.39 mmol). Purify by reverse phase chromatography [Column: Symmetry C18, 19×300 mm, flow rate 30 mL/min, eluting with water with 0.1% TFA/acetonitrile (19:1 to 3:7 gradient)] followed by SCX chromatography to obtain 7-chloro-6-(1,2-dimethyl-1H-imidazol-4-ylthiomethyl)-2,3,4,5-tetrahydro-1H-benzo[d]azepine. Use a method similar to the General Procedure 2-4 to obtain the title compound as a white solid (90 mg, 50% 2 steps). MS (ES+) m/z: 322.2 (M+H)⁺.

Example 34

7-Chloro-6-(5-ethyl-1H-1,3,4-triazol-2-ylthiomethyl)-2,3,4,5-tetrahydro-1H-benzo[d]azepine Succinate

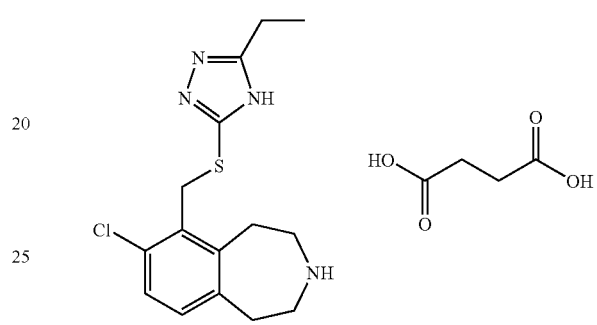

Dissolve 5-ethyl-1H-1,3,4-triazole-2-thione (92 mg, 0.71 mmol) in anhydrous DMF (5 mL). Add sodium hydride (40 mg, 0.925 mmol, 60% dispersion in mineral oil) at room temperature under a nitrogen atmosphere and stir for 10 min. Add a solution of 3-tert-butoxycarbonyl-7-chloro-6-chloromethyl-2,3,4,5-tetrahydro-1H-benzo[d]azepine (210 mg, 0.65 mmol) in anhydrous DMF (5 mL) at room temperature over 3 min and stir under nitrogen for 18 h. Quench with saturated aqueous NH$_4$Cl (ca. 1 mL) and pour into water (100 mL). Extract the aqueous phase with EtOAc (3×25 mL) and wash the combined organic extracts with brine. Dry the organic solution over Na$_2$SO$_4$, filter and concentrate in vacuo to obtain crude 3-tert-butoxycarbonyl-7-chloro-6-(5-ethyl-1H-1,3,4-triazol-2-ylthiomethyl)-2,3,4,5-tetrahydro-1H-benzo[d]azepine (200 mg, 73%) suitable for use without further purification. MS (ES+) m/z: 423 (M+H)⁺.

Use a method similar to the General Procedure 1 to deprotect 3-tert-butoxycarbonyl-7-chloro-6-(5-ethyl-1H-1,3,4-triazol-2-ylthiomethyl)-2,3,4,5-tetrahydro-1H-benzo[d] azepine (200 mg, 0.47 mmol). Purify by SCX chromatography eluting successively with DCM, methanol and 2M ammonia in methanol, followed by silica gel chromatography (12 g) eluting with DCM/2M ammonia in methanol (1:0 to 4:1 gradient over 30 min) to obtain 7-chloro-6-(5-ethyl-1H-1,3,4-triazol-2-ylthiomethyl)-2,3,4,5-tetrahydro-1H-benzo[d]azepine (175 mg, 88%) as a yellow oil. Use a method similar to the General Procedure 2-1 to obtain the title compound as an off-white solid (230 mg, 96%). MS (ES+) m/z: 323 (M+H)⁺.

Examples 35-37

Examples 35-37 may be prepared essentially as described in Example 34 using 3-tert-butoxycarbonyl-7-chloro-6-chloromethyl-2,3,4,5-tetrahydro-1H-benzo[d]azepine and the appropriately substituted 1H-1,3,4-triazole-2-thione. Overall yields and MS (ES+) data are shown in the Table below.

| Ex. | Structure | Compound | Yield (%) | MS (ES+) m/z |
|---|---|---|---|---|
| 35 | 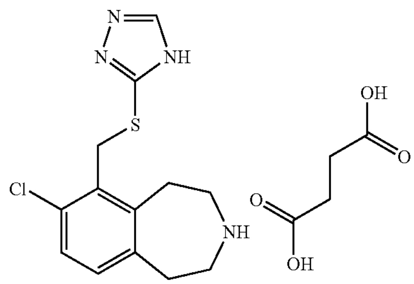 | 7-Chloro-6-(1H-1,3,4-triazol-2-ylthiomethyl)-2,3,4,5-tetrahydro-1H-benzo[d]azepine Succinate | 48 | 295 (M + H)+ |
| 36 | 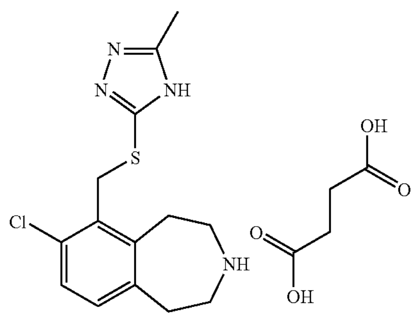 | 7-Chloro-6-(5-methyl-1H-1,3,4-triazol-2-ylthiomethyl)-2,3,4,5-tetrahydro-1H-benzo[d]azepine Succinate | 47 | 309 (M + H)+ |
| 37 | 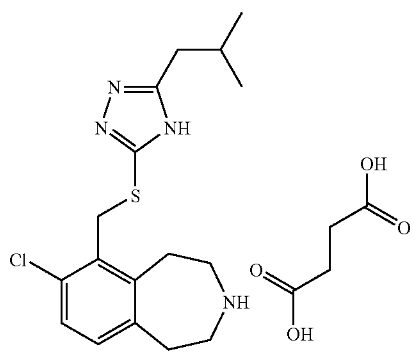 | 7-Chloro-6-(5-iso-butyl-1H-1,3,4-triazol-2-ylthiomethyl)-2,3,4,5-tetrahydro-1H-benzo[d]azepine Succinate | 32 | 351 (M + H)+ |

Example 38

7-Chloro-6-(3H-[1,2,3]triazol-4-ylthiomethyl)-2,3,4,5-tetrahydro-1H-benzo[d]azepine Succinate

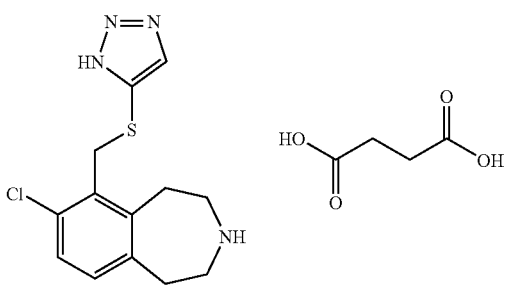

Slurry 1H-[1,2,3]triazole-5-thiol sodium salt (465 mg, 3.78 mmol) in anhydrous DMF (20 mL). Add a solution of 3-tert-butoxycarbonyl-7-chloro-6-chloromethyl-2,3,4,5-tetrahydro-1H-benzo[d]azepine (1.1 g, 3.4 mmol) in anhydrous DMF (10 mL) dropwise over 10 min under nitrogen. Stir at room temperature for 3 h. Quench by addition of saturated NH$_4$Cl (100 mL). Extract with EtOAc (3×50 mL) and dry the combined organic extracts with water and brine. Dry the organic phase over Na$_2$SO$_4$, filter and concentrate in vacuo to obtain 3-tert-butoxycarbonyl-7-chloro-6-(3H-[1,2,3]triazol-4-ylthiomethyl)-2,3,4,5-tetrahydro-1H-benzo[d]azepine (1.2 g, 90%) as a yellow oil suitable for use without further purification.

Use a method similar to the General Procedure 1 to deprotect 3-tert-butoxycarbonyl-7-chloro-6-(3H-[1,2,3]triazol-4-ylthiomethyl)-2,3,4,5-tetrahydro-1H-benzo[d]azepine (0.7 g, 1.78 mmol). Purify the crude mixture by SCX chromatography (5 g) eluting successively with DCM, methanol, and 2M ammonia in methanol, followed by chromatography on silica gel (12 g) eluting with 2M ammonia in methanol/DCM (0:1 to 1:4 over 30 min) to obtain 7-chloro-6-(3H-[1,2,3]triazol-4-ylthiomethyl)-2,3,4,5-tetrahydro-1H-benzo[d]azepine (296 mg, 57%) as an off-white solid.

Use a method similar to the General Procedure 2-1, using 7-chloro-6-(3H-[1,2,3]triazol-4-ylthiomethyl)-2,3,4,5-tetrahydro-1H-benzo[d]azepine (296 mg, 1 mmol) to obtain an oily solid (410 mg, 99%). Recrystallize from methanol to afford the title compound as an off-white powder (108 mg, 26%). MS (ES+) m/z: 295 (M+H)+.

Example 39

7-Chloro-6-(3-methyl-3H-[1,2,3]triazol-4-ylthiomethyl)-2,3,4,5-tetrahydro-1H-benzo[d]azepine Succinate

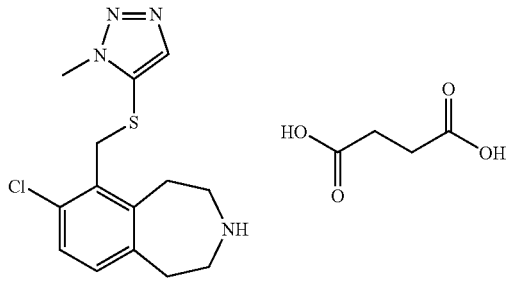

Dissolve 3-tert-butoxycarbonyl-7-chloro-6-(3H-[1,2,3]triazol-4-ylthiomethyl)-2,3,4,5-tetrahydro-1H-benzo[d]azepine (0.5 g, 1.39 mmol) in acetone (10 mL). Add $K_2CO_3$ (1.39 g, 13.9 mmol) followed by methyl iodide (86 µL, 1.39 mmol) with vigorous stirring under nitrogen and stir for 1 h. Filter off the solids and wash with acetone and EtOAc and concentrate the filtrate in vacuo. Purify by reverse phase HPLC (Vydac® C18 column, 5.0×25 cm; eluting with a gradient of 10% acetonitrile in 0.3% TFA/water to 100% acetonitrile over 90 min; flow rate 45 mL/min) to obtain two fractions. Concentrate each fraction in vacuo and dry under high vacuum at 50° C. overnight. First fraction eluted at ca. 40% acetonitrile in 0.3% TFA/$H_2O$, and contained 3-tert-butoxycarbonyl-7-chloro-6-(3-methyl-3H-[1,2,3]triazol-4-ylthiomethyl)-2,3,4,5-tetrahydro-1H-benzo[d]azepine (65.1 mg, 25%). Second fraction eluted at 80% acetonitrile in 0.3% TFA/$H_2O$, and contained 3-tert-butoxycarbonyl-7-chloro-6-(2-methyl-2H-[1,2,3]triazol-4-ylthiomethyl)-2,3,4,5-tetrahydro-1H-benzo[d]azepine (58.8 mg, 23%).

Use a method similar to the General Procedure 1 to deprotect 3-tert-butoxycarbonyl-7-chloro-6-(3-methyl-3H-[1,2,3]triazol-4-ylthiomethyl)-2,3,4,5-tetrahydro-1H-benzo[d]azepine (65.1 mg, 0.16 mmol). Purify by SCX chromatography (500 mg) eluting successively with DCM, methanol, and 2M ammonia in methanol, followed by chromatography on silica gel (4 g) eluting with 2M ammonia in methanol/DCM (1:99 to 1:9 over 30 min) to obtain 7-chloro-6-(3-methyl-3H-[1,2,3]triazol-4-ylthiomethyl)-2,3,4,5-tetrahydro-1H-benzo[d]azepine (45 mg, 92%) as a brown oil. Use a method similar to the General Procedure 2-1 using 7-chloro-6-(3-methyl-3H-[1,2,3]triazol-4-ylthiomethyl)-2,3,4,5-tetrahydro-1H-benzo[d]azepine (45 mg, 0.146 mmol) to obtain the title compound (60 mg, 96%) as an off-white foam. MS (ES+), m/z: 309 (M+H)⁺.

Example 40

7-Chloro-6-(2-methyl-2H-[1,2,3]triazol-4-ylthiomethyl)-2,3,4,5-tetrahydro-1H-benzo[d]azepine Succinate

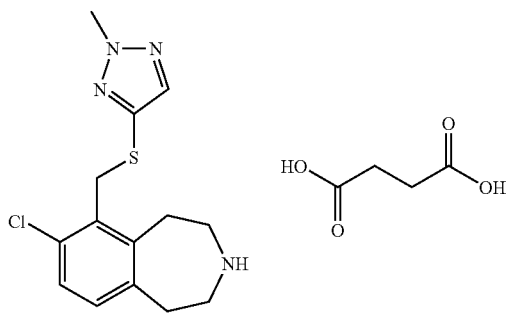

Use a method similar to the General Procedure 1 to deprotect 3-tert-butoxycarbonyl-7-chloro-6-(2-methyl-2H-[1,2,3]triazol-4-ylthiomethyl)-2,3,4,5-tetrahydro-1H-benzo[d]azepine (58.8 mg, 0.14 mmol). Purify by SCX chromatography (0.5 g) eluting successively with DCM, methanol, and 2M ammonia in methanol, followed by chromatography on silica gel (4 g) eluting with 2M ammonia in methanol/DCM (0.1:99.9 to 1:9 gradient over 30 min) to obtain 7-chloro-6-(2-methyl-2H-[1,2,3]triazol-4-ylthiomethyl)-2,3,4,5-tetrahydro-1H-benzo[d]azepine (41.5 mg, 96%). Use a method similar to the General Procedure 2-1, using 7-chloro-6-(2-methyl-2H-[1,2,3]triazol-4-ylthiomethyl)-2,3,4,5-tetrahydro-1H-benzo[d]azepine (41.5 mg, 0.135 mmol) to obtain the title compound (54 mg, 94%) as an off-white solid. MS (ES+) m/z: 309 (M+H)⁺.

Example 41

6-Benzylthiomethyl-7-chloro-2,3,4,5-tetrahydro-1H-benzo[d]azepine Succinate

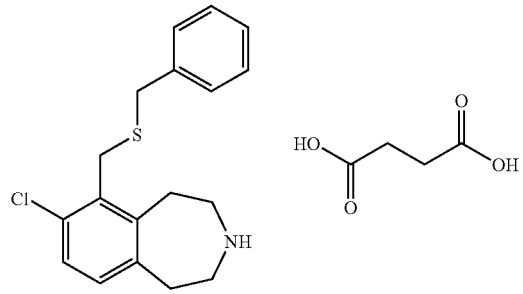

Dissolve benzylmercaptan (230 mg, 1.84 mmol) in anhydrous DMF (5 mL). Add sodium hydride (100 mg, 2.5 mmol, 60% dispersion in mineral oil) and stir the mixture for 10 min. Add then a solution of 3-tert-butoxycarbonyl-7-chloro-6-chloromethyl-2,3,4,5-tetrahydro-1H-benzo[d]azepine (550 mg, 1.67 mmol) in anhydrous DMF (1 mL). Stir under nitrogen at room temperature overnight. Pour reaction mixture into water (150 mL) and extract with DCM (3×50 mL). Wash the combined organic extracts with brine, dry over $Na_2SO_4$, filter and concentrate in vacuo to afford crude 6-benzylthiomethyl-3-tert-butoxycarbonyl-7-chloro-2,3,4,5-tetrahydro-1H-benzo[d]azepine as a yellow oil (1.13 g) suitable for use without additional purification.

Use a method similar to the General Procedure 1 to deprotect 6-benzylthiomethyl-3-tert-butoxycarbonyl-7-chloro-2,3,4,5-tetrahydro-1H-benzo[d]azepine (1.1 g crude material). Purify by SCX chromatography (5 g) eluting successively with DCM, methanol, and 7M ammonia in methanol followed by chromatography on silica gel (12 g) eluting with DCM/2M ammonia in methanol (1:0 to 4:1 gradient over 35 min) to obtain 6-benzylthiomethyl-7-chloro-2,3,4,5-tetrahydro-1H-benzo[d]azepine (260 mg, 51% over 2 steps) as a colorless oil. Use a method similar to the General Procedure 2-1 to obtain the title compound as an off-white solid (340 mg, 95%). MS (ES+) m/z: 318 (M+H)⁺.

Example 42

7-Chloro-6-(pyridin-2-ylmethylthiomethyl)-2,3,4,5-tetrahydro-1H-benzo[d]azepine Succinate

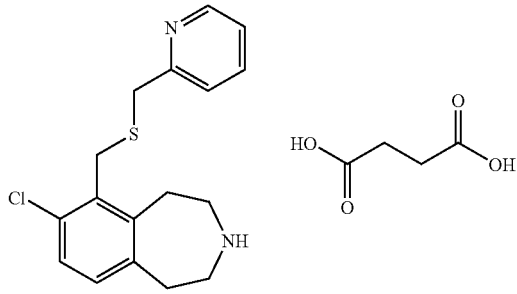

Evaporate a solution of 2-pyridine methanethiol (2.5 mL, 10% in EtOH) in vacuo to obtain neat 2-pyridine methanethiol (250 mg). Immediately dissolve 2-pyridine methanethiol (230 mg, 1.84 mmol) in anhydrous DMF (5 mL) under an atmosphere of nitrogen. Add sodium hydride (100 mg, 2.5 mmol, 60% dispersion in mineral oil) and stir for 10 min. Add a solution of 3-tert-butoxycarbonyl-7-chloro-6-chloromethyl-2,3,4,5-tetrahydro-1H-benzo[d]azepine (550 mg, 1.67 mmol) in anhydrous DMF (1 mL) and stir under nitrogen for 2 h. Quench reaction by slow addition of water (10 mL), dilute up to 150 mL with water and extract with DCM (3×50 mL). Wash the combined organic extracts with brine, dry over Na$_2$SO$_4$, filter and concentrate in vacuo. Purify by chromatography on silica gel (40 g) eluting with hexane/EtOAc (9:1 to 1:1 gradient over 60 min, 40 mL/min) to obtain 3-tert-butoxycarbonyl-7-chloro-6-(pyridin-2-ylmethylthiomethyl)-2,3,4,5-tetrahydro-1H-benzo[d]azepine (275 mg, 40%) as a light yellow syrup.

Use a method similar to the General Procedure 1 to deprotect 3-tert-butoxycarbonyl-7-chloro-6-(pyridin-2-ylmethylthiomethyl)-2,3,4,5-tetrahydro-1H-benzo[d]azepine (275 mg, 0.66 mmol). Purify by SCX chromatography (5 g) eluting successively with DCM, methanol and 7M ammonia in methanol followed by chromatography on silica gel (12 g) eluting with DCM/2M ammonia in methanol (1:0 to 9:1 gradient over 30 min) to obtain 7-chloro-6-(pyridin-2-ylmethylthiomethyl)-2,3,4,5-tetrahydro-1H-benzo[d]azepine (190 mg, 91%) as a colorless oil. Use a method similar to the General Procedure 2-1 to obtain the title compound as an off-white solid (259 mg, 99%). MS (ES+) m/z: 319 (M+H)$^+$.

Example 43

7-Chloro-6-(4,5-dihydro-thiazol-2-ylthiomethyl)-2,3,4,5-tetrahydro-1H-benzo[d]azepine Succinate

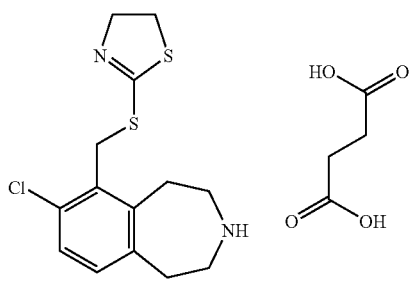

To a solution of 2-mercaptothiazoline (0.3 g, 2.5 mmol) in anhydrous DMF (8.5 mL) at room temperature add sodium hydride (0.1 g, 2.6 mmol, 60% dispersion in mineral oil) in portions. After stirring at room temperature for 10 min, add a solution of 3-tert-butoxycarbonyl-7-chloro-6-chloromethyl-2,3,4,5-tetrahydro-1H-benzo[d]azepine (0.74 g, 2.3 mmol) in anhydrous DMF (5.6 mL). Stir at room temperature overnight and quench the reaction mixture with 10% aqueous NaHCO$_3$ (14 mL). Extract the mixture twice with EtOAc. Dry the combined organic extracts over Na$_2$SO$_4$, filter and concentrate in vacuo. Dissolve the residue in DCM, load the solution on to a RediSep® column (40 g) and purify the crude mixture by preparative liquid chromatography (100:0 to 95:5 hexane/EtOAc over 30 min; 95:5 hexane/EtOAc over 3 min; 95:5 to 75:25 hexane/EtOAc over 30 min; 75:25 hexane/EtOAc over 3 min; 35 mL/min) to afford 3-tert-butoxycarbonyl-7-chloro-6-(4,5-dihydro-thiazol-2-ylthiomethyl)-2,3,4,5-tetrahydro-1H-benzo[d]azepine (0.77 g, 83%). MS (ES+) m/z: 413.1 (M+H)$^+$.

To a solution of 3-tert-butoxycarbonyl-7-chloro-6-(4,5-dihydro-thiazol-2-ylthiomethyl)-2,3,4,5-tetrahydro-1H-benzo[d]azepine (0.77 g, 1.9 mmol) in anhydrous DCM (41 mL) at room temperature add trifluoroacetic acid (37.7 mL) and stir the solution at room temperature overnight. Concentrate in vacuo and elute the residue through a SCX column (10 g). Dissolve the residue in DCM, load the solution on to a RediSep® column (40 g) and purify the crude mixture by preparative liquid chromatography (linear gradient: 100:0 to 90:10 DCM/2M ammonia in methanol over 30 min; 35 mL/min) to afford 7-chloro-6-(4,5-dihydro-thiazol-2-ylthiomethyl)-2,3,4,5-tetrahydro-1H-benzo[d]azepine (0.58 g, 100%). MS (ES+) m/z: 313.1 (M+H)$^+$.

To a solution of 7-chloro-6-(4,5-dihydro-thiazol-2-ylthiomethyl)-2,3,4,5-tetrahydro-1H-benzo[d]azepine (0.57 g, 1.8 mmol) in absolute ethanol (10 mL), add succinic acid (0.217 g, 1.83 mmol). After acid dissolves, concentrate the reaction mixture in vacuo. Combine the residue with MTBE, concentrate in vacuo several times and dry under high vacuum at room temperature overnight to obtain the title compound (0.79 g, 100%) as a white foam. MS (ES+) m/z/z: 313.0 (M+H)$^+$.

Example 44

7-Chloro-6-[5-(cyclopropylmethyl-amino)-[1,3,4]thiadiazol-2-ylthiomethyl]-2,3,4,5-tetrahydro-1H-benzo[d]azepine Succinate

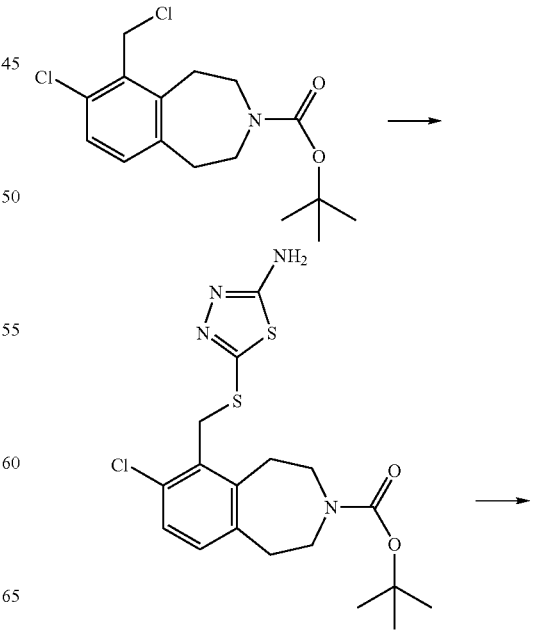

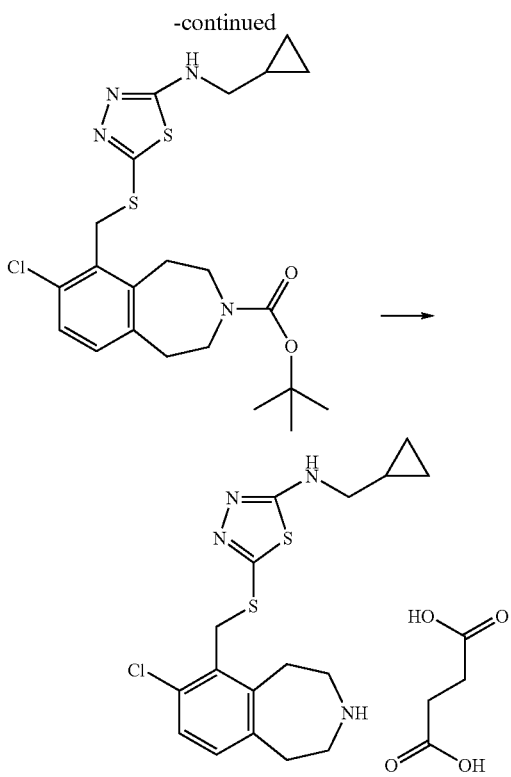

6-(5-Amino-[1,3,4]thiadiazol-2-ylthiomethyl)-3-tert-butoxycarbonyl-7-chloro-2,3,4,5-tetrahydro-1H-benzo[d]azepine: To a mixture of 5-amino-1,3,4-thiadiazole-2-thiol (0.33 g, 2.5 mmol) in anhydrous DMF (8.5 mL) at room temperature add sodium hydride (0.1 g, 2.6 mmol, 60% dispersion in mineral oil) in portions. After stirring at room temperature for 10 min, add a solution of 3-tert-butoxycarbonyl-7-chloro-6-chloromethyl-2,3,4,5-tetrahydro-1H-benzo[d]azepine (0.75 g, 2.3 mmol) in anhydrous DMF (5.6 mL). Stir at room temperature overnight and quench the reaction mixture with 10% aqueous NaHCO$_3$ (25 mL). Extract the mixture with DCM (100 mL). Dry the organic phase over Na$_2$SO$_4$, filter and concentrate in vacuo. Dissolve the residue in DCM, load the solution on to a RediSep® column (40 g) and purify the crude mixture by preparative liquid chromatography (hexane over 10 min; 100:0 to 50:50 hexane/EtOAc over 23 min; 50:50 to 0:100 hexane/EtOAc over 33 min; 35 mL/min) to obtain an oil. Add EtOAc (16 mL) to precipitate product. After stirring overnight, filter the slurry, wash the solid with EtOAc (10 mL) and dry to obtain the desired intermediate (0.583 g, 61%) as a white solid. MS (ES+) m/z: 427.1 (M+H)$^+$.

3-tert-Butoxycarbonyl-7-chloro-6-[5-(cyclopropylmethyl-amino)-[1,3,4]thiadiazol-2-ylthiomethyl]-2,3,4,5-tetrahydro-1H-benzo[d]azepine: To a solution of 6-(5-amino-[1,3,4]thiadiazol-2-ylthiomethyl)-3-tert-butoxycarbonyl-7-chloro-2,3,4,5-tetrahydro-1H-benzo[d]azepine (0.252 g, 0.59 mmol) in anhydrous DCE (1 mL), add a solution of cyclopropane carboxaldehyde (0.083 g, 1.2 mmol) in anhydrous DCE (1 mL) at room temperature. Add sodium tris(acetoxy)borohydride (0.38 g, 1.8 mmol) and a solution of glacial acetic acid (0.20 mL, 3.5 mmol) in anhydrous DCE (1 mL) to the reaction mixture at room temperature. Heat at reflux overnight, cool the reaction mixture to room temperature and add saturated aqueous NaHCO$_3$ (25 mL) to the mixture. After stirring at room temperature for 1 h, extract the two-phase mixture with DCM (2×50 mL). Dry the combined organic extracts over Na$_2$SO$_4$, filter and concentrate in vacuo. Dissolve the residue in DCM, load the solution on to a RediSep® column (40 g) and purify the crude mixture by preparative liquid chromatography (100:0 to 95:5 hexane/EtOAc over 33 min; 95:5 to 50:50 hexane/EtOAc over 33 min; 50:50 to 0:100 hexane/EtOAc over 30 min; 35 mL/min) to afford the desired intermediate (0.087 g, 31%). MS (ES+) m/z: 481.2 (M+H)$^+$.

7-Chloro-6-[5-(cyclopropylmethyl-amino)-[1,3,4]thiadiazol-2-ylthiomethyl]-2,3,4,5-tetrahydro-1H-benzo[d]azepine Succinate: To a solution of 3-tert-butoxycarbonyl-7-chloro-6-[5-(cyclopropylmethyl-amino)-[1,3,4]thiadiazol-2-ylthiomethyl]-2,3,4,5-tetrahydro-1H-benzo[d]azepine (0.082 g, 0.171 mmol) in anhydrous DCM (3.5 mL) at room temperature add trifluoroacetic acid (3.5 mL) and stir the solution at room temperature overnight. Concentrate in vacuo and elute the residue through a SCX column (20 g). Dissolve the residue in DCM, load the solution on to a RediSep® column (12 g) and purify the crude mixture by preparative liquid chromatography (100:0 to 90:10 DCM/2M ammonia in methanol over 33 min; 35 mL/min) to afford 7-chloro-6-[5-(cyclopropylmethyl-amino)-[1,3,4]thiadiazol-2-ylthiomethyl]-2,3,4,5-tetrahydro-1H-benzo[d]azepine (0.051 g, 78%). MS (ES+) m/z: 381.1 (M+H)$^+$. To a solution of 7-chloro-6-[5-(cyclopropylmethyl-amino)-[1,3,4]thiadiazol-2-ylthiomethyl]-2,3,4,5-tetrahydro-1H-benzo[d]azepine (0.044 g, 0.116 mmol) in absolute ethanol (5 mL), add succinic acid (0.014 g, 0.116 mmol). After acid dissolves, concentrate the reaction mixture in vacuo. Combine the residue with MTBE, concentrate in vacuo several times and dry under high vacuum at room temperature overnight to obtain the title compound (0.058 g, 100%) as a white foam. MS (ES+) m/z: 381.0 (M+H)$^+$.

Example 45

7-Chloro-6-[2-(cyclopropylmethyl-amino)-thiazol-5-ylthiomethyl]-2,3,4,5-tetrahydro-1H-benzo[d]azepine Succinate

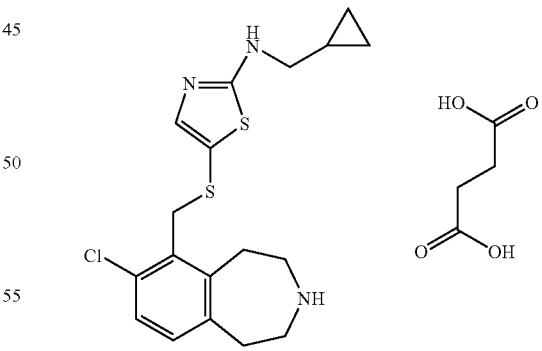

To a solution of 3-tert-butoxycarbonyl-7-chloro-6-mercaptomethyl-2,3,4,5-tetrahydro-1H-benzo[d]azepine (0.202 g, 0.617 mmol) and N-(5-bromothiazol-2-yl)-cyclopropylmethylamine (0.14 g, 0.62 mmol) in anhydrous DMF (6.2 mL) at room temperature add cesium carbonate (0.22 g, 0.68 mmol). Stir at room temperature overnight and partition the reaction mixture between saturated aqueous NaHCO$_3$ (50 mL) and DCM (100 mL). Dry the organic extract over Na$_2$SO$_4$, filter and concentrate in vacuo. Dissolve the residue in DCM, load the solution on to an Analogix® column (40 g) and purify the crude intermediate by preparative liquid chromatography (100:0 to 75:25 hexane/EtOAc over 30 min; 75:25 to 50:50 hexane/EtOAc over 33 min; 35 mL/min) to afford 3-tert-butoxycarbonyl-7-chloro-6-[2-(cyclopropylmethyl-amino)-thiazol-5-ylthiomethyl]-2,3,4,5-tetrahydro-1H-benzo[d]azepine (0.129 g, 44%). MS (ES+) m/z: 480.2 (M+H)$^+$.

To a solution of 3-tert-butoxycarbonyl-7-chloro-6-[2-(cyclopropylmethyl-amino)-thiazol-5-ylthiomethyl]-2,3,4,5-tetrahydro-1H-benzo[d]azepine (0.113 g, 0.237 mmol) in anhydrous DCM (4.9 mL) at room temperature add trifluoroacetic acid (4.9 mL) and stir the solution at room temperature overnight. Concentrate in vacuo and elute the residue through a SCX column (20 g). Dissolve the residue in DCM, load the solution on to an Analogix® column (40 g) and purify the crude mixture by preparative liquid chromatography (100:0 to 90:10 DCM/2M ammonia in methanol over 30 min; 90:10 DCM/2M ammonia in methanol over 33 min; 35 mL/min) to afford 7-chloro-6-[2-(cyclopropylmethyl-amino)-thiazol-5-ylthiomethyl]-2,3,4,5-tetrahydro-1H-benzo[d]azepine (0.075 g, 83%). MS (ES+) m/z: 380.1 (M+H)$^+$.

To a solution of 7-chloro-6-[2-(cyclopropylmethyl-amino)-thiazol-5-ylthiomethyl]-2,3,4,5-tetrahydro-1H-benzo[d]azepine (0.055 g, 0.144 mmol) in absolute ethanol (5 mL) add succinic acid (0.017 g, 0.144 mmol). After acid dissolves, concentrate the reaction mixture in vacuo. Combine the residue with MTBE, concentrate in vacuo several times and dry under high vacuum at room temperature overnight to obtain the title compound (0.072 g, 100%) as a white foam. MS (ES+) m/z: 380.0 (M+H)$^+$.

Example 46

6-(5-Amino-[1,2,4]thiadiazol-3-ylthiomethyl)-7-chloro-2,3,4,5-tetrahydro-1H-benzo[d]azepine Succinate

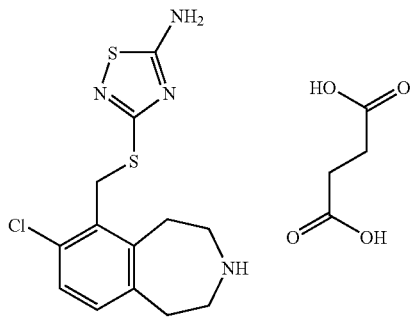

To a solution of 3-tert-butoxycarbonyl-6-carbamimidoylthiomethyl-7-chloro-2,3,4,5-tetrahydro-1H-benzo[d]azepine hydrochloride (0.510 g, 1.256 mmol) in methanol (12.5 mL) at room temperature add solid sodium methoxide (0.14 g, 2.5 mmol) and then KSCN (0.12 g, 1.3 mmol). After cooling the reaction mixture to 0° C., add a solution of bromine (0.20 g, 1.3 mmol) in methanol (4 mL) dropwise. Stir the reaction mixture at room temperature overnight. Concentrate the reaction mixture in vacuo and partition the residue between DCM (100 mL) and water (50 mL). Extract the aqueous phase with DCM (50 mL). Dry the combined organic extracts over Na$_2$SO$_4$, filter and concentrate in vacuo. Dissolve the residue in DCM/methanol, add silica gel (5 g) and concentrate to a powder. Load the powder on to a dry column attached to a RediSep® column (40 g) and purify the crude mixture by preparative liquid chromatography (100:0 to 95:5 DCM/2M ammonia in methanol over 33 min; 95:5 to 80:20 DCM/2M ammonia in methanol over 33 min; 35 mL/min) to afford 6-(5-amino-[1,2,4]thiadiazol-3-ylthiomethyl)-3-tert-butoxycarbonyl-7-chloro-2,3,4,5-tetrahydro-1H-benzo[d]azepine (0.229 g, 43%). MS (ES+) m/z: 427.2 (M+H)$^+$.

To a solution of 6-(5-amino-[1,2,4]thiadiazol-3-ylthiomethyl)-3-tert-butoxycarbonyl-7-chloro-2,3,4,5-tetrahydro-1H-benzo[d]azepine (0.186 g, 0.436 mmol) in anhydrous DCM (10 mL) at room temperature add trifluoroacetic acid (10 mL) and stir the solution at room temperature overnight. Concentrate in vacuo and elute the residue through a SCX column (20 g). Dissolve the residue in DCM/methanol, add silica gel (5 g) and concentrate to a powder. Load the powder on to a dry column attached to a RediSep® column (40 g) and purify the crude mixture by preparative liquid chromatography (100:0 to 80:20 DCM/2M ammonia in methanol over 33 min; 80:20 DCM/2M ammonia in methanol over 33 min; 35 mL/min) to afford 6-(5-amino-[1,2,4]thiadiazol-3-ylthiomethyl)-7-chloro-2,3,4,5-tetrahydro-1H-benzo[d]azepine (0.102 g, 72%). MS (ES+) m/z: 327.1 (M+H)$^+$.

Add succinic acid (0.035 g, 0.299 mmol) to a mixture of 6-(5-amino-[1,2,4]thiadiazol-3-ylthiomethyl)-7-chloro-2,3,4,5-tetrahydro-1H-benzo[d]azepine (0.098 g, 0.299 mmol) in absolute ethanol (5 mL), DCM (5 mL) and methanol (2 mL) at room temperature. Concentrate the reaction mixture in vacuo. Combine the residue with methanol (5 mL) and DCM (5 mL) and concentrate in vacuo. Combine the residue with MTBE (5 mL) and concentrate three times to afford a white solid. Dry under high vacuum at room temperature overnight to afford the title compound (0.133 g, 100%) as a white solid. MS (ES+) m/z: 327.0 (M+H)$^+$.

Example 47

7-Chloro-6-(2-methyl-3H-imidazol-4-ylthiomethyl)-2,3,4,5-tetrahydro-1H-benzo[d]azepine (L)-Tartrate

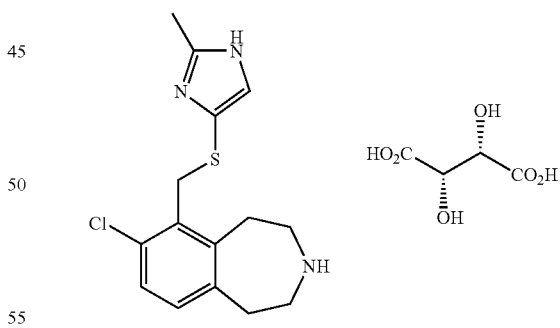

Add lithium hydroxide hydrate (42 mg, 1 mmol) to a stirred solution of 4-acetylsulfanyl-1-tert-butoxycarbonyl-2-methyl-imidazole (290 mg, 1.13 mmol) and 6-bromomethyl-3-tert-butoxycarbonyl-7-chloro-2,3,4,5-tetrahydro-1H-benzo[d]azepine (368 mg, 0.98 mmol) in methanol (12 mL) and stir the resulting mixture for 30 min. Partition the mixture between EtOAc and water and extract the aqueous phase three times with EtOAc. Dry the combined organic extracts over MgSO$_4$, filter, and concentrate in vacuo. Purify the crude mixture by chromatography on silica gel (40 g) eluting with hexane/EtOAc [100:0 (5 min), 19:1 (5 min), 85:15 (5 min), 4:1; flow rate: 50 mL/min] to give 3-tert-butoxycarbonyl-7-chloro-6-(2-methyl-3H-imidazol-4-ylthiomethyl)-2,3,4,5-tetrahydro-1H-benzo[d]azepine (310 mg, 54%). MS (ES+) m/z: 508 (M+H)$^+$.

Dissolve 3-tert-butoxycarbonyl-7-chloro-6-(2-methyl-3H-imidazol-4-ylthiomethyl)-2,3,4,5-tetrahydro-1H-benzo[d]azepine (306 mg, 0.602 mmol) in methanol (20 mL) and bubble the resulting solution with hydrogen chloride gas for 5 min. Cap the flask and stir at room temperature overnight. Concentrate the mixture in vacuo. Purify the crude product by chromatography on silica gel (40 g) eluting with a step gradient of DCM/(chloroform:methanol:concentrated NH$_4$OH) [100:0 (5 min), 19:1 (5 min), 9:1 (5 min), 4:1 (5 min), 3:2 (5 min), 1:1; flow rate: 28 mL/min] to provide 7-chloro-6-(2-methyl-3H-imidazol-4-ylthiomethyl)-2,3,4,5-tetrahydro-1H-benzo[d]azepine (193 mg, 100%). MS (ES+) m/z: 308 (M+H)$^+$.

Dissolve 7-chloro-6-(2-methyl-3H-imidazol-4-ylthiomethyl)-2,3,4,5-tetrahydro-1H-benzo[d]azepine (193 mg, 0.63 mmol) in methanol (12 mL) and water (1 mL) and add L-(+)-tartaric acid (94 mg, 0.63 mmol). Stir the mixture for 1 h and concentrate the mixture in vacuo. Dissolve in water, and freeze dry the solution to provide the title compound (32 mg, 100%). MS (APCI) m/z: 308 (M+H)$^+$.

Example 48

7-Chloro-6-{4-[2-(cyclopropylmethyl-amino)-thiazol-4-yl]-phenylthiomethyl}-2,3,4,5-tetrahydro-1H-benzo[d]azepine Succinate

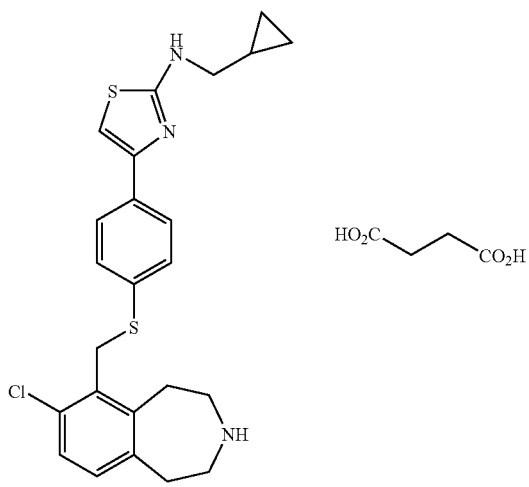

To a solution of 3-tert-butoxycarbonyl-7-chloro-6-mercaptomethyl-2,3,4,5-tetrahydro-1H-benzo[d]azepine (0.051 g, 0.155 mmol) in dry dioxane (0.7 mL) add N-[4-(4-bromophenyl)-thiazol-2-yl]-cyclopropylmethylamine (0.043 g, 0.14 mmol), tris(dibenzylideneacetone)dipalladium(0) (3.2 mg, 0.0035 mmol), Xantphos (4.1 mg, 0.014 mmol) and diisopropylethylamine (0.049 mL, 0.28 mmol) at room temperature. Purge the reaction mixture with nitrogen and heat the mixture at 100° C. overnight. Cool the reaction mixture to room temperature, dilute with DCM (50 mL) and filter through Celite®. Concentrate the filtrate in vacuo. Dissolve the residue in DCM, load the solution on to a RediSep® column (40 g) and purify the crude mixture by preparative liquid chromatography (0:100 to 25:75 EtOAc/hexane over 33 min; 35 mL/min) to afford 3-tert-butoxycarbonyl-7-chloro-6-{4-[2-(cyclopropylmethyl-amino)-thiazol-4-yl]-phenylthiomethyl}-2,3,4,5-tetrahydro-1H-benzo[d]azepine (0.076 g, 97%) as a colorless oil.

To a solution of 3-tert-butoxycarbonyl-7-chloro-6-{4-[2-(cyclopropylmethyl-amino)-thiazol-4-yl]-phenylthiomethyl}-2,3,4,5-tetrahydro-1H-benzo[d]azepine (0.305 g, 0.548 mmol) in dry DCM (12.6 mL) at room temperature add trifluoroacetic acid (12.6 mL) and stir the solution at room temperature overnight. Concentrate in vacuo and elute the residue through a SCX column (20 g). Dissolve the residue in DCM, load the solution on to a RediSep® column (40 g) and purify the crude mixture by preparative liquid chromatography (100:0 to 95:5 DCM/2M ammonia in methanol over 33 min; 95:5 to 90:10 DCM/2M ammonia in methanol over 33 min; 35 mL/min) to afford 7-chloro-6-{4-[2-(cyclopropylmethyl-amino)-thiazol-4-yl]-phenylthiomethyl}-2,3,4,5-tetrahydro-1H-benzo[d]azepine (0.215 g, 86%) as an off-white foam.

Add succinic acid (0.053 g, 0.453 mmol) to a mixture of 7-chloro-6-{4-[2-(cyclopropylmethyl-amino)-thiazol-4-yl]-phenylthiomethyl}-2,3,4,5-tetrahydro-1H-benzo[d]azepine (0.207 g, 0.452 mmol) in absolute ethanol (10 mL) at room temperature and stir for 1 h. Concentrate the reaction mixture in vacuo. Combine the residue with MTBE (5 mL) and concentrate three times to afford a pale yellow foam. Dry under high vacuum at room temperature overnight to obtain the title compound (0.259 g, 99%) as a pale yellow foam. MS (ES+) m/z: 456.0 (M+H)$^+$.

Example 49

7-Chloro-6-{5-[2-(cyclopropylmethyl-amino)-thiazol-4-yl]-pyridin-2-ylthiomethyl}-2,3,4,5-tetrahydro-1H-benzo[d]azepine Succinate

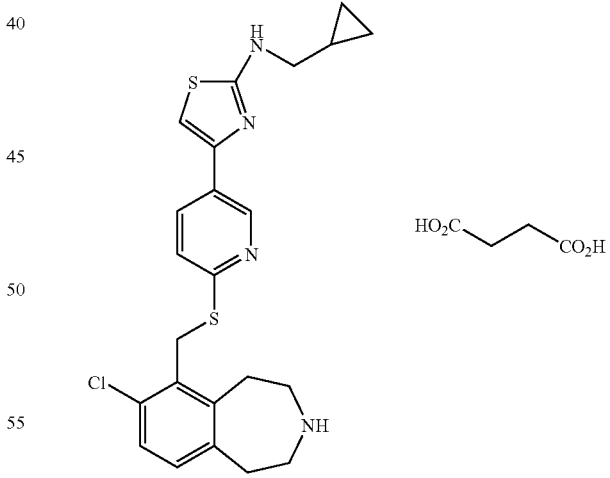

To a solution of 3-tert-butoxycarbonyl-7-chloro-6-mercaptomethyl-2,3,4,5-tetrahydro-1H-benzo[d]azepine (0.078 g, 0.239 mmol) in anhydrous dioxane (1.1 mL), add N-[4-(6-bromo-pyridin-3-yl)-thiazol-2-yl]-cyclopropylmethylamine (0.067 g, 0.218 mmol), tris(dibenzylideneacetone)dipalladium(0) (5 mg, 0.0055 mmol), Xantphos (6.3 mg, 0.011 mmol) and diisopropylethylamine (0.076 mL, 0.44 mmol) at room temperature. Purge the reaction mixture with nitrogen and heat the mixture at 100° C. overnight. Cool the reaction mixture to room temperature. Dilute with DCM (50 mL) and filter through Celite®. Concentrate the filtrate in vacuo. Dissolve the residue in DCM, load the solution on to a RediSep® column (40 g) and purify the crude mixture by preparative liquid chromatography (0:100 to 25:75 EtOAc/hexane over 33 min; 35 mL/min) to afford 3-tert-butoxycarbonyl-7-chloro-6-{5-[2-(cyclopropylmethyl-amino)-thiazol-4-yl]-pyridin-2-ylthiomethyl}-2,3,4,5-tetrahydro-1H-benzo[d]azepine (0.113 g, 94%) as a pale yellow foam. MS (ES+) m/z: 557.2 (M+H)$^+$.

To a solution of 3-tert-butoxycarbonyl-7-chloro-6-{5-[2-(cyclopropylmethyl-amino)-thiazol-4-yl]-pyridin-2-ylthiomethyl}-2,3,4,5-tetrahydro-1H-benzo[d]azepine (0.386 g, 0.693 mmol) in anhydrous DCM (16 mL) at room temperature add trifluoroacetic acid (15.9 mL) and stir the solution at room temperature overnight. Concentrate in vacuo and elute the residue through a SCX column (20 g). Dissolve the residue in DCM, load the solution on to a RediSep° column (40 g) and purify the crude mixture by preparative liquid chromatography (100:0 to 95:5 DCM/2M ammonia in methanol over 33 min; 95:5 to 90:10 DCM/2M ammonia in methanol over 33 min; 35 mL/min) to afford 7-chloro-6-{5-[2-(cyclopropylmethyl-amino)-thiazol-4-yl]-pyridin-2-ylthiomethyl}-2,3,4,5-tetrahydro-1H-benzo[d]azepine (0.315 g, 99%). MS (ES+) m/z: 457.1 (M+H)$^+$.

Add succinic acid (0.073 g, 0.619 mmol) to a mixture of 7-chloro-6-{5-[2-(cyclopropylmethyl-amino)-thiazol-4-yl]-pyridin-2-ylthiomethyl}-2,3,4,5-tetrahydro-1H-benzo[d]azepine (0.282 g, 0.618 mmol) in methanol (5 mL) at room temperature. Concentrate the reaction mixture in vacuo. Combine the residue with MTBE (5 mL) and concentrate three times to afford a pale yellow foam. Dry under high vacuum at room temperature overnight to obtain the title compound (0.348 g, 98%) as a pale yellow foam. MS (ES+) m/z: 457.0 (M+H)$^+$.

The compounds of the present invention are relatively selective for the 5-HT$_{2C}$ receptor. The compounds of the present invention are particularly relatively selective for the 5-HT$_{2C}$ receptor in comparison to other 5-HT receptor subtypes and specifically the 5-HT$_{2A}$ and 5-HT$_{2B}$ receptors. This selectivity is demonstrated in the following agonist activity assays and receptor binding assays.

Agonist Activity Assays (G Alpha g-GTPγ[$^{35}$S] Binding Assays)

The 5-HT$_2$ receptors are functionally coupled to specific G-proteins. Agonist activation of 5-HT$_2$ G-protein-coupled receptors results in the release of GDP from the α-subunit (G alpha q or G alpha i) of the G-protein and the subsequent binding of GTP. The binding of the stable analog GTPγ[$^{35}$S] is an indicator of receptor activation (i.e. agonist activity).

The G alpha q-GTPγ[$^{35}$S] binding assay is used to determine the in vitro potency (EC$_{50}$) and maximal efficacy (E$_{max}$, normalized to the 5-HT response) of a test compound at the 5-HT$_{2A}$, 5-HT$_{2B}$, and 5-HT$_{2C}$ receptors. The area under the dose response curve (AUC) is also determined for each receptor subtype and used to measure the test compound's selectivity for the 5-HT$_{2C}$ receptor over the 5-HT$_{2A}$ and 5-HT$_{2B}$ receptors, expressed as Selectivity Ratios (AUC 2C/2A and AUC 2C/2B, respectively). The Selectivity Ratios allow the assessment of selectivity based on both potency and efficacy. A selectivity measure that incorporates both potency and efficacy at the 5-HT$_{2C}$ receptor, as compared to the 5-HT$_{2A}$ and 5-HT$_{2B}$ receptors, is considered important due to the adverse events associated with 5-HT$_{2A}$ and 5-HT$_{2B}$ agonist activity (see introduction).

Membrane Preparation: Grow AV12 cells stably transfected with the human 5-HT$_{2A}$, 5-HT$_{2B}$, or 5-HT$_{2C}$ receptors in suspension, harvest by centrifugation, wash the cell pellet with phosphate buffered saline, pH 7.4, pellet the cells again, remove the supernatant, freeze the cell pellet on dry ice and store at −70° C. Thaw stock cell pellet and resuspend in 50 mM Tris, pH 7.4, aliquot into 1-2 mL volumes and refreeze at −70° C. for subsequent assays. (As is appreciated in the art, optimal cell quantities used per aliquot will vary with the individual transfected cell line used. In one embodiment, 5-HT$_{2A}$ and 5-HT$_{2C}$ transfected cells are typically used at about 6×10$^8$ cells per aliquot, while 5-HT$_{2B}$ cells are typically used at about 7.5×10$^8$ cells per aliquot).

On the day of assay, thaw membranes, wash the membranes with assay buffer (50 mM Tris-HCl (pH 7.4), 10 mM MgCl$_2$, 100 mM NaCl, and 0.2 mM EDTA), resuspend in assay buffer and incubate for 10 min. at 37° C. to hydrolyze any residual endogenous 5-HT. Wash the membranes again with assay buffer, and resuspend in assay buffer at a concentration to provide aliquots of about 1-4×10$^6$ cell equivalents per well (typically about 1-2×10$^6$ cell equivalents for assays with 5-HT$_{2A}$ or 5-HT$_{2C}$ receptor assays, and about 3-4×10$^6$ cell equivalents for assays with 5-HT$_{2B}$ receptor assays). Homogenize the cells with a tissue grinder and use the homogenate directly in the assay as described below.

G alpha q-GTPγ[$^{35}$] Binding Assays: The immunoadsorption scintillation proximity assay (ISPA) of [$^{35}$S]-GTPγS binding to G alpha q is modified from published conditions (DeLapp et al, JPET 289 (1999) 946-955). Dissolve test compounds in DMSO and dilute in assay buffer to provide a range of concentrations to generate a concentration response curve. In wells of a 96 well microtiter plate, mix diluted test compound, GDP (0.1 µM final concentration), and [$^{35}$S]-GTPγS (between 0.5 and 1.0 nM final concentration). Add an aliquot of membranes to the incubation mixture and mix the plates to initiate agonist stimulation of the nucleotide exchange (200 µl final volume). Incubate the microtiter plates for 30 min. at room temperature. Quench the incubation with IGEPAL® CA-630 detergent (0.27% final concentration). Add affinity purified polyclonal rabbit anti-G alpha q antibody (about 1-2 mg per well), and anti-rabbit Ig scintillation proximity assay beads (Amersham; about 1.25 mg per well; 300 µl final volume). Seal the plates and incubate the mixture for 3 h at room temperature. Centrifuge the microtiter plates briefly to pellet beads. Quantitate the GTPγ[$^{35}$S] binding by microtiter plate scintillation spectrometry (Wallac Trilux MicroBeta™ scintillation counter).

Data Analysis: For each concentration response curve for a test compound at a given receptor, analyze the data with GraphPad Prism™ software (v3.02; GraphPad Software, San Diego, Calif.) running on a personal computer with MicroSoft Windows OS®, using nonlinear regression analysis curve fitting to determine the EC$_{50}$ and E$_{max}$ (normalized to 5-HT control curves). Determine the Area Under the agonist concentration-response Curve (AUC) with GraphPad Prism™ by the trapezoidal method.

To calculate the Selectivity Ratios, first, determine the AUC for the test compound for each receptor subtype as described above. Second, normalize the AUC's at each receptor subtype relative to the AUC determined for 5-HT at that receptor. The normalized AUC for a test compound at a given receptor is therefore expressed as a percentage of the AUC determined for 5-HT at that receptor. For example:

$$5HT_{2A}\text{Normalized } AUC = a = \frac{\left(\begin{array}{c} AUC_{test\ compound}\ \text{at} \\ 5HT_{2A}\ \text{receptor} \end{array}\right)}{\left(AUC_{5\text{-}HT}\ \text{at } 5HT_{2A}\ \text{receptor}\right)} \times 100\%$$

$$5HT_{2B}\text{Normalized } AUC = b = \frac{\left(\begin{array}{c} AUC_{test\ compound}\ \text{at} \\ 5HT_{2B}\ \text{receptor} \end{array}\right)}{\left(AUC_{5\text{-}HT}\ \text{at } 5HT_{2B}\ \text{receptor}\right)} \times 100\%$$

$$5HT_{2C}\text{Normalized } AUC = c = \frac{\left(\begin{array}{c} AUC_{test\ compound}\ \text{at} \\ 5HT_{2C}\ \text{receptor} \end{array}\right)}{\left(AUC_{5\text{-}HT}\ \text{at } 5HT_{2C}\ \text{receptor}\right)} \times 100\%$$

Third, calculate the Selectivity Ratios for the test compound as follows:

Selectivity Ratio for $5\text{-}HT_{2C}$ receptor/$5\text{-}HT_{2A}$ receptor (AUC 2C/2A)=c/a Selectivity Ratio for $5\text{-}HT_{2C}$ receptor/$5\text{-}HT_{2B}$ receptor (AUC 2C/2B)=c/b For reference purposes, the AUC 2C/2A and AUC 2C/2B for 5-HT are each 1.0. Likewise, the ratios for mCPP (meta-chlorophenylpiperazine) are tested and are found to be 2.1 and 2.1 respectively.

Representative compounds of the present invention are tested in the G alpha q-GTPγ[$^{35}$S] assays for the $5\text{-}HT_{2A}$, $5\text{-}HT_{2B}$, and $5\text{-}HT_{2C}$ receptors essentially as described above and are found to be a highly potent and selective agonists of the $5\text{-}HT_{2C}$ receptor, with $EC_{50}$'s typically less than or equal to 250 nM, and AUC 2C/2A and AUC 2C/2B ratios typically greater than 1.5. Preferred compounds are those with EC50's less than or equal to 100 nM, and AUC 2C/2A and AUC 2C/2B ratios greater than or equal to 2.0. More preferred are those with EC50's less than or equal to 50 nM, and AUC 2C/2A and AUC 2C/2B ratios greater than or equal to 3.0.

Ligand Binding Assays

The ligand binding affinity of the compounds of the present invention to the $5\text{-}HT_{2C}$ receptor subtype is measured essentially as described by Wainscott (Wainscott, et al., *Journal of Pharmacology and Experimental Therapeutics*, 276:720-727 (1996)). Data is analyzed by nonlinear regression analysis on the concentration response curves using the four parameter logistic equation described by DeLean (DeLean, et al, *Molecular Pharmacology*, 21, 5-16 (1982)). $IC_{50}$ values are converted to $K_i$ values using the Cheng-Prusoff equation (Cheng, et al., *Biochem. Pharmacol.*, 22, 3099-3108 (1973)).

Representative compounds of the present invention are tested essentially as described above and are found to have excellent affinity for the $5\text{-}HT_{2C}$ receptor, with $K_i$'s typically less than or equal to about 250 nM. Preferred compounds are those with $K_i$'s of less than or equal to about 100 nM. More preferred are those with $K_i$'s less than or equal to 50 nM.

Affinities for other receptor subtypes can readily be determined by slight modification of the above described radioligand receptor binding assay using cells transfected with the desired receptor in place of cells transfected with the $5\text{-}HT_{2C}$ receptor subtype and using an appropriate radioligand. The binding affinities for representative compounds of the present invention for a variety of receptors are determined in such assays and the compounds are found to have surprisingly higher affinity for the $5\text{-}HT_{2C}$ receptor. Affinity for the $5\text{-}HT_{2C}$ receptor is found to be significantly higher than for other 5-HT receptor subtypes, and notably higher than the $5\text{-}HT_{2A}$ and $5\text{-}HT_{2B}$ receptor subtypes. Preferred compounds are those with $IC_{50}$'s equal to or greater than 300 nM for the alpha 1 and alpha 2 adrenergic receptors and equal to or greater than 500 nM for $D_1$ and $D_2$ dopaminergic receptors. More preferred compounds are those with $IC_{50}$'s equal to or greater than 1000 nM for the alpha 1 and alpha 2 adrenergic receptors and the $D_1$ and $D_2$ dopaminergic receptors. Still more preferred are those compounds with $IC_{50}$'s equal to or greater than 3000 nM for the alpha 1 and alpha 2 adrenergic receptors and the $D_1$ and $D_2$ dopaminergic receptors.

For the above in vitro assays, exemplified compounds are assayed and found to have either an $EC_{50}$ or a $K_i$ value of equal to or less than 50 nM, and to have AUC 2C/2A and AUC 2C/2B ratios of greater than or equal to 2.0. Exemplified compounds are assayed and found to typically have alpha 1 and alpha 2 adrenergic receptor $IC_{50}$'s equal to or greater than 300 nM, and $D_1$ and $D_2$ dopaminergic receptor $IC_{50}$'s equal to or greater than 500 nM.

Rat Feeding Assays

The ability of the compounds of the present invention to treat obesity is demonstrated by testing in acute and chronic rat feeding assays.

Animals: Obtain male Long-Evans rats (Harlan Sprague-Dawley, Indianapolis, Ind.) that are approximately one hundred-days old and have been maintained on a calorie rich diet since weaning (TD 95217, 40% calories from fat; Teklad, Madison, Wis.). House the rats individually with a 12 h: 12 h light:dark cycle (lights on from about 22:00 h to about 10:00 h) and maintain rats on the same diet (TD 95217) with free access to water, for about 1-2 weeks to acclimate the rats to the environment. Dose rats orally with vehicle (10% acacia with 0.15% saccharin in water) once daily for at least 1 day (typically 1-2 days) to acclimate the rats to the procedures. Randomize the rats into groups so each group has similar mean body weights.

Calorimetric Acute Feeding Assay: At approximately 8:00 h on the day of assay, weigh each rat and transfer to individual chambers of an open circuit calorimetry system (Oxymax, Columbus Instruments International Corporation; Columbus, Ohio), with free access to food (pre-weighed) and water, and begin measuring $VO_2$ and $VCO_2$. At approximately 10:00 h, dose rats orally with vehicle or test compound, return them to their calorimetry chambers, and continue measuring $VO_2$ and $VCO_2$ at regular time intervals (approximately hourly). At approximately 8:00 h the following day, measure rat body weight and the remaining food, assuming the difference in weight of food is equal to the mass of food consumed. Calculate the 24 h energy expenditure (EE) and respiratory quotient (RQ) essentially as described in Chen, Y. and Heiman, M. L., Regulatory Peptide, 92:113-119 (2000). EE during light photoperiod is indicative of the resting metabolic rate and RQ is indicative of the fuel source the animal utilizes (pure carbohydrate metabolism gives an RQ of about 1.0, pure fat metabolism gives an RQ of about 0.7, mixed carbohydrate and fat metabolism gives intermediate values for RQ). Calculate EE as the product of calorific value (CV) and $VO_2$ per body weight (kg); where CV=3.815+1.232*RQ, and RQ is the ratio of $CO_2$ produced ($VCO_2$) to $O_2$ consumed ($VO_2$). Caloric intake is calculated as (mass of 24 h food intake in grams)×(physiological fuel value of the diet in kilocalorie/g) per kg of body weight.

Acute Feeding Assay with a selective $5\text{-}HT_{2C}$ receptor antagonist: The above calorimetric acute feeding assay is conducted with the following modifications. Open circuit calorimetry systems are not used and only the 24 h periodic food intake and body weight are measured. Three groups of rats are used with the first group receiving a subcutaneous dose of saline (0.5 mL) about 15 minutes prior to the oral dose of vehicle, the second group receiving a subcutaneous dose of saline (0.5 mL) about 15 minutes prior to the oral dose of test compound in vehicle, and the third group receiving a subcutaneous injection of a selective $5\text{-HT}_{2C}$ receptor antagonist, 6-chloro-5-methyl-N-{2-[(2-methylpyridin-3-yl-oxy)pyridin-5-yl]aminocarbonyl}-2,3-dihydroindole (3 mg/Kg, in 35% cyclodextrin, 0.5 mL), about 15 min. prior to the oral dose of test compound in vehicle.

Chronic Feeding Assay: At between approximately 8:00 h and 10:00 h on day one of the assay, weigh and orally dose each rat with vehicle or test compound and return the animal to its home cage, with free access to food (pre-weighed) and water. For each of days 2-15, at between approximately 8:00 h and 10:00 h, measure rat body weight and the weight of food consumed in the last 24 h period, and administer daily oral dose of test compound or vehicle. On days –2 and 15 measure total fat mass and lean mass by nuclear magnetic resonance (NMR) using an EchoMRI™ system (Echo Medical Systems, Houston Tex.). (See Frank C. Tinsley, Gersh Z. Taicher, and Mark L. Heiman, "Evaluation of a New Quantitative Magnetic Resonance (QMR) Method for Mouse Whole Body Composition Analysis", Obesity Research, submitted May 1, 2003.)

Representative compounds of the present invention are tested in acute and chronic feeding assays essentially as described above. In the acute assays, the compounds are found to significantly reduce 24 h food intake, which effect is blocked by pre-administration of the $5\text{-HT}_{2C}$ receptor antagonist. The compounds also are found to dose-dependently reduce RQ without significantly changing the energy expenditure during the light photo-period. Thus the compounds are found to reduce caloric intake and increase the proportion of fuel deriving from fat utilization, without significantly changing the resting metabolic rate. In the chronic assay, the compounds are found to significantly decrease cumulative food intake and cumulative body weight change in a dose-dependent manner compared to control animals. The decrease in body weight is found to be due to loss of adipose tissue while lean body mass is not changed.

The ability of the $5\text{-HT}_{2C}$ receptor agonists of the present invention to treat obsessive/compulsive disorder is demonstrated by testing in a variety of in vivo assays as follows:

Marble Burying Assay

Marble burying in mice has been used to model anxiety disorders including obsessive-compulsive disorders (OCD) due to ethological study of the behavior (e.g. Gyertyan I. "Analysis of the marble burying response: Marbles serve to measure digging rather than evoke burying", *Behavioural Pharmacology* 6: 24-31, (1995)) and due to the pharmacological effects of clinical standards (c.f., Njung'E K. Handley S L. "Evaluation of marble-burying behavior as a model of anxiety", *Pharmacology, Biochemistry & Behavior.* 38: 63-67, (1991)); Borsini F., Podhorna J., and Marazziti, D. "Do animal models of anxiety predict anxiolytic effects of antidepressants?", *Psychopharmacology* 163: 121-141, (2002)). Thus, drugs used in the treatment of generalized anxiety in humans (e.g. benzodiazepines) as well as compounds used to treat OCD (e.g. SSRIs like fluoxetine) decrease burying.

House experimentally-naïve male, NIH Swiss mice (Harlan Sprague-Dawley, Indianapolis, Ind.) weighing between 28-35 g in groups of 12 for at least three days prior to testing in a vivarium with 12 h light and dark cycles. Conduct experiments during the light cycle in a dimly lit experimental testing room. Dose mice with vehicle or test compound and, after a specified pretreatment interval (generally 30 min.), place each mouse individually on a rotorod (Ugo Basile 7650) operating at a speed of 6 revolutions/min. and observe for falling. After 2 min. on the rotorod, place the mice individually in a 17×28×12 cm high plastic tub with 5 mm sawdust shavings on the floor that are covered with 20 blue marbles (1.5 cm diameter) placed in the center. After 30 min., count the number of marbles buried (⅔ covered with sawdust). Assess the test compound's effect on marble burying with Dunnett's test and the effect on rotorod performance by Fisher's exact test.

Clinically effective standard compounds suppress marble burying at doses that are devoid of motor-impairing effects as measured on the rotorod. The in vivo efficacy of $5\text{HT}_{2C}$ compounds at the $5\text{HT}_{2C}$ receptor is confirmed by the prevention of effects of the $5\text{HT}_{2C}$ agonists on marble burying by co-administration of the $5\text{HT}_{2C}$ receptor antagonist, 6-chloro-5-methyl-N-{2-[(2-methylpyridin-3-yl-oxy)pyridin-5-yl]aminocarbonyl}-2,3-dihydroindole.

Representative compounds of the present invention are assayed in the marble burying assay essentially as described and are surprisingly found to reduce burying behavior in the test mice. The reduction of burying behavior is found to be blocked by co-administration of the $5\text{-HT}_{2C}$ antagonist. In contrast to the compounds of the present invention, the anxiolytic compound chlordiazepoxide and the antipsychotic compound chlorpromazine decrease marble burying only at doses that also disrupt rotorod performance.

Nestlet Shredding

Mice naturally will construct nests of material available in their living environment. Since this behavior is obsessive in nature, it has been used to model OCD (Xia Li, Denise Morrow and Jeffrey M. Witkin, "Decreases in nestlet shredding of mice by serotonin uptake inhibitors: comparison with marble burying", Psychopharmacology, submitted Jul. 14, 2003). House experimentally-naïve male, NIH Swiss mice (Harlan Sprague-Dawley, Indianapolis, Ind.) weighing between 28-35 g in groups of 12 for at least three days prior to testing in a vivarium with a 12 h light/dark cycle. Conduct experiments during the light cycle in an experimental room with normal overhead fluorescent lighting. Dose mice with vehicle or test compound and after a specified pretreatment interval (generally 30 min.), place the mice individually in a 17×28×12 cm high plastic tub with about 5 mm sawdust shavings on the floor along with a pre-weighed multi-ply gauze pad (51 mm square). After 30 min., weigh the remainder of the gauze pad not removed by the mouse. Determine the weight of the gauze used for nestlet construction by subtraction. Compare the results for test compound treated mice to the results for vehicle control treated mice with Dunnett's test.

Clinically effective OCD treatment standard compounds suppress nestlet shredding at doses that are devoid of motor-impairing effects as measured by the rotorod test. The in vivo efficacy of $5\text{HT}_2\text{C}$ compounds at the $5\text{HT}_{2C}$ receptor is confirmed by the prevention of effects of the $5\text{HT}_{2C}$ agonists on nestlet shredding by co-administration of the $5\text{HT}_{2C}$ receptor antagonist, 6-chloro-5-methyl-N-{2-[(2-methylpyridin-3-yl-oxy)pyridin-5-yl]aminocarbonyl}-2,3-dihydroindole.

Representative compounds of the present invention are assayed essentially as described above and are surprisingly found to suppress nestlet shredding at doses that are devoid of motor-impairing effects as measured by the rotorod test.

In contrast to the compounds of the present invention, the anxiolytic chlordiazepoxide and the psychomotor stimulant d-amphetamine decreases nestlet shredding only at doses that produce motoric side effects (depression or stimulation, respectively).

Schedule-Induced Polydipsia

Food-deprived rats exposed to intermittent presentations of food will drink amounts of water that are far in excess of their normal daily intake and in excess of their intake when given all of their food at one time (Falk J L. "Production of polydipsia in normal rats by an intermittent food schedule", *Science* 133: 195-196, (1961)). This excessive behavior is persistent and has been used to model OCD.

Maintain Wistar rats on a food restricted diet (to maintain 85% free feeding weight), but with free access to water. Train the rats in a behavioral testing chamber to press a lever to receive a food pellet under a fixed interval schedule, such that the rats are rewarded with a 45 mg food pellet the first time they press a lever after a 120 second interval has elapsed. The fixed interval is then reset to 120 seconds and the process repeated. Thus, during a 90 min. test session, the rats can earn a maximum of 45 pellets. The behavioral chamber is also equipped with a water bottle that is weighed before and after the session to determine the amount of water consumed.

Administer test compounds on Tuesdays and Fridays. Determine control day performances on Thursdays. Administer compounds either orally at 60 min. before the beginning of a test session, or subcutaneously at 20 min. before the beginning of a test session. Compare the rates of lever pressing and water consumption for each animal's performance during sessions after test compound treatment with that animal's performance during control sessions, expressed as a percent of the control rate. Average the individual percent of control rates for each dose and calculate the standard error of the mean.

Clinically effective OCD treatment standard compounds (e.g. chlomipramine, fluoxetine) suppress schedule-induced polydipsia without producing notable changes in motor patterns, food intake, or behavior the following day. The in vivo efficacy of $5HT_{2C}$ compounds at the $5HT_{2C}$ receptor is confirmed by the prevention of effects of the $5HT_{2C}$ agonists on excessive drinking by co-administration of the $5HT_{2C}$ receptor antagonist, 6-chloro-5-methyl-N-{2-[(2-methylpyridin-3-yl-oxy)pyridin-5-yl]aminocarbonyl}-2,3-dihydroindole.

Representative compounds of the present invention are assayed in the schedule-induced polydipsia assay essentially as described above and are surprisingly found to suppress schedule-induced polydipsia without producing notable changes in motor patterns, food intake, or behavior the following day. The behavior suppression is blocked by co-administration of the $5\text{-HT}_{2C}$ antagonist.

In contrast to the compounds of the present invention, the psychomotor stimulant d-amphetamine decreases excessive drinking only at behaviorally stimulating doses and these effects are not prevented by the $5HT_{2C}$ receptor antagonist.

While it is possible to administer compounds employed in the methods of this invention directly without any formulation, the compounds are usually administered in the form of pharmaceutical compositions comprising a pharmaceutically acceptable excipient and at least one compound of Formula I or a pharmaceutically acceptable salt thereof. These compositions can be administered by a variety of routes including oral, rectal, transdermal, subcutaneous, intravenous, intramuscular, and intranasal. The compounds employed in the methods of this invention are effective as both injectable and oral compositions. Such compositions are prepared in a manner well known in the pharmaceutical art. See, e.g. REMINGTON'S PHARMACEUTICAL SCIENCES, (16th ed. 1980).

In making the compositions employed in the present invention the active ingredient is usually mixed with at least one excipient, diluted by at least one excipient, or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The compounds are generally effective over a wide dosage range. For examples, dosages per day normally fall within the range of about 0.01 to about 30 mg/kg. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat.

No. 5,023,252, issued Jun. 11, 1991, herein incorporated by reference. Such patches may be constructed for continuous, pulsatile, or on demand delivery of pharmaceutical agents.

Under some circumstances, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compound employed, the type of pharmacokinetic profile desired from the route of administration, and the state of the patient.

We claim:
1. A compound of Formula I:

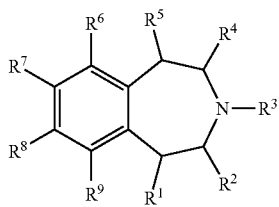

I where:
$R^1$ is hydrogen;
$R^2$, $R^3$, and $R^4$ are each hydrogen;
$R^5$ is hydrogen;
$R^6$ is —$(C_1$-$C_3)$alkyl-S—$(C_0$-$C_3)$alkyl-$R^{10}$, —$(C_1$-$C_3)$alkyl-$NR^{12}$—$(C_0$-$C_3)$alkyl-$R^{11}$, or —$(C_1$-$C_3)$alkyl-O—$(C_0$-$C_3)$alkyl-$R^{13}$;
$R^7$ is chloro;
$R^8$ is hydrogen;
$R^9$ is hydrogen;
$R^{10}$ is
  a) an aromatic heterocycle substituent selected from the group consisting of tetrazolyl, 1,2,3-thiadiazolyl, 1,3,4-thiadiazolyl, 1,2,4-thiadiazolyl, 1,2,3-oxadiazolyl, 1,3,4-oxadiazolyl, and 1,2,4-oxadiazolyl, any one of which may optionally be substituted with a substituent selected from the group consisting of $(C_1$-$C_4)$alkyl optionally substituted with 1 to 5 fluoro substituents, $Ph^1$-$(C_0$-$C_3)$alkyl, $Ar^1$—$(C_0$-$C_3)$alkyl, $(C_1$-$C_4)$alkyl-C(O)—, $Ph^1$-$(C_0$-$C_3)$alkyl-C(O)—, $Ar^1$—$(C_0$-$C_3)$alkyl-C(O)—, $(C_1$-$C_4)$alkyl-$NR^{12}$—$(C_0$-$C_3)$alkyl- optionally substituted on the on the and $(C_1$-$C_4)$alkyl moiety with 1 to 5 fluoro substituents, $(C_3$-$C_7)$cycloalkyl-$(C_0$-$C_3)$alkyl-$NR^{12}$—$(C_0$-$C_3)$alkyl, $Ph^1$-$(C_0$-$C_3)$alkyl-$NR^{12}$—$(C_0$-$C_3)$alkyl, $Ar^1$—$(C_0$-$C_3)$alkyl-$NR^{12}$—$(C_0$-$C_3)$alkyl;

b) an aromatic heterocycle substituent selected from the group consisting of imidazolyl, thiazolyl, isothiazolyl, thiophenyl, pyrazolyl, oxazolyl, isoxazolyl, 1,2,3-triazolyl, 1,2,4-triazolyl, or a heterocycle selected from thiazolinyl, any one of which may be optionally substituted with one to two substituents selected from the group consisting of
  $(C_1$-$C_6)$alkyl optionally substituted with 1 to 6 fluoro substituents,
  $Ph^1$-$(C_0$-$C_3)$alkyl optionally substituted on the alkyl moiety with 1 to 6 fluoro substituents,
  $Ar^1$—$(C_0$-$C_3)$alkyl optionally substituted on the alkyl moiety with 1 to 6 fluoro substituents,
  $(C_1$-$C_6)$alkyl-C(O)—,
  $Ph^1$-$(C_0$-$C_3)$alkyl-C(O)—,
  $Ar^1$—$(C_0$-$C_3)$alkyl-C(O)—,
  $(C_1$-$C_6)$alkyl-NH—C(O)— optionally substituted with 1 to 6 fluoro substituents,
  $Ph^1$-$(C_0$-$C_3)$alkyl-NH—C(O)— optionally substituted on the alkyl moiety with 1 to 6 fluoro substituents, and
  $Ar^1$—$(C_0$-$C_3)$alkyl-NH—C(O)— optionally substituted on the alkyl moiety with 1 to 6 fluoro substituents,
  or optionally substituted on ring carbon atoms with one or two substituents selected from the group consisting of
  halo,
  cyano,
  $(C_1$-$C_6)$alkyl-CH=CH— optionally substituted with 1 to 6 fluoro substituents,
  $(C_1$-$C_6)$alkoxy optionally substituted with 1 to 6 fluoro substituents,
  $(C_1$-$C_6)$alkylthio optionally substituted with 1 to 6 fluoro substituents,
  $Ph^1$-$(C_0$-$C_3)$alkylthio,
  $(C_1$-$C_6)$alkyl-$NR^{12}$—$(C_0$-$C_3)$alkyl- optionally substituted on the $(C_1$-$C_6)$alkyl moiety with 1 to 6 fluoro substituents,
  $(C_3$-$C_7)$cycloalkyl-$(C_0$-$C_3)$alkyl-$NR^{12}$—$(C_0$-$C_3)$alkyl,
  $Ph^1$-$(C_0$-$C_3)$alkyl-$NR^{12}$—$(C_0$-$C_3)$alkyl-,
  $Ar^1$—$(C_0$-$C_3)$alkyl-$NR^{12}$—$(C_0$-$C_3)$alkyl-,
  $Het^1$-$(C_0$-$C_3)$alkyl-,
  $(C_1$-$C_6)$alkyl-C(O)—NH—,
  $Ph^1$-$(C_0$-$C_3)$alkyl-C(O)—NH—,
  $Ar^1$—$(C_0$-$C_3)$alkyl-C(O)—NH—,
  $(C_1$-$C_6)$alkyl-O—C(O)—NH— optionally substituted with 1 to 6 fluoro substituents,
  $Ph^1$-$(C_0$-$C_3)$alkyl-O—C(O)—NH— optionally substituted on the alkyl moiety with 1 to 6 fluoro substituents, and
  $Ar^1$—$(C_0$-$C_3)$alkyl-O—C(O)—NH— optionally substituted on the alkyl moiety with 1 to 6 fluoro substituents,
  or optionally substituted on two adjacent ring atoms with a bivalent 3 to 4 carbon hydrocarbon substituent which, together with the ring atoms to which it is attached, form a benzene ring or a partially saturated five- or six-membered ring;

c) phenyl optionally substituted with:
  i) 1 to 5 independently selected halo substituents; or
  ii) 1 to 3 substituents independently selected from the group consisting of halo, cyano, —$SCF_3$, nitro, hydroxy, $(C_1$-$C_6)$alkyl optionally further substituted with 1 to 6 fluoro substituents, and $(C_1-C_6)$ alkoxy optionally further substituted with 1 to 6 fluoro substituents; or iii) 0, 1, or 2 substituents independently selected from the group consisting of halo, cyano, —$SCF_3$, methyl, —$CF_3$, methoxy, —$OCF_3$, nitro, and hydroxy, together with one substituent selected from the group consisting of $(C_3-C_7)$cycloalkyl-$(C_0-C_5)$alkyl optionally substituted on the alkyl moiety with 1 to 6 fluoro substituents and optionally substituted independently on the cycloalkyl moiety with 1 to 6 substituents selected from fluoro and methyl provided that no more than 2 substituents are methyl, $Ph^1$-$(C_0-C_5)$alkyl, $Ar^1$—$(C_0-C_5)$alkyl, thiazolyl-$(C_0-C_1)$alkyl optionally substituted with a substituent independently selected from the group consisting of halo, $(C_1-C_6)$alkyl optionally further substituted with 1 to 6 fluoro substituents, $(C_1-C_6)$alkyl-$NR^{12}$—$(C_0-C_3)$alkyl- optionally substituted on the $(C_1-C_6)$alkyl moiety with 1 to 6 fluoro substituents, and $(C_3-C_7)$cycloalkyl-$(C_0-C_3)$alkyl-$NR^{12}$—$(C_0-C_3)$alkyl, $(C_1-C_6)$alkyl-CH=CH— optionally substituted with 1 to 6 fluoro substituents, $(C_3-C_7)$cycloalkyl-$(C_0-C_3)$alkyl-CH=CH— optionally substituted with 1 to 6 fluoro substituents on alkyl and optionally substituted independently on the cycloalkyl moiety with 1 to 6 substituents selected from fluoro and methyl provided that no more than 2 substituents are methyl, $(C_1-C_6)$alkyl-S—$(C_0-C_5)$alkyl optionally substituted on the $(C_1-C_6)$alkyl moiety with 1 to 6 fluoro substituents, $(C_3-C_7)$cycloalkyl-$(C_0-C_3)$alkyl-S—$(C_0-C_5)$alkyl, $Ph^1$-$(C_0-C_3)$alkyl-S—$(C_0-C_5)$alkyl, $Ar^1$—$(C_0-C_3)$alkyl-S—$(C_0-C_5)$alkyl, $(C_1-C_6)$alkyl-O—$(C_0-C_5)$alkyl optionally substituted on the $(C_1-C_6)$alkyl moiety with 1 to 6 fluoro substituents, $(C_3-C_7)$cycloalkyl-$(C_0-C_3)$alkyl-O—$(C_0-C_5)$alkyl, $Ph^1$-$(C_0-C_3)$alkyl-O—$(C_0-C_5)$alkyl, $Ar^1$—$(C_0-C_3)$alkyl-O—$(C_0-C_5)$alkyl, $(C_1-C_6)$alkyl-$SO_2$—$(C_0-C_5)$alkyl optionally substituted on the $(C_1-C_6)$alkyl moiety with 1 to 6 fluoro substituents, $(C_3-C_7)$cycloalkyl-$(C_0-C_3)$alkyl-$SO_2$—$(C_0-C_5)$alkyl, $Ph^1$-$(C_0-C_3)$alkyl-$SO_2$—$(C_0-C_5)$alkyl, $Ar^1$—$(C_0-C_3)$alkyl-$SO_2$—$(C_0-C_5)$alkyl, $(C_1-C_6)$alkyl-C(O)—$(C_0-C_5)$alkyl, $(C_3-C_7)$cycloalkyl-$(C_0-C_3)$alkyl-C(O)—$(C_0-C_5)$alkyl, $Ph^1$-$(C_0-C_3)$alkyl-C(O)—$(C_0-C_5)$alkyl, $Ar^1$—$(C_0-C_3)$alkyl-C(O)—$(C_0-C_5)$alkyl, $(C_1-C_6)$alkyl-NH—$(C_0-C_5)$alkyl optionally substituted on the $(C_1-C_6)$alkyl moiety with 1 to 6 fluoro substituents, $(C_3-C_7)$cycloalkyl-$(C_0-C_3)$alkyl-NH—$(C_0-C_5)$alkyl, $Ph^1$-$(C_0-C_3)$alkyl-NH—$(C_0-C_5)$alkyl, $Ar^1$—$(C_0-C_3)$alkyl-NH—$(C_0-C_5)$alkyl, $Het^1$-$(C_0-C_3)$alkyl-, $(C_1-C_6)$alkyl-NH—C(O)—$(C_0-C_5)$alkyl optionally substituted on the $(C_1-C_6)$alkyl moiety with 1 to 6 fluoro substituents, $(C_3-C_7)$cycloalkyl-$(C_0-C_3)$alkyl-NH—C(O)—$(C_0-C_5)$alkyl, $Ph^1$-$(C_0-C_3)$alkyl-NH—C(O)—$(C_0-C_5)$alkyl, $Ar^1$—$(C_0-C_3)$alkyl-NH—C(O)—$(C_0-C_5)$alkyl, $(C_1-C_6)$alkyl-$(C_0-C_3)$alkyl-C(O)—NH—$(C_0-C_5)$alkyl, $(C_3-C_7)$cycloalkyl-C(O)—NH—$(C_0-C_5)$alkyl, $Ph^1$-$(C_0-C_3)$alkyl-C(O)—NH—$(C_0-C_5)$alkyl, $Ar^1$—$(C_0-C_3)$alkyl-C(O)—NH—$(C_0-C_5)$alkyl, $(C_1-C_6)$alkyl-NH—$SO_2$—$(C_0-C_5)$alkyl optionally substituted on the $(C_1-C_6)$alkyl moiety with 1 to 6 fluoro substituents, $(C_3-C_7)$cycloalkyl-$(C_0-C_3)$alkyl-NH—$SO_2$—$(C_0-C_5)$alkyl, $(C_1-C_6)$alkyl-$SO_2$—NH—$(C_0-C_5)$alkyl, $(C_3-C_7)$cycloalkyl-$(C_0-C_3)$alkyl-$SO_2$—NH—$(C_0-C_5)$alkyl;

d) an aromatic heterocycle substituent selected from the group consisting of pyridyl, pyridazinyl, pyrimidinyl, pyrazinyl, any of which may be optionally substituted with 1 or 2 substituents independently selected from the group consisting of halo, cyano, —$SCF_3$, methyl, —$CF_3$, methoxy, —$OCF_3$, nitro, hydroxy, and optionally further substituted with a substituent selected from the group consisting of $(C_3-C_7)$cycloalkyl-$(C_0-C_5)$alkyl optionally further substituted on the alkyl moiety with 1 to 6 fluoro substituents and optionally substituted independently on the cycloalkyl moiety with 1 to 6 substituents selected from fluoro and methyl provided that no more than 2 substituents are methyl, $Ph^1$-$(C_0-C_5)$alkyl, $Ar^1$—$(C_0-C_5)$alkyl, thiazolyl-$(C_0-C_1)$alkyl optionally substituted with a substituent independently selected from the group consisting of halo, $(C_1-C_6)$alkyl optionally further substituted with 1 to 6 fluoro substituents, $(C_1-C_6)$alkyl-$NR^{12}$—$(C_0-C_3)$alkyl- optionally substituted on the $(C_1-C_6)$alkyl moiety with 1 to 6 fluoro substituents, and $(C_3-C_7)$cycloalkyl-$(C_0-C_3)$alkyl-$NR^{12}$—$(C_0-C_3)$alkyl, $(C_1-C_6)$alkyl-CH=CH— optionally substituted with 1 to 6 fluoro substituents, $(C_3-C_7)$cycloalkyl-$(C_0-C_3)$alkyl-CH=CH— optionally substituted with 1 to 6 fluoro substituents on alkyl and optionally substituted independently on the cycloalkyl moiety with 1 to 6 substituents selected from fluoro and methyl provided that no more than 2 substituents are methyl, $(C_1-C_6)$alkyl-S—$(C_0-C_5)$alkyl optionally substituted on the $(C_1-C_6)$alkyl moiety with 1 to 6 fluoro substituents, $(C_3-C_7)$cycloalkyl-$(C_0-C_3)$alkyl-S—$(C_0-C_5)$alkyl, $Ph^1$-$(C_0-C_3)$alkyl-S—$(C_0-C_5)$alkyl, $Ar^1$—$(C_0-C_3)$alkyl-S—$(C_0-C_5)$alkyl, $(C_1-C_6)$alkyl-O—$(C_0-C_5)$alkyl optionally substituted on the $(C_1-C_6)$alkyl moiety with 1 to 6 fluoro substituents, $(C_3-C_7)$cycloalkyl-$(C_0-C_3)$alkyl-O—$(C_0-C_5)$alkyl, $Ph^1$-$(C_0-C_3)$alkyl-O—$(C_0-C_5)$alkyl, $Ar^1$—$(C_0-C_3)$alkyl-O—$(C_0-C_5)$alkyl, $(C_1-C_6)$alkyl-$SO_2$—$(C_0-C_5)$alkyl optionally substituted on the $(C_1-C_6)$alkyl moiety with 1 to 6 fluoro substituents, ($C_3$-$C_7$)cycloalkyl-($C_0$-$C_3$)alkyl-$SO_2$—($C_0$-$C_5$)alkyl,
$Ph^1$-($C_0$-$C_3$)alkyl-$SO_2$—($C_0$-$C_5$)alkyl,
$Ar^1$—($C_0$-$C_3$)alkyl-$SO_2$—($C_0$-$C_5$)alkyl,
($C_1$-$C_6$)alkyl-C(O)—($C_0$-$C_5$)alkyl,
($C_3$-$C_7$)cycloalkyl-($C_0$-$C_3$)alkyl-C(O)—($C_0$-$C_5$)alkyl,
$Ph^1$-($C_0$-$C_3$)alkyl-C(O)—($C_0$-$C_5$)alkyl,
$Ar^1$—($C_0$-$C_3$)alkyl-C(O)—($C_0$-$C_5$)alkyl,
($C_1$-$C_6$)alkyl-NH—($C_0$-$C_5$)alkyl optionally substituted on the ($C_1$-$C_6$)alkyl moiety with 1 to 6 fluoro substituents,
($C_3$-$C_7$)cycloalkyl-($C_0$-$C_3$)alkyl-NH—($C_0$-$C_5$)alkyl,
$Ph^1$-($C_0$-$C_3$)alkyl-NH—($C_0$-$C_5$)alkyl,
$Ar^1$—($C_0$-$C_3$)alkyl-NH—($C_0$-$C_5$)alkyl,
$Het^1$-($C_0$-$C_5$)alkyl-,
($C_1$-$C_6$)alkyl-NH—C(O)—($C_0$-$C_5$)alkyl optionally substituted on the ($C_1$-$C_6$)alkyl moiety with 1 to 6 fluoro substituents,
($C_3$-$C_7$)cycloalkyl-($C_0$-$C_3$)alkyl-NH—C(O)—($C_0$-$C_5$)alkyl,
$Ph^1$-($C_0$-$C_3$)alkyl-NH—C(O)—($C_0$-$C_5$)alkyl,
$Ar^1$—($C_0$-$C_3$)alkyl-NH—C(O)—($C_0$-$C_5$)alkyl,
($C_1$-$C_6$)alkyl-C(O)—NH—($C_0$-$C_5$)alkyl,
($C_3$-$C_7$)cycloalkyl-($C_0$-$C_3$)alkyl-C(O)—NH—($C_0$-$C_5$)alkyl,
$Ph^1$-($C_0$-$C_3$)alkyl-C(O)—NH—($C_0$-$C_5$)alkyl,
$Ar^1$—($C_0$-$C_3$)alkyl-C(O)—NH—($C_0$-$C_5$)alkyl; or
e) alpha-naphthalyl, quinolin-2-yl, quinolin-3-yl, or quinolin-4-yl;

$R^{11}$ is
a) phenyl optionally substituted with:
  i) 1 to 5 independently selected halo substituents; or
  ii) 1 to 3 substituents independently selected from the group consisting of halo, cyano, methyl, —$CF_3$, —$SCF_3$, methoxy, nitro, and hydroxy; or
  iii) 0, 1 or 2 substituents independently selected from the group consisting of halo, cyano, methyl, —$CF_3$, —$SCF_3$, methoxy, nitro, and hydroxy and further substituted with a substituent selected from the group consisting of:
    ($C_1$-$C_6$)alkyl optionally further substituted with 1 to 6 fluoro substituents,
    ($C_1$-$C_6$)alkyl-O—($C_0$-$C_5$)alkyl optionally further substituted with 1 to 6 fluoro substituents,
    ($C_1$-$C_6$)alkyl-CH=CH— optionally substituted with 1 to 6 fluoro substituents,
    ($C_3$-$C_7$)cycloalkyl-($C_0$-$C_3$)alkyl-CH=CH— optionally substituted with 1 to 6 fluoro substituents on alkyl and optionally substituted independently on the cycloalkyl moiety with 1 to 6 substituents selected from fluoro and methyl provided that no more than 2 substituents are methyl,
    ($C_3$-$C_7$)cycloalkyl-($C_0$-$C_3$)alkyl-O—($C_0$-$C_5$)alkyl,
    $Ph^1$-($C_0$-$C_3$)alkyl-O—($C_0$-$C_5$)alkyl,
    $Ar^1$—($C_0$-$C_3$)alkyl-O—($C_0$-$C_5$)alkyl,
    ($C_1$-$C_6$)alkyl-S—($C_0$-$C_5$)alkyl optionally substituted on the ($C_1$-$C_6$)alkyl moiety with 1 to 6 fluoro substituents,
    ($C_3$-$C_7$)cycloalkyl-($C_0$-$C_3$)alkyl-S—($C_0$-$C_5$)alkyl,
    $Ph^1$-($C_0$-$C_3$)alkyl-S—($C_0$-$C_5$)alkyl,
    $Ar^1$—($C_0$-$C_3$)alkyl-S—($C_0$-$C_5$)alkyl,
    ($C_1$-$C_6$)alkyl-$SO_2$—($C_0$-$C_5$)alkyl optionally substituted on the ($C_1$-$C_6$)alkyl moiety with 1 to 6 fluoro substituents,
    ($C_3$-$C_7$)cycloalkyl-($C_0$-$C_3$)alkyl-$SO_2$—($C_0$-$C_5$)alkyl,
    $Ph^1$-($C_0$-$C_3$)alkyl-$SO_2$—($C_0$-$C_5$)alkyl,
    $Ar^1$—($C_0$-$C_3$)alkyl-$SO_2$—($C_0$-$C_5$)alkyl,
    ($C_1$-$C_6$)alkyl-C(O)—($C_0$-$C_5$)alkyl,
    ($C_3$-$C_7$)cycloalkyl-($C_0$-$C_3$)alkyl-C(O)—($C_0$-$C_5$)alkyl,
    $Ph^1$-($C_0$-$C_3$)alkyl-C(O)—($C_0$-$C_5$)alkyl,
    $Ar^1$—($C_0$-$C_3$)alkyl-C(O)—($C_0$-$C_5$)alkyl,
    ($C_1$-$C_6$)alkyl-NH—($C_0$-$C_5$)alkyl optionally substituted on the ($C_1$-$C_6$)alkyl moiety with 1 to 6 fluoro substituents,
    ($C_3$-$C_7$)cycloalkyl-($C_0$-$C_3$)alkyl-NH—($C_0$-$C_5$)alkyl,
    $Ph^1$-($C_0$-$C_3$)alkyl-NH—($C_0$-$C_5$)alkyl,
    $Ar^1$—($C_0$-$C_3$)alkyl-NH—($C_0$-$C_5$)alkyl,
    ($C_1$-$C_6$)alkyl-NH—C(O)—($C_0$-$C_5$)alkyl optionally substituted on the ($C_1$-$C_6$)alkyl moiety with 1 to 6 fluoro substituents,
    ($C_3$-$C_7$)cycloalkyl-($C_0$-$C_3$)alkyl-NH—C(O)—($C_0$-$C_5$)alkyl,
    $Ph^1$-($C_0$-$C_3$)alkyl-NH—C(O)—($C_0$-$C_5$)alkyl,
    $Ar^1$—($C_0$-$C_3$)alkyl-NH—C(O)—($C_0$-$C_5$)alkyl,
    $Het^1$-($C_0$-$C_5$)alkyl-,
    ($C_1$-$C_6$)alkyl-C(O)—NH—($C_0$-$C_5$)alkyl,
    ($C_3$-$C_7$)cycloalkyl-($C_0$-$C_3$)alkyl-C(O)—NH—($C_0$-$C_5$)alkyl,
    $Ph^1$-($C_0$-$C_3$)alkyl-C(O)—NH—($C_0$-$C_5$)alkyl, and
    $Ar^1$—($C_0$-$C_3$)alkyl-C(O)—NH—($C_0$-$C_5$)alkyl;
b) pyridyl optionally substituted with
  i) 1 to 3 substituents independently selected from the group consisting of halo, cyano, methyl, —$CF_3$, —$SCF_3$, methoxy, nitro, and hydroxy; or
  ii) 0, 1 or 2 substituents independently selected from the group consisting of halo, cyano, methyl, —$CF_3$, —$SCF_3$, methoxy, nitro, and hydroxy, and further substituted with a substituent selected from the group consisting of:
    ($C_1$-$C_6$)alkyl optionally further substituted with 1 to 6 fluoro substituents,
    ($C_1$-$C_6$)alkyl-O—($C_0$-$C_5$)alkyl optionally further substituted with 1 to 6 fluoro substituents,
    ($C_1$-$C_6$)alkyl-CH=CH— optionally substituted with 1 to 6 fluoro substituents,
    ($C_3$-$C_7$)cycloalkyl-($C_0$-$C_3$)alkyl-CH=CH— optionally substituted with 1 to 6 fluoro substituents on alkyl and optionally substituted independently on the cycloalkyl moiety with 1 to 6 substituents selected from fluoro and methyl provided that no more than 2 substituents are methyl,
    ($C_3$-$C_7$)cycloalkyl-($C_0$-$C_3$)alkyl-O—($C_0$-$C_5$)alkyl,
    $Ph^1$-($C_0$-$C_3$)alkyl-O—($C_0$-$C_5$)alkyl,
    ($C_1$-$C_6$)alkyl-S—($C_0$-$C_5$)alkyl optionally substituted on the ($C_1$-$C_6$)alkyl moiety with 1 to 6 fluoro substituents,
    ($C_3$-$C_7$)cycloalkyl-($C_0$-$C_3$)alkyl-S—($C_0$-$C_5$)alkyl,
    $Ph^1$-($C_0$-$C_3$)alkyl-S—($C_0$-$C_5$)alkyl,
    ($C_1$-$C_6$)alkyl-$SO_2$—($C_0$-$C_5$)alkyl optionally substituted on the ($C_1$-$C_6$)alkyl moiety with 1 to 6 fluoro substituents,
    ($C_3$-$C_7$)cycloalkyl-($C_0$-$C_3$)alkyl-$SO_2$—($C_0$-$C_5$)alkyl,
    $Ph^1$-($C_0$-$C_3$)alkyl-$SO_2$—($C_0$-$C_5$)alkyl,
    ($C_1$-$C_6$)alkyl-C(O)—($C_0$-$C_5$)alkyl, $(C_3-C_7)$cycloalkyl-$(C_0-C_3)$alkyl-C(O)—$(C_0-C_5)$alkyl,
Ph$^1$-$(C_0-C_3)$alkyl-C(O)—$(C_0-C_5)$alkyl,
$(C_1-C_6)$alkyl-NH—$(C_0-C_5)$alkyl optionally substituted on the $(C_1-C_6)$alkyl moiety with 1 to 6 fluoro substituents,
$(C_3-C_7)$cycloalkyl-$(C_0-C_3)$alkyl-NH—$(C_0-C_5)$alkyl,
Ph$^1$-$(C_0-C_3)$alkyl-NH—$(C_0-C_5)$alkyl,
$(C_1-C_6)$alkyl-NH—C(O)—$(C_0-C_5)$alkyl optionally substituted on the $(C_1-C_6)$alkyl moiety with 1 to 6 fluoro substituents,
$(C_3-C_7)$cycloalkyl-$(C_0-C_3)$alkyl-NH—C(O)—$(C_0-C_5)$alkyl,
Ph$^1$-$(C_0-C_3)$alkyl-NH—C(O)—$(C_0-C_5)$alkyl,
$(C_1-C_6)$alkyl-C(O)—NH—$(C_0-C_5)$alkyl,
$(C_3-C_7)$cycloalkyl-$(C_0-C_3)$alkyl-C(O)—NH—$(C_0-C_5)$alkyl, and
Ph$^1$-$(C_0-C_3)$alkyl-C(O)—NH—$(C_0-C_5)$alkyl;
c) pyridazinyl optionally substituted with 1 or 2 substituents independently selected from the group consisting of halo, cyano, hydroxy, $(C_1-C_6)$alkyl optionally further substituted with 1 to 6 fluoro substituents, $(C_1-C_6)$alkoxy optionally further substituted with 1 to 6 fluoro substituents; and $(C_1-C_6)$alkylthio optionally further substituted with 1 to 6 fluoro substituents; or
d) a five-membered aromatic heterocycle selected from the group of thiophenyl, thiazole, isothiazole optionally substituted with 1 or 2 substituents independently selected from the group consisting of halo, cyano, hydroxy, $(C_1-C_6)$alkyl optionally further substituted with 1 to 6 fluoro substituents, $(C_1-C_6)$alkoxy optionally further substituted with 1 to 6 fluoro substituents, $(C_1-C_6)$alkylthio optionally further substituted with 1 to 6 fluoro substituents, $(C_1-C_6)$alkylamino optionally further substituted with 1 to 6 fluoro substituents, and $(C_1-C_6)$alkyl-C(O)—;

R$^{12}$ is hydrogen or methyl

R$^{13}$ is a) phenyl optionally substituted with:
  i) 1 to 5 independently selected halo substituents; or
  ii) 1 to 3 substituents independently selected from the group consisting of halo, cyano, —SCF$_3$, nitro, hydroxy, $(C_1-C_6)$alkyl optionally further substituted with 1 to 6 fluoro substituents, and $(C_1-C_6)$alkoxy optionally further substituted with 1 to 6 fluoro substituents; or
  iii) 0, 1, or 2 substituents independently selected from the group consisting of halo, cyano, —SCF$_3$, methyl, —CF$_3$, methoxy, —OCF$_3$, nitro, and hydroxy, together with one substituent selected from the group consisting of
    $(C_3-C_7)$cycloalkyl-$(C_0-C_5)$alkyl optionally substituted on the alkyl moiety with 1 to 6 fluoro substituents and optionally substituted independently on the cycloalkyl moiety with 1 to 6 substituents selected from fluoro and methyl provided that no more than 2 substituents are methyl,
    Ph$^1$-$(C_0-C_5)$alkyl,
    Ar$^1$—$(C_0-C_5)$alkyl,
    $(C_1-C_6)$alkyl-CH=CH— optionally substituted with 1 to 6 fluoro substituents, $(C_3-C_7)$cycloalkyl-$(C_0-C_3)$alkyl-CH=CH— optionally substituted with 1 to 6 fluoro substituents on alkyl and optionally substituted independently on the cycloalkyl moiety with 1 to 6 substituents selected from fluoro and methyl provided that no more than 2 substituents are methyl,
    $(C_1-C_6)$alkyl-S—$(C_0-C_5)$alkyl optionally substituted on the $(C_1-C_6)$alkyl moiety with 1 to 6 fluoro substituents,
    $(C_3-C_7)$cycloalkyl-$(C_0-C_3)$alkyl-S—$(C_0-C_5)$alkyl,
    Ph$^1$-$(C_0-C_3)$alkyl-S—$(C_0-C_5)$alkyl,
    Ar$^1$—$(C_0-C_3)$alkyl-S—$(C_0-C_5)$alkyl,
    $(C_1-C_6)$alkyl-O—$(C_0-C_5)$alkyl optionally substituted on the $(C_1-C_6)$alkyl moiety with 1 to 6 fluoro substituents,
    $(C_3-C_7)$cycloalkyl-$(C_0-C_3)$alkyl-O—$(C_0-C_5)$alkyl,
    Ph$^1$-$(C_0-C_3)$alkyl-O—$(C_0-C_5)$alkyl,
    Ar$^1$—$(C_0-C_3)$alkyl-O—$(C_0-C_5)$alkyl,
    $(C_1-C_6)$alkyl-SO$_2$—$(C_0-C_5)$alkyl optionally substituted on the $(C_1-C_6)$alkyl moiety with 1 to 6 fluoro substituents,
    $(C_3-C_7)$cycloalkyl-$(C_0-C_3)$alkyl-SO$_2$—$(C_0-C_5)$alkyl,
    Ph$^1$-$(C_0-C_3)$alkyl-SO$_2$—$(C_0-C_5)$alkyl,
    Ar$^1$—$(C_0-C_3)$alkyl-SO$_2$—$(C_0-C_5)$alkyl,
    $(C_1-C_6)$alkyl-C(O)—$(C_0-C_5)$alkyl,
    $(C_3-C_7)$cycloalkyl-$(C_0-C_3)$alkyl-C(O)—$(C_0-C_5)$alkyl,
    Ph$^1$-$(C_0-C_3)$alkyl-C(O)—$(C_0-C_5)$alkyl,
    Ar$^1$—$(C_0-C_3)$alkyl-C(O)—$(C_0-C_5)$alkyl,
    $(C_1-C_6)$alkyl-NH—$(C_0-C_5)$alkyl optionally substituted on the $(C_1-C_6)$alkyl moiety with 1 to 6 fluoro substituents,
    $(C_3-C_7)$cycloalkyl-$(C_0-C_3)$alkyl-NH—$(C_0-C_5)$alkyl,
    Ph$^1$-$(C_0-C_3)$alkyl-NH—$(C_0-C_5)$alkyl,
    Ar$^1$—$(C_0-C_3)$alkyl-NH—$(C_0-C_5)$alkyl,
    Het$^1$-$(C_0-C_3)$alkyl-,
    $(C_1-C_6)$alkyl-NH—C(O)—$(C_0-C_5)$alkyl optionally substituted on the $(C_1-C_6)$alkyl moiety with 1 to 6 fluoro substituents,
    $(C_3-C_7)$cycloalkyl-$(C_0-C_3)$alkyl-NH—C(O)—$(C_0-C_5)$alkyl,
    Ph$^1$-$(C_0-C_3)$alkyl-NH—C(O)—$(C_0-C_5)$alkyl,
    Ar$^1$—$(C_0-C_3)$alkyl-NH—C(O)—$(C_0-C_5)$alkyl,
    $(C_1-C_6)$alkyl-$(C_0-C_3)$alkyl-C(O)—NH—$(C_0-C_5)$alkyl,
    $(C_3-C_7)$cycloalkyl-C(O)—NH—$(C_0-C_5)$alkyl,
    Ph$^1$-$(C_0-C_3)$alkyl-C(O)—NH—$(C_0-C_5)$alkyl,
    Ar$^1$—$(C_0-C_3)$alkyl-C(O)—NH—$(C_0-C_5)$alkyl,
    $(C_1-C_6)$alkyl-NH—SO$_2$—$(C_0-C_5)$alkyl optionally substituted on the $(C_1-C_6)$alkyl moiety with 1 to 6 fluoro substituents,
    $(C_3-C_7)$cycloalkyl-$(C_0-C_3)$alkyl-NH—SO$_2$—$(C_0-C_5)$alkyl,
    $(C_1-C_6)$alkyl-SO$_2$—NH—$(C_0-C_5)$alkyl,
    $(C_3-C_7)$cycloalkyl-$(C_0-C_3)$alkyl-SO$_2$—NH—$(C_0-C_5)$alkyl; or
b) thiophenyl optionally substituted with one to two substituents selected from the group consisting of
  halo,
  cyano,
  $(C_1-C_6)$alkyl optionally substituted with 1 to 6 fluoro substituents,
  Ph$^1$-$(C_0-C_3)$alkyl optionally substituted on the alkyl moiety with 1 to 6 fluoro substituents,
  Ar$^1$—$(C_0-C_3)$alkyl optionally substituted on the alkyl moiety with 1 to 6 fluoro substituents,
  $(C_1-C_6)$alkyl-C(O)—,
  Ph$^1$-$(C_0-C_3)$alkyl-C(O)—,
  Ar$^1$—$(C_0-C_3)$alkyl-C(O)—,
  $(C_1-C_6)$alkyl-NH—C(O)— optionally substituted with 1 to 6 fluoro substituents, Ph$^1$-(C$_0$-C$_3$)alkyl-NH—C(O)— optionally substituted on the alkyl moiety with 1 to 6 fluoro substituents, Ar$^1$—(C$_0$-C$_3$)alkyl-NH—C(O)— optionally substituted on the alkyl moiety with 1 to 6 fluoro substituents, (C$_1$-C$_6$)alkyl-CH=CH— optionally substituted with 1 to 6 fluoro substituents, (C$_1$-C$_6$)alkoxy optionally substituted with 1 to 6 fluoro substituents, (C$_1$-C$_6$)alkylthio optionally substituted with 1 to 6 fluoro substituents, Ph$^1$-(C$_0$-C$_3$)alkylthio, (C$_1$-C$_6$)alkyl-NR$^{12}$—(C$_0$-C$_3$)alkyl- optionally substituted on the (C$_1$-C$_6$)alkyl moiety with 1 to 6 fluoro substituents, (C$_3$-C$_7$)cycloalkyl-(C$_0$-C$_3$)alkyl-NR$^{12}$—(C$_0$-C$_3$)alkyl, Ph$^1$-(C$_0$-C$_3$)alkyl-NR$^{12}$—(C$_0$-C$_3$)alkyl-, Ar$^1$—(C$_0$-C$_3$)alkyl-NR$^{12}$—(C$_0$-C$_3$)alkyl-, Het$^1$-(C$_0$-C$_3$)alkyl-, (C$_1$-C$_6$)alkyl-C(O)—NH—, Ph$^1$-(C$_0$-C$_3$)alkyl-C(O)—NH—, Ar$^1$—(C$_0$-C$_3$)alkyl-C(O)—NH—, (C$_1$-C$_6$)alkyl-O—C(O)—NH— optionally substituted with 1 to 6 fluoro substituents, Ph$^1$-(C$_0$-C$_3$)alkyl-O—C(O)—NH— optionally substituted on the alkyl moiety with 1 to 6 fluoro substituents, and Ar$^1$—(C$_0$-C$_3$)alkyl-O—C(O)—NH— optionally substituted on the alkyl moiety with 1 to 6 fluoro substituents;

Ar$^1$ is pyridyl, optionally substituted with 1 to 4 independently selected halo substituents, or with 1 to 3 substituents independently selected from the group consisting of halo, cyano, hydroxy, acetyl, methyl, —CF$_3$, methoxy, —OCF$_3$, methylthio, —SCF$_3$;

Ph$^1$ is phenyl optionally substituted with 1 to 5 independently selected halo substituents, or with 1 to 3 substituents independently selected from the group consisting of halo, cyano, hydroxy, acetyl, methylthio, —SCF$_3$, (C$_1$-C$_6$)alkyl optionally further substituted with 1 to 6 fluoro substituents, and (C$_1$-C$_6$)alkoxy optionally further substituted with 1 to 6 fluoro substituents;

Het$^1$ is a saturated, nitrogen-containing heterocycle substituent selected from the group consisting of pyrrolidinyl, piperidinyl, homopiperidinyl, morpholinyl, thiomorpholinyl, homomorpholinyl, and homothiomorpholinyl, any of which may optionally be substituted with (C$_1$-C$_6$)alkyl or with 2 methyl substituents;

or a pharmaceutically acceptable salt thereof.

2. A compound of Formula (Ia):

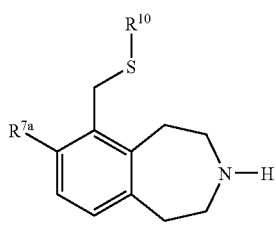

Ia wherein

R$^{7a}$ is chloro; and

R$^{10}$ is a) an aromatic heterocycle substituent selected from the group consisting of tetrazolyl, 1,2,3-thiadiazolyl, 1,3,4-thiadiazolyl, 1,2,4-thiadiazolyl, 1,2,3-oxadiazolyl, 1,3,4-oxadiazolyl, and 1,2,4-oxadiazolyl, any one of which may optionally be substituted with a substituent selected from the group consisting of (C$_1$-C$_4$)alkyl optionally substituted with 1 to 5 fluoro substituents, Ph$^1$-(C$_0$-C$_3$)alkyl, Ar$^1$—(C$_0$-C$_3$)alkyl, (C$_1$-C$_4$)alkyl-C(O)—, Ph$^1$-(C$_0$-C$_3$)alkyl-C(O)—, Ar$^1$—(C$_0$-C$_3$)alkyl-C(O)—, (C$_1$-C$_4$)alkyl-NR$^{12}$—(C$_0$-C$_3$)alkyl- optionally substituted on the on the and (C$_1$-C$_4$)alkyl moiety with 1 to 5 fluoro substituents, (C$_3$-C$_7$)cycloalkyl-(C$_0$-C$_3$)alkyl-NR$^{12}$—(C$_0$-C$_3$)alkyl, Ph$^1$-(C$_0$-C$_3$)alkyl-NR$^{12}$—(C$_0$-C$_3$)alkyl, Ar$^1$—(C$_0$-C$_3$)alkyl-NR$^{12}$—(C$_0$-C$_3$)alkyl;

b) an aromatic heterocycle substituent selected from the group consisting of imidazolyl, thiazolyl, isothiazolyl, thiophenyl, pyrazolyl, oxazolyl, isoxazolyl, 1,2,3-triazolyl, 1,2,4-triazolyl, or a heterocycle selected from thiazolinyl, any one of which may be optionally substituted with one to two substituents selected from the group consisting of (C$_1$-C$_6$)alkyl optionally substituted with 1 to 6 fluoro substituents, Ph$^1$-(C$_0$-C$_3$)alkyl optionally substituted on the alkyl moiety with 1 to 6 fluoro substituents, Ar$^1$—(C$_0$-C$_3$)alkyl optionally substituted on the alkyl moiety with 1 to 6 fluoro substituents, (C$_1$-C$_6$)alkyl-C(O)—, Ph$^1$-(C$_0$-C$_3$)alkyl-C(O)—, Ar$^1$—(C$_0$-C$_3$)alkyl-C(O)—, (C$_1$-C$_6$)alkyl-NH—C(O)— optionally substituted with 1 to 6 fluoro substituents, Ph$^1$-(C$_0$-C$_3$)alkyl-NH—C(O)— optionally substituted on the alkyl moiety with 1 to 6 fluoro substituents, and Ar$^1$—(C$_0$-C$_3$)alkyl-NH—C(O)— optionally substituted on the alkyl moiety with 1 to 6 fluoro substituents, or optionally substituted on ring carbon atoms with one or two substituents selected from the group consisting of halo, cyano, (C$_1$-C$_6$)alkyl-CH=CH— optionally substituted with 1 to 6 fluoro substituents, (C$_1$-C$_6$)alkoxy optionally substituted with 1 to 6 fluoro substituents, (C$_1$-C$_6$)alkylthio optionally substituted with 1 to 6 fluoro substituents, Ph$^1$-(C$_0$-C$_3$)alkylthio, (C$_1$-C$_6$)alkyl-NR$^{12}$—(C$_0$-C$_3$)alkyl- optionally substituted on the (C$_1$-C$_6$)alkyl moiety with 1 to 6 fluoro substituents, (C$_3$-C$_7$)cycloalkyl-(C$_0$-C$_3$)alkyl-NR$^{12}$—(C$_0$-C$_3$)alkyl, Ph$^1$-(C$_0$-C$_3$)alkyl-NR$^{12}$—(C$_0$-C$_3$)alkyl-, Ar$^1$—(C$_0$-C$_3$)alkyl-NR$^{12}$—(C$_0$-C$_3$)alkyl-, Het$^1$-(C$_0$-C$_3$)alkyl-, (C$_1$-C$_6$)alkyl-C(O)—NH—, Ph$^1$-(C$_0$-C$_3$)alkyl-C(O)—NH—, Ar$^1$—(C$_0$-C$_3$)alkyl-C(O)—NH—, (C$_1$-C$_6$)alkyl-O—C(O)—NH— optionally substituted with 1 to 6 fluoro substituents, Ph$^1$-(C$_0$-C$_3$)alkyl-O—C(O)—NH— optionally substituted on the alkyl moiety with 1 to 6 fluoro substituents, and
Ar$^1$—(C$_0$-C$_3$)alkyl-O—C(O)—NH— optionally substituted on the alkyl moiety with 1 to 6 fluoro substituents,
or optionally substituted on two adjacent ring atoms with a bivalent 3 to 4 carbon hydrocarbon substituent which, together with the ring atoms to which it is attached, form a benzene ring or a partially saturated five- or six-membered ring;
c) phenyl optionally substituted with:
  i) 1 to 5 independently selected halo substituents; or
  ii) 1 to 3 substituents independently selected from the group consisting of halo, cyano, —SCF$_3$, nitro, hydroxy, (C$_1$-C$_6$)alkyl optionally further substituted with 1 to 6 fluoro substituents, and (C$_1$-C$_6$)alkoxy optionally further substituted with 1 to 6 fluoro substituents; or
  iii) 0, 1, or 2 substituents independently selected from the group consisting of halo, cyano, —SCF$_3$, methyl, —CF$_3$, methoxy, —OCF$_3$, nitro, and hydroxy, together with one substituent selected from the group consisting of
    (C$_3$-C$_7$)cycloalkyl-(C$_0$-C$_5$)alkyl optionally substituted on the alkyl moiety with 1 to 6 fluoro substituents and optionally substituted independently on the cycloalkyl moiety with 1 to 6 substituents selected from fluoro and methyl provided that no more than 2 substituents are methyl,
    Ph$^1$-(C$_0$-C$_5$)alkyl,
    Ar$^1$—(C$_0$-C$_5$)alkyl,
    thiazolyl-(C$_0$-C$_1$)alkyl optionally substituted with a substituent independently selected from the group consisting of halo, (C$_1$-C$_6$)alkyl optionally further substituted with 1 to 6 fluoro substituents, (C$_1$-C$_6$)alkyl-NR$^{12}$—(C$_0$-C$_3$)alkyl- optionally substituted on the (C$_1$-C$_6$)alkyl moiety with 1 to 6 fluoro substituents, and (C$_3$-C$_7$)cycloalkyl-(C$_0$-C$_3$)alkyl-NR$^{12}$—(C$_0$-C$_3$)alkyl,
    (C$_1$-C$_6$)alkyl-CH=CH— optionally substituted with 1 to 6 fluoro substituents, (C$_3$-C$_7$)cycloalkyl-(C$_0$-C$_3$)alkyl-CH=CH— optionally substituted with 1 to 6 fluoro substituents on alkyl and optionally substituted independently on the cycloalkyl moiety with 1 to 6 substituents selected from fluoro and methyl provided that no more than 2 substituents are methyl,
    (C$_1$-C$_6$)alkyl-S—(C$_0$-C$_5$)alkyl optionally substituted on the (C$_1$-C$_6$)alkyl moiety with 1 to 6 fluoro substituents,
    (C$_3$-C$_7$)cycloalkyl-(C$_0$-C$_3$)alkyl-S—(C$_0$-C$_5$)alkyl,
    Ph$^1$-(C$_0$-C$_3$)alkyl-S—(C$_0$-C$_5$)alkyl,
    Ar$^1$—(C$_0$-C$_3$)alkyl-S—(C$_0$-C$_5$)alkyl,
    (C$_1$-C$_6$)alkyl-O—(C$_0$-C$_5$)alkyl optionally substituted on the (C$_1$-C$_6$)alkyl moiety with 1 to 6 fluoro substituents,
    (C$_3$-C$_7$)cycloalkyl-(C$_0$-C$_3$)alkyl-O—(C$_0$-C$_5$)alkyl,
    Ph$^1$-(C$_0$-C$_3$)alkyl-O—(C$_0$-C$_5$)alkyl,
    Ar$^1$—(C$_0$-C$_3$)alkyl-O—(C$_0$-C$_5$)alkyl,
    (C$_1$-C$_6$)alkyl-SO$_2$—(C$_0$-C$_5$)alkyl optionally substituted on the (C$_1$-C$_6$)alkyl moiety with 1 to 6 fluoro substituents,
    (C$_3$-C$_7$)cycloalkyl-(C$_0$-C$_3$)alkyl-SO$_2$—(C$_0$-C$_5$)alkyl,
    Ph$^1$-(C$_0$-C$_3$)alkyl-SO$_2$—(C$_0$-C$_5$)alkyl,
    Ar$^1$—(C$_0$-C$_3$)alkyl-SO$_2$—(C$_0$-C$_5$)alkyl,
    (C$_1$-C$_6$)alkyl-C(O)—(C$_0$-C$_5$)alkyl,
    (C$_3$-C$_7$)cycloalkyl-(C$_0$-C$_3$)alkyl-C(O)—(C$_0$-C$_5$)alkyl,
    Ph$^1$-(C$_0$-C$_3$)alkyl-C(O)—(C$_0$-C$_5$)alkyl,
    Ar$^1$—(C$_0$-C$_3$)alkyl-C(O)—(C$_0$-C$_5$)alkyl,
    (C$_1$-C$_6$)alkyl-NH—(C$_0$-C$_5$)alkyl optionally substituted on the (C$_1$-C$_6$)alkyl moiety with 1 to 6 fluoro substituents,
    (C$_3$-C$_7$)cycloalkyl-(C$_0$-C$_3$)alkyl-NH—(C$_0$-C$_5$)alkyl,
    Ph$^1$-(C$_0$-C$_3$)alkyl-NH—(C$_0$-C$_5$)alkyl,
    Ar$^1$—(C$_0$-C$_3$)alkyl-NH—(C$_0$-C$_5$)alkyl,
    Het$^1$-(C$_0$-C$_3$)alkyl-,
    (C$_1$-C$_6$)alkyl-NH—C(O)—(C$_0$-C$_5$)alkyl optionally substituted on the (C$_1$-C$_6$)alkyl moiety with 1 to 6 fluoro substituents,
    (C$_3$-C$_7$)cycloalkyl-(C$_0$-C$_3$)alkyl-NH—C(O)—(C$_0$-C$_5$)alkyl,
    Ph$^1$-(C$_0$-C$_3$)alkyl-NH—C(O)—(C$_0$-C$_5$)alkyl,
    Ar$^1$—(C$_0$-C$_3$)alkyl-NH—C(O)—(C$_0$-C$_5$)alkyl,
    (C$_1$-C$_6$)alkyl-(C$_0$-C$_3$)alkyl-C(O)—NH—(C$_0$-C$_5$)alkyl,
    (C$_3$-C$_7$)cycloalkyl-C(O)—NH—(C$_0$-C$_5$)alkyl,
    Ph$^1$-(C$_0$-C$_3$)alkyl-C(O)—NH—(C$_0$-C$_5$)alkyl,
    Ar$^1$—(C$_0$-C$_3$)alkyl-C(O)—NH—(C$_0$-C$_5$)alkyl,
    (C$_1$-C$_6$)alkyl-NH—SO$_2$—(C$_0$-C$_5$)alkyl optionally substituted on the (C$_1$-C$_6$)alkyl moiety with 1 to 6 fluoro substituents,
    (C$_3$-C$_7$)cycloalkyl-(C$_0$-C$_3$)alkyl-NH—SO$_2$—(C$_0$-C$_5$)alkyl,
    (C$_1$-C$_6$)alkyl-SO$_2$—NH—(C$_0$-C$_5$)alkyl,
    (C$_3$-C$_7$)cycloalkyl-(C$_0$-C$_3$)alkyl-SO$_2$—NH—(C$_0$-C$_5$)alkyl;
d) an aromatic heterocycle substituent selected from the group consisting of pyridyl, pyridazinyl, pyrimidinyl, pyrazinyl, any of which may be optionally substituted with 1 or 2 substituents independently selected from the group consisting of halo, cyano, —SCF$_3$, methyl, —CF$_3$, methoxy, —OCF$_3$, nitro, hydroxy, and optionally further substituted with a substituent selected from the group consisting of
  (C$_3$-C$_7$)cycloalkyl-(C$_0$-C$_5$)alkyl optionally further substituted on the alkyl moiety with 1 to 6 fluoro substituents and optionally substituted independently on the cycloalkyl moiety with 1 to 6 substituents selected from fluoro and methyl provided that no more than 2 substituents are methyl,
  Ph$^1$-(C$_0$-C$_5$)alkyl,
  Ar$^1$—(C$_0$-C$_5$)alkyl,
  thiazolyl-(C$_0$-C$_1$)alkyl optionally substituted with a substituent independently selected from the group consisting of halo, (C$_1$-C$_6$)alkyl optionally further substituted with 1 to 6 fluoro substituents, (C$_1$-C$_6$)alkyl-NR$^{12}$—(C$_0$-C$_3$)alkyl- optionally substituted on the (C$_1$-C$_6$)alkyl moiety with 1 to 6 fluoro substituents, and (C$_3$-C$_7$)cycloalkyl-(C$_0$-C$_3$)alkyl-NR$^{12}$—(C$_0$-C$_3$)alkyl,
  (C$_1$-C$_6$)alkyl-CH=CH— optionally substituted with 1 to 6 fluoro substituents,
  (C$_3$-C$_7$)cycloalkyl-(C$_0$-C$_3$)alkyl-CH=CH— optionally substituted with 1 to 6 fluoro substituents on alkyl and optionally substituted independently on the cycloalkyl moiety with 1 to 6 substituents selected from fluoro and methyl provided that no more than 2 substituents are methyl, (C₁-C₆)alkyl-S—(C₀-C₅)alkyl optionally substituted on the (C₁-C₆)alkyl moiety with 1 to 6 fluoro substituents,
(C₃-C₇)cycloalkyl-(C₀-C₃)alkyl-S—(C₀-C₅)alkyl,
Ph¹-(C₀-C₃)alkyl-S—(C₀-C₅)alkyl,
Ar¹—(C₀-C₃)alkyl-S—(C₀-C₅)alkyl,
(C₁-C₆)alkyl-O—(C₀-C₅)alkyl optionally substituted on the (C₁-C₆)alkyl moiety with 1 to 6 fluoro substituents,
(C₃-C₇)cycloalkyl-(C₀-C₃)alkyl-O—(C₀-C₅)alkyl,
Ph¹-(C₀-C₃)alkyl-O—(C₀-C₅)alkyl,
Ar¹—(C₀-C₃)alkyl-O—(C₀-C₅)alkyl,
(C₁-C₆)alkyl-SO₂—(C₀-C₅)alkyl optionally substituted on the (C₁-C₆)alkyl moiety with 1 to 6 fluoro substituents,
(C₃-C₇)cycloalkyl-(C₀-C₃)alkyl-SO₂—(C₀-C₅)alkyl,
Ph¹-(C₀-C₃)alkyl-SO₂—(C₀-C₅)alkyl,
Ar¹—(C₀-C₃)alkyl-SO₂—(C₀-C₅)alkyl,
(C₁-C₆)alkyl-C(O)—(C₀-C₅)alkyl,
(C₃-C₇)cycloalkyl-(C₀-C₃)alkyl-C(O)—(C₀-C₅)alkyl,
Ph¹-(C₀-C₃)alkyl-C(O)—(C₀-C₅)alkyl,
Ar¹—(C₀-C₃)alkyl-C(O)—(C₀-C₅)alkyl,
(C₁-C₆)alkyl-NH—(C₀-C₅)alkyl optionally substituted on the (C₁-C₆)alkyl moiety with 1 to 6 fluoro substituents,
(C₃-C₇)cycloalkyl-(C₀-C₃)alkyl-NH—(C₀-C₅)alkyl,
Ph¹-(C₀-C₃)alkyl-NH—(C₀-C₅)alkyl,
Ar¹—(C₀-C₃)alkyl-NH—(C₀-C₅)alkyl,
Het¹-(C₀-C₅)alkyl-,
(C₁-C₆)alkyl-NH—C(O)—(C₀-C₅)alkyl optionally substituted on the (C₁-C₆)alkyl moiety with 1 to 6 fluoro substituents,
(C₃-C₇)cycloalkyl-(C₀-C₃)alkyl-NH—C(O)—(C₀-C₅)alkyl,
Ph¹-(C₀-C₃)alkyl-NH—C(O)—(C₀-C₅)alkyl,
Ar¹—(C₀-C₃)alkyl-NH—C(O)—(C₀-C₅)alkyl,
(C₁-C₆)alkyl-C(O)—NH—(C₀-C₅)alkyl,
(C₃-C₇)cycloalkyl-(C₀-C₃)alkyl-C(O)—NH—(C₀-C₅)alkyl,
Ph¹-(C₀-C₃)alkyl-C(O)—NH—(C₀-C₅)alkyl,
Ar¹—(C₀-C₃)alkyl-C(O)—NH—(C₀-C₅)alkyl; or
e) alpha-naphthalyl, quinolin-2-yl, quinolin-3-yl, or quinolin-4-yl;
R¹² is hydrogen or methyl;
Ar¹ is pyridyl, optionally substituted with 1 to 4 independently selected halo substituents, or with 1 to 3 substituents independently selected from the group consisting of halo, cyano, hydroxy, acetyl, methyl, —CF₃, methoxy, —OCF₃, methylthio, —SCF₃;
Ph¹ is phenyl optionally substituted with 1 to 5 independently selected halo substituents, or with 1 to 3 substituents independently selected from the group consisting of halo, cyano, hydroxy, acetyl, methylthio, —SCF₃, (C₁-C₆)alkyl optionally further substituted with 1 to 6 fluoro substituents, and (C₁-C₆)alkoxy optionally further substituted with 1 to 6 fluoro substituents;
Het¹ is a saturated, nitrogen-containing heterocycle substituent selected from the group consisting of pyrrolidinyl, piperidinyl, homopiperidinyl, morpholinyl, thiomorpholinyl, homomorpholinyl, and homothiomorpholinyl, any of which may optionally be substituted with (C₁-C₆)alkyl or with 2 methyl substituents;
or a pharmaceutically acceptable salt thereof.

3. A compound of Formula (Ib):

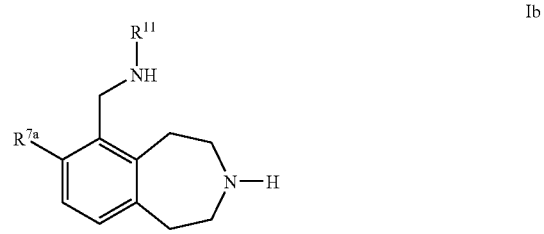

Ib wherein
R⁷ᵃ chloro;
R¹¹ is;
a) phenyl optionally substituted with:
  i) 1 to 5 independently selected halo substituents; or
  ii) 1 to 3 substituents independently selected from the group consisting of halo, cyano, methyl, —CF₃, —SCF₃, methoxy, nitro, and hydroxy; or
  iii) 0, 1 or 2 substituents independently selected from the group consisting of halo, cyano, methyl, —CF₃, —SCF₃, methoxy, nitro, and hydroxy and further substituted with a substituent selected from the group consisting of:
  (C₁-C₆)alkyl optionally further substituted with 1 to 6 fluoro substituents,
  (C₁-C₆)alkyl-O—(C₀-C₅)alkyl optionally further substituted with 1 to 6 fluoro substituents,
  (C₁-C₆)alkyl-CH═CH— optionally substituted with 1 to 6 fluoro substituents,
  (C₃-C₇)cycloalkyl-(C₀-C₃)alkyl-CH═CH— optionally substituted with 1 to 6 fluoro substituents on alkyl and optionally substituted independently on the cycloalkyl moiety with 1 to 6 substituents selected from fluoro and methyl provided that no more than 2 substituents are methyl,
  (C₃-C₇)cycloalkyl-(C₀-C₃)alkyl-O—(C₀-C₅)alkyl,
  Ph¹-(C₀-C₃)alkyl-O—(C₀-C₅)alkyl,
  Ar¹—(C₀-C₃)alkyl-O—(C₀-C₅)alkyl,
  (C₁-C₆)alkyl-S—(C₀-C₅)alkyl optionally substituted on the (C₁-C₆)alkyl moiety with 1 to 6 fluoro substituents,
  (C₃-C₇)cycloalkyl-(C₀-C₃)alkyl-S—(C₀-C₅)alkyl,
  Ph¹-(C₀-C₃)alkyl-S—(C₀-C₅)alkyl,
  Ar¹—(C₀-C₃)alkyl-S—(C₀-C₅)alkyl,
  (C₁-C₆)alkyl-SO₂—(C₀-C₅)alkyl optionally substituted on the (C₁-C₆)alkyl moiety with 1 to 6 fluoro substituents,
  (C₃-C₇)cycloalkyl-(C₀-C₃)alkyl-SO₂—(C₀-C₅)alkyl,
  Ph¹-(C₀-C₃)alkyl-SO₂—(C₀-C₅)alkyl,
  Ar¹—(C₀-C₃)alkyl-SO₂—(C₀-C₅)alkyl,
  (C₁-C₆)alkyl-C(O)—(C₀-C₅)alkyl,
  (C₃-C₇)cycloalkyl-(C₀-C₃)alkyl-C(O)—(C₀-C₅)alkyl,
  Ph¹-(C₀-C₃)alkyl-C(O)—(C₀-C₅)alkyl,
  Ar¹—(C₀-C₃)alkyl-C(O)—(C₀-C₅)alkyl,
  (C₁-C₆)alkyl-NH—(C₀-C₅)alkyl optionally substituted on the (C₁-C₆)alkyl moiety with 1 to 6 fluoro substituents, ($C_3$-$C_7$)cycloalkyl-($C_0$-$C_3$)alkyl-NH—($C_0$-$C_5$)alkyl,
$Ph^1$-($C_0$-$C_3$)alkyl-NH—($C_0$-$C_5$)alkyl,
$Ar^1$—($C_0$-$C_3$)alkyl-NH—($C_0$-$C_5$)alkyl,
($C_1$-$C_6$)alkyl-NH—C(O)—($C_0$-$C_5$)alkyl optionally substituted on the ($C_1$-$C_6$)alkyl moiety with 1 to 6 fluoro substituents,
($C_3$-$C_7$)cycloalkyl-($C_0$-$C_3$)alkyl-NH—C(O)—($C_0$-$C_5$)alkyl,
$Ph^1$-($C_0$-$C_3$)alkyl-NH—C(O)—($C_0$-$C_5$)alkyl,
$Ar^1$—($C_0$-$C_3$)alkyl-NH—C(O)—($C_0$-$C_5$)alkyl,
$Het^1$-($C_0$-$C_5$)alkyl-,
($C_1$-$C_6$)alkyl-C(O)—NH—($C_0$-$C_5$)alkyl,
($C_3$-$C_7$)cycloalkyl-($C_0$-$C_3$)alkyl-C(O)—NH—($C_0$-$C_5$)alkyl,
$Ph^1$-($C_0$-$C_3$)alkyl-C(O)—NH—($C_0$-$C_5$)alkyl, and
$Ar^1$—($C_0$-$C_3$)alkyl-C(O)—NH—($C_0$-$C_5$)alkyl;
b) pyridyl optionally substituted with
  i) 1 to 3 substituents independently selected from the group consisting of halo, cyano, methyl, —$CF_3$, —$SCF_3$, methoxy, nitro, and hydroxy; or
  ii) 0, 1 or 2 substituents independently selected from the group consisting of halo, cyano, methyl, —$CF_3$, —$SCF_3$, methoxy, nitro, and hydroxy, and further substituted with a substituent selected from the group consisting of:
    ($C_1$-$C_6$)alkyl optionally further substituted with 1 to 6 fluoro substituents,
    ($C_1$-$C_6$)alkyl-O—($C_0$-$C_5$)alkyl optionally further substituted with 1 to 6 fluoro substituents,
    ($C_1$-$C_6$)alkyl-CH=CH— optionally substituted with 1 to 6 fluoro substituents,
    ($C_3$-$C_7$)cycloalkyl-($C_0$-$C_3$)alkyl-CH=CH— optionally substituted with 1 to 6 fluoro substituents on alkyl and optionally substituted independently on the cycloalkyl moiety with 1 to 6 substituents selected from fluoro and methyl provided that no more than 2 substituents are methyl,
    ($C_3$-$C_7$)cycloalkyl-($C_0$-$C_3$)alkyl-O—($C_0$-$C_5$)alkyl,
    $Ph^1$-($C_0$-$C_3$)alkyl-O—($C_0$-$C_5$)alkyl,
    ($C_1$-$C_6$)alkyl-S—($C_0$-$C_5$)alkyl optionally substituted on the ($C_1$-$C_6$)alkyl moiety with 1 to 6 fluoro substituents,
    ($C_3$-$C_7$)cycloalkyl-($C_0$-$C_3$)alkyl-S—($C_0$-$C_5$)alkyl,
    $Ph^1$-($C_0$-$C_3$)alkyl-S—($C_0$-$C_5$)alkyl,
    ($C_1$-$C_6$)alkyl-$SO_2$—($C_0$-$C_5$)alkyl optionally substituted on the ($C_1$-$C_6$)alkyl moiety with 1 to 6 fluoro substituents,
    ($C_3$-$C_7$)cycloalkyl-($C_0$-$C_3$)alkyl-$SO_2$—($C_0$-$C_5$)alkyl,
    $Ph^1$-($C_0$-$C_3$)alkyl-$SO_2$—($C_0$-$C_5$)alkyl,
    ($C_1$-$C_6$)alkyl-C(O)—($C_0$-$C_5$)alkyl,
    ($C_3$-$C_7$)cycloalkyl-($C_0$-$C_3$)alkyl-C(O)—($C_0$-$C_5$)alkyl,
    $Ph^1$-($C_0$-$C_3$)alkyl-C(O)—($C_0$-$C_5$)alkyl,
    ($C_1$-$C_6$)alkyl-NH—($C_0$-$C_5$)alkyl optionally substituted on the ($C_1$-$C_6$)alkyl moiety with 1 to 6 fluoro substituents,
    ($C_3$-$C_7$)cycloalkyl-($C_0$-$C_3$)alkyl-NH—($C_0$-$C_5$)alkyl,
    $Ph^1$-($C_0$-$C_3$)alkyl-NH—($C_0$-$C_5$)alkyl,
    ($C_1$-$C_6$)alkyl-NH—C(O)—($C_0$-$C_5$)alkyl optionally substituted on the ($C_1$-$C_6$)alkyl moiety with 1 to 6 fluoro substituents,
    ($C_3$-$C_7$)cycloalkyl-($C_0$-$C_3$)alkyl-NH—C(O)—($C_0$-$C_5$)alkyl,
    $Ph^1$-($C_0$-$C_3$)alkyl-NH—C(O)—($C_0$-$C_5$)alkyl,
    ($C_1$-$C_6$)alkyl-C(O)—NH—($C_0$-$C_5$)alkyl,
    ($C_3$-$C_7$)cycloalkyl-($C_0$-$C_3$)alkyl-C(O)—NH—($C_0$-$C_5$)alkyl, and
    $Ph^1$-($C_0$-$C_3$)alkyl-C(O)—NH—($C_0$-$C_5$)alkyl;
c) pyridazinyl optionally substituted with 1 or 2 substituents independently selected from the group consisting of halo, cyano, hydroxy, ($C_1$-$C_6$)alkyl optionally further substituted with 1 to 6 fluoro substituents, ($C_1$-$C_6$)alkoxy optionally further substituted with 1 to 6 fluoro substituents; and ($C_1$-$C_6$)alkylthio optionally further substituted with 1 to 6 fluoro substituents; or
d) a five-membered aromatic heterocycle selected from the group of thiophenyl, thiazole, isothiazole optionally substituted with 1 or 2 substituents independently selected from the group consisting of halo, cyano, hydroxy, ($C_1$-$C_6$)alkyl optionally further substituted with 1 to 6 fluoro substituents, ($C_1$-$C_6$)alkoxy optionally further substituted with 1 to 6 fluoro substituents, ($C_1$-$C_6$)alkylthio optionally further substituted with 1 to 6 fluoro substituents, ($C_1$-$C_6$)alkylamino optionally further substituted with 1 to 6 fluoro substituents, and ($C_1$-$C_6$)alkyl-C(O)—;

$Ar^1$ is pyridyl, optionally substituted with 1 to 4 independently selected halo substituents, or with 1 to 3 substituents independently selected from the group consisting of halo, cyano, hydroxy, acetyl, methyl, —$CF_3$, methoxy, —$OCF_3$, methylthio, —$SCF_3$;

$Ph^1$ is phenyl optionally substituted with 1 to 5 independently selected halo substituents, or with 1 to 3 substituents independently selected from the group consisting of halo, cyano, hydroxy, acetyl, methylthio, —$SCF_3$, ($C_1$-$C_6$)alkyl optionally further substituted with 1 to 6 fluoro substituents, and ($C_1$-$C_6$)alkoxy optionally further substituted with 1 to 6 fluoro substituents;

$Het^1$ is a saturated, nitrogen-containing heterocycle substituent selected from the group consisting of pyrrolidinyl, piperidinyl, homopiperidinyl, morpholinyl, thiomorpholinyl, homomorpholinyl, and homothiomorpholinyl, any of which may optionally be substituted with ($C_1$-$C_6$)alkyl or with 2 methyl substituents;

or a pharmaceutically acceptable salt thereof.

4. A compound of Formula (Ic):

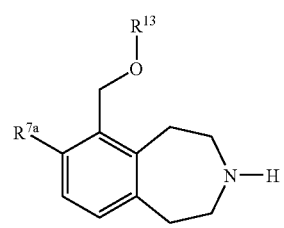

Ic wherein
$R^{7a}$ is chloro;
$R^{13}$ is
  a) phenyl optionally substituted with: i) 1 to 5 independently selected halo substituents; or
     ii) 1 to 3 substituents independently selected from the group consisting of halo, cyano, —SCF$_3$, nitro, hydroxy, (C$_1$-C$_6$)alkyl optionally further substituted with 1 to 6 fluoro substituents, and (C$_1$-C$_6$)alkoxy optionally further substituted with 1 to 6 fluoro substituents; or
     iii) 0, 1, or 2 substituents independently selected from the group consisting of halo, cyano, —SCF$_3$, methyl, —CF$_3$, methoxy, —OCF$_3$, nitro, and hydroxy, together with one substituent selected from the group consisting of
        (C$_3$-C$_7$)cycloalkyl-(C$_0$-C$_5$)alkyl optionally substituted on the alkyl moiety with 1 to 6 fluoro substituents and optionally substituted independently on the cycloalkyl moiety with 1 to 6 substituents selected from fluoro and methyl provided that no more than 2 substituents are methyl,
        Ph$^1$-(C$_0$-C$_5$)alkyl,
        Ar$^1$—(C$_0$-C$_5$)alkyl,
        (C$_1$-C$_6$)alkyl-CH═CH— optionally substituted with 1 to 6 fluoro substituents, (C$_3$-C$_7$)cycloalkyl-(C$_0$-C$_3$)alkyl-CH═CH— optionally substituted with 1 to 6 fluoro substituents on alkyl and optionally substituted independently on the cycloalkyl moiety with 1 to 6 substituents selected from fluoro and methyl provided that no more than 2 substituents are methyl,
        (C$_1$-C$_6$)alkyl-S—(C$_0$-C$_5$)alkyl optionally substituted on the (C$_1$-C$_6$)alkyl moiety with 1 to 6 fluoro substituents,
        (C$_3$-C$_7$)cycloalkyl-(C$_0$-C$_3$)alkyl-S—(C$_0$-C$_5$)alkyl,
        Ph$^1$-(C$_0$-C$_3$)alkyl-S—(C$_0$-C$_5$)alkyl,
        Ar$^1$—(C$_0$-C$_3$)alkyl-S—(C$_0$-C$_5$)alkyl,
        (C$_1$-C$_6$)alkyl-O—(C$_0$-C$_5$)alkyl optionally substituted on the (C$_1$-C$_6$)alkyl moiety with 1 to 6 fluoro substituents,
        (C$_3$-C$_7$)cycloalkyl-(C$_0$-C$_3$)alkyl-O—(C$_0$-C$_5$)alkyl,
        Ph$^1$-(C$_0$-C$_3$)alkyl-O—(C$_0$-C$_5$)alkyl,
        Ar$^1$—(C$_0$-C$_3$)alkyl-O—(C$_0$-C$_5$)alkyl,
        (C$_1$-C$_6$)alkyl-SO$_2$—(C$_0$-C$_5$)alkyl optionally substituted on the (C$_1$-C$_6$)alkyl moiety with 1 to 6 fluoro substituents,
        (C$_3$-C$_7$)cycloalkyl-(C$_0$-C$_3$)alkyl-SO$_2$—(C$_0$-C$_5$)alkyl,
        Ph$^1$-(C$_0$-C$_3$)alkyl-SO$_2$—(C$_0$-C$_5$)alkyl,
        Ar$^1$—(C$_0$-C$_3$)alkyl-SO$_2$—(C$_0$-C$_5$)alkyl,
        (C$_1$-C$_6$)alkyl-C(O)—(C$_0$-C$_5$)alkyl,
        (C$_3$-C$_7$)cycloalkyl-(C$_0$-C$_3$)alkyl-C(O)—(C$_0$-C$_5$)alkyl,
        Ph$^1$-(C$_0$-C$_3$)alkyl-C(O)—(C$_0$-C$_5$)alkyl,
        Ar$^1$—(C$_0$-C$_3$)alkyl-C(O)—(C$_0$-C$_5$)alkyl,
        (C$_1$-C$_6$)alkyl-NH—(C$_0$-C$_5$)alkyl optionally substituted on the (C$_1$-C$_6$)alkyl moiety with 1 to 6 fluoro substituents,
        (C$_3$-C$_7$)cycloalkyl-(C$_0$-C$_3$)alkyl-NH—(C$_0$-C$_5$)alkyl,
        Ph$^1$-(C$_0$-C$_3$)alkyl-NH—(C$_0$-C$_5$)alkyl,
        Ar$^1$—(C$_0$-C$_3$)alkyl-NH—(C$_0$-C$_5$)alkyl,
        Het$^1$-(C$_0$-C$_3$)alkyl-,
        (C$_1$-C$_6$)alkyl-NH—C(O)—(C$_0$-C$_5$)alkyl optionally substituted on the (C$_1$-C$_6$)alkyl moiety with 1 to 6 fluoro substituents,
        (C$_3$-C$_7$)cycloalkyl-(C$_0$-C$_3$)alkyl-NH—C(O)—(C$_0$-C$_5$)alkyl,
        Ph$^1$-(C$_0$-C$_3$)alkyl-NH—C(O)—(C$_0$-C$_5$)alkyl,
        Ar$^1$—(C$_0$-C$_3$)alkyl-NH—C(O)—(C$_0$-C$_5$)alkyl,
        (C$_1$-C$_6$)alkyl-(C$_0$-C$_3$)alkyl-C(O)—NH—(C$_0$-C$_5$)alkyl,
        (C$_3$-C$_7$)cycloalkyl-C(O)—NH—(C$_0$-C$_5$)alkyl,
        Ph$^1$-(C$_0$-C$_3$)alkyl-C(O)—NH—(C$_0$-C$_5$)alkyl,
        Ar$^1$—(C$_0$-C$_3$)alkyl-C(O)—NH—(C$_0$-C$_5$)alkyl,
        (C$_1$-C$_6$)alkyl-NH—SO$_2$—(C$_0$-C$_5$)alkyl optionally substituted on the (C$_1$-C$_6$)alkyl moiety with 1 to 6 fluoro substituents,
        (C$_3$-C$_7$)cycloalkyl-(C$_0$-C$_3$)alkyl-NH—SO$_2$—(C$_0$-C$_5$)alkyl,
        (C$_1$-C$_6$)alkyl-SO$_2$—NH—(C$_0$-C$_5$)alkyl,
        (C$_3$-C$_7$)cycloalkyl-(C$_0$-C$_3$)alkyl-SO$_2$—NH—(C$_0$-C$_5$)alkyl; or
  b) thiophenyl optionally substituted with one to two substituents selected from the group consisting of
     halo,
     cyano,
     (C$_1$-C$_6$)alkyl optionally substituted with 1 to 6 fluoro substituents,
     Ph$^1$-(C$_0$-C$_3$)alkyl optionally substituted on the alkyl moiety with 1 to 6 fluoro substituents,
     Ar$^1$—(C$_0$-C$_3$)alkyl optionally substituted on the alkyl moiety with 1 to 6 fluoro substituents,
     (C$_1$-C$_6$)alkyl-C(O)—,
     Ph$^1$-(C$_0$-C$_3$)alkyl-C(O)—,
     Ar$^1$—(C$_0$-C$_3$)alkyl-C(O)—,
     (C$_1$-C$_6$)alkyl-NH—C(O)— optionally substituted with 1 to 6 fluoro substituents,
     Ph$^1$-(C$_0$-C$_3$)alkyl-NH—C(O)— optionally substituted on the alkyl moiety with 1 to 6 fluoro substituents,
     Ar$^1$—(C$_0$-C$_3$)alkyl-NH—C(O)— optionally substituted on the alkyl moiety with 1 to 6 fluoro substituents,
     (C$_1$-C$_6$)alkyl-CH═CH— optionally substituted with 1 to 6 fluoro substituents,
     (C$_1$-C$_6$)alkoxy optionally substituted with 1 to 6 fluoro substituents,
     (C$_1$-C$_6$)alkylthio optionally substituted with 1 to 6 fluoro substituents,
     Ph$^1$-(C$_0$-C$_3$)alkylthio,
     (C$_1$-C$_6$)alkyl-NR$^{12}$—(C$_0$-C$_3$)alkyl- optionally substituted on the (C$_1$-C$_6$)alkyl moiety with 1 to 6 fluoro substituents,
     (C$_3$-C$_7$)cycloalkyl-(C$_0$-C$_3$)alkyl-NR$^{12}$—(C$_0$-C$_3$)alkyl,
     Ph$^1$-(C$_0$-C$_3$)alkyl-NR$^{12}$—(C$_0$-C$_3$)alkyl-,
     Ar$^1$—(C$_0$-C$_3$)alkyl-NR$^{12}$—(C$_0$-C$_3$)alkyl-,
     Het$^1$-(C$_0$-C$_3$)alkyl-,
     (C$_1$-C$_6$)alkyl-C(O)—NH—,
     Ph$^1$-(C$_0$-C$_3$)alkyl-C(O)—NH—,
     Ar$^1$—(C$_0$-C$_3$)alkyl-C(O)—NH—,
     (C$_1$-C$_6$)alkyl-O—C(O)—NH— optionally substituted with 1 to 6 fluoro substituents,
     Ph$^1$-(C$_0$-C$_3$)alkyl-O—C(O)—NH— optionally substituted on the alkyl moiety with 1 to 6 fluoro substituents, and
     Ar$^1$—(C$_0$-C$_3$)alkyl-O—C(O)—NH— optionally substituted on the alkyl moiety with 1 to 6 fluoro substituents;

$R^{12}$ is hydrogen or methyl;

$Ar^1$ is pyridyl, optionally substituted with 1 to 4 independently selected halo substituents, or with 1 to 3 substituents independently selected from the group consisting of halo, cyano, hydroxy, acetyl, methyl, —$CF_3$, methoxy, —$OCF_3$, methylthio, —$SCF_3$;

$Ph^1$ is phenyl optionally substituted with 1 to 5 independently selected halo substituents, or with 1 to 3 substituents independently selected from the group consisting of halo, cyano, hydroxy, acetyl, methylthio, —$SCF_3$, ($C_1$-$C_6$)alkyl optionally further substituted with 1 to 6 fluoro substituents, and ($C_1$-$C_6$)alkoxy optionally further substituted with 1 to 6 fluoro substituents;

$Het^1$ is a saturated, nitrogen-containing heterocycle substituent selected from the group consisting of pyrrolidinyl, piperidinyl, homopiperidinyl, morpholinyl, thiomorpholinyl, homomorpholinyl, and homothiomorpholinyl, any of which may optionally be substituted with ($C_1$-$C_6$)alkyl or with 2 methyl substituents;

or a pharmaceutically acceptable salt thereof.

5. A pharmaceutical composition comprising a compound according to claim 1, or a pharmaceutically acceptable salt thereof, as an active ingredient in association with a pharmaceutically acceptable carrier, diluent or excipient.

\* \* \* \* \*